US012656343B2

(12) United States Patent
Toler et al.

(10) Patent No.: US 12,656,343 B2
(45) Date of Patent: Jun. 16, 2026

(54) BIOMARKERS OF EARLY OSTEOARTHRITIS

(71) Applicant: CD DIAGNOSTICS, INC., Claymont, DE (US)

(72) Inventors: Krista Toler, Pierceton, IN (US); James W. Stave, Bear, DE (US); Michael Brown, Warsaw, IN (US); Carolina Sepulveda, Glen Mills, PA (US); Tony Joaquim, Mount Laurel, NJ (US)

(73) Assignee: CD DIAGNOSTICS, INC., Claymont, DE (US)

( * ) Notice: Subject to any disclaimer, the term of this patent is extended or adjusted under 35 U.S.C. 154(b) by 1081 days.

(21) Appl. No.: 17/770,541

(22) PCT Filed: Oct. 29, 2020

(86) PCT No.: PCT/US2020/057967
§ 371 (c)(1),
(2) Date: Apr. 20, 2022

(87) PCT Pub. No.: WO2021/087116
PCT Pub. Date: May 6, 2021

(65) Prior Publication Data
US 2022/0390466 A1 Dec. 8, 2022

Related U.S. Application Data

(60) Provisional application No. 63/010,756, filed on Apr. 16, 2020, provisional application No. 62/928,114, filed on Oct. 30, 2019.

(51) Int. Cl.
*G01N 33/569* (2006.01)
*G01N 33/487* (2006.01)
(Continued)

(52) U.S. Cl.
CPC ..... *G01N 33/56972* (2013.01); *G01N 33/487* (2013.01); *G01N 33/6893* (2013.01);
(Continued)

(58) Field of Classification Search
CPC .......... G01N 33/56972; G01N 33/487; G01N 33/6893; G01N 33/6887;
(Continued)

(56) References Cited

U.S. PATENT DOCUMENTS 8,058,013 B2 11/2011 Karl et al.
2011/0218116 A1 9/2011 Cook et al.
(Continued)

FOREIGN PATENT DOCUMENTS

WO 2021087116 5/2021
WO WO-2021087116 A1 5/2021

OTHER PUBLICATIONS

U.S. Appl. No. 17/573,843, filed Jan. 12, 2022, Pre-Surgical Diagnostic Tool Using Biomarkers to Evaluate the Risk Factors of Post Surgical Complications.
(Continued)

*Primary Examiner* — Kathryn Elizabeth Limbaugh
(74) *Attorney, Agent, or Firm* — Schwegman Lundberg & Woessner, P.A.

(57) ABSTRACT

Biomarkers are used in compositions, combinations, systems, and methods for diagnosing, staging, and monitoring and/or treatment of osteoarthritis. The biomarkers discriminate osteoarthritis from rheumatoid arthritis, crystalline arthritis, septic arthritis, and/or traumatic injury, and can be used in a differential diagnosis of joint pain and/or joint inflammation.

20 Claims, 105 Drawing Sheets

(51) Int. Cl.
    *G01N 33/68*      (2006.01)
    *G16H 50/20*     (2018.01)

(52) U.S. Cl.
    CPC ..... *G16H 50/20* (2018.01); *G01N 2333/5421* (2013.01); *G01N 2333/78* (2013.01); *G01N 2800/102* (2013.01); *G01N 2800/105* (2013.01)

(58) Field of Classification Search
    CPC ....... G01N 2333/5421; G01N 2333/78; G01N 2800/102; G01N 2800/105; G16H 50/20
    See application file for complete search history.

(56) References Cited

U.S. PATENT DOCUMENTS

| | | |
|---|---|---|
| 2018/0045737 A1 | 2/2018 | Deirmengian et al. |
| 2022/0137048 A1 | 5/2022 | Thai-paquette et al. |

OTHER PUBLICATIONS

"International Application Serial No. PCT/US2020/057967, International Search Report mailed Feb. 23, 2021", 5 pgs.

"International Application Serial No. PCT/US2020/057967, Written Opinion mailed Feb. 23, 2021", 7 pgs.

Pantsulaia, I, et al., "Association between radiographic hand osteoarthritis and RANKL, OPG and inflammatory markers", Osteoarthritis and Cartilage, Bailliere Tindall, London, GB, vol. 18, No. 11, (Nov. 1, 2010), 1448-1453.

Pilichou, A, et al., "High levels of synovial fluid osteoprotegerin (OPG) and increased serum ratio of receptor activator of nuclear factor-@kB ligand (RANKL) to OPG correlate with disease severity in patients with primary knee osteoarthritis", Clinical Biochemistry, Elsevier Inc, US, CA, vol. 41, No. 9, (Jun. 1, 2008), 746-749.

"International Application Serial No. PCT US2020 057967, International Preliminary Report on Patentability mailed May 12, 2022", 9 pgs.

"Protocols Used in Molecular Biology", eds. Singh, S.K., and Kumar, D., Benthan Science ISBN: 9789811439292 available at researchgate.net., (2020), 70 pgs.

Ausubel, "Current Protocols in Molecular Biology", John Wiley and Sons, New York, N.Y.,, (2003), pp. 1934-3647.

Healy, William L., "Complications of total knee arthroplasty: standardized list and definitions of the Knee Society.", The Association of Bone and Joint Surgeons, (Jul. 19, 2012), 6 pgs.

Pantsulaia, I, "Association between radiographic hand osteoarthritis and RANKL, OPG and inflammatory markers", Osteoarthritis and Cartilage, Bailliere Tindall, London, GB, vol. 18, No. 11, (Nov. 1, 2010), 1448-1453.

Pilichou, A, "High levels of synovial fluid osteoprotegerin (OPG) and increased serum ratio of receptor activator of nuclear factor-@kB ligand (RANKL) to OPG correlate with disease severity in patients with primary knee osteoarthritis", Clinical Biochemistry, Elsevier Inc, US, CA, vol. 41, No. 9, (Jun. 1, 2008), 746-749.

Villanueva, "Automated serum peptide profiling", Nature Protocols vol. 1 (2), (2006), 881-891.

"European Application Serial No. 20808604.1, Response to Communication pursuant to Rules 161(1) and 162 EPC filed Dec. 19, 2022", 13 pgs.

"European Application Serial No. 20808604.1, Communication Pursuant to Article 94(3) EPC mailed Feb. 6, 2025", 6 pgs.

"European Application Serial No. 20808604.1, Response filed Jun. 4, 2025 to Communication Pursuant to Article 94(3) EPC mailed Feb. 6, 2025", 214 pgs.

"U.S. Appl. No. 17/573,843, Non Final Office Action mailed Oct. 1, 2025", 20 pgs.

Heard, Bryan J., et al., "A computational method to differentiate normal individuals, osteoarthritis and rheumatoid arthritis patients using serum biomarkers", J. R. Soc. Interface 11: Apr. 28, 2014, (2014), 1-9.

Martadiani, E. D., et al., "High level of serum cartilage oligomeric matrix protein and plasma interleukin-6 increase the risk of ultrasound-detected synovial inflammation in knee osteoarthritis", Bali Med. J. 6(1), (2017), 23-30.

MMP-13

TIMP-1

MMP-13

TIMP1

| MARKER | OA VS. ALL | | | | OA VS. RA | | | | OA VS. TRAUMA | | | |
|---|---|---|---|---|---|---|---|---|---|---|---|---|
| | AUC | CUTOFF | SENSITIVITY | SPECIFICITY | AUC | CUTOFF | SENSITIVITY | SPECIFICITY | AUC | CUTOFF | SENSITIVITY | SPECIFICITY |
| COMP | 0.895 | >3697 | 85.2 | 89.5 | 0.933 | >3609 | 85.2 | 100.0 | 0.872 | >3697 | 85.2 | 82.9 |
| IL-8 | 0.963 | <406.0 | 92.6 | 96.5 | 0.959 | <603.5 | 94.4 | 95.5 | 0.966 | <367.0 | 90.7 | 100.0 |
| CRP | 0.956 | <2.550 | 92.0 | 94.7 | 0.939 | <2.550 | 92.0 | 86.4 | 0.967 | <2.700 | 92.0 | 100.0 |
| MMP-9 | 0.952 | <19191 | 96.3 | 89.5 | 0.911 | <9056 | 90.7 | 86.4 | 0.978 | <34212 | 96.3 | 100.0 |
| OPG | 0.877 | >6079 | 73.0 | 88.6 | 0.801 | >6598 | 70.3 | 82.6 | 0.959 | >4586 | 91.9 | 95.2 |
| OPN | 0.877 | >13063 | 97.3 | 76.7 | 0.786 | >8094 | 100.0 | 625.2 | 0.981 | >13063 | 97.3 | 90.0 |
| MMP3 | 0.875 | <2.53 E6 | 82.1 | 90.9 | 0.854 | <2.53 E6 | 82.1 | 82.6 | 0.898 | <2.69 E6 | 82.1 | 100.0 |
| IL6 | 0.966 | <2752 | 97.3 | 86.1 | 0.941 | <2128 | 91.9 | 82.6 | 0.995 | <2823 | 97.3 | 100.0 |
| OC | 0.873 | >4110 | 82.1 | 83.3 | 0.876 | <4512 | 75.0 | 90.9 | 0.870 | >2356 | 96.4 | 75.0 |
| PDGF | 0.938 | <287.0 | 100.0 | 88.1 | 0.929 | <287.0 | 100.0 | 86.4 | 0.948 | <513.0 | 100.0 | 90.0 |
| NGAL | 0.843 | <156699 | 96.4 | 81.0 | 0.731 | <156699 | 96.4 | 63.6 | 0.966 | <1903366 | 96.4 | 100.0 |

FIG. 24

WOMAC STIFFNESS CFB vs. COMP/IL-8 RATIO BY KL GRADE

KELLGREN-LAWRENCE GRADE AT BASELINE ● 2 ◆ 3 ■ 4

COMP/IL-8 RATIO

CHANGE IN WOMAC STIFFNESS

| NUMBER | BATCH | COHORT | KL SCORE | ANTI-CCP (U/mL) | RF (IU/mL) | RA ALGORITHM TERTIARY ANALYSIS | COMP (ng/mL) | IL-8 (pg/mL) | COMP/IL-8 (ng/pg) | OSTEOARTHRITIS ALGORITHM |
|---|---|---|---|---|---|---|---|---|---|---|
| 1 | 1 | CA | NA | BQL | <10 | NEGATIVE | 3283 | AQL | 0.1 | NEGATIVE |
| 2 | 1 | CA | NA | BQL | <10 | NEGATIVE | 4423 | 3048.269 | 1.5 | NEGATIVE |
| 3 | 1 | CA | NA | BQL | <10 | NEGATIVE | 3057 | 387.292 | 7.9 | POSITIVE |
| 4 | 1 | CA | NA | BQL | <10 | NEGATIVE | 8589 | 1293.817 | 6.6 | NEGATIVE |
| 5 | 1 | CA | NA | BQL | <10 | NEGATIVE | 3148 | 1461.113 | 2.0 | POSITIVE |
| 6 | 1 | CA | NA | BQL | <10 | NEGATIVE | 6991 | 1506.445 | 4.6 | POSITIVE |
| 7 | 1 | CA | NA | BQL | <10 | NEGATIVE | 7138 | 413.13 | 17.3 | NEGATIVE |
| 8 | 1 | CA | NA | BQL | <10 | NEGATIVE | 8671 | 1441.431 | 6.0 | NEGATIVE |
| 9 | 1 | CA | NA | BQL | <10 | NEGATIVE | 3881 | 1395.752 | 2.8 | NEGATIVE |
| 10 | 1 | CA | NA | BQL | <10 | NEGATIVE | BQL | 7903.13 | NIL | NEGATIVE |
| 11 | 1 | CA | NA | BQL | <10 | NEGATIVE | 2947 | 932.422 | 3.2 | NEGATIVE |
| 12 | 1 | CA | NA | BQL | <10 | NEGATIVE | 3429 | 1398.846 | 2.5 | NEGATIVE |
| 13 | 1 | CA | NA | BQL | <10 | NEGATIVE | BQL | 10380.4 | NIL | NEGATIVE |
| 14 | 1 | CA | NA | BQL | <10 | NEGATIVE | 2172 | 640.583 | 3.4 | NEGATIVE |
| 15 | 1 | CA | NA | BQL | <10 | NEGATIVE | 4760 | 3564.889 | 1.3 | NEGATIVE |
| 16 | 1 | CA | NA | BQL | <10 | NEGATIVE | 2355 | 1328.769 | 1.8 | NEGATIVE |
| 17 | 1 | CA | NA | BQL | <10 | NEGATIVE | 2925 | AQL | 0.1 | NEGATIVE |
| 18 | 1 | CA | NA | BQL | <10 | NEGATIVE | 1738 | 3750.832 | 0.5 | NEGATIVE |
| 19 | 1 | CA | NA | BQL | <10 | NEGATIVE | 1792 | 30484.07 | 0.1 | NEGATIVE |
| 20 | 1 | CA | NA | BQL | <10 | NEGATIVE | 6441 | 191.727 | 33.6 | POSITIVE |
| 21 | 1 | CA | NA | BQL | <10 | NEGATIVE | 4202 | 5698.53 | 0.7 | NEGATIVE |
| 22 | 1 | CA | NA | BQL | <10 | NEGATIVE | 2898 | 4612.736 | 0.6 | NEGATIVE |
| 23 | 1 | CA | NA | BQL | <10 | NEGATIVE | 5451 | 447.47 | 1.1 | POSITIVE |
| 24 | 1 | CA | NA | BQL | <10 | NEGATIVE | 2649 | 6580.14 | 1.2 | NEGATIVE |
| 25 | 1 | CA | NA | BQL | <10 | NEGATIVE | 2792 | 1933.128 | 2.7 | NEGATIVE |

FIG. 42A-1

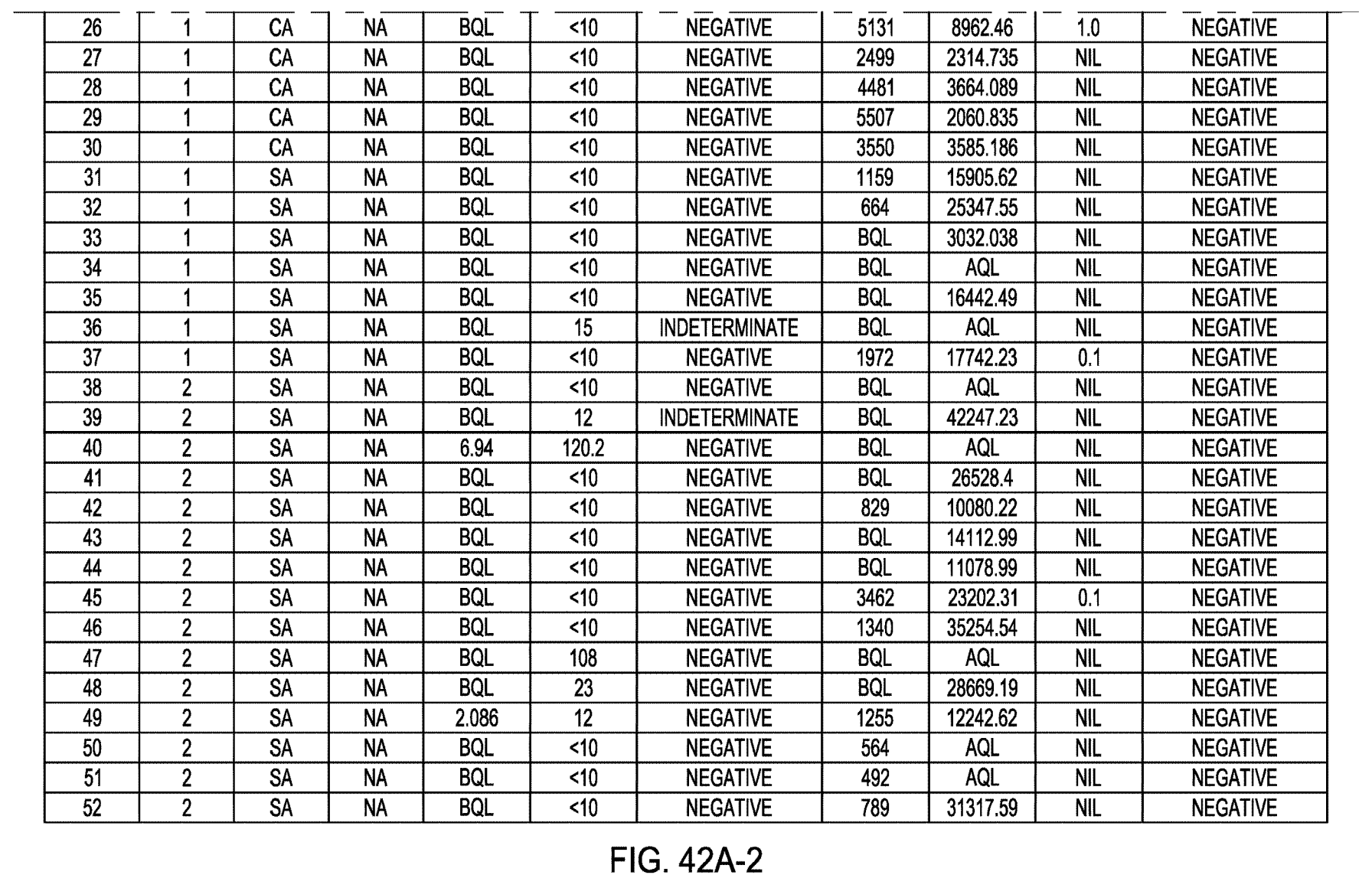

| | | | | | | | | | | |
|---|---|---|---|---|---|---|---|---|---|---|
| 26 | 1 | CA | NA | BQL | <10 | NEGATIVE | 5131 | 8962.46 | 1.0 | NEGATIVE |
| 27 | 1 | CA | NA | BQL | <10 | NEGATIVE | 2499 | 2314.735 | NIL | NEGATIVE |
| 28 | 1 | CA | NA | BQL | <10 | NEGATIVE | 4481 | 3664.089 | NIL | NEGATIVE |
| 29 | 1 | CA | NA | BQL | <10 | NEGATIVE | 5507 | 2060.835 | NIL | NEGATIVE |
| 30 | 1 | CA | NA | BQL | <10 | NEGATIVE | 3550 | 3585.186 | NIL | NEGATIVE |
| 31 | 1 | SA | NA | BQL | <10 | NEGATIVE | 1159 | 15905.62 | NIL | NEGATIVE |
| 32 | 1 | SA | NA | BQL | <10 | NEGATIVE | 664 | 25347.55 | NIL | NEGATIVE |
| 33 | 1 | SA | NA | BQL | <10 | NEGATIVE | BQL | 3032.038 | NIL | NEGATIVE |
| 34 | 1 | SA | NA | BQL | <10 | NEGATIVE | BQL | AQL | NIL | NEGATIVE |
| 35 | 1 | SA | NA | BQL | <10 | NEGATIVE | BQL | 16442.49 | NIL | NEGATIVE |
| 36 | 1 | SA | NA | BQL | 15 | INDETERMINATE | BQL | AQL | NIL | NEGATIVE |
| 37 | 1 | SA | NA | BQL | <10 | NEGATIVE | 1972 | 17742.23 | 0.1 | NEGATIVE |
| 38 | 2 | SA | NA | BQL | <10 | NEGATIVE | BQL | AQL | NIL | NEGATIVE |
| 39 | 2 | SA | NA | BQL | 12 | INDETERMINATE | BQL | 42247.23 | NIL | NEGATIVE |
| 40 | 2 | SA | NA | 6.94 | 120.2 | NEGATIVE | BQL | AQL | NIL | NEGATIVE |
| 41 | 2 | SA | NA | BQL | <10 | NEGATIVE | BQL | 26528.4 | NIL | NEGATIVE |
| 42 | 2 | SA | NA | BQL | <10 | NEGATIVE | 829 | 10080.22 | NIL | NEGATIVE |
| 43 | 2 | SA | NA | BQL | <10 | NEGATIVE | BQL | 14112.99 | NIL | NEGATIVE |
| 44 | 2 | SA | NA | BQL | <10 | NEGATIVE | BQL | 11078.99 | NIL | NEGATIVE |
| 45 | 2 | SA | NA | BQL | <10 | NEGATIVE | 3462 | 23202.31 | 0.1 | NEGATIVE |
| 46 | 2 | SA | NA | BQL | <10 | NEGATIVE | 1340 | 35254.54 | NIL | NEGATIVE |
| 47 | 2 | SA | NA | BQL | 108 | NEGATIVE | BQL | AQL | NIL | NEGATIVE |
| 48 | 2 | SA | NA | BQL | 23 | NEGATIVE | BQL | 28669.19 | NIL | NEGATIVE |
| 49 | 2 | SA | NA | 2.086 | 12 | NEGATIVE | 1255 | 12242.62 | NIL | NEGATIVE |
| 50 | 2 | SA | NA | BQL | <10 | NEGATIVE | 564 | AQL | NIL | NEGATIVE |
| 51 | 2 | SA | NA | BQL | <10 | NEGATIVE | 492 | AQL | NIL | NEGATIVE |
| 52 | 2 | SA | NA | BQL | <10 | NEGATIVE | 789 | 31317.59 | NIL | NEGATIVE |

FIG. 42A-2

| NUMBER | BATCH | COHORT | KL SCORE | ANTI-CCP (U/mL) | RF (IU/mL) | RA ALGORITHM TERTIARY ANALYSIS | COMP (ng/mL) | IL-8 (pg/mL) | COMP/IL-8 (ng/pg) | OSTEOARTHRITIS ALGORITHM |
|---|---|---|---|---|---|---|---|---|---|---|
| 53 | 2 | SA | NA | BQL | <10 | NEGATIVE | 929 | AQL | NIL | NEGATIVE |
| 54 | 2 | SA | NA | BQL | <10 | NEGATIVE | 64 | AQL | NIL | NEGATIVE |
| 55 | 2 | SA | NA | 201.114 | 441.7 | POSITIVE | 836 | 16606.54 | NIL | NEGATIVE |
| 56 | 2 | SA | NA | BQL | <10 | NEGATIVE | 277 | 14915.89 | NIL | NEGATIVE |
| 57 | 2 | SA | NA | BQL | <10 | NEGATIVE | 3564 | 14307.16 | 0.2 | NEGATIVE |
| 58 | 2 | SA | NA | BQL | <10 | NEGATIVE | 279 | AQL | NIL | NEGATIVE |
| 59 | 2 | SA | NA | BQL | <10 | NEGATIVE | 101 | 26182.37 | NIL | NEGATIVE |
| 60 | 2 | SA | NA | BQL | <10 | NEGATIVE | 33 | 49402.66 | NIL | NEGATIVE |
| 61 | 2 | UNK | NA | BQL | <10 | NEGATIVE | 10635 | 520.387 | 20.4 | POSITIVE |
| 62 | 2 | UNK | NA | BQL | <10 | NEGATIVE | 4843 | BQL | 48.0 | POSITIVE |
| 63 | 2 | UNK | NA | BQL | <10 | NEGATIVE | 6031 | 1788.154 | 3.4 | NEGATIVE |
| 64 | 2 | UNK | NA | BQL | <10 | NEGATIVE | 3722 | 610.02 | 6.1 | POSITIVE |
| 65 | 2 | UNK | NA | 171.018 | 28 | POSITIVE | 513 | 2910.311 | NIL | NEGATIVE |
| 66 | 2 | UNK | NA | BQL | <10 | NEGATIVE | 2498 | 121.165 | 20.6 | POSITIVE |
| 67 | 2 | UNK | NA | BQL | <10 | NEGATIVE | 3103 | 2173.717 | 1.4 | NEGATIVE |
| 68 | 2 | UNK | NA | BQL | <10 | NEGATIVE | 1354 | 3253.475 | NIL | NEGATIVE |
| 69 | 2 | UNK | NA | BQL | <10 | NEGATIVE | 6727 | 538.41 | 12.5 | POSITIVE |
| 70 | 2 | UNK | NA | BQL | <10 | NEGATIVE | 824 | 3896.974 | NIL | NEGATIVE |
| 71 | 2 | UNK | NA | BQL | <10 | NEGATIVE | 4873 | 2124.46 | 2.3 | NEGATIVE |
| 72 | 2 | UNK | NA | BQL | <10 | POSITIVE | 2132 | 612.283 | 3.5 | POSITIVE |
| 73 | 2 | UNK | NA | BQL | 36 | POSITIVE | 1651 | AQL | 0.0 | NEGATIVE |
| 74 | 2 | UNK | NA | BQL | <10 | NEGATIVE | 3585 | 4321.035 | 0.8 | NEGATIVE |
| 75 | 2 | UNK | NA | BQL | <10 | NEGATIVE | 1068 | 7262.37 | NIL | NEGATIVE |
| 76 | 2 | UNK | NA | BQL | <10 | NEGATIVE | 4323 | 1658.895 | 2.6 | NEGATIVE |
| 77 | 2 | UNK | NA | BQL | <10 | NEGATIVE | 3307 | 1297.165 | 2.5 | NEGATIVE |
| 78 | 2 | UNK | NA | BQL | <10 | NEGATIVE | 6897 | 847.522 | 8.1 | POSITIVE |

FIG. 42B-1

| | | | | | | | | | | |
|---|---|---|---|---|---|---|---|---|---|---|
| 79 | 2 | UNK | NA | BQL | <10 | NEGATIVE | 11050 | 198.659 | 55.6 | POSITIVE |
| 80 | 2 | UNK | NA | BQL | 12 | INDETERMINATE | 1064 | 10278.76 | NIL | NEGATIVE |
| 81 | 2 | OA | 2 | BQL | <10 | NEGATIVE | 3302 | BQL | 32.7 | POSITIVE |
| 82 | 2 | OA | 3 | BQL | <10 | NEGATIVE | 4686 | BQL | 46.4 | POSITIVE |
| 83 | 2 | OA | 4 | BQL | <10 | NEGATIVE | 4367 | 699.21 | 6.2 | POSITIVE |
| 84 | 2 | OA | 4 | BQL | <10 | NEGATIVE | 4995 | 149.729 | 33.4 | POSITIVE |
| 85 | 2 | OA | 2 | BQL | <10 | NEGATIVE | 1675 | 2089.436 | 0.8 | NEGATIVE |
| 86 | 2 | OA | 4 | BQL | <10 | NEGATIVE | 3920 | 1531.144 | 2.6 | NEGATIVE |
| 87 | 2 | OA | 3 | BQL | <10 | NEGATIVE | 3488 | BQL | 34.5 | POSITIVE |
| 88 | 2 | OA | 3 | BQL | 15 | NEGATIVE | 3995 | 117.861 | 33.9 | POSITIVE |
| 89 | 2 | OA | 4 | BQL | <10 | NEGATIVE | 3890 | 2959.19 | 1.3 | NEGATIVE |
| 90 | 2 | OA | 4 | BQL | <10 | NEGATIVE | 1998 | BQL | 19.8 | POSITIVE |
| 91 | 2 | OA | 3 | BQL | 12 | NEGATIVE | 4239 | BQL | 42.0 | POSITIVE |
| 92 | 2 | OA | 3 | 6.94 | 120.2 | NEGATIVE | 9565 | 192.737 | 49.6 | POSITIVE |
| 93 | 2 | OA | 2 | BQL | <10 | NEGATIVE | 3321 | BQL | 32.9 | POSITIVE |
| 94 | 2 | OA | NR | BQL | <10 | NEGATIVE | 4752 | BQL | 47.0 | POSITIVE |
| 95 | 2 | OA | 3 | BQL | <10 | NEGATIVE | 4658 | BQL | 46.1 | POSITIVE |
| 96 | 2 | OA | 3 | BQL | <10 | NEGATIVE | 4594 | BQL | 45.5 | POSITIVE |
| 97 | 2 | OA | 3 | BQL | <10 | NEGATIVE | 2645 | BQL | 26.2 | POSITIVE |
| 98 | 2 | OA | 3 | BQL | <10 | NEGATIVE | 2586 | BQL | 25.6 | POSITIVE |
| 99 | 2 | OA | NR | BQL | 108 | NEGATIVE | 3916 | 208.83 | 18.8 | POSITIVE |
| 100 | 2 | OA | 4 | BQL | 23 | NEGATIVE | 2882 | BQL | 28.5 | POSITIVE |
| 101 | 2 | OA | 3 | 2.086 | 12 | NEGATIVE | 3461 | BQL | 34.3 | POSITIVE |
| 102 | 2 | OA | 4 | BQL | <10 | NEGATIVE | 4071 | 784.724 | 5.2 | POSITIVE |
| 103 | 2 | OA | NR | BQL | <10 | NEGATIVE | 7460 | BQL | 73.9 | POSITIVE |
| 104 | 2 | OA | 2 | BQL | <10 | NEGATIVE | 4897 | BQL | 48.5 | POSITIVE |
| 105 | 2 | OA | 3 | BQL | <10 | NEGATIVE | 6139 | 169.878 | 36.1 | POSITIVE |
| 106 | 2 | OA | 3 | BQL | <10 | NEGATIVE | 3404 | BQL | 33.7 | POSITIVE |

FIG. 42B-2

| NUMBER | BATCH | COHORT | KL SCORE | ANTI-CCP (U/mL) | RF (IU/mL) | RA ALGORITHM TERTIARY ANALYSIS | COMP (ng/mL) | IL-8 (pg/mL) | COMP/IL-8 (ng/pg) | OSTEOARTHRITIS ALGORITHM |
|---|---|---|---|---|---|---|---|---|---|---|
| 107 | 2 | OA | 4 | BQL | <10 | NEGATIVE | 4756 | 685.147 | 6.9 | POSITIVE |
| 108 | 2 | OA | 4 | BQL | <10 | NEGATIVE | 4041 | 325.631 | 12.4 | POSITIVE |
| 109 | 2 | OA | 3 | BQL | <10 | NEGATIVE | 3891 | BQL | 38.5 | POSITIVE |
| 110 | 2 | OA | 3 | BQL | <10 | NEGATIVE | 5051 | 123.144 | 41.0 | POSITIVE |
| 111 | 2 | OA | 3 | BQL | <10 | NEGATIVE | 2885 | BQL | 28.6 | POSITIVE |
| 112 | 3 | UNK | NA | BQL | <10 | NEGATIVE | 1363 | 6859.44 | NIL | NEGATIVE |
| 113 | 3 | UNK | NA | BQL | <10 | NEGATIVE | 2707 | 689.939 | 3.9 | NEGATIVE |
| 114 | 3 | UNK | NA | BQL | <10 | NEGATIVE | 4664 | 12692.21 | 0.4 | NEGATIVE |
| 115 | 3 | UNK | NA | BQL | <10 | NEGATIVE | 2956 | 149.324 | 19.8 | POSITIVE |
| 116 | 3 | UNK | NA | BQL | <10 | NEGATIVE | 5517 | 808.674 | 6.8 | POSITIVE |
| 117 | 3 | UNK | NA | AQL | 47 | NEGATIVE | 726 | 6134.85 | NIL | NEGATIVE |
| 118 | 3 | UNK | NA | BQL | <10 | NEGATIVE | 6224 | 450.264 | 13.8 | POSITIVE |
| 119 | 3 | UNK | NA | BQL | <10 | NEGATIVE | 6280 | 119.049 | 52.8 | POSITIVE |
| 120 | 3 | UNK | NA | BQL | <10 | NEGATIVE | BQL | 153644.9 | NIL | NEGATIVE |
| 121 | 3 | UNK | NA | BQL | <10 | NEGATIVE | 1152 | 7841.65 | NIL | NEGATIVE |
| 122 | 3 | UNK | NA | BQL | <10 | NEGATIVE | 2196 | 22186.91 | 0.1 | NEGATIVE |
| 123 | 3 | UNK | NA | BQL | 11 | INDETERMINATE | 5401 | 168.53 | 32.0 | POSITIVE |
| 124 | 3 | UNK | NA | BQL | 16 | INDETERMINATE | 18890 | 552.177 | 34.2 | POSITIVE |
| 125 | 3 | UNK | NA | BQL | <10 | NEGATIVE | 786 | 1708.383 | NIL | NEGATIVE |
| 126 | 3 | UNK | NA | BQL | <10 | NEGATIVE | 3924 | 625.339 | 6.3 | POSITIVE |
| 127 | 3 | UNK | NA | BQL | <10 | NEGATIVE | 1085 | 1999.425 | NIL | NEGATIVE |
| 128 | 3 | UNK | NA | BQL | <10 | NEGATIVE | 2497 | 1522.446 | 1.6 | NEGATIVE |
| 129 | 3 | UNK | NA | BQL | <10 | NEGATIVE | 4437 | 1777.446 | 2.5 | NEGATIVE |
| 130 | 3 | UNK | NA | BQL | <10 | NEGATIVE | 3707 | 645.713 | 5.7 | POSITIVE |
| 131 | 3 | UNK | NA | BQL | <10 | NEGATIVE | 3562 | 1041.513 | 3.4 | NEGATIVE |
| 132 | 3 | UNK | NA | BQL | <10 | NEGATIVE | 739 | 24367.74 | NIL | NEGATIVE |

FIG. 42C-1

| | | | | | | | | | |
|---|---|---|---|---|---|---|---|---|---|
| 133 | 3 | UNK | NA | BQL | <10 | NEGATIVE | 5035 | 1403.943 | 3.6 | NEGATIVE |
| 134 | 3 | UNK | NA | BQL | <10 | NEGATIVE | 5376 | 161.602 | 33.3 | POSITIVE |
| 135 | 3 | UNK | NA | BQL | <10 | NEGATIVE | 7250 | 1163.226 | 6.2 | POSITIVE |
| 136 | 3 | UNK | NA | BQL | <10 | NEGATIVE | 3821 | 259.614 | 14.7 | POSITIVE |
| 137 | 3 | UNK | NA | BQL | 12 | NEGATIVE | 6299 | 904.202 | 7.0 | POSITIVE |
| 138 | 3 | UNK | NA | BQL | <10 | INDETERMINATE | 1797 | 503.153 | 3.6 | NEGATIVE |
| 139 | 3 | UNK | NA | 35.575 | <10 | INDETERMINATE | 4672 | 639.758 | 7.3 | POSITIVE |
| 140 | 3 | UNK | NA | BQL | <10 | NEGATIVE | 893 | 8151.6 | NIL | NEGATIVE |
| 141 | 3 | UNK | NA | BQL | 38 | INDETERMINATE | 3189 | 756.431 | 4.2 | NEGATIVE |
| 142 | 3 | UNK | NA | BQL | <10 | NEGATIVE | 1658 | 888.176 | 1.9 | NEGATIVE |
| 143 | 3 | UNK | NA | BQL | <10 | NEGATIVE | 3240 | 1191.15 | 2.7 | NEGATIVE |
| 144 | 3 | UNK | NA | BQL | <10 | NEGATIVE | 2082 | 3691.37 | 0.1 | NEGATIVE |
| 145 | 3 | UNK | NA | BQL | <10 | NEGATIVE | 2612 | 1154.291 | 2.3 | NEGATIVE |
| 146 | 3 | UNK | NA | 6.94 | <10 | NEGATIVE | 976 | 1118.229 | NIL | NEGATIVE |
| 147 | 3 | UNK | NA | BQL | <10 | NEGATIVE | 4631 | BQL | 45.9 | POSITIVE |
| 148 | 3 | UNK | NA | BQL | <10 | NEGATIVE | 3324 | 399.31 | 8.3 | POSITIVE |
| 149 | 3 | UNK | NA | BQL | <10 | NEGATIVE | 2642 | 8616.87 | 0.3 | NEGATIVE |
| 150 | 3 | UNK | NA | BQL | <10 | NEGATIVE | 6323 | BQL | 62.6 | POSITIVE |
| 151 | 3 | UNK | NA | BQL | <10 | NEGATIVE | 2460 | 3344.845 | 0.7 | NEGATIVE |
| 152 | 3 | OA | 2 | BQL | <10 | NEGATIVE | 1632 | 135.735 | 12.0 | POSITIVE |
| 153 | 3 | OA | 3 | BQL | <10 | NEGATIVE | 3964 | 734.937 | 5.4 | POSITIVE |
| 154 | 3 | OA | 4 | BQL | <10 | NEGATIVE | 2015 | 195.774 | 10.3 | POSITIVE |
| 155 | 3 | OA | 4 | 2.086 | <10 | NEGATIVE | 5857 | BQL | 58.0 | POSITIVE |
| 156 | 3 | OA | 4 | BQL | <10 | NEGATIVE | 2715 | BQL | 26.9 | POSITIVE |
| 157 | 3 | OA | 3 | BQL | <10 | NEGATIVE | 1756 | BQL | 17.4 | POSITIVE |
| 158 | 3 | OA | 4 | BQL | <10 | NEGATIVE | 4101 | 1377.962 | 3.0 | NEGATIVE |
| 159 | 3 | OA | 4 | BQL | <10 | NEGATIVE | 3491 | 277.632 | 12.6 | POSITIVE |
| 160 | 3 | OA | 4 | BQL | <10 | NEGATIVE | 2576 | BQL | 25.5 | POSITIVE |

FIG. 42C-2

| NUMBER | BATCH | COHORT | KL SCORE | ANTI-CCP (U/mL) | RF (IU/mL) | RA ALGORITHM TERTIARY ANALYSIS | COMP (ng/mL) | IL-8 (pg/mL) | COMP/IL-8 (ng/pg) | OSTEOARTHRITIS ALGORITHM |
|---|---|---|---|---|---|---|---|---|---|---|
| 161 | 3 | OA | 2 | BQL | <10 | NEGATIVE | 3350 | 455.041 | 7.4 | POSITIVE |
| 162 | 3 | OA | 3 | BQL | <10 | NEGATIVE | 3800 | BQL | 37.6 | POSITIVE |
| 163 | 3 | OA | 3 | BQL | <10 | NEGATIVE | 3177 | BQL | 31.5 | POSITIVE |
| 164 | 3 | OA | 3 | BQL | <10 | NEGATIVE | 4270 | BQL | 42.3 | POSITIVE |
| 165 | 3 | OA | 3 | BQL | <10 | NEGATIVE | 3288 | 630.277 | 5.2 | POSITIVE |
| 166 | 3 | OA | 3 | BQL | <10 | NEGATIVE | 5820 | BQL | 57.6 | POSITIVE |
| 167 | 3 | OA | 4 | BQL | <10 | NEGATIVE | 4343 | 675.123 | 6.4 | POSITIVE |
| 168 | 3 | OA | 3 | BQL | <10 | NEGATIVE | 4859 | 367.249 | 13.2 | POSITIVE |
| 169 | 3 | OA | 2 | BQL | <10 | NEGATIVE | 4291 | BQL | 42.5 | POSITIVE |
| 170 | 3 | OA | 4 | BQL | <10 | NEGATIVE | 3463 | 387.638 | 8.9 | POSITIVE |
| 171 | 3 | OA | 3 | BQL | <10 | NEGATIVE | 1420 | 3953.54 | NIL | NEGATIVE |
| 172 | 3 | OA | 3 | BQL | <10 | NEGATIVE | 1633 | 472.276 | 3.5 | NEGATIVE |
| 173 | 3 | OA | 4 | BQL | <10 | NEGATIVE | 4084 | BQL | 40.4 | POSITIVE |
| 174 | 3 | OA | 4 | BQL | <10 | NEGATIVE | 2786 | 1740.298 | 1.6 | NEGATIVE |
| 175 | 3 | RA | NA | 127.732 | 145.6 | POSITIVE | 14870 | 2594.722 | 5.7 | POSITIVE |
| 176 | 3 | RA | NA | 9.368 | 139.4 | POSITIVE | 4257 | 114.395 | 37.2 | POSITIVE |
| 177 | 3 | RA | NA | 3.051 | <10 | INDETERMINATE | 470 | 127.917 | NIL | NEGATIVE |
| 178 | 3 | RA | NA | BQL | <10 | NEGATIVE | 2643 | 1999.088 | 1.3 | NEGATIVE |
| 179 | 3 | RA | NA | BQL | <10 | NEGATIVE | 2515 | 2941.287 | 0.9 | NEGATIVE |
| 180 | 3 | RA | NA | BQL | <10 | NEGATIVE | 2077 | 27572.56 | 0.1 | NEGATIVE |
| 181 | 3 | RA | NA | BQL | <10 | NEGATIVE | 2275 | 2184.736 | 1.0 | NEGATIVE |
| 182 | 3 | RA | NA | BQL | <10 | NEGATIVE | 2619 | 368.617 | 7.1 | POSITIVE |
| 183 | 3 | RA | NA | BQL | <10 | NEGATIVE | 2564 | 900.226 | 2.6 | NEGATIVE |
| 184 | 3 | RA | NA | BQL | <10 | NEGATIVE | BQL | 69201.1 | NIL | NEGATIVE |
| 185 | 4 | RA | NA | BQL | <10 | NEGATIVE | 2157 | 2508.297 | 0.9 | NEGATIVE |
| 186 | 4 | RA | NA | BQL | <10 | NEGATIVE | 7910 | BQL | 78.3 | POSITIVE |

FIG. 42D-1

| | | | | | | | | | | |
|---|---|---|---|---|---|---|---|---|---|---|
| 187 | 4 | RA | NA | BQL | <10 | NEGATIVE | 5609 | BQL | 55.5 | POSITIVE |
| 188 | 4 | RA | NA | BQL | <10 | NEGATIVE | 18685 | 175.326 | 106.6 | POSITIVE |
| 189 | 4 | RA | NA | BQL | <10 | NEGATIVE | 6278 | 274.039 | 22.9 | POSITIVE |
| 190 | 4 | RA | NA | BQL | <10 | NEGATIVE | 2006 | 24146.87 | 0.1 | NEGATIVE |
| 191 | 4 | RA | NA | BQL | <10 | NEGATIVE | 1717 | 36236.88 | 0.0 | NEGATIVE |
| 192 | 4 | RA | NA | BQL | <10 | NEGATIVE | 1968 | 24721.78 | 0.1 | NEGATIVE |
| 193 | 4 | RA | NA | BQL | <10 | NEGATIVE | 2421 | 34811.86 | 0.1 | NEGATIVE |
| 194 | 4 | RA | NA | AQL | 76.2 | POSITIVE | 1249 | 27555.2 | NIL | NEGATIVE |
| 195 | 4 | RA | NA | BQL | <10 | NEGATIVE | 2400 | 642.383 | 3.7 | NEGATIVE |
| 196 | 4 | RA | NA | BQL | 38.3 | POSITIVE | BQL | 22231.51 | NIL | NEGATIVE |
| 197 | 4 | RA | NA | BQL | <10 | NEGATIVE | BQL | 145.836 | NIL | NEGATIVE |
| 198 | 4 | RA | NA | BQL | <10 | INDETERMINATE | BQL | BQL | NIL | NEGATIVE |
| 199 | 4 | RA | NA | BQL | <10 | NEGATIVE | BQL | BQL | NIL | NEGATIVE |
| 200 | 4 | RA | NA | 6.94 | <10 | INDETERMINATE | BQL | BQL | NIL | NEGATIVE |
| 201 | 4 | RA | NA | BQL | <10 | NEGATIVE | BQL | 433.865 | NIL | NEGATIVE |
| 202 | 4 | RA | NA | BQL | <10 | INDETERMINATE | BQL | BQL | NIL | NEGATIVE |
| 203 | 4 | RA | NA | BQL | <10 | NEGATIVE | BQL | 362.518 | NIL | NEGATIVE |
| 204 | 4 | RA | NA | BQL | 11.1 | POSITIVE | BQL | BQL | NIL | NEGATIVE |
| 205 | 4 | RA | NA | BQL | 13.8 | POSITIVE | BQL | BQL | NIL | NEGATIVE |
| 206 | 4 | RA | NA | BQL | 15.8 | POSITIVE | BQL | BQL | NIL | NEGATIVE |
| 207 | 4 | RA | NA | BQL | <10 | INDETERMINATE | BQL | 116.823 | NIL | NEGATIVE |
| 208 | 4 | RA | NA | BQL | <10 | NEGATIVE | BQL | BQL | NIL | NEGATIVE |
| 209 | 4 | RA | NA | 2.086 | <10 | INDETERMINATE | BQL | BQL | NIL | NEGATIVE |
| 210 | 4 | RA | NA | BQL | <10 | NEGATIVE | BQL | 150.145 | NIL | NEGATIVE |
| 211 | 4 | RA | NA | BQL | <10 | NEGATIVE | BQL | BQL | NIL | NEGATIVE |
| 212 | 4 | RA | NA | BQL | 70.1 | POSITIVE | BQL | BQL | NIL | NEGATIVE |
| 213 | 4 | RA | NA | BQL | <10 | NEGATIVE | BQL | BQL | NIL | NEGATIVE |
| 214 | 4 | RA | NA | BQL | <10 | NEGATIVE | BQL | BQL | NIL | NEGATIVE |

FIG. 42D-2

| NUMBER | BATCH | COHORT | KL SCORE | ANTI-CCP (U/mL) | RF (IU/mL) | RA ALGORITHM TERTIARY ANALYSIS | COMP (ng/mL) | IL-8 (pg/mL) | COMP/IL-8 (ng/pg) | OSTEOARTHRITIS ALGORITHM |
|---|---|---|---|---|---|---|---|---|---|---|
| 215 | 4 | RA | NA | 2.152 | <10 | INDETERMINATE | BQL | BQL | NIL | NEGATIVE |
| 216 | 4 | RA | NA | BQL | <10 | NEGATIVE | BQL | 173.106 | NIL | NEGATIVE |
| 217 | 4 | RA | NA | BQL | <10 | NEGATIVE | BQL | 103.411 | NIL | NEGATIVE |
| 218 | 4 | RA | NA | BQL | 10.9 | INDETERMINATE | BQL | BQL | NIL | NEGATIVE |
| 219 | 4 | RA | NA | 4.581 | <10 | INDETERMINATE | BQL | BQL | NIL | NEGATIVE |
| 220 | 4 | RA | NA | BQL | <10 | NEGATIVE | BQL | 454.663 | NIL | NEGATIVE |
| 221 | 4 | RA | NA | BQL | <10 | NEGATIVE | BQL | BQL | NIL | NEGATIVE |
| 222 | 4 | RA | NA | BQL | <10 | NEGATIVE | BQL | BQL | NIL | NEGATIVE |
| 223 | 4 | RA | NA | BQL | 10.4 | INDETERMINATE | BQL | BQL | NIL | NEGATIVE |
| 224 | 4 | RA | NA | 21.594 | <10 | INDETERMINATE | BQL | BQL | NIL | NEGATIVE |
| 225 | 4 | RA | NA | 2.076 | 12.1 | NEGATIVE | BQL | BQL | NIL | NEGATIVE |
| 226 | 4 | RA | NA | 2.053 | 12.3 | NEGATIVE | BQL | BQL | NIL | NEGATIVE |
| 227 | 4 | RA | NA | BQL | 533.9 | NEGATIVE | 532 | 11394.82 | NIL | NEGATIVE |
| 228 | 4 | RA | NA | BQL | <10 | NEGATIVE | 2771 | 2525.23 | 1.1 | NEGATIVE |
| 229 | 4 | RA | NA | BQL | <10 | NEGATIVE | 2462 | 2290.56 | 1.1 | NEGATIVE |
| 230 | 4 | RA | NA | BQL | <10 | NEGATIVE | 9797 | 3182.906 | 3.1 | NEGATIVE |
| 231 | 4 | RA | NA | BQL | <10 | NEGATIVE | 7469 | 3458.174 | 2.2 | NEGATIVE |
| 232 | 4 | RA | NA | BQL | <10 | NEGATIVE | 6380 | 7017.25 | 0.9 | NEGATIVE |
| 233 | 4 | RA | NA | BQL | <10 | NEGATIVE | 584 | 1425.192 | NIL | NEGATIVE |
| 234 | 4 | RA | NA | BQL | <10 | NEGATIVE | 1586 | 3004.767 | 0.5 | NEGATIVE |

WHERE
NA: NOT APPLICABLE
NR: NOT REPORTED
AQL: ABOVE QUANTITATION LIMIT
BQL: BELOW QUANTITATION LIMIT
NIL: NULL OR ZERO VALUES

FIG. 42E n = 54 OA (CONDITION POSITIVE) AND
117 RA, CA, AND NSA (CONDITION NEGATIVE)

| NUMBER | BATCH | COHORT | TOTAL NUCLEATED CELL COUNT (CELL/μL) | RBC (CELL/μL) | NEUTROPHILS % | MONONUCLEAR CELLS |
|--------|-------|--------|------|------|------|------|
| 1 | 1 | CA | 11499 | 10000 | 92.7 | 7.3 |
| 2 | 1 | CA | 3700 | 20000 | 91.7 | 8.3 |
| 3 | 1 | CA | 475 | 1000 | 23 | 77 |
| 4 | 1 | CA | 1925 | 1000 | 48.9 | 51.1 |
| 5 | 1 | CA | 4093 | 4000 | 77.7 | 22.3 |
| 6 | 1 | CA | 733 | 0 | 46.1 | 53.9 |
| 7 | 1 | CA | 485 | 30000 | 38.3 | 61.7 |
| 8 | 1 | CA | 375 | 1000 | 14.7 | 85.3 |
| 9 | 1 | CA | 727 | 3000 | 9.5 | 90.5 |
| 10 | 1 | CA | 18898 | 7000 | 82.7 | 17.3 |
| 11 | 1 | CA | 252 | 0 | 36.7 | 63.3 |
| 12 | 1 | CA | 401 | 5000 | 19.1 | 80.9 |
| 13 | 1 | CA | 76044 | 4000 | 90.8 | 9.2 |
| 14 | 1 | CA | 1343 | 6000 | 5.3 | 94.7 |
| 15 | 1 | CA | 19670 | 1000 | 86.8 | 13.2 |
| 16 | 1 | CA | 4866 | 3000 | 55.7 | 44.3 |
| 17 | 1 | CA | 20841 | 14000 | 95.1 | 4.9 |
| 18 | 1 | CA | 2105 | 1000 | 39.8 | 60.2 |
| 19 | 1 | CA | 4355 | 211000 | 62.7 | 37.3 |
| 20 | 1 | CA | 276 | 1000 | 16.4 | 83.6 |
| 21 | 1 | CA | 9366 | 3000 | 84.6 | 15.4 |
| 22 | 1 | CA | 26961 | 1000 | 93.3 | 6.7 |
| 23 | 1 | CA | 2098 | 1000 | 37.6 | 62.4 |
| 24 | 1 | CA | 2244 | 57000 | 41.2 | 58.8 |
| 25 | 1 | CA | 350 | 2000 | 26.8 | 73.2 |
| 26 | 1 | CA | 1092 | 1000 | 59.6 | 40.4 |
| 27 | 1 | CA | 3350 | 1000 | 73.7 | 26.3 |
| 28 | 1 | CA | 4824 | 2000 | 60.7 | 39.3 |
| 29 | 1 | CA | 358 | 2000 | 26.7 | 73.3 |
| 30 | 1 | CA | 2504 | 7000 | 25.8 | 74.2 |
| 31 | 1 | SA | 2773 | 9000 | 75.6 | 24.4 |
| 32 | 1 | SA | 44970 | 40000 | 98.1 | 1.9 |

FIG. 44A

| NUMBER | BATCH | COHORT | TOTAL NUCLEATED CELL COUNT (CELL/µL) | RBC (CELL/µL) | NEUTROPHILS % | MONONUCLEAR CELLS |
|---|---|---|---|---|---|---|
| 33 | 1 | SA | 29548 | 4000 | 95.2 | 4.8 |
| 34 | 1 | SA | 32018 | 3000 | 95 | 5 |
| 35 | 1 | SA | 15090 | 3000 | 92.4 | 7.6 |
| 36 | 1 | SA | 56807 | 23000 | 96.1 | 3.9 |
| 37 | 1 | SA | 13716 | 15000 | 77.9 | 22.1 |
| 38 | 2 | SA | 50718 | 13000 | 95.3 | 4.7 |
| 39 | 2 | SA | 50819 | 20000 | 94.7 | 5.3 |
| 40 | 2 | SA | 54686 | 66000 | 95.1 | 4.9 |
| 41 | 2 | SA | 41544 | 21000 | 89.4 | 10.6 |
| 42 | 2 | SA | 60438 | 2000 | 96.1 | 3.9 |
| 43 | 2 | SA | 45892 | 10000 | 93.1 | 6.9 |
| 44 | 2 | SA | 59465 | 11000 | 95.9 | 4.1 |
| 45 | 2 | SA | 14672 | 4000 | 72.8 | 27.2 |
| 46 | 2 | SA | 27496 | 3000 | 79.2 | 20.8 |
| 47 | 2 | SA | 21252 | 34000 | 82.6 | 17.4 |
| 48 | 2 | SA | 32571 | 26000 | 91.9 | 8.1 |
| 49 | 2 | SA | 15989 | 15000 | 89.7 | 10.3 |
| 50 | 2 | SA | 84861 | 12000 | 58.7 | 41.3 |
| 51 | 2 | SA | 18500 | 29000 | 89.2 | 10.8 |
| 52 | 2 | SA | 18153 | 6000 | 86.1 | 13.9 |
| 53 | 2 | SA | 7192 | 3000 | 53.3 | 46.7 |
| 54 | 2 | SA | 38058 | 24000 | 95.5 | 4.5 |
| 55 | 2 | SA | 9712 | 24000 | 67.8 | 32.2 |
| 56 | 2 | SA | 8573 | 35000 | 91.4 | 8.6 |
| 57 | 2 | SA | 6966 | 4000 | 52.9 | 47.1 |
| 58 | 2 | SA | 26940 | 19000 | 98 | 2 |
| 59 | 2 | SA | 30486 | 4000 | 95.2 | 4.8 |
| 60 | 2 | SA | 43214 | 50000 | 94.1 | 5.9 |
| 61 | 2 | UNK | 731 | 4000 | 32 | 68 |
| 62 | 2 | UNK | 357 | 0 | 71.1 | 28.9 |
| 63 | 2 | UNK | 5466 | 130000 | 78.3 | 21.7 |
| 64 | 2 | UNK | 530 | 1000 | 16.6 | 83.4 |
| 65 | 2 | UNK | 537 | 57000 | 41.7 | 58.3 |
| 66 | 2 | UNK | 263 | 1000 | 19.1 | 80.9 |
| 67 | 2 | UNK | 114 | 2000 | 8.7 | 91.3 |

FIG. 44B

| NUMBER | BATCH | COHORT | TOTAL NUCLEATED CELL COUNT (CELL/µL) | RBC (CELL/µL) | NEUTROPHILS % | MONONUCLEAR CELLS |
|---|---|---|---|---|---|---|
| 68 | 2 | UNK | 7144 | 2000 | 91.8 | 8.2 |
| 69 | 2 | UNK | 932 | 75000 | 72.6 | 27.4 |
| 70 | 2 | UNK | 13667 | 7000 | 85.5 | 14.5 |
| 71 | 2 | UNK | 306 | 15000 | 16.4 | 83.6 |
| 72 | 2 | UNK | 3073 | 223000 | 69.6 | 30.4 |
| 73 | 2 | UNK | 9295 | 1000 | 78.6 | 21.4 |
| 74 | 2 | UNK | 1265 | 2000 | 60.3 | 39.7 |
| 75 | 2 | UNK | 25392 | 3000 | 91.1 | 8.9 |
| 76 | 2 | UNK | 216 | 24000 | 27.3 | 72.7 |
| 77 | 2 | UNK | 926 | 15000 | 15.1 | 84.9 |
| 78 | 2 | UNK | 198 | 4000 | 27.9 | 72.1 |
| 79 | 2 | UNK | 128 | 0 | 32.8 | 67.2 |
| 80 | 2 | UNK | 14304 | 4000 | 57.6 | 42.4 |
| 81 | 3 | UNK | 19867 | 18000 | 91.2 | 8.8 |
| 82 | 3 | UNK | 505 | 3000 | 27.1 | 72.9 |
| 83 | 3 | UNK | 367 | 0 | 25.6 | 74.4 |
| 84 | 3 | UNK | 417 | 3000 | 23.9 | 76.1 |
| 85 | 3 | UNK | 836 | 225000 | 17.2 | 82.8 |
| 86 | 3 | UNK | 3318 | 126000 | 68.4 | 31.6 |
| 87 | 3 | UNK | 516 | 4000 | 18.5 | 81.5 |
| 88 | 3 | UNK | 127 | 1000 | 14.4 | 85.6 |
| 89 | 3 | UNK | 58292 | 64000 | 80 | 20 |
| 90 | 3 | UNK | 13297 | 1000 | 91.7 | 8.3 |
| 91 | 3 | UNK | 9175 | 2000 | 14.7 | 85.3 |
| 92 | 3 | UNK | 442 | 81000 | 33.3 | 66.7 |
| 93 | 3 | UNK | 347 | 85000 | 33 | 67 |
| 94 | 3 | UNK | 1291 | 7000 | 29.9 | 70.1 |
| 95 | 3 | UNK | 363 | 62000 | 27.2 | 72.8 |
| 96 | 3 | UNK | 1263 | 34000 | 27.8 | 72.2 |
| 97 | 3 | UNK | 281 | 23000 | 26.8 | 73.2 |
| 98 | 3 | UNK | 1103 | 1000 | 46 | 54 |
| 99 | 3 | UNK | 452 | 1000 | 17 | 83 |
| 100 | 3 | UNK | 362 | 6000 | 16.4 | 83.6 |
| 101 | 3 | UNK | 3662 | 4000 | 66.4 | 33.6 |
| 102 | 3 | UNK | 865 | 8000 | 15.1 | 84.9 |

FIG. 44C

| NUMBER | BATCH | COHORT | TOTAL NUCLEATED CELL COUNT (CELL/µL) | RBC (CELL/µL) | NEUTROPHILS % | MONONUCLEAR CELLS |
|---|---|---|---|---|---|---|
| 103 | 3 | UNK | 283 | 0 | 53.3 | 46.7 |
| 104 | 3 | UNK | 219 | 38000 | 44.7 | 55.3 |
| 105 | 3 | UNK | 228 | 0 | 2.2 | 97.8 |
| 106 | 3 | UNK | 776 | 3000 | 22.7 | 77.3 |
| 107 | 3 | UNK | 380 | 1000 | 46.5 | 53.5 |
| 108 | 3 | UNK | 279 | 1000 | 21.4 | 78.6 |
| 109 | 3 | UNK | 10953 | 25000 | 83.3 | 16.7 |
| 110 | 3 | UNK | 445 | 1000 | 11.7 | 88.3 |
| 111 | 3 | UNK | 1217 | 43000 | 57.4 | 42.6 |
| 112 | 3 | UNK | 596 | 9000 | 39.9 | 60.1 |
| 113 | 3 | UNK | 282 | 220000 | 56.1 | 43.9 |
| 114 | 3 | UNK | 7822 | 5000 | 57.3 | 42.7 |
| 115 | 3 | UNK | 11369 | 15000 | 25.7 | 74.3 |
| 116 | 3 | UNK | 459 | 82000 | 32.7 | 67.3 |
| 117 | 3 | UNK | 12918 | 7000 | 17.6 | 82.4 |
| 118 | 3 | UNK | 96 | 1000 | 8.2 | 91.8 |
| 119 | 3 | UNK | 252 | 1000 | 11.8 | 88.2 |
| 120 | 3 | UNK | 359 | 6000 | 23.5 | 76.5 |

FIG. 44D

| BLINDED ID | COHORT | CRYSTAL ID |
|---|---|---|
| 081 | NSA | INTRACELLULAR CPPD CRYSTALS |
| 017 | NSA | INTRACELLULAR CPPD CRYSTALS |
| 243 | NSA | INTRACELLULAR CPPD CRYSTALS |
| 239 | NSA | INTRACELLULAR AND EXTRACELLULAR MSU CRYSTALS |
| 175 | NSA | INTRACELLULAR CPPD CRYSTALS |
| 265 | NSA | INTRACELLULAR AND EXTRACELLULAR CPPD CRYSTALS |
| 266 | NSA | INTRACELLULAR CPPD CRYSTALS |
| 070 | NSA | INTRACELLULAR AND EXTRACELLULAR MSU CRYSTALS |
| 056 | NSA | INTRACELLULAR AND EXTRACELLULAR CPPD CRYSTALS |
| 092 | NSA | INTRACELLULAR CPPD CRYSTALS |
| 087 | NSA | INTRACELLULAR AND EXTRACELLULAR CPPD CRYSTALS |
| 182 | RA | CPPD CRYSTALS |
| 112 | RA | MSU CRYSTALS |
| 126 | RA | CPPD CRYSTALS |
| 32 | RA | CPPD CRYSTALS |
| 228 | RA | CHOLESTEROL |
| 68 | RA | MSU CRYSTALS |
| 198 | RA | MSU CRYSTALS |
| 146 | RA | MSU CRYSTALS |
| 218 | RA | MSU CRYSTALS |
| 154 | RA | MSU CRYSTALS |
| 254 | RA | MSU CRYSTALS |
| 127 | RA | MSU CRYSTALS |
| 143 | RA | MSU CRYSTALS |
| 102 | RA | CHOLESTEROL |
| 113 | RA | CHOLESTEROL |
| 132 | RA | CHOLESTEROL |
| 194 | RA | MSU CRYSTALS |
| 106 | RA | MSU CRYSTALS |
| 233 | RA | MSU CRYSTALS |
| 199 | RA | MSU CRYSTALS |
| 246 | RA | MSU CRYSTALS |
| 188 | RA | MSU CRYSTALS |
| 76 | RA | MSU CRYSTALS |
| 261 | RA | MSU CRYSTALS |
| 28 | RA | MSU CRYSTALS |
| 11 | RA | MSU CRYSTALS |
| 30 | RA | MSU CRYSTALS |
| 187 | RA | MSU CRYSTALS |

FIG. 45A

| BLINDED ID | COHORT | CRYSTAL ID |
|---|---|---|
| 37 | RA | MSU CRYSTALS |
| 160 | RA | MSU CRYSTALS |
| 144 | RA | MSU CRYSTALS |
| 190 | RA | MSU CRYSTALS |
| 156 | RA | CPPD CRYSTALS |

FIG. 45B

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 136 | CA | -0.019 | 0.696 | NON-COMPROMISED | 1.141 | 66.6 | INDETERMINATE | 4.854 | REFLEX |
| 270 | CA | -0.004 | 0.766 | NON-COMPROMISED | 2.52 | 44 | INDETERMINATE | 3.983 | REFLEX |
| 167 | CA | -0.002 | 0.598 | NON-COMPROMISED | 0.091 | 17.7 | NEGATIVE | 0.104 | NEGATIVE |
| 035 | CA | -0.006 | 0.644 | NON-COMPROMISED | 0.135 | 28.4 | NEGATIVE | 0.26 | NEGATIVE |
| 222 | CA | -0.005 | 0.707 | NON-COMPROMISED | 0.213 | 33.7 | NEGATIVE | 1.175 | REFLEX |
| 062 | CA | -0.007 | 0.473 | NON-COMPROMISED | 0.125 | 19.2 | NEGATIVE | 0.136 | NEGATIVE |
| 021 | CA | 0.065 | 0.614 | NON-COMPROMISED | 0.067 | 28 | NEGATIVE | 0.093 | NEGATIVE |
| 185 | CA | 0.008 | 0.558 | NON-COMPROMISED | 0.101 | 21.1 | NEGATIVE | 0.052 | NEGATIVE |
| 051 | CA | 0.009 | 0.599 | NON-COMPROMISED | 0.091 | 16.3 | NEGATIVE | 0.057 | NEGATIVE |
| 227 | CA | -0.001 | 0.652 | NON-COMPROMISED | 0.85 | 67.2 | NEGATIVE | 1.806 | REFLEX |
| 084 | CA | -0.005 | 0.492 | NON-COMPROMISED | 0.054 | 21.8 | NEGATIVE | 0.014 | NEGATIVE |
| 157 | CA | -0.001 | 0.634 | NON-COMPROMISED | 0.081 | 32.5 | NEGATIVE | 0.052 | NEGATIVE |
| 115 | CA | -0.005 | 0.797 | NON-COMPROMISED | 0.593 | 85.2 | NEGATIVE | 6.056 | REFLEX |
| 043 | CA | 0.023 | 0.596 | NON-COMPROMISED | 0.075 | 28.9 | NEGATIVE | 0.029 | NEGATIVE |

FIG. 46A

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 273 | CA | -0.005 | 0.661 | NON-COMPROMISED | 0.19 | 57.9 | NEGATIVE | 3.27 | REFLEX |
| 209 | CA | -0.006 | 0.796 | NON-COMPROMISED | 0.678 | 31.7 | NEGATIVE | 0.94 | NEGATIVE |
| 236 | CA | -0.007 | 0.716 | NON-COMPROMISED | 0.78 | 66.1 | NEGATIVE | 4.347 | REFLEX |
| 220 | CA | -0.007 | 0.79 | NON-COMPROMISED | 0.14 | 28 | NEGATIVE | 0.208 | NEGATIVE |
| 078 | CA | 0.026 | 0.574 | NON-COMPROMISED | 0.561 | 86.3 | NEGATIVE | 0.823 | NEGATIVE |
| 025 | CA | -0.01 | 0.597 | NON-COMPROMISED | 0.086 | 24 | NEGATIVE | 0.125 | NEGATIVE |
| 120 | CA | -0.007 | 0.654 | NON-COMPROMISED | 0.769 | 61 | NEGATIVE | 3.684 | REFLEX |
| 108 | CA | 0.002 | 0.681 | NON-COMPROMISED | 0.346 | 89 | NEGATIVE | 1.002 | REFLEX |
| 007 | CA | -0.008 | 0.636 | NON-COMPROMISED | 0.186 | 26.4 | NEGATIVE | 0.326 | NEGATIVE |
| 294 | CA | 0.006 | 0.998 | NON-COMPROMISED | 0.212 | 28.2 | NEGATIVE | 0.106 | NEGATIVE |
| 297 | CA | 0.1 | 0.667 | NON-COMPROMISED | 0.072 | 48.9 | NEGATIVE | 0.067 | NEGATIVE |
| 312 | CA | 0.003 | 0.706 | NON-COMPROMISED | 0.216 | 51.4 | NEGATIVE | 0.425 | NEGATIVE |
| 240 | CA | -0.007 | 0.762 | NON-COMPROMISED | 0.793 | 37.8 | NEGATIVE | 1.557 | REFLEX |
| 306 | CA | -0.007 | 0.778 | NON-COMPROMISED | 0.309 | 30.3 | NEGATIVE | 1.543 | REFLEX |
| 221 | CA | -0.008 | 0.711 | NON-COMPROMISED | 0.115 | 16.9 | NEGATIVE | 0.045 | NEGATIVE |
| 274 | CA | -0.012 | 0.722 | NON-COMPROMISED | 0.248 | 34.5 | NEGATIVE | 0.144 | NEGATIVE |

FIG. 46B

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 077 | SA | -0.001 | 0.598 | NON-COMPROMISED | 1.475 | 71.7 | POSITIVE | 2.704 | REFLEX |
| 081 | SA | 0.035 | 0.884 | NON-COMPROMISED | 3.282 | 116.6 | POSITIVE | 5.57 | REFLEX |
| 017 | SA | -0.006 | 0.725 | NON-COMPROMISED | 1.193 | 114.7 | POSITIVE | 4.86 | REFLEX |
| 095 | SA | -0.002 | 0.72 | NON-COMPROMISED | 2.111 | 94.1 | POSITIVE | 4.625 | REFLEX |
| 243 | SA | -0.005 | 0.627 | NON-COMPROMISED | 2.054 | 83.7 | POSITIVE | 3.372 | REFLEX |
| 048 | SA | -0.001 | 0.883 | NON-COMPROMISED | 3.269 | 164.8 | POSITIVE | 6.101 | REFLEX |
| 239 | SA | -0.008 | 0.797 | NON-COMPROMISED | 1.932 | 72.4 | POSITIVE | 3.945 | REFLEX |
| 299 | SA | 0.005 | 0.797 | NON-COMPROMISED | 2.437 | 70.6 | POSITIVE | 5.147 | REFLEX |
| 175 | SA | 0.005 | 0.93 | NON-COMPROMISED | 3.225 | 224.9 | POSITIVE | 4.511 | REFLEX |
| 265 | SA | 0.016 | 0.861 | NON-COMPROMISED | 3.753 | 152.6 | POSITIVE | 4.045 | REFLEX |
| 224 | SA | -0.001 | 0.826 | NON-COMPROMISED | 3.269 | 112.3 | POSITIVE | 4.861 | REFLEX |
| 266 | SA | -0.005 | 0.671 | NON-COMPROMISED | 1.263 | 148.5 | POSITIVE | 6.05 | REFLEX |
| 308 | SA | -0.006 | 0.655 | NON-COMPROMISED | 2.916 | 114.1 | POSITIVE | 1.622 | REFLEX |
| 285 | SA | -0.004 | 0.812 | NON-COMPROMISED | 4.652 | 143.2 | POSITIVE | 3.795 | REFLEX |
| 070 | SA | -0.001 | 0.622 | NON-COMPROMISED | 1.041 | 107.5 | POSITIVE | 3.27 | REFLEX |
| 114 | SA | -0.008 | 0.767 | NON-COMPROMISED | 2.37 | 141.5 | POSITIVE | 4.415 | REFLEX |

FIG. 46C

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 279 | SA | 0 | 0.807 | NON-COMPROMISED | 3.503 | 135.1 | POSITIVE | 4.584 | REFLEX |
| 253 | SA | -0.003 | 0.604 | NON-COMPROMISED | 2.259 | 121.6 | POSITIVE | 4.478 | REFLEX |
| 107 | SA | 0.014 | 0.697 | NON-COMPROMISED | 1.857 | 78.4 | POSITIVE | 4.293 | REFLEX |
| 238 | SA | 0.017 | 0.823 | NON-COMPROMISED | 3.473 | 191 | POSITIVE | 4.686 | REFLEX |
| 258 | SA | 0.031 | 0.832 | NON-COMPROMISED | 2.863 | 128.7 | POSITIVE | 6.279 | REFLEX |
| 056 | SA | 0.009 | 0.768 | NON-COMPROMISED | 3.405 | 129.6 | POSITIVE | 5.223 | REFLEX |
| 104 | SA | -0.016 | 0.755 | NON-COMPROMISED | 1.482 | 118.4 | POSITIVE | 2.572 | REFLEX |
| 010 | SA | 0.009 | 0.841 | NON-COMPROMISED | 3.491 | 161.8 | POSITIVE | 5.878 | REFLEX |
| 075 | SA | 0.019 | 0.769 | NON-COMPROMISED | 1.322 | 81.9 | POSITIVE | 3.287 | REFLEX |
| 092 | SA | 0.035 | 0.845 | NON-COMPROMISED | 3.156 | 96.4 | POSITIVE | 5.015 | REFLEX |
| 268 | SA | -0.01 | 0.987 | NON-COMPROMISED | 1.243 | 75.6 | POSITIVE | 2.539 | REFLEX |
| 087 | SA | 0.005 | 0.741 | NON-COMPROMISED | 1.723 | 116.5 | POSITIVE | 6.622 | REFLEX |
| 241 | SA | -0.007 | 0.823 | NON-COMPROMISED | 1.672 | 81.7 | POSITIVE | 6.467 | REFLEX |
| 097 | SA | 0.046 | 1.079 | NON-COMPROMISED | 1.874 | 159.2 | POSITIVE | 5.673 | REFLEX |
| 006 | UNK | 0.029 | 0.525 | NON-COMPROMISED | 0.108 | 19.7 | NEGATIVE | 0.109 | NEGATIVE |
| 049 | UNK | -0.007 | 0.495 | NON-COMPROMISED | 0.105 | 24.7 | NEGATIVE | 0.155 | NEGATIVE |

FIG. 46D

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 169 | UNK | 0.482 | 0.772 | NON-COMPROMISED | 0.847 | 40.3 | NEGATIVE | 1.933 | REFLEX |
| 225 | UNK | -0.006 | 0.824 | NON-COMPROMISED | 0.095 | 26.4 | NEGATIVE | 0.106 | NEGATIVE |
| 044 | UNK | 2.271 | 0.811 | NON-COMPROMISED | 1.28 | 24 | INDETERMINATE | 0.3 | NEGATIVE |
| 223 | UNK | 0.001 | 0.563 | NON-COMPROMISED | 0.076 | 14.5 | NEGATIVE | 0.051 | NEGATIVE |
| 001 | UNK | 0 | 0.475 | NON-COMPROMISED | 0.058 | 23.2 | NEGATIVE | 0.02 | NEGATIVE |
| 174 | UNK | -0.011 | 0.939 | NON-COMPROMISED | 0.598 | 49 | NEGATIVE | 0.794 | NEGATIVE |
| 277 | UNK | 0.103 | 0.675 | NON-COMPROMISED | 0.08 | 21.6 | NEGATIVE | 0.211 | NEGATIVE |
| 101 | UNK | 0.013 | 0.584 | NON-COMPROMISED | 1.496 | 68.1 | INDETERMINATE | 3.849 | REFLEX |
| 237 | UNK | 0.108 | 0.78 | NON-COMPROMISED | 0.066 | 35.2 | NEGATIVE | 0.048 | NEGATIVE |
| 046 | UNK | 0.117 | 0.593 | NON-COMPROMISED | 0.105 | 34.5 | NEGATIVE | 0.322 | NEGATIVE |
| 040 | UNK | -0.007 | 0.849 | NON-COMPROMISED | 0.632 | 48.6 | NEGATIVE | 2.769 | REFLEX |
| 079 | UNK | 0.01 | 0.601 | NON-COMPROMISED | 0.123 | 21.5 | NEGATIVE | 0.294 | NEGATIVE |
| 141 | UNK | -0.006 | 0.754 | NON-COMPROMISED | 0.347 | 43.3 | NEGATIVE | 4.426 | REFLEX |
| 023 | UNK | 0.479 | 0.539 | NON-COMPROMISED | 0.078 | 23.1 | NEGATIVE | 0.031 | NEGATIVE |
| 168 | UNK | 0.088 | 0.712 | NON-COMPROMISED | 0.144 | 23.5 | NEGATIVE | 0.111 | NEGATIVE |
| 205 | UNK | -0.003 | 0.554 | NON-COMPROMISED | 0.075 | 17.8 | NEGATIVE | 0.08 | NEGATIVE |

FIG. 46E

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 022 | UNK | 0.013 | 0.527 | NON-COMPROMISED | 0.057 | 30.4 | NEGATIVE | 0.025 | NEGATIVE |
| 264 | UNK | -0.005 | 0.665 | NON-COMPROMISED | 0.674 | 53.8 | NEGATIVE | 3.044 | REFLEX |
| 086 | OA | 0.005 | 0.399 | NON-COMPROMISED | 0.109 | 10.1 | NEGATIVE | 0.019 | NEGATIVE |
| 202 | OA | -0.001 | 0.561 | NON-COMPROMISED | 0.104 | 31.6 | NEGATIVE | 0.020 | NEGATIVE |
| 176 | OA | 0.002 | 0.578 | NON-COMPROMISED | 0.107 | 19.6 | NEGATIVE | 0.021 | NEGATIVE |
| 300 | OA | 0.014 | 0.488 | NON-COMPROMISED | 0.103 | 14.7 | NEGATIVE | 0.018 | NEGATIVE |
| 096 | OA | 0.003 | 0.645 | NON-COMPROMISED | 1.558 | 21.7 | INDETERMINATE | 2.172 | REFLEX |
| 196 | OA | 0.007 | 0.47 | NON-COMPROMISED | 0.105 | 15.1 | NEGATIVE | 0.019 | NEGATIVE |
| 255 | OA | -0.001 | 0.454 | NON-COMPROMISED | 0.111 | 16.0 | NEGATIVE | 0.058 | NEGATIVE |
| 180 | OA | 0.003 | 0.45 | NON-COMPROMISED | 0.111 | 14.5 | NEGATIVE | 0.029 | NEGATIVE |
| 066 | OA | 0.077 | 0.536 | NON-COMPROMISED | 0.110 | 15.7 | NEGATIVE | 0.035 | NEGATIVE |
| 039 | OA | 0.006 | 0.465 | NON-COMPROMISED | 0.103 | 26.7 | NEGATIVE | 0.022 | NEGATIVE |
| 118 | OA | -0.004 | 0.517 | NON-COMPROMISED | 0.105 | 15.9 | NEGATIVE | 0.022 | NEGATIVE |
| 125 | OA | 0.156 | 0.64 | NON-COMPROMISED | 0.114 | 26.2 | NEGATIVE | 0.121 | NEGATIVE |
| 213 | OA | -0.001 | 0.579 | NON-COMPROMISED | 0.108 | 18.0 | NEGATIVE | 0.032 | NEGATIVE |
| 189 | OA | 0.001 | 0.439 | NON-COMPROMISED | 0.108 | 16.4 | NEGATIVE | 0.023 | NEGATIVE |

FIG. 46F

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 090 | OA | -0.002 | 0.514 | NON-COMPROMISED | 0.101 | 21.8 | NEGATIVE | 0.020 | NEGATIVE |
| 197 | OA | 0.002 | 0.476 | NON-COMPROMISED | 0.137 | 35.3 | NEGATIVE | 0.033 | NEGATIVE |
| 129 | OA | 0.636 | 0.506 | NON-COMPROMISED | 0.114 | 16.5 | NEGATIVE | 0.046 | NEGATIVE |
| 226 | OA | -0.001 | 0.424 | NON-COMPROMISED | 0.103 | 16.5 | NEGATIVE | 0.020 | NEGATIVE |
| 291 | OA | -0.002 | 0.467 | NON-COMPROMISED | 0.104 | 12.9 | NEGATIVE | 0.022 | NEGATIVE |
| 314 | OA | 0.046 | 0.474 | NON-COMPROMISED | 0.104 | 17.8 | NEGATIVE | 0.019 | NEGATIVE |
| 177 | OA | -0.002 | 0.469 | NON-COMPROMISED | 0.103 | 23.7 | NEGATIVE | 0.019 | NEGATIVE |
| 138 | OA | -0.001 | 0.427 | NON-COMPROMISED | 0.105 | 18.6 | NEGATIVE | 0.023 | NEGATIVE |
| 181 | OA | -0.005 | 0.532 | NON-COMPROMISED | 0.104 | 30.3 | NEGATIVE | 0.018 | NEGATIVE |
| 263 | OA | -0.002 | 0.483 | NON-COMPROMISED | 0.108 | 36.4 | NEGATIVE | 0.021 | NEGATIVE |
| 281 | OA | -0.002 | 0.543 | NON-COMPROMISED | 0.115 | 12.5 | NEGATIVE | 0.017 | NEGATIVE |
| 186 | OA | 0.019 | 0.493 | NON-COMPROMISED | 0.102 | 13.7 | NEGATIVE | 0.017 | NEGATIVE |
| 005 | OA | 0.000 | 0.578 | NON-COMPROMISED | 0.112 | 19.8 | NEGATIVE | 0.040 | NEGATIVE |
| 089 | OA | 0.08 | 0.554 | NON-COMPROMISED | 0.171 | 13.8 | NEGATIVE | 0.093 | NEGATIVE |
| 173 | OA | 0.091 | 0.627 | NON-COMPROMISED | 0.105 | 22.9 | NEGATIVE | 0.025 | NEGATIVE |
| 069 | OA | 0.123 | 0.411 | NON-COMPROMISED | 0.104 | 22.2 | NEGATIVE | 0.067 | NEGATIVE |

FIG. 46G

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 073 | OA | -0.002 | 0.559 | NON-COMPROMISED | 0.116 | 25.9 | NEGATIVE | 0.020 | NEGATIVE |
| 091 | UNK | -0.002 | 0.883 | NON-COMPROMISED | 1.147 | 60.9 | INDETERMINATE | 4.295 | REFLEX |
| 230 | UNK | 0.066 | 0.766 | NON-COMPROMISED | 0.089 | 30.5 | NEGATIVE | 0.041 | NEGATIVE |
| 310 | UNK | -0.01 | 0.702 | NON-COMPROMISED | 0.073 | 20.8 | NEGATIVE | 0.056 | NEGATIVE |
| 059 | UNK | -0.009 | 0.837 | NON-COMPROMISED | 0.07 | 13.1 | NEGATIVE | 0.019 | NEGATIVE |
| 016 | UNK | 0.136 | 0.619 | NON-COMPROMISED | 0.099 | 19.3 | NEGATIVE | 0.065 | NEGATIVE |
| 009 | UNK | 0 | 0.716 | NON-COMPROMISED | 0.255 | 37.6 | NEGATIVE | 0.829 | NEGATIVE |
| 131 | UNK | 0.098 | 0.525 | NON-COMPROMISED | 0.1 | 15.9 | NEGATIVE | 0.083 | NEGATIVE |
| 155 | UNK | 0.012 | 0.663 | NON-COMPROMISED | 0.063 | 21.8 | NEGATIVE | 0.03 | NEGATIVE |
| 147 | UNK | 0.05 | 0.783 | NON-COMPROMISED | 3.278 | 2 | INDETERMINATE | 5.175 | REFLEX |
| 047 | UNK | -0.006 | 0.708 | NON-COMPROMISED | 0.765 | 59.7 | NEGATIVE | 4.464 | REFLEX |
| 085 | UNK | -0.002 | 0.645 | NON-COMPROMISED | 0.112 | 83.1 | NEGATIVE | 0.147 | NEGATIVE |
| 244 | UNK | 0.167 | 0.508 | NON-COMPROMISED | 0.092 | 33.1 | NEGATIVE | 0.05 | NEGATIVE |
| 249 | UNK | 2.307 | 0.551 | NON-COMPROMISED | 0.106 | 28.2 | NEGATIVE | 0.017 | NEGATIVE |
| 130 | UNK | 0.126 | 0.638 | NON-COMPROMISED | 0.091 | 52 | NEGATIVE | 0.118 | NEGATIVE |
| 015 | UNK | 0.014 | 0.568 | NON-COMPROMISED | 0.066 | 22.7 | NEGATIVE | 0.042 | NEGATIVE |

FIG. 46H

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 026 | UNK | -0.072 | 0.686 | NON-COMPROMISED | 0.119 | 53.8 | NEGATIVE | 0.286 | NEGATIVE |
| 063 | UNK | 0.007 | 0.638 | NON-COMPROMISED | 0.104 | 34.3 | NEGATIVE | 0.082 | NEGATIVE |
| 313 | UNK | -0.005 | 0.666 | NON-COMPROMISED | 0.183 | 17.8 | NEGATIVE | 0.281 | NEGATIVE |
| 200 | UNK | -0.005 | 0.648 | NON-COMPROMISED | 0.095 | 13.8 | NEGATIVE | 0.052 | NEGATIVE |
| 133 | UNK | 0.2 | 0.429 | NON-COMPROMISED | 0.067 | 31 | NEGATIVE | 0.026 | NEGATIVE |
| 067 | UNK | 0.011 | 0.802 | NON-COMPROMISED | 0.25 | 32.8 | NEGATIVE | 0.632 | NEGATIVE |
| 166 | UNK | -0.004 | 0.643 | NON-COMPROMISED | 0.102 | 19.5 | NEGATIVE | 0.102 | NEGATIVE |
| 252 | UNK | -0.007 | 0.404 | NON-COMPROMISED | 0.139 | 13.8 | NEGATIVE | 0.07 | NEGATIVE |
| 307 | UNK | 0.429 | 0.645 | NON-COMPROMISED | 0.091 | 47.5 | NEGATIVE | 0.039 | NEGATIVE |
| 315 | UNK | -0.007 | 0.644 | NON-COMPROMISED | 0.143 | 15 | NEGATIVE | 0.038 | NEGATIVE |
| 123 | UNK | -0.004 | 0.537 | NON-COMPROMISED | 0.082 | 24.1 | NEGATIVE | 0.068 | NEGATIVE |
| 053 | UNK | 0.009 | 0.664 | NON-COMPROMISED | 0.084 | 24.3 | NEGATIVE | 0.091 | NEGATIVE |
| 309 | UNK | -0.158 | 0.756 | NON-COMPROMISED | 0.156 | 33.3 | NEGATIVE | 0.037 | NEGATIVE |
| 012 | UNK | -0.004 | 0.637 | NON-COMPROMISED | 0.641 | 52.3 | NEGATIVE | 2.886 | REFLEX |
| 184 | UNK | -0.11 | 0.758 | NON-COMPROMISED | 0.075 | 25 | NEGATIVE | 0.045 | NEGATIVE |
| 140 | UNK | 0.008 | 0.87 | NON-COMPROMISED | 0.128 | 20.6 | NEGATIVE | 0.107 | NEGATIVE |

FIG. 46I

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 287 | UNK | -0.007 | 0.746 | NON-COMPROMISED | 0.08 | 25 | NEGATIVE | 0.072 | NEGATIVE |
| 151 | UNK | 0.002 | 0.744 | NON-COMPROMISED | 0.551 | 72.5 | NEGATIVE | 0.419 | NEGATIVE |
| 191 | UNK | 0.151 | 0.866 | NON-COMPROMISED | 0.058 | 43.6 | NEGATIVE | 0.061 | NEGATIVE |
| 036 | UNK | -0.008 | 0.82 | NON-COMPROMISED | 0.158 | 51 | NEGATIVE | 0.741 | NEGATIVE |
| 216 | UNK | 0 | 0.552 | NON-COMPROMISED | 0.094 | 20.7 | NEGATIVE | 0.027 | NEGATIVE |
| 163 | UNK | 0.002 | 0.736 | NON-COMPROMISED | 0.094 | 15.7 | NEGATIVE | 0.042 | NEGATIVE |
| 208 | UNK | 0.002 | 0.519 | NON-COMPROMISED | 0.097 | 29.2 | NEGATIVE | 0.036 | NEGATIVE |
| 269 | UNK | 1.053 | 0.755 | NON-COMPROMISED | 0.078 | 22.3 | NEGATIVE | 0.042 | NEGATIVE |
| 232 | UNK | -0.012 | 0.872 | NON-COMPROMISED | 0.31 | 56 | NEGATIVE | 0.363 | NEGATIVE |
| 134 | OA | 0.006 | 0.608 | NON-COMPROMISED | 0.062 | 7.8 | NEGATIVE | 0.058 | NEGATIVE |
| 088 | OA | 0.126 | 0.537 | NON-COMPROMISED | 0.068 | 30.8 | NEGATIVE | 0.051 | NEGATIVE |
| 278 | OA | 0.076 | 0.538 | NON-COMPROMISED | 0.063 | 15.0 | NEGATIVE | 0.046 | NEGATIVE |
| 080 | OA | 0.014 | 0.608 | NON-COMPROMISED | 0.067 | 26.7 | NEGATIVE | 0.045 | NEGATIVE |
| 290 | OA | 0 | 0.411 | NON-COMPROMISED | 0.066 | 22.8 | NEGATIVE | 0.028 | NEGATIVE |
| 004 | OA | -0.003 | 0.482 | NON-COMPROMISED | 0.071 | 12.9 | NEGATIVE | 0.051 | NEGATIVE |
| 083 | OA | -0.003 | 0.56 | NON-COMPROMISED | 0.07 | 16.5 | NEGATIVE | 0.039 | NEGATIVE |

FIG. 46J

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 041 | OA | -0.001 | 0.525 | NON-COMPROMISED | 0.057 | 36.2 | NEGATIVE | 0.037 | NEGATIVE |
| 008 | OA | -0.002 | 0.564 | NON-COMPROMISED | 0.058 | 15.5 | NEGATIVE | 0.056 | NEGATIVE |
| 002 | OA | 0 | 0.534 | NON-COMPROMISED | 0.071 | 14.2 | NEGATIVE | 0.125 | NEGATIVE |
| 212 | OA | 0.008 | 0.583 | NON-COMPROMISED | 0.083 | 14.4 | NEGATIVE | 0.044 | NEGATIVE |
| 034 | OA | -0.005 | 0.505 | NON-COMPROMISED | 0.082 | 25.9 | NEGATIVE | 0.066 | NEGATIVE |
| 082 | OA | 0.005 | 0.458 | NON-COMPROMISED | 0.076 | 19.1 | NEGATIVE | 0.079 | NEGATIVE |
| 210 | OA | 0.002 | 0.482 | NON-COMPROMISED | 0.072 | 20.5 | NEGATIVE | 0.036 | NEGATIVE |
| 231 | OA | 0.11 | 0.36 | NON-COMPROMISED | 0.08 | 21.8 | NEGATIVE | 0.038 | NEGATIVE |
| 311 | OA | 0.004 | 0.458 | NON-COMPROMISED | 0.061 | 32.5 | NEGATIVE | 0.032 | NEGATIVE |
| 295 | OA | -0.002 | 0.55 | NON-COMPROMISED | 0.067 | 19.9 | NEGATIVE | 0.102 | NEGATIVE |
| 055 | OA | -0.002 | 0.396 | NON-COMPROMISED | 0.074 | 21.9 | NEGATIVE | 0.033 | NEGATIVE |
| 064 | OA | 0.006 | 0.493 | NON-COMPROMISED | 0.09 | 30.0 | NEGATIVE | 0.079 | NEGATIVE |
| 111 | OA | -0.004 | 0.689 | NON-COMPROMISED | 1.937 | 19.4 | INDETERMINATE | 1.984 | REFLEX |
| 020 | OA | -0.008 | 0.465 | NON-COMPROMISED | 0.077 | 20.1 | NEGATIVE | 0.035 | NEGATIVE |
| 171 | OA | 0.02 | 0.502 | NON-COMPROMISED | 0.083 | 21.4 | NEGATIVE | 0.035 | NEGATIVE |
| 245 | OA | 0.644 | 0.538 | NON-COMPROMISED | 1.86 | 32.0 | INDETERMINATE | 1.724 | REFLEX |

FIG. 46K

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 182 | RA | 1.694 | 0.619 | NON-COMPROMISED | 0.086 | 38.8 | NEGATIVE | 0.102 | NEGATIVE |
| 248 | RA | 0.029 | 0.317 | DILUTED | 0.113 | 8.2 | NEGATIVE | 0.086 | NEGATIVE |
| 018 | RA | -0.001 | 0.283 | DILUTED | 0.118 | 5.9 | NEGATIVE | 0.114 | NEGATIVE |
| 257 | RA | 0.118 | 0.623 | NON-COMPROMISED | 1.646 | 103.7 | POSITIVE | 2.926 | REFLEX |
| 303 | RA | 0.313 | 0.761 | NON-COMPROMISED | 2.639 | 106.9 | POSITIVE | 5.17 | REFLEX |
| 302 | RA | 0.408 | 0.744 | NON-COMPROMISED | 2.959 | 101.8 | POSITIVE | 5.653 | REFLEX |
| 094 | RA | 0.238 | 0.667 | NON-COMPROMISED | 1.65 | 95.8 | POSITIVE | 3.155 | REFLEX |
| 286 | RA | 0.147 | 0.535 | NON-COMPROMISED | 0.233 | 21.1 | NEGATIVE | 0.619 | NEGATIVE |
| 112 | RA | 0.121 | 0.563 | NON-COMPROMISED | 1.073 | 68.1 | INDETERMINATE | 1.912 | REFLEX |
| 024 | RA | 0.074 | 0.914 | NON-COMPROMISED | 3.162 | 280.7 | POSITIVE | 5.973 | REFLEX |
| 162 | RA | 0.41 | 0.593 | NON-COMPROMISED | 2.276 | 65.0 | INDETERMINATE | 2.473 | REFLEX |
| 61 | RA | -0.002 | 0.443 | NON-COMPROMISED | 0.071 | 23.9 | NEGATIVE | 0.02 | NEGATIVE |
| 126 | RA | 0.015 | 0.503 | NON-COMPROMISED | 0.069 | 23.5 | NEGATIVE | 0.032 | NEGATIVE |
| 42 | RA | 0.002 | 0.522 | NON-COMPROMISED | 0.077 | 18.6 | NEGATIVE | 0.045 | NEGATIVE |
| 32 | RA | 0.022 | 0.587 | NON-COMPROMISED | 0.085 | 17.2 | NEGATIVE | 0.043 | NEGATIVE |
| 250 | RA | 0.498 | 0.625 | NON-COMPROMISED | 2.243 | 78.3 | POSITIVE | 3.144 | REFLEX |

FIG. 46L

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 65 | RA | 0.512 | 0.634 | NON-COMPROMISED | 2.891 | 73.1 | POSITIVE | 3.53 | REFLEX |
| 119 | RA | 0.487 | 0.623 | NON-COMPROMISED | 2.33 | 64.1 | INDETERMINATE | 2.985 | REFLEX |
| 54 | RA | 0.49 | 0.622 | NON-COMPROMISED | 2.758 | 76.5 | POSITIVE | 3.14 | REFLEX |
| 29 | RA | 0.083 | 0.647 | NON-COMPROMISED | 2.565 | 18.7 | INDETERMINATE | 2.835 | REFLEX |
| 121 | RA | 16.684 | 0.944 | NON-COMPROMISED | 0.203 | 34 | NEGATIVE | 0.449 | NEGATIVE |
| 122 | RA | 0.194 | 0.863 | NON-COMPROMISED | 2.04 | 109.8 | POSITIVE | 3.077 | REFLEX |
| 228 | RA | 0.038 | 0.89 | NON-COMPROMISED | 0.3 | 51.3 | NEGATIVE | 0.059 | NEGATIVE |
| 68 | RA | 0.007 | 0.859 | NON-COMPROMISED | 0.296 | 76.6 | NEGATIVE | 0.086 | NEGATIVE |
| 198 | RA | -0.01 | 0.771 | NON-COMPROMISED | 0.398 | 30.3 | NEGATIVE | 0.227 | NEGATIVE |
| 146 | RA | -0.008 | 0.95 | NON-COMPROMISED | 0.281 | 64.6 | NEGATIVE | 0.076 | NEGATIVE |
| 72 | RA | 0.017 | 0.852 | NON-COMPROMISED | 0.211 | 76.4 | NEGATIVE | 0.091 | NEGATIVE |
| 218 | RA | 0 | 0.859 | NON-COMPROMISED | 0.312 | 53.5 | NEGATIVE | 0.071 | NEGATIVE |
| 154 | RA | 0.017 | 0.867 | NON-COMPROMISED | 0.193 | 66 | NEGATIVE | 0.044 | NEGATIVE |
| 254 | RA | 0.008 | 0.808 | NON-COMPROMISED | 0.346 | 55.1 | NEGATIVE | 0.054 | NEGATIVE |
| 127 | RA | -0.004 | 0.874 | NON-COMPROMISED | 0.58 | 58.2 | NEGATIVE | 0.104 | NEGATIVE |
| 150 | RA | 0.002 | 0.955 | NON-COMPROMISED | 0.508 | 65.7 | NEGATIVE | 0.08 | NEGATIVE |

FIG. 46M

| BLINDED ID | COHORT | HEMOGLOBIN | A280 | SPECIMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 143 | RA | 0.014 | 0.834 | NON-COMPROMISED | 0.467 | 72.4 | NEGATIVE | 0.131 | NEGATIVE |
| 102 | RA | 0.02 | 0.845 | NON-COMPROMISED | 0.502 | 43.1 | NEGATIVE | 0.113 | NEGATIVE |
| 113 | RA | 0.006 | 0.807 | NON-COMPROMISED | 0.527 | 59.4 | NEGATIVE | 0.085 | NEGATIVE |
| 132 | RA | 0.018 | 0.88 | NON-COMPROMISED | 0.338 | 58.5 | NEGATIVE | 0.066 | NEGATIVE |
| 194 | RA | 0.013 | 0.701 | NON-COMPROMISED | 0.358 | 19.9 | NEGATIVE | 0.067 | NEGATIVE |
| 106 | RA | -0.042 | 1.394 | CONTAMINATED | 0.236 | 24.5 | NEGATIVE | 0.055 | NEGATIVE |
| 233 | RA | -0.005 | 0.747 | NON-COMPROMISED | 0.245 | 29.7 | NEGATIVE | 0.064 | NEGATIVE |
| 199 | RA | -0.014 | 0.792 | NON-COMPROMISED | 0.228 | 28.8 | NEGATIVE | 0.064 | NEGATIVE |
| 50 | RA | 0.101 | 0.816 | NON-COMPROMISED | 0.248 | 17.7 | NEGATIVE | 0.063 | NEGATIVE |
| 246 | RA | 0.005 | 0.784 | NON-COMPROMISED | 0.437 | 58.7 | NEGATIVE | 0.412 | NEGATIVE |
| 188 | RA | 0.015 | 0.763 | NON-COMPROMISED | 0.281 | 74 | NEGATIVE | 0.169 | NEGATIVE |
| 76 | RA | -0.005 | 0.856 | NON-COMPROMISED | 0.27 | 52.8 | NEGATIVE | 0.059 | NEGATIVE |
| 261 | RA | -0.002 | 0.974 | NON-COMPROMISED | 1.016 | 90.6 | POSITIVE | 0.068 | NEGATIVE |
| 28 | RA | 0.032 | 0.812 | NON-COMPROMISED | 1.482 | 70.8 | POSITIVE | 0.107 | NEGATIVE |
| 11 | RA | -0.013 | 0.93 | NON-COMPROMISED | 0.301 | 81.6 | NEGATIVE | 0.058 | NEGATIVE |
| 30 | RA | 0.012 | 0.841 | NON-COMPROMISED | 0.277 | 51.1 | NEGATIVE | 0.061 | NEGATIVE |

FIG. 46N

| BLINDED ID | COHORT | HEMOGLOBIN | A280 | SPECMEN INTEGRITY | ALPHA DEFENSIN S/CO | LACTATE | SEPTIC DEFSIN RESULT | HNE S/CO | HNE RESULT (OA/RA SAMPLES) |
|---|---|---|---|---|---|---|---|---|---|
| 187 | RA | -0.012 | 0.786 | NON-COMPROMISED | 0.385 | 49.5 | NEGATIVE | 0.074 | NEGATIVE |
| 37 | RA | 0.025 | 0.917 | NON-COMPROMISED | 0.287 | 83.6 | NEGATIVE | 0.073 | NEGATIVE |
| 160 | RA | -0.004 | 0.841 | NON-COMPROMISED | 0.35 | 59.6 | NEGATIVE | 0.087 | NEGATIVE |
| 144 | RA | -0.004 | 0.871 | NON-COMPROMISED | 0.278 | 57 | NEGATIVE | 0.065 | NEGATIVE |
| 13 | RA | 0.031 | 0.697 | NON-COMPROMISED | 1.375 | 56.7 | INDETERMINATE | 1.883 | REFLEX |
| 203 | RA | 0.509 | 0.598 | NON-COMPROMISED | 0.11 | 50.2 | NEGATIVE | 0.178 | NEGATIVE |
| 211 | RA | 0.191 | 0.544 | NON-COMPROMISED | 0.127 | 48.8 | NEGATIVE | 0.196 | NEGATIVE |
| 190 | RA | 0.021 | 0.653 | NON-COMPROMISED | 1.994 | 25.1 | INDETERMINATE | 2.337 | REFLEX |
| 195 | RA | 0.014 | 0.614 | NON-COMPROMISED | 1.951 | 24 | INDETERMINATE | 2.412 | REFLEX |
| 156 | RA | 0.003 | 0.565 | NON-COMPROMISED | 3.939 | 148.5 | POSITIVE | 6.008 | REFLEX |
| 135 | RA | 0.001 | 0.543 | NON-COMPROMISED | 0.281 | 58.9 | NEGATIVE | 0.502 | NEGATIVE |
| 109 | RA | 0.339 | 0.6 | NON-COMPROMISED | 2.283 | 67.5 | INDETERMINATE | 2.143 | REFLEX |

FIG. 46O

| TEST NAME | RESULTS | UNITS | FLAG | CLINICAL DECISION LIMITS |
|---|---|---|---|---|
| SYNOVASURE OSTEOARTHRITIS (OA) | POSITIVE | | ABNORMAL | RUN BY: NA |
| COMP, SYNOVIAL FLUID | 10635 | ng/mL | HIGH | >1500 |
| IL-8, SYNOBIAL FLUID | 540.4 | pg/mL | | |
| COMP/IL-8* | 19.7 | ng/pg | HIGH | >4.3 |
| *COMP/IL-8 RATIO IS CALCULATED ONLY WHEN COMP>1500 ng/mL | | | | |
| SYNOVASURE RHEUMATOID ARTHRITIS (RA) | NEGATIVE | | | RUN BY: NA |
| ANTI-CCP, SYNOVIAL FLUID | NEGATIVE | | | |
| RHEUMATOID FACTOR, SYNOVIAL FLUID | <10 | IU/mL | | ≥10 |
| SYNOVASURE CRYSTALLINE ARTHRITIS (CA) | NEGATIVE | | | RUN BY: NA |
| CRYSTAL ID, SYNOVIAL FLUID | | | | |
| NO CRYSTALS FOUND | | | | |
| SYNOVASURE NATIVE SPEPTIC ARTHRITIS (NSA) | | | | |
| CELL COUNT/DIFF, SYNOVIAL FLUID | | | | RUN BY: NA |
| RED BLOOD CELL COUNT | 4000 | /μL | | |
| TOTAL NUCLEATED CELL COUNT | 731 | /μL | | >3000 |
| NEUTROPHILS | 32 | % | | >70 |
| MONONUCLEAR CELLS | 68 | % | | |

FIG. 47A

| TEST NAME | RESULTS | UNITS | FLAG | CLINICAL DECISION LIMITS |
|---|---|---|---|---|
| SYNOVASURE OSTEOARTHRITIS (OA) | NEGATIVE | | | RUN BY: NA |
| COMP, SYNOVIAL FLUID | 1354 | ng/mL | | > 1500 |
| IL-8, SYNOBIAL FLUID | 3253.5 | pg/mL | | |
| COMP/IL-8* | | ng/pg | | > 4.3 |
| *COMP/IL-8 RATIO IS CALCULATED ONLY WHEN COMP>1500 ng/mL | | | | |
| SYNOVASURE RHEUMATOID ARTHRITIS (RA) | NEGATIVE | | | RUN BY: NA |
| ANTI-CCP, SYNOVIAL FLUID | NEGATIVE | | | |
| RHEUMATOID FACTOR, SYNOVIAL FLUID | <10 | IU/mL | | ≥10 |
| SYNOVASURE CRYSTALLINE ARTHRITIS (CA) | NEGATIVE | | | RUN BY: NA |
| CRYSTAL ID, SYNOVIAL FLUID | | | | |
| NO CRYSTALS FOUND | | | | |
| SYNOVASURE NATIVE SPEPTIC ARTHRITIS (NSA) | | | | RUN BY: NA |
| CELL COUNT/DIFF, SYNOVIAL FLUID | | | | |
| RED BLOOD CELL COUNT | 2000 | /µL | | |
| TOTAL NUCLEATED CELL COUNT | 7144 | /µL | HIGH | > 3000 |
| NEUTROPHILS | 91.8 | % | HIGH | > 70 |
| MONONUCLEAR CELLS | 8.2 | % | | |
| SYNOVASURE ALPHA DEFENSIN NSA* | NEGATIVE | | | RUN BY: SG ON 9/29/2018 7:28 AM |
| ALPHA-DEFENSINS-SF | 0.598 | | | |
| LACTATE | 49 | mg/dL | | |

*ALPHA DEFENSIN NSA ALGORITHM IS TESTED AND REPORTED WHEN TOTAL NUCLEATED CELL COUNT OR % NEUTROPHILS IS HIGH

FIG. 47B

| TEST NAME | RESULTS | UNITS | FLAG | CLINICAL DECISION LIMITS |
|---|---|---|---|---|
| SYNOVASURE OSTEOARTHRITIS (OA) | INDETERMINATE# | | ABNORMAL | RUN BY: NA |
| COMP, SYNOVIAL FLUID | 5035 | ng/mL | HIGH | > 1500 |
| IL-8, SYNOBIAL FLUID | 1403.9 | pg/mL | | |
| COMP/IL-8* | 3.6 | ng/pg | | > 4.3 |
| *COMP/IL-8 RATIO IS CALCULATED ONLY WHEN COMP>1500 ng/mL #INDETERMINATE RESULTS SUGGEST CARTILAGE DAMAGE AND ELEVATED INFLAMMATORY STATUS | | | | |
| SYNOVASURE RHEUMATOID ARTHRITIS (RA) | NEGATIVE | | | RUN BY: NA |
| ANTI-CCP, SYNOVIAL FLUID | NEGATIVE | | | |
| RHEUMATOID FACTOR, SYNOVIAL FLUID | <10 | IU/mL | | ≥10 |
| SYNOVASURE CRYSTALLINE ARTHRITIS (CA) | NEGATIVE | | | RUN BY: NA |
| CRYSTAL ID, SYNOVIAL FLUID | | | | |
| NO CRYSTALS FOUND | | | | |
| SYNOVASURE NATIVE SPEPTIC ARTHRITIS (NSA) | | | | RUN BY: NA |
| CELL COUNT/DIFF, SYNOVIAL FLUID | | | | |
| RED BLOOD CELL COUNT | 8000 | /µL | | |
| TOTAL NUCLEATED CELL COUNT | 865 | /µL | | > 3000 |
| NEUTROPHILS | 15.1 | % | | > 70 |
| MONONUCLEAR CELLS | 84.9 | % | | |

FIG. 47C

| TEST NAME | RESULTS | UNITS | FLAG | CLINICAL DECISION LIMITS |
|---|---|---|---|---|
| SYNOVASURE OSTEOARTHRITIS (OA) | INDETERMINATE# | | ABNORMAL | RUN BY: NA |
| COMP, SYNOVIAL FLUID | 1797 | ng/mL | HIGH | >1500 |
| IL-8, SYNOBIAL FLUID | 503.2 | pg/mL | | |
| COMP/IL-8* | 3.6 | ng/pg | | >4.3 |
| *COMP/IL-8 RATIO IS CALCULATED ONLY WHEN COMP>1500 ng/mL | | | | |
| #INDETERMINATE RESULTS SUGGEST CARTILAGE DAMAGE AND ELEVATED INFLAMMATORY STATUS | | | | |
| SYNOVASURE RHEUMATOID ARTHRITIS (RA) | INDETERMINATE^ | | | RUN BY: NA |
| ANTI-CCP, SYNOVIAL FLUID | NEGATIVE | | | |
| RHEUMATOID FACTOR, SYNOVIAL FLUID | 12 | IU/mL | HIGH | ≥10 |
| #INDETERMINATE RESULTS SUGGESTS RA WHEN ANTI-CCP IS POSITIVE | | | | |
| SYNOVASURE CRYSTALLINE ARTHRITIS (CA) | NEGATIVE | | | RUN BY: NA |
| CRYSTAL ID, SYNOVIAL FLUID | | | | |
| NO CRYSTALS FOUND | | | | |
| SYNOVASURE NATIVE SPEPTIC ARTHRITIS (NSA) | | | | RUN BY: NA |
| CELL COUNT/DIFF, SYNOVIAL FLUID | | | | |
| RED BLOOD CELL COUNT | 1000 | /µL | | |
| TOTAL NUCLEATED CELL COUNT | 380 | /µL | | >3000 |
| NEUTROPHILS | 46.5 | % | | >70 |
| MONONUCLEAR CELLS | 53.5 | % | | |

FIG. 47D

| TEST NAME | RESULTS | UNITS | FLAG | CLINICAL DECISION LIMITS |
|---|---|---|---|---|
| SYNOVASURE OSTEOARTHRITIS (OA) | POSITIVE | | ABNORMAL | RUN BY: NA |
| COMP, SYNOVIAL FLUID | 3324 | ng/mL | HIGH | > 1500 |
| IL-8, SYNOBIAL FLUID | 399.31 | pg/mL | | |
| COMP/IL-8* | 8.3 | ng/pg | HIGH | > 4.3 |
| *COMP/IL-8 RATIO IS CALCULATED ONLY WHEN COMP>1500 ng/mL | | | | |
| SYNOVASURE RHEUMATOID ARTHRITIS (RA) | NEGATIVE | | | RUN BY: NA |
| ANTI-CCP, SYNOVIAL FLUID | NEGATIVE | | | |
| RHEUMATOID FACTOR, SYNOVIAL FLUID | <10 | IU/mL | | ≥10 |
| SYNOVASURE CRYSTALLINE ARTHRITIS (CA) | NEGATIVE | | | RUN BY: NA |
| CRYSTAL ID, SYNOVIAL FLUID | | | | |
| NO CRYSTALS FOUND | | | | |
| SYNOVASURE NATIVE SPEPTIC ARTHRITIS (NSA) | | | | RUN BY: NA |
| CELL COUNT/DIFF, SYNOVIAL FLUID | | | | |
| RED BLOOD CELL COUNT | 7000 | /μL | | |
| TOTAL NUCLEATED CELL COUNT | 12918 | /μL | | > 3000 |
| NEUTROPHILS | 17.6 | % | | |
| MONONUCLEAR CELLS | 82.4 | % | | > 70 |
| SYNOVASURE ALPHA DEFENSIN NSA* | NEGATIVE | | | RUN BY: SG ON 9/29/2018 7:28 AM |
| ALPHA-DEFENSINS-SF | 0.094 | | | |
| L-LACTATE | 15.7 | mg/dL | | |

*ALPHA DEFENSIN NSA ALGORITHM IS TESTED AND REPORTED WHEN TOTAL NUCLEATED CELL COUNT OR % NEUTROPHILS IS HIGH

FIG. 47E

OSTEOARTHRITIS SAMPLES: SECONDARY SCREENING FOR SELECTED BIOMARKERS

VALUES IN AGREEMENT WITH CUT-OFFS FOR OSTEOARTHRITIS, ↑OUT OF RANGE, PUT IN A SENTINEL VALUE WHICH IS ASSAY SPECIFIC, ^EXTRAPOLATED ABOVE HIGH STANDARD, v EXTRAPOLATED BELOW LOWEST STANDARD

| Sample ID | Sex | Age | AD S/CO | CRP mg/L | HNE S/CO | MMP9 pg/ml | MMP3 pg/ml | OPG pg/ml | OPN pg/ml | IL6 pg/ml | IL8 pg/ml | PDGF pg/ml | NGAL pg/ml | OC pg/ml | COMP ng/ml |
|---|---|---|---|---|---|---|---|---|---|---|---|---|---|---|---|
| OA1 | F | 75 | | | | 1169* | | | | | 43.2* | | | | 6514* |
| OA2 | M | 53 | 0.07 | 0.9* | 0.04 | 2072* | | | | | 31.8* | | | | 9583* |
| OA3 | M | 72 | 0.07 | 0.6* | 0.04 | 7064* | | | | | 32.4* | | | | 3951* |
| OA4 | M | 65 | | | 0.06 | 2185* | | | | | 111.9* | | | | 4356* |
| OA5 | M | 74 | 0.07 | 1.2* | 0.04 | 494* | | | | | 53.1* | | | | 5948* |
| OA6 | M | 78 | 0.65 | 0.6* | 0.03 | 606* | | | | | 100.2* | | | | 5866* |
| OA8 | F | 67 | | | | 450* | | | | | 21.1* | | | | 2582* |
| OA9 | M | 55 | | | | 450* | | | | | 26.3* | | | | 1660* |
| OA10 | M | 76 | 0.099 | 0.5* | 0.03 | 3033* | | | | | 40.3* | | | | 8006* |
| OA11 | F | 59 | 0.100 | 1.1* | 0.04 | 450* | | | | | 34.0* | | | | 3789* |
| OA13 | | | 0.111 | 1.6* | | 5414* | | | | | 58.6* | | | | 718* |
| OA14 | | | 0.101 | 0.5* | | 7121* | | | | | 43.5* | | | | 10338* |
| OA18 | | | 0.096 | 1.1* | 0.039 | 829* | 936642* | 22016* | 64941* | 1808* | 107* | 2* | 58211* | 12025* | 6767* |
| OA19 | | | 0.103 | 1.9* | 0.084 | 3071* | 1567500* | 8449* | 30277* | 68* | 31* | 12* | 48421* | 4147* | 5896* |
| OA20 | | | 0.099 | 0.5* | 0.048 | 1045* | 938652* | 5242 | 33585* | 453* | 9* | 165* | 28426* | 2564 | 6517* |
| OA21 | | | 0.098 | 0.5* | 0.038 | 829* | 455119* | 3190 | 14540* | 84* | 7* | 2* | 37319* | 2652 | 5663* |
| OA22 | | | 0.100 | 0.9* | 0.047 | 1698* | 848187* | 12534* | 64639* | 143* | 10* | 12* | 49136* | 8091* | 6716* |
| OA23 | F | 73 | 0.132 | 0.8* | 0.208 | 11328* | 1235900* | 7399* | 65333* | 276* | 126* | 52* | 121532* | 13164* | 100656* |
| OA24 | | | 0.100 | 0.5* | 0.035 | 295* | 2330900* | 12261* | 26986* | 29* | 8* | 2* | 51655* | 5505* | 5324* |
| OA25 | F | 78 | 0.096 | 1.0* | 0.033 | 721* | 1902800* | 6095* | 13084* | 304* | 16* | 22* | 31343* | 9722* | 2416* |
| OA26 | | | 0.102 | 0.5* | 0.049 | 2850* | 1318100* | 16264* | 48139* | 349* | 16* | 62* | 65385* | 6800* | 5222* |
| OA27 | M | 82 | 0.106 | 0.8* | 0.033 | 3680* | 1024100* | 7071* | 47715* | 148* | 10* | 2* | 43961* | 1828 | 6546* |
| OA28 | | | 0.098 | 1.0* | 0.073 | 507* | 314616* | 12505* | 28643* | 222* | 9* | 2* | 59408* | 3824 | 7572* |
| OA29 | M | 66 | 0.107 | 0.8* | 0.051 | 4680* | 4753100 | 9168* | 71506* | 538* | 349* | 2* | 43430* | 3467 | 4916* |
| OA30 | | | 0.096 | 0.5* | 0.089 | 15267 | 1565600* | 10721* | 23211* | 162* | 31* | 187* | 124266* | 11102* | 5002* |

FIG. 48A

| Sample ID | Sex | Age | AD S/CO | CRP mg/L | HNE S/CO | MMP9 pg/ml | MMP3 pg/ml | OPG pg/ml | OPN pg/ml | IL6 pg/ml | IL8 pg/ml | PDGF pg/ml | NGAL pg/ml | OC pg/ml | COMP ng/ml |
|---|---|---|---|---|---|---|---|---|---|---|---|---|---|---|---|
| OA31 | M | 85 | 0.098 | 8.7 | 0.043 | 4068* | 1541900* | 16264* | 295999* | 1991* | 387* | 2* | 87284* | 4221* | 8087* |
| OA32 | | | 0.112 | 0.6* | 0.063 | 13151* | 5070000 | 3166 | 62227* | 929* | 538 | 2* | 69830* | 10052* | 2524* |
| OA33 | F | 65 | 0.097 | 0.5* | 0.045 | 4124* | 1720600* | 9082* | 52042* | 155* | 677 | 32* | 50641* | 17734* | 5615* |
| OA34 | F | 73 | 0.108 | 0.5* | 0.048 | 2906* | 15232000 | 5307 | 76316* | 2347* | 72* | 2* | 59632* | 6685* | 3125* |
| OA35 | F | 80 | 0.100 | 0.6* | 0.045 | 614* | 897242* | 8859* | 32916* | 583* | 46* | 2* | 110323* | 5761* | 5109* |
| OA36 | F | 75 | 0.104 | 0.5* | 0.055 | 2630* | 1041200* | 8311* | 62800* | 271* | 48* | 32* | 45362* | 11054* | 3810* |
| OA37 | M | 68 | 0.759 | 2.4* | 1.686 | 97741 | 11836000 | 6715* | 620625* | 3851 | 1395 | 32* | 64684 | 13314* | 3997* |
| OA38 | M | 73 | 0.094 | 0.8* | 0.052 | 2245* | 775937* | 17726* | 38579* | 456* | 3* | 32* | 83965* | 7721* | 8136* |
| OA39 | F | 70 | 0.098 | 0.6* | 0.058 | 3846* | 2367500* | 5504 | 41177* | 1304* | 33* | 72* | 79152* | 6893* | 5318* |
| OA40 | M | 75 | 0.096 | 0.6* | 0.040 | 5350* | 183896* | 10009* | 449923* | 356* | 57* | 12* | 89742* | 20900* | 12580* |
| OA41 | F | 68 | 0.095 | 0.5* | 0.047 | 5070* | 4291300 | 2026 | 26786* | 1108* | 44* | 2* | 52068* | 15921* | 5113* |
| OA42 | M | 64 | 0.103 | 0.5* | 0.041 | 1262* | 362334* | 5156 | 17905* | 36* | 18* | 32* | 48496* | 4560* | 6146* |
| OA43 | M | 77 | 0.098 | 0.5* | 0.033 | 721* | 197008* | 11433* | 39665* | 35* | 6* | 12* | 52631* | 6363* | 8052* |
| OA44 | F | 67 | 0.097 | 0.5* | 0.046 | 1153* | 137524* | 4741 | 42223* | 88* | 18* | 32* | 21439* | 4823* | 6070* |
| OA45 | M | 69 | 0.095 | 0.6* | 0.038 | 829* | 364978* | 7342* | 29495* | 160* | 7* | 12* | 65347* | 7952* | 6783* |
| OA47 | M | 67 | 0.097 | 2.3* | 0.050 | 7863* | | | | | 18.9* | | | | 76 |
| OA48 | F | 57 | 0.101 | 1.0* | 0.041 | 4222* | | | | | 24.5* | | | | 7778* |
| OA49 | F | 45 | 0.097 | 0.5* | 0.037 | 5812* | | | | | 40* | | | | 3833* |
| OA50 | M | 76 | 0.096 | 0.9* | 0.063 | 5698* | | | | | 50* | | | | 7197* |
| OA51 | F | 88 | 0.123 | 0.5* | 0.079 | 6040* | | | | | 97* | | | | 4126* |
| OA52 | F | 71 | 0.100 | 8.1 | 0.037 | 1620* | | | | | 37* | | | | 7238* |
| OA54 | M | 70 | | 0.6* | | 1252* | | | | | 114* | | | | 844 |
| OA55 | M | 69 | | 0.5* | | 2763* | | | | | 53* | | | | 13290* |
| OA56 | M | 63 | | 0.5* | | 3871* | | | | | 23* | | | | 9243* |
| OA57 | M | 63 | | 0.5* | | 1115* | | | | | 17* | | | | 15486* |
| OA58 | F | 49 | | 2.0* | | 4042* | | | | | 16* | | | | 4060* |
| OA59 | F | 62 | | 20.5 | | 449584 | | | | | 2705 | | | | 184 |
| OA60 | M | 72 | | 1.1* | | 2155* | | | | | 40* | | | | 6416* |
| OA61 | M | 59 | | 4.0 | | 5271* | | | | | 20* | | | | 5383* |

FIG. 48B

RHEUMATOID ARTHRITIS SAMPLES: SECONDARY SCREENING FOR SELECTED BIOMARKERS

VALUES IN AGREEMENT WITH CUT-OFFS FOR OSTEOARTHRITIS, †OUT OF RANGE, PUT IN A SENTINEL VALUE WHICH IS ASSAY SPECIFIC, ^EXTRAPOLATED ABOVE HIGH STANDARD, v EXTRAPOLATED BELOW LOWEST STANDARD

| Sample ID | Sex | Age | AD S/CO | CRP mg/L | HNE S/CO | MMP9 pg/ml | MMP3 pg/ml | OPG pg/ml | OPN pg/ml | IL6 pg/ml | IL8 pg/ml | PDGF pg/ml | NGAL pg/ml | OC pg/ml | COMP ng/ml |
|---|---|---|---|---|---|---|---|---|---|---|---|---|---|---|---|
| BRH1040288 | F | 82 | 2.237 | 17.4 | 1.479 | 282067 | 4207900 | 6063 | 700† | 12682 | 2936 | 16679 | 2780900 | 560† | 139 |
| BRH1040289 | F | 69 | 1.216 | 10.8 | 0.859 | 202201 | 3016500 | 6481* | 700† | 8006 | 1519 | 7033 | 1020500 | 1482 | 143 |
| BRH1040290 | M | 66 | 2.686 | 667.8 | 2.533 | 407891 | 20852000 | 3322 | 1424 | 14844 | 3810 | 12388 | 8100000^ | 560† | 951 |
| BRH1040291 | M | 62 | 1.656 | 12.6 | 1.605 | 253061 | 29200000^ | 5418 | 48018* | 13384 | 2105 | 3467 | 2496300 | 4147* | 2503* |
| BRH1040292 | M | 80 | 0.748 | 12.3 | 0.931 | 225065 | 10271000 | 4600 | 44122* | 11804 | 2412 | 3585 | 844953 | 2001 | 3429* |
| BRH1040293 | F | 88 | 2.555 | 14.9 | 2.536 | 397023 | 52300000^ | 3884 | 700† | 16371 | 5041 | 6353 | 10300000^ | 2934 | 818 |
| BRH1040294 | F | 88 | 2.599 | 33.9 | 2.411 | 375901 | 15256000 | 3861 | 1685 | 16124 | 4643 | 3728 | 15000000^ | 560† | 784 |
| BRH1040295 | F | 68 | 2.518 | 11.9 | 2.259 | 337863 | 16859000 | 3801 | 700† | 15477 | 4896 | 2059 | 4000000^ | 3016 | 704 |
| BRH1040296 | F | 77 | 2.670 | 17.3 | 2.452 | 347584 | 15539000 | 3730 | 700† | 14335 | 5214 | 8036 | 6400000^ | 1642 | 1031 |
| BRH1040297 | F | 71 | 2.417 | 15.5 | 2.392 | 382747 | 19760000 | 3666 | 782v | 14224 | 4742 | 5405 | 2999500 | 2681 | 912 |
| BRH1048231 | M | 65 | 0.132 | 13.8 | 0.066 | 14923* | 4773500 | 8740* | 100575* | 850* | 819 | 1411 | 94563* | 18233* | 1528 |
| BRH1048232 | M | 58 | 0.082 | 1.0* | 0.042 | 5070* | 3360700 | 4853 | 700† | 296* | 669 | 1971 | 19150* | 560† | 658 |
| BRH1048233 | M | 80 | 0.084 | 0.8* | 0.050 | 10590* | 21138000 | 5572 | 17905* | 642* | 3578 | 4213 | 22794* | 6040* | 3181* |
| BRH1048234 | M | 67 | 0.098 | 2.7 | 0.403 | 3680* | 2688600 | 5782 | 27718* | 3157 | 2010 | 103* | 30283* | 3363 | 1270 |
| BRH1048235 | M | 70 | 0.835 | 18.8 | 0.946 | 138168 | 7165300 | 1982 | 7503 | 6391 | 13120 | 504 | 533946 | 560† | 648 |
| BRH1048236 | M | 72 | 0.314 | 3.0 | 0.085 | 36894 | 1672100* | 4920 | 700† | 2264* | 9598 | 1862 | 189131 | 560† | 463 |
| BRH1048237 | M | 59 | 0.994 | 9.6 | 0.401 | 93561 | 411251* | 3576 | 700† | 3527 | 770 | 387 | 627677 | 560† | 91 |
| BRH1048238 | M | 68 | 0.089 | 17.0 | 0.050 | 41763 | 19306000 | 7097* | 40684* | 6088 | 29* | 1016 | 40117* | 4464* | 2823* |
| BRH1048239 | M | 74 | 0.083 | 1.7* | 0.044 | 10249* | 1107500* | 7728* | 4505 | 705* | 736 | 1750 | 41681* | 935 | 1813* |
| BRH1048240 | M | 75 | 0.273 | 25.7 | 0.289 | 45463 | 19322000 | 7676* | 211028* | 6259 | 2509 | 1184 | 344398 | 3849 | 3343* |
| BRH1048241 | M | 80 | 0.194 | 12.7 | 0.199 | 23114 | 957117* | 5017 | 5637 | 6248 | 1115 | 20000^ | 99487* | 3596 | 1543 |
| BRH1048242 | F | 55 | 0.094 | 8.1 | 0.050 | 1425* | 4154500 | 5963 | 112959* | 2315* | 3219 | 20000^ | 34849* | 3673 | 2990* |

FIG. 48C

TRAUMA/INJURY SAMPLES: SECONDARY SCREENING FOR SELECTED BIOMARKERS

VALUES IN AGREEMENT WITH CUT-OFFS FOR OSTEOARTHRITIS, †OUT OF RANGE, PUT IN A SENTINEL VALUE WHICH IS ASSAY SPECIFIC, ^EXTRAPOLATED ABOVE HIGH STANDARD, ∨EXTRAPOLATED BELOW LOWEST STANDARD

| Sample ID | Sex | Age | AD S/CO | CRP mg/L | HNE S/CO | MMP9 pg/ml | MMP3 pg/ml | OPG pg/ml | OPN pg/ml | IL6 pg/ml | IL8 pg/ml | PDGF pg/ml | NGAL pg/ml | OC pg/ml | COMP ng/ml |
|---|---|---|---|---|---|---|---|---|---|---|---|---|---|---|---|
| BRH1040273 | M | 67 | 0.154 | 8.8 | 0.189 | 157063 | 4637000 | 1610 | 21489* | 3941 | 542 | 7647 | 256405 | 560† | 282 |
| BRH1040274 | F | 62 | 0.425 | 7.4 | 0.379 | 114139 | 7782100 | 3073 | 3916 | 4219 | 1005 | 2362 | 562232 | 560† | 805 |
| BRH1040275 | F | 62 | 0.247 | 6.4 | 0.306 | 108020 | 6898500 | 2835 | 4142 | 3713 | 605 | 3762 | 434125 | 1054 | 947 |
| BRH1040276 | M | 51 | 0.310 | 9.4 | 0.351 | 262177 | 6315900 | 3056 | 6890 | 3678 | 954 | 5538 | 507944 | 9534* | 924 |
| BRH1040277 | F | 49 | 0.408 | 9.8 | 0.394 | 116858 | 6994800 | 3079 | 5947 | 3730 | 814 | 2716 | 589705 | 560† | 1025 |
| BRH1040278 | F | 57 | 0.441 | 20.6 | 0.405 | 184887 | 8500600 | 3777 | 8914 | 4689 | 755 | 2760 | 578416 | 560† | 884 |
| BRH1040279 | F | 56 | 0.177 | 3.2 | 0.190 | 10195 | 4934900 | 5249 | 4784 | 4677 | 642 | 2608 | 363649 | 2101 | 361 |
| BRH1040280 | M | 72 | 0.168 | 11.3 | 0.204 | 159571 | 3018100 | 2106 | 13042 | 5639 | 489 | 5030 | 347942 | 12196* | 398 |
| BRH1040281 | F | 67 | 0.189 | 3.0 | 0.261 | 95585 | 5096200 | 3328 | 6190 | 5767 | 922 | 967 | 377129 | 718 | 428 |
| BRH1040282 | M | 59 | 0.205 | 3.6 | 0.206 | 68323 | 4510600 | 2733 | 7338 | 7733 | 604 | 32* | 523703 | 560† | 416 |
| BRH1040283 | M | 51 | 0.178 | 7.8 | 0.212 | 83756 | 4251100 | 1752 | 5121 | 6573 | 385* | 979 | 354717 | 3390 | 322 |
| BRH1040284 | F | 54 | 0.180 | 34.5 | 0.218 | 140359 | 3245700 | 2018 | 7557 | 5897 | 429 | 942 | 328814 | 11537* | 310 |
| BRH1040285 | M | 54 | 0.186 | 12.1 | 0.230 | 189431 | 6443900 | 2176 | 8405 | 6659 | 818 | 8773 | 435659 | 1755 | 351 |
| BRH1040286 | M | 49 | 0.193 | 4.3 | 0.233 | 106544 | 6070500 | 2966 | 10462 | 9833 | 1173 | 1584 | 536264 | 2166 | 558 |
| BRH1040287 | F | 45 | 0.191 | 3.3 | 0.212 | 96156 | 7346200 | 4400 | 7720 | 7733 | 748 | 2644 | 412052 | 560† | 354 |
| BRH1048208 | F | 62 | 0.286 | 6.2 | 0.263 | 108534 | 7439900 | 2581 | 3190 | 3299 | 900 | 3408 | 434528 | 798 | 878 |
| BRH1048216 | F | 67 | 0.185 | 3.0 | 0.199 | 71339 | 4170300 | 2674 | 4784 | 4608 | 545 | 839 | 279863 | 560† | 253 |
| BRH1048217 | F | 59 | 0.204 | 4.0 | 0.221 | 53156 | 5555800 | 2528 | 5382 | 6352 | 425 | OOR | 327118 | 560† | 334 |
| BRH1048218 | M | 51 | 0.168 | 8.5 | 0.232 | 93119 | 9428800 | 1955 | 586 | 7096 | 580 | 1016 | 391707 | 4073 | 313 |
| BRH1048219 | M | 44 | 0.466 | 25.4 | 0.439 | 156386 | 16424000 | 4525 | 19687* | 9344 | 1116 | 1678 | 783901 | 1755 | 317 |
| BRH1058059 | F | 46 |  | 7.5 |  | 109742 |  |  |  |  | 53280 |  |  |  | 3605* |
| BRH1058060 | F | 47 |  | 7.8 |  | 138188 |  |  |  |  | 4444 |  |  |  | 4519* |
| BRH1058061 | F | 93 |  | 39.3 |  | 262243 |  |  |  |  | 72383^ |  |  |  | 3566* |
| BRH1058062 | F | 66 |  | 17.9 |  | 154438 |  |  |  |  | 30749 |  |  |  | 2502* |
| BRH1058063 | F | 72 |  | 27.8 |  | 201898 |  |  |  |  | 24212 |  |  |  | 123 |

FIG. 48D

| Sample ID | Sex | Age | AD S/CO | CRP mg/L | HNE S/CO | MMP9 pg/ml | MMP3 pg/ml | OPG pg/ml | OPN pg/ml | IL6 pg/ml | IL8 pg/ml | PDGF pg/ml | NGAL pg/ml | OC pg/ml | COMP ng/ml |
|---|---|---|---|---|---|---|---|---|---|---|---|---|---|---|---|
| BRH1058064 | F | 59 | | 14.8 | | 244336 | | | | | 5165 | | | | 164 |
| BRH1058065 | F | 62 | | 22.6 | | 240329 | | | | | 5413 | | | | 886 |
| BRH1058066 | F | 72 | | 15.2 | | 376491 | | | | | 2165 | | | | 113 |
| BRH1058067 | M | 63 | | 15.1 | | 288641 | | | | | 1364 | | | | 4693* |
| BRH1058068 | M | 67 | | 23.0 | | 234563 | | | | | 2424 | | | | 10553* |
| BRH1058069 | M | 75 | | 16.1 | | 276013 | | | | | 1246 | | | | 5014* |
| BRH1058070 | F | 72 | | 18.0 | | 363155 | | | | | 1536 | | | | 7657* |
| BRH1058071 | F | 34 | | 23.0 | | 320709 | | | | | 2231 | | | | 5548* |
| BRH1058072 | M | 62 | | 16.7 | | 301685 | | | | | 1859 | | | | 65 |
| BRH1058073 | M | 54 | | 22.2 | | 264681 | | | | | 2137 | | | | 1799* |

FIG. 48E

ROC ANALYSIS OF 11 BIOMARKERS DISCRIMINATING OA FROM RA, TRAUMA/INJURY OR A COMBINED GROUP OF RA AND TRAUMA/INJURY

| Biomarker | OA vs All | | | | OA vs RA | | | | OA vs Trauma | | | |
|---|---|---|---|---|---|---|---|---|---|---|---|---|
| | AUC | Cut-off | Sensitivity | Specificity | AUC | Cut-off | Sensitivity | Specificity | AUC | Cut-off | Sensitivity | Specificity |
| COMP | 0.895 | >3697 | 85.2 | 89.5 | 0.933 | >3609 | 85.2 | 100.0 | 0.872 | >3697 | 85.2 | 82.9 |
| IL-8 | 0.963 | <406.0 | 92.6 | 96.5 | 0.959 | <603.5 | 94.4 | 95.5 | 0.966 | <367.0 | 90.7 | 100.0 |
| CRP | 0.956 | <2.550 | 92.0 | 94.7 | 0.939 | <2.550 | 92.0 | 86.4 | 0.967 | <2.700 | 92.0 | 100.0 |
| MMP-9 | 0.952 | <19291 | 96.3 | 89.5 | 0.911 | <9056 | 90.7 | 86.4 | 0.978 | <34212 | 96.3 | 100.0 |
| OPG | 0.877 | >6079 | 73.0 | 88.6 | 0.801 | >6598 | 70.3 | 82.6 | 0.959 | >4586 | 91.9 | 95.2 |
| OPN | 0.877 | >13063 | 97.3 | 76.7 | 0.786 | >8094 | 100.0 | 625.2 | 0.981 | >13063 | 97.3 | 90.0 |
| MMP-3 | 0.875 | <2.53E6 | 82.1 | 90.9 | 0.854 | <2.53E6 | 82.1 | 82.6 | 0.898 | <2.69E6 | 92.1 | 100.0 |
| IL-6 | 0.966 | <2752 | 97.3 | 86.1 | 0.941 | <2128 | 91.9 | 82.6 | 0.995 | <2823 | 97.3 | 100.0 |
| OC | 0.873 | >4110 | 82.1 | 83.3 | 0.876 | >4512 | 75.0 | 90.0 | 0.870 | >2365 | 96.4 | 75.0 |
| PDGF | 0.938 | <287.0 | 100.0 | 88.1 | 0.929 | <287.0 | 100.0 | 86.4 | 0.948 | <513.0 | 100.0 | 90.0 |
| NGAL | 0.843 | <156699 | 96.4 | 81.0 | 0.731 | <156699 | 96.4 | 63.6 | 0.966 | <190336 | 96.4 | 100.0 |

FIG. 49

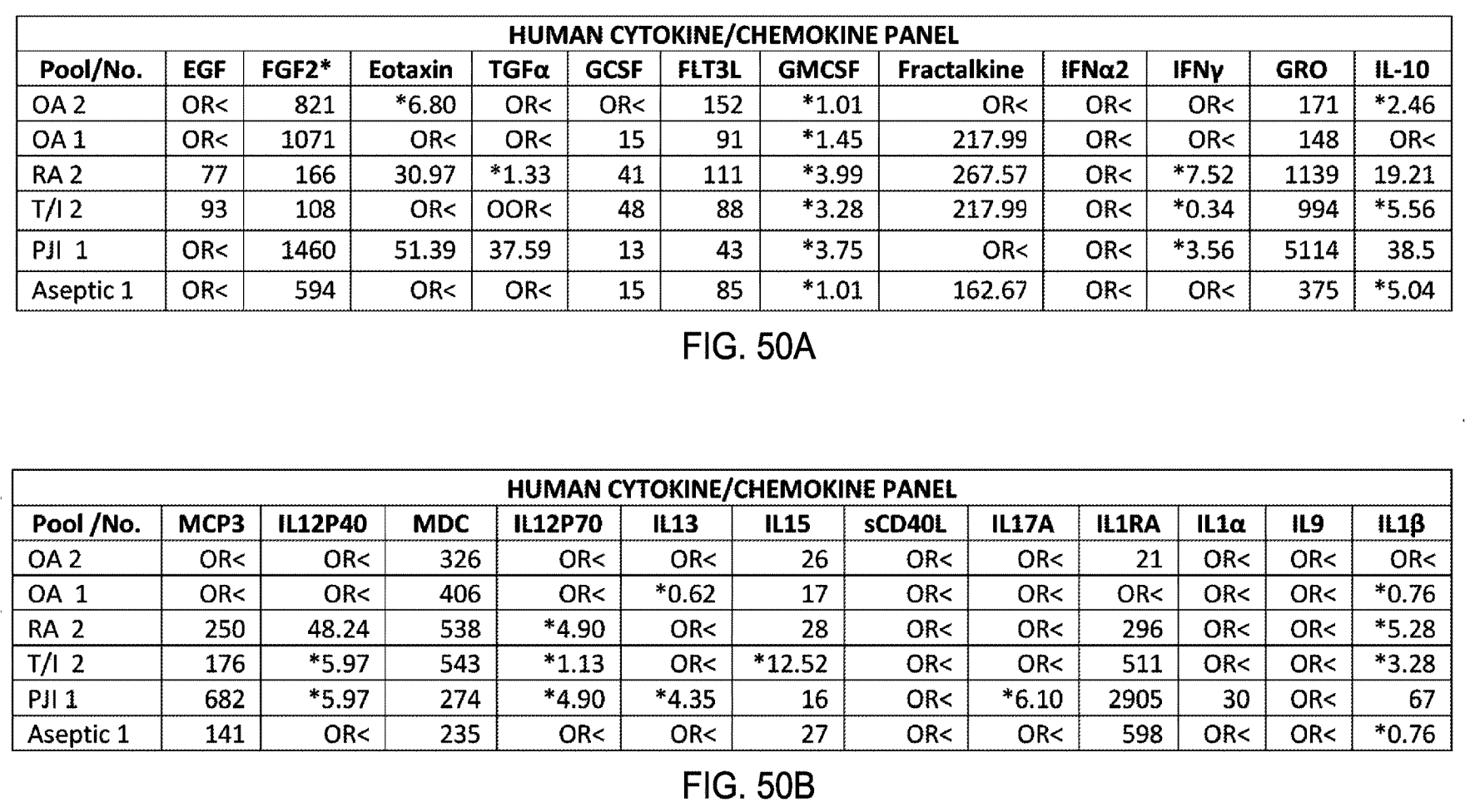

HUMAN CYTOKINE/CHEMOKINE PANEL

| Pool/No. | EGF | FGF2* | Eotaxin | TGFα | GCSF | FLT3L | GMCSF | Fractalkine | IFNα2 | IFNγ | GRO | IL-10 |
|---|---|---|---|---|---|---|---|---|---|---|---|---|
| OA 2 | OR< | 821 | *6.80 | OR< | OR< | 152 | *1.01 | OR< | OR< | OR< | 171 | *2.46 |
| OA 1 | OR< | 1071 | OR< | OR< | 15 | 91 | *1.45 | 217.99 | OR< | OR< | 148 | OR< |
| RA 2 | 77 | 166 | 30.97 | *1.33 | 41 | 111 | *3.99 | 267.57 | OR< | *7.52 | 1139 | 19.21 |
| T/I 2 | 93 | 108 | OR< | OOR< | 48 | 88 | *3.28 | 217.99 | OR< | *0.34 | 994 | *5.56 |
| PJI 1 | OR< | 1460 | 51.39 | 37.59 | 13 | 43 | *3.75 | OR< | OR< | *3.56 | 5114 | 38.5 |
| Aseptic 1 | OR< | 594 | OR< | OR< | 15 | 85 | *1.01 | 162.67 | OR< | OR< | 375 | *5.04 |

FIG. 50A

HUMAN CYTOKINE/CHEMOKINE PANEL

| Pool/No. | MCP3 | IL12P40 | MDC | IL12P70 | IL13 | IL15 | sCD40L | IL17A | IL1RA | IL1α | IL9 | IL1β |
|---|---|---|---|---|---|---|---|---|---|---|---|---|
| OA 2 | OR< | OR< | 326 | OR< | OR< | 26 | OR< | OR< | 21 | OR< | OR< | OR< |
| OA 1 | OR< | OR< | 406 | OR< | *0.62 | 17 | OR< | OR< | OR< | OR< | OR< | *0.76 |
| RA 2 | 250 | 48.24 | 538 | *4.90 | OR< | 28 | OR< | OR< | 296 | OR< | OR< | *5.28 |
| T/I 2 | 176 | *5.97 | 543 | *1.13 | OR< | *12.52 | OR< | OR< | 511 | OR< | OR< | *3.28 |
| PJI 1 | 682 | *5.97 | 274 | *4.90 | *4.35 | 16 | OR< | *6.10 | 2905 | 30 | OR< | 67 |
| Aseptic 1 | 141 | OR< | 235 | OR< | OR< | 27 | OR< | OR< | 598 | OR< | OR< | *0.76 |

FIG. 50B

HUMAN CYTOKINE/CHEMOKINE PANEL

| Pool /No. | IL2 | IL3 | IL4 | IL5 | IL6 | IL7 | IL8 | IP10 | MCP1 | MIP1α | MIPβ | TNFα |
|---|---|---|---|---|---|---|---|---|---|---|---|---|
| OA 2 | OR< | OR< | OR< | *2.56 | 275 | OR< | 225 | 547 | 1851 | *24.36 | 32 | *1.44 |
| OA 1 | OR< | OR< | OR< | *2.79 | 400 | OR< | 45 | 1895 | 1362 | *31.18 | 95 | OR< |
| RA 2 | OR< | OR< | 1043 | *3.41 | 8173 | 28.27 | 5921 | 791 | 3251 | 101 | 61 | *5.86 |
| T/I 2 | OR< | OR< | 1410 | *4.51 | 2740 | OR< | 1306 | 5023 | 1477 | 82 | 90 | *4.23 |
| PJI 1 | OR< | OR< | OR< | *7.31 | 50762 | 47.71 | 50100 | 790 | 3236 | 335 | 29 | *12.0 |
| Aseptic 1 | OR< | OR< | OR< | *2.90 | 169 | OR< | 584 | 5810 | 6079 | 62 | 698 | *0.05 |

FIG. 50C

SOLUBLE CYTOKINE/CHEMOKINE RECEPTOR PANEL

| Pool/No. | sCD30 | sEGFR | Sgp130 | sIL1R1 | sIL1RII | sIL4R | sIL6R |
|---|---|---|---|---|---|---|---|
| OA 2 | *16.19 | 23509 | 82919 | *49.18 | 53214 | 15642 | 9113 |
| OA 1 | *16.19 | 20147 | 85306 | *29.11 | 52726 | 9529 | 8079 |
| RA 2 | *53.07 | 48091 | 150748 | *65.34 | 99420 | 16509 | 16695 |
| T/I 2 | *29.59 | 22497 | 75616 | *39.26 | 49047 | 14192 | 7545 |
| PJI 1 | *22.89 | 9205 | 48123 | *15.00 | 28664 | 1770 | 5702 |
| Aseptic 1 | *19.54 | 38676 | 105553 | *52.45 | 72114 | 10448 | 9885 |

HUMAN CYTOKINE/CHEMOKINE PANEL

| Pool/No. | TNFβ | VEGF | PDGFAA | PDGFAB PDGFBB | RANTES |
|---|---|---|---|---|---|
| OA 2 | *0.39 | 413 | 31 | 39 | 161 |
| OA 1 | OR< | 282 | 20 | 4 | 102 |
| RA 2 | *4.17 | 778 | 1040 | 8200 | 3339 |
| T/I 2 | *4.39 | 271 | 860 | 4110 | 1747 |
| PJI 1 | *3.32 | 4994 | 41 | OR< | 2517 |
| Aseptic 1 | *0.13 | 766 | 124 | 29 | 306 |

FIG. 50D

| Pool/No. | SOLUBLE CYTOKINE/CHEMOKINE RECEPTOR PANEL | | | | | MMP PANEL 1 | | | | MMP PANEL 2 | | |
| | sRAGE | sTNFRI | sTNFRII | sVEGFR1 | sVEGFR2 | sVEGFR3 | MMP3 | MMP12 | MMP13 | MMP1 | MMP2 | MM7 |
|---|---|---|---|---|---|---|---|---|---|---|---|---|
| OA 2 | *8.52 | 3946 | 6710 | *626.81 | 2372.27 | *16.05 | 2.74E+06 | OR< | OR< | 82380 | 277410 | 2071 |
| OA 1 | *12.21 | 3540 | 6377 | *626.81 | 2645.44 | OR< | 2.84E+06 | OR< | OR< | 66010 | 271260 | 975 |
| RA 2 | *31.51 | 5402 | 36014 | 3303.39 | 19969.71 | *157.46 | 2.72E+07 | 156.0 | 170.5 | 182916 | 661055 | 4026 |
| T/I 2 | 14.02 | 3817 | 17442 | 1240.14 | 3873.06 | *40.44 | 1.12E+07 | OR< | OR< | 346337 | 384422 | 2833 |
| PJI 1 | *0.58 | 3912 | 27050 | 4737.49 | *1002.72 | *16.05 | 5.91E+06 | 1058.8 | 3287.4 | 98093 | 1199900 | 2935 |
| Aseptic 1 | *21.13 | 8665 | 19018 | 3736.14 | 3736.76 | *16.05 | 1.89E+05 | 17397.8 | 20326.0 | 44479 | 425288 | 22825 |

FIG. 50E

| Pool/No. | MMP PANEL 2 | | TIMP PANEL | | | | NGAL | BONE METABOLISM PANEL | | | | |
|---|---|---|---|---|---|---|---|---|---|---|---|---|
| | MMP9 | MMP10 | TIMP1 | TIMP2 | TIMP3 | TIMP4 | NGAL | ACTH | DKK1 | IL6 | Insulin | Leptin |
| OA 2 | 2147 | 93876 | 511247 | 131025 | 10608 | 84.75 | 61612 | OR< | 295 | 661 | OR< | 15198 |
| OA 1 | 16511 | 91295 | 459251 | 114217 | 5045 | OR< | 42518 | OR< | 240 | 869 | OR< | 5711 |
| RA 2 | 264651 | 309911 | 221261 | 102821 | 2289 | 113.86 | 2126400 | OR< | 770 | 17647 | OR< | 4792 |
| T/I 2 | 93589 | 160281 | 209690 | 62254 | 764 | 52.61 | 395228 | OR< | 813 | 6648 | OR< | 8929 |
| PJI 1 | 4.14E+10 | 1.38E+10 | 285322 | 42928 | 2009 | *20.26 | 2.73E+07 | OR< | 93 | 124183 | OR< | 376 |
| Aseptic 1 | 79539 | 175884 | 465207 | 151061 | 22580 | OR< | 70652 | OR< | 64 | 363 | OR< | 7628 |

FIG. 50F

| Pool/No. | BONE METABOLISM PANEL | | | | | | | | RANKL | MMP9/COMPLEXED WITH | | COMP ng/ml |
|---|---|---|---|---|---|---|---|---|---|---|---|---|
| | TNFα | OPG | OC | OPN | SOST | IL1β | PTH | FGF23 | RANKL | TIMP1 | NGAL | |
| OA 2 | *0.78 | 11825 | 5918 | 57761 | 2146 | OR< | *17.47 | OR< | OR< | OR< | 3109 | 5172.75986 |
| OA 1 | OR< | 7498 | 7925 | 26356 | 1582 | OR< | 22 | OR< | 101 | ND | ND | ND |
| RA 2 | 2 | 4732 | OR< | 6220 | 2714 | *0.83 | 24 | OR< | 58 | 664700 | 408842 | 766.205837 |
| T/I 2 | 1 | 3299 | 3967 | 7851 | 1000 | *0.58 | *8.25 | OR< | OR< | 113400 | 49312 | 467.793139 |
| PJI 1 | 3 | 816 | 5714 | 5960 | 330 | 22 | *8.25 | OR< | 135 | ND | ND | ND |
| Aseptic 1 | *0.61 | 730 | 13858 | 572269 | 673 | OR< | *8.25 | OR< | 1834 | ND | ND | ND |

ND – NOT DONE
OR< - OUT OF RANGE LOW
* - EXTRAPOLATED BELOW LOW STANDARD

FIG. 50G

BIOMARKERS OF EARLY OSTEOARTHRITIS

CLAIM OF PRIORITY

This application is a U.S. National Stage Application under 35 U.S.C. 371 from International Application Serial No. PCT/US2020/057967, filed on Oct. 29, 2020, and published as WO 2021/087116 A1 on May 6, 2021, which claims the benefit of U.S. Provisional Patent Application Ser. No. 62/928,114, filed on Oct. 30, 2019, and also claims the benefit of U.S. Provisional Patent Application Ser. No. 63/010,756, filed on Apr. 16, 2020, the benefit of priority of each of which is claimed hereby, and each of which is incorporated by reference herein in its entirety.

TECHNICAL FIELD

The disclosure is directed to methods, compositions, and systems for detection, diagnosis, prognosis, disease staging, and/or monitoring progression and/or treatment of joint injuries, disorders, and diseases and the assessment of the usefulness and efficacy of therapeutic compositions or methods to treat such injuries, joint damage and arthritic diseases.

BRIEF SUMMARY OF BACKGROUND

This section provides background information related to the present disclosure, but such background information is not admitted as being prior art. Arthritis is defined by the Arthritis Foundation as a group of diseases affecting the joints that can cause inflammation, pain, or joint disease. More than 100 rheumatic diseases exist, with osteoarthritis (OA) being the most common. Although rheumatic diseases are characterized as musculoskeletal inflammation, OA has been described as a noninflammatory arthropathy. In OA classical signs of inflammation, e.g., marked infiltration of inflammatory cells into joint tissues and the presence of few neutrophils in the synovial fluid, are absent. Yet, there is clear evidence for an inflammatory component in OA pathogenesis. Osteoarthritis is a progressive degenerative joint disease characterized by loss of cartilage and underlying bony changes. Osteoarthritis of the knee affects the entire joint, including cartilage, ligaments, bone, and joint lining. Driven by underlying inflammation, pain is the most common reason patients seek treatment for OA. Researchers are actively seeking biomarkers to detect osteoarthritis (OA) using genomic, transcriptomic, and proteomic methodologies. Detection, diagnosis, staging, and prognosis of OA is of particular interest because this information can inform treatment decisions. Biomarkers have been identified that are known to be associated with OA, but there is still no definitive diagnostic test for detecting OA at any stage of the disease.

Brief Description of Problem Solved

Currently, the diagnosis of OA relies on clinical history and evaluation, with radiographs often used to confirm the diagnosis. Typically, advanced imaging and joint fluid analysis is not needed. These methods may be sufficient to identify clear-cut cases of established OA, but current OA diagnostic methods lack the capability of detecting comorbidities in the affected joint, such as crystalline arthritis (CA, presence of monosodium urate (MSU) crystals or calcium pyrophosphate dihydrate (CPP or CPPD) crystals, rheumatoid arthritis (RA), or septic arthritis, e.g., native septic arthritis (NSA) and periprosthetic joint infection (PJI), and do not provide any insight into the OA phenotype. An inability to objectively measure disease severity and rate of progression has hindered the development of new OA treatments. The traditional method of diagnosing OA does not provide the clinician with sufficient information to establish a targeted, patient-specific treatment approach. This results in many patients experiencing long term pain, functional impairment, and progression to end-stage disease due to unavailable or ineffective OA treatment.

The high prevalence of OA makes it an obvious leading hypothesis for causes of unspecified knee pain, particularly when paired with an atypical clinical presentation of an alternative arthropathy and/or X-ray evidence of joint space narrowing and osteophytes. Under these circumstances, a patient may be misdiagnosed as having OA when they do not actually have the disease. Alternatively, a patient may be diagnosed with and treated for primary OA when, in fact, the OA is either secondary to another type of arthritis or OA is the primary disease but another type of arthritis is also affecting the joint. Rheumatoid arthritis, CA, injury/trauma, and/or septic arthritis (NSA or PJI, collectively SA) can contribute to an inaccurate or incomplete diagnosis of knee pain/inflammation as being due to OA.

The intersecting signs and symptoms of the arthritis types included in a differential diagnosis of OA, as well as the high rate of concomitant presentation of more than one type of arthritis, indicates that the complete picture of the cause for the pain and/or inflammation/effusion in a joint cannot truly be known without synovial fluid analysis. Currently, despite the clear need, there is no single panel of synovial fluid tests that provide information on the arthritis types necessary for a valid differential diagnosis of OA, namely osteoarthritis, rheumatoid arthritis, crystalline arthritis (gout and pseudogout), and septic arthritis (native septic arthritis or periprosthetic joint infection).

Brief Listing of Advantages

There is a significant unmet medical need for early and/or better OA interventions, but the development of new treatment options and appropriate use of existing treatment options is dependent on an accurate and complete diagnosis of the disease. Research has demonstrated that OA can coexist with other inflammatory arthritis types, which may sometimes remain undetected while a patient fails to achieve satisfactory treatment outcomes. Additionally, there is clear evidence that OA has been misdiagnosed and mistreated as RA. Hence, there is a clear need for tools to advance more informed diagnoses and better medical decision making.

The present inventors have developed biomarkers, compositions, algorithms, methods to aid clinicians in clarifying the differential diagnosis of osteoarthritis, rheumatoid arthritis, crystalline arthritis, and infectious arthritis in synovial fluid of patients experiencing joint pain and/or inflammation, and ensure the possibility of alternative or additional diagnoses are evaluated, particularly in cases where the clinical presentation may not be clear. Biomarkers, compositions, algorithms, and methods of the present patent disclosure enable a valid and complete diagnosis of OA using well-known immunoassay diagnostic technologies, without the need for radiographic confirmation and can aid clinicians in clarifying the differential diagnosis of OA, and ensure the evaluation of alternative or additional diagnoses, particularly in cases where the clinical presentation may not be clear-cut. Accurate and complete diagnosis provides the best foundation for informing treatment decision and treatment success. Biomarkers, compositions, algorithms, and methods of the present patent disclosure provide a valid and complete differential diagnosis of the most common sources of unspecified joint pain and/or inflammation, e.g. whether due to OA, RA, CA, SA, or a combination of two or more of these disorders, thereby giving clinicians the information necessary for selection of the pharmacological and other interventions that are most appropriate and helpful to treating the specific arthropathy(ies) that are present in each patient. The interplay between OA and other arthritic conditions is complex and may change over the course of disease. The biomarkers, algorithms, methods, and compositions disclosed herein also to provide clinicians with the ability to monitor the progression of joint disease, and the efficacy of therapeutic interventions.

SUMMARY OF THE TECHNICAL DETAILS

The protein biomarkers of the present invention were identified using ELISA and highly multiplexed immunoassays to identify different proteins in synovial fluid samples from 9 different patient groups including samples from early OA, middle stage OA, and late stage OA. Protein biomarkers have been identified from this analysis that are useful for making diagnostic immunoassays, for evaluating synovial fluid samples and diagnosing joint pain or joint inflammation.

SUMMARY OF THE INVENTION

This summary is intended to provide an overview of subject matter of the present patent application. It is not intended to provide an exclusive or exhaustive explanation of the invention or its full scope or all its features. The detailed description is included to provide further information about the present patent application.

The present inventors have recognized that a valid diagnosis of joint pain and/or joint inflammation can be performed by analysing synovial fluid for the presence of one or more biomarkers, and the levels of one or a combination of biomarkers in synovial fluid can be used to determine if osteoarthritis is present, if one or more joint diseases other than osteoarthritis are present in the joint, or if osteoarthritis is concurrently present with one or more other diseases in the joint. The methods, algorithms, systems, and compositions disclosed herein are useful in diagnosing, staging, monitoring disease progression, and treatment of osteoarthritis and other arthropathies. To further illustrate the compositions, combinations, methods, algorithms, and systems disclosed herein, a non-limiting list of aspects of the invention provided here:

Aspect 1 can include or use a method of evaluating a synovial fluid, comprising: determining a level of a first biomarker in a synovial fluid sample extracted from a painful or inflamed joint of a subject, the first biomarker selected from cartilage oligomeric matrix protein (COMP), osteopontin (OPN), osteoprotegerin (OPG), and osteocalcin (OC); determining a level of a second biomarker in the synovial fluid sample, the second biomarker selected from interleukin-8 (IL-8), interleukin-6 (IL-6), C-reactive protein (CRP), matrix metalloproteinase-9 (MMP-9), matrix metalloproteinase-3 (MMP3), neutrophil gelatinase-associated lipocalin (NGAL), and a platelet-derived growth factor (PDGF); determining a sample biomarker ratio of the levels of first biomarker and the second biomarker in the synovial fluid sample; and comparing the sample biomarker ratio to a reference ratio of the levels of the first biomarker and the second biomarker in a reference synovial fluid.

Aspect 2 can include or use or can optionally be combined with the subject matter of Aspect 1 to optionally include or use a method wherein when the sample biomarker ratio is greater than or equal to the reference ratio the subject is confirmed to have osteoarthritis.

Aspect 3 can include or use or can optionally be combined with the subject matter of any one or a combination of Aspects 1 through 2 to optionally include or use a method further comprising determining the presence of a third biomarker in the synovial fluid sample when the sample biomarker ratio is less than the reference ratio.

Aspect 4 can include or use or can optionally be combined with the subject matter of any one or any combination of Aspects 1 through 3 to optionally include or use a method wherein when the level of the first biomarker in the synovial fluid sample is less than a reference level of the first biomarker osteoarthritis can be excluded from a diagnosis of the subject's joint pain or inflammation.

Aspect 5 can include or use or can optionally be combined with the subject matter of any one or any combination of Aspects 1 through 4 to optionally include or use a method wherein when the level of the second biomarker in the synovial fluid sample is greater than or equal to a reference level of the second biomarker an inflammatory arthropathy or traumatic injury is present in the subject's joint.

Aspect 6 can include or use or can optionally be combined with the subject matter of any one or any combination of Aspects 1 through 5 to optionally include or use a method of evaluating a synovial fluid, comprising: determining a level of a first biomarker in a synovial fluid sample extracted from a painful or inflamed joint of a subject, the first biomarker selected from cartilage oligomeric matrix protein (COMP), osteopontin (OPN), osteoprotegerin (OPG), and osteocalcin (OC); comparing the level of the first biomarker in the synovial fluid sample to a reference level of the first biomarker; and determining a level of a second biomarker in the synovial fluid sample when the level of the first biomarker is greater than or equal to the reference level of the first biomarker, the second biomarker selected from interleukin-8 (IL-8), interleukin-6 (IL-6), C-reactive protein (CRP), matrix metalloproteinase-9 (MMP-9), matrix metalloproteinase-3 (MMP3), neutrophil gelatinase-associated lipocalin (NGAL), and a platelet-derived growth factor (PDGF).

Aspect 7 can include or use or can optionally be combined with the subject matter of any one or any combination of Aspects 1 through 6 to optionally include or use a method further comprising comparing the level of the second biomarker to a reference level of the second biomarker.

Aspect 8 can include or use or can optionally be combined with the subject matter of any one or any combination of Aspects 1 through 7 to optionally include or use a method further comprising determining a biomarker ratio of the level of the first biomarker and the level of the second biomarker in the synovial fluid sample and comparing the biomarker ratio with a reference ratio of the levels of the first biomarker and the second biomarker in the reference.

Aspect 9 can include or use or can optionally be combined with the subject matter of any one or any combination of Aspects 1 through 8 to optionally include or use a method wherein when the level of the first biomarker in the synovial fluid sample is less than the reference level of the first biomarker osteoarthritis is excluded from a diagnosis of the subject's joint pain or joint inflammation.

Aspect 10 can include or use a method of evaluating joint pain or joint inflammation in a subject, comprising: determining a level of cartilage oligomeric matrix protein (COMP) in a synovial fluid sample obtained from the joint; and determining a level of interleukin-8 (IL-8) in the synovial fluid sample when the level of COMP is greater than or equal to 1,500 ng/mL or determining the presence of anti-cyclic citrullinated peptide (anti-CCP) or rheumatoid factor (RF) in the synovial fluid sample when the level of COMP is less than 1,500 ng/mL.

Aspect 11 can include or use or can optionally be combined with the subject matter of any one or any combination of Aspects 1 through 10 to optionally include or use a method further comprising determining the presence of or absence of monosodium urate (MSU) crystals or calcium pyrophosphate dihydrate (CPPD) crystals in the synovial fluid sample.

Aspect 12 can include or use or can optionally be combined with the subject matter of any one or any combination of Aspects 1 through 11 to optionally include or use a method further comprising determining a red blood cell (RBC) count, a white blood cell (WBC) count, the percentage of polymorphonuclear WBCs, the presence of alphadefensin (AD), the presence of lactate, or the presence of neutrophil elastase in the synovial fluid sample.

Aspect 13 can include or use or can optionally be combined with the subject matter of any one or any combination of Aspects 1 through 12 to optionally include or use a method further comprising determining the absorbance at 280 nm (A280) of the synovial fluid sample and comparing the A280 of the sample with a reference A280.

Aspect 14 an include or use or can optionally be combined with the subject matter of any one or any combination of Aspects 1 through 13 to optionally include or use a method wherein when the level of COMP is less than 1,500 ng/mL osteoarthritis is excluded from a diagnosis of the subject's joint pain or joint inflammation.

Aspect 15 can include or use or can optionally be combined with the subject matter of any one or any combination of Aspects 1 through 14 to optionally include or use a method further comprising determining a concentration ratio of COMP:IL-8 when the level of COMP is greater than or equal to 1,500 ng/mL.

Aspect 16 can include or use or can optionally be combined with the subject matter of any one or any combination of Aspects 1 through 15 to optionally include or use a method wherein a concentration ratio of COMP:IL-8 greater than or equal to 2.0 ng/pg or greater than or equal to 2,000 indicates the subject has osteoarthritis.

Aspect 17 can include or use or can optionally be combined with the subject matter of any one or any combination of Aspects 1 through 16 to optionally include or use a method wherein a level of IL-8 less than 600 pg/mL indicates the subject does not have an inflammatory arthropathy or an acute traumatic injury to the joint.

Aspect 18 can include or use or can optionally be combined with the subject matter of any one or any combination of Aspects 1 through 17 to optionally include or use a method further comprising treating the subject for osteoarthritis when the level of COMP is greater than or equal to 1,500 ng/mL.

Aspect 19 can include or use or can optionally be combined with the subject matter of any one or any combination of Aspects 1 through 18 to optionally include or use a method further comprising treating the subject for an inflammatory arthropathy or acute traumatic injury when the level of COMP is less than 1,500 ng/mL.

Aspect 20 can include or use or can optionally be combined with the subject matter of any one or any combination of Aspects 1 through 19 to optionally include or use a method further comprising treating the subject for an inflammatory arthropathy when a concentration ratio of COMP:IL-8 is less than 4.3 ng/pg or less than 4300, or treating the subject for osteoarthritis when the ratio of COMP:IL-8 is greater than or equal to 4.3 ng/pg or greater than or equal to 4300.

Aspect 21 can include or use, or can optionally be combined with any portion or a combination of portions of any one or more of Aspects 1 through 20, subject matter that can include means for performing any one or more of the functions of Aspects 1 through 20, or a machine-readable medium including instructions that, when performed by a machine, cause the machine to perform any one or more of the functions of Aspects 1 through 20.

Further areas of applicability will become apparent from the description provided herein. The description and specific aspects of the invention in this overview are intended for purposes of illustration only and are not intended to limit the scope of the present disclosure.

BRIEF DESCRIPTION OF THE FIGURES

In the figures, which are not necessarily drawn to scale, like numerals may describe similar components in different views. Like numerals having different letter suffixes may represent different instances of similar components. The figures illustrate generally, by way of example, but not by way of limitation, various aspects discussed in the present document. The figures described herein are for illustrative purposes only of selected examples and not all possible examples or implementations, and these drawings are not intended to limit the scope of the present disclosure.

The following abbreviations shall be used throughout the figures: OA=osteoarthritis; OA KL 1,2=osteoarthritis stage Kellgren-Lawrence (KL) 1,2; OA KL 2,3=osteoarthritis stage KL 2,3; OA KL4=osteoarthritis KL stage 4; RA=rheumatoid arthritis; Aseptic=not infected; MOM=metal on metal inflammation; MOP=metal on plastic inflammation; Trauma=acute trauma or injury to the joint; PJI=periprosthetic joint infection; NSA or Nat. Inf.=native septic arthritis or native infection; gout=monosodium urate (MSU) crystal disease; CPP or CPPD=calcium pyrophosphate dihydrate crystal disease; C/O=cutoff level of a biomarker to discriminate OA from one or more of the other disease states to discriminate a particular stage of OA form another stage of OA. A dotted-line or a dashed-line in a graph or scatter plot denotes a cutoff (C/O) value for a biomarker to discriminate OA from one or more other disease states.

FIG. 1A compares OA and separate disease states; Cutoff (C/O)>4220 pg/mL, Sensitivity 1.0, Specificity 0.95. FIG. 1B compares OA to MOM, PJI and Aseptic combined; C/O>4464 pg/mL, Sensitivity 0.95, Specificity 1.0.

FIG. 2A compares OA to separate disease states. FIG. 2B compares OA to MOM, MOP, PJI and Aseptic combined; C/O>4464 pg/mL, Sensitivity 1.0, Specificity 0.96.

FIG. 2A compares OA and disease states. FIG. 1B compares OA to MOM, MOP, PJI and Aseptic combined; C/O<150.1, Sensitivity 1.0, Specificity 0.96.

FIG. 5A illustrates IL-8 with C/O<1000 (RA alone and a C/O<400 for all. FIG. 5B illustrates IL-6 with a C/O<2,000 pg/mL. FIG. 5C illustrates CRP with C/O<3 mg/dL. FIG. 5D illustrates PDGF with C/O<1,000 pg/mL. FIG. 5E illustrates MMP-9 with C/O<1,000 pg/mL. FIG. 5F illustrates MMP-3 with C/O<3×10$^6$ pg/mL. FIG. 5G illustrates OPG with C/O>4,000 pg/mL. FIG. 5H illustrates OPN in with C/O>10,000 pg/mL. FIG. 5I illustrates COMP with C/O>3,000 ng/mL.

FIG. 6A illustrates COMP and IL-8 with COMP C/O>1600 ng/mL; IL-8 C/O<600 pg/mL; Sensitivity 90.7; Specificity 98.0. FIG. 6B illustrates COMP and CRP with COMP C/O>1600 ng/mL; CRP C/O<2.55 mg/dL; Sensitivity 88.9; Specificity 96.0. FIG. 5C illustrates COMP and MMP-9 with COMP C/O>1600 ng/mL; MMP-9 C/O<9000 pg/mL; Sensitivity 87.0; Specificity 97.9. FIG. 6D illustrates COMP and PDGF with COMP C/O>1600 ng/mL; PDGF C/O<87 pg/mL; Sensitivity 88.9; Specificity 98.5.

FIG. 7A illustrates MMP-9. FIG. 7B illustrates IL-8. FIG. 7C illustrates COMP.

FIG. 8A illustrates IL-6; FIG. 8B illustrates IL-8. FIG. 8C illustrates PDGF; FIG. 8D illustrates RANTES. FIG. 8E illustrates sTNFRII. FIG. 8F illustrates sVEGFR2.

FIG. 10A illustrates a plot of CRTAC1. FIG. 10B illustrates a plot of CLEC3B. FIG. 10C illustrates a bar graph of CRTAC1.

FIG. 11A illustrates Lumican. FIG. 11B illustrates Galectin 3BP. FIG. 11C illustrates Afamin.

FIG. 12A illustrates MMP-1. FIG. 12B illustrates MMP-3. FIG. 12C illustrates MMP-9. FIG. 12D illustrates MMP-12. FIG. 12E illustrates MMP-13. FIG. 12F illustrates TIMP1.

FIG. 13A illustrates IL-8 with C/O<1,000 pg/mL. FIG. 13B illustrates IL-6 with C/O<2,000 pg/mL. FIG. 13C illustrates CRP in synovial fluid samples with C/O<3 mg/dL. FIG. 13D illustrates PDGF with C/O<1,000 pg/mL. FIG. 13E illustrates MMP-9 with C/O<1,000 pg/mL. FIG. 13F illustrates MMP-3 with C/O<3×10$^6$ pg/mL.

FIG. 14A illustrates OPG. FIG. 14B illustrates OPN. FIG. 14C illustrates OC.

FIG. 15A illustrates GPC5. FIG. 15B illustrates MMP-8. FIG. 15C illustrates TNFS9. FIG. 15D illustrates CXCL1.

FIG. 16A illustrates MMP-9 with C/O<2×10$^4$ pg/mL. FIG. 16B illustrates IL-8 with C/O<400 pg/mL. FIG. 16C illustrates COMP with C/O>3,000 ng/mL. Dotted line indicates C/O to discriminate OA from CA.

FIG. 17A illustrates FRZB. FIG. 17B illustrates Glypican 5. FIG. 17C illustrates NKp30. FIG. 17D illustrates Galectin 3. FIG. 17E illustrates Clusterin. FIG. 17F illustrates Leptin. FIG. 17G illustrates FOLR2. FIG. 17H illustrates Albumin.

FIG. 18A illustrates MMP-1. FIG. 18B illustrates MMP-3. FIG. 18C illustrate MMP-9. FIG. 18D illustrates MMP-12. FIG. 18E illustrates MMP-13. FIG. 18F illustrates TIMP1.

FIG. 19A illustrates OPG. FIG. 19B illustrates OPN. FIG. 19C illustrates OC.

FIG. 21A is a plot of individual synovial fluid samples with C/O>3000 ng/mL. FIG. 21B illustrates a receiver operating characteristic (ROC) graph for COMP.

FIG. 22A illustrates C1C2 with C/O>0.06 μg/mL. FIG. 22B illustrates C2C with C/O>100 ng/mL.

FIG. 23A is a plot of IL-8 with C/O<800 pg/mL (OA vs. RA) and C/O<400 pg/mL (OA vs. All). FIG. 23B illustrates a ROC graph for IL-8. FIG. 23C is a plot of CRP with C/O<3.0 mg/dL. FIG. 23D is a ROC graph for CRP. FIG. 23E is a plot of MMP-9 with C/O<10,000 pg/mL (OA vs. RA) and C/O<11,000 pg/mL (OA vs. All). FIG. 23F is a ROC graph for MMP-9.

FIG. 24 illustrates a table of various biomarkers to discriminate OA vs. RA, OA vs. Trauma/Injury, and OA vs. All (RA and T/I). AUC=area under the curve.

FIG. 25A illustrates IL=6 with C/O<3000 pg/mL. FIG. 25B illustrates MMP-3 with C/O<3×10$^6$ pg/mL. FIG. 25C illustrates NGAL with C/O<2×10$^5$ pg/mL.

FIG. 28A illustrates COMP:IL-8 ratio for individual disease states. FIG. 28B illustrates COMP:IL-8 ratio for OA and ratio for RA, NSA and CA samples combined. COMP:IL-8 ratio C/O>3.0.

FIG. 33A illustrates IL-8 with C/O<600 pg/mL. FIG. 33B illustrates IL-8 levels in COMP positive samples, with C/O<700 pg/mL.

FIG. 34A illustrates COMP:IL-8 ratios.

FIG. 34B illustrates and expanded plot of FIG. 34A COMP:IL-8 ratios with C/O>2. Units of COMP and IL-8 are not considered in calculating ratios.

FIG. 37A illustrates sample integrity testing. FIG. 37B illustrates methods of determining the inflammatory or non-inflammatory status of a sample. FIG. 37C illustrates methods of screening samples for biomarkers of OA, according to one aspect COMP is the illustrated biomarker but is representative of individual OA biomarker and any combination of OA biomarkers. FIG. 37D illustrates an example of a method of screening a synovial fluid sample for a biomarker (e.g., COMP) and comparing to a reference level of the biomarker, and/or determining a biomarker ratio. FIG. 37E illustrates methods of determining biomarkers of RA (e.g., anti-CCP and RFs) in a sample. FIG. 37F methods of determining biomarkers of RA (e.g., anti-CCP and RFs). FIG. 37G illustrates methods of determining the presence of biomarkers of CA (e.g., MSU crystals and CPP crystals) in a sample.

FIGS. 42A-42E illustrate tables of results of one or more aspects (OA and RA algorithm data) of a method of evaluating synovial fluid samples.

FIGS. 44A-44D illustrate tables of the results of one or more aspects (RBC and WBC counts) of a method of evaluating synovial fluid samples. FIG. 44A is a table of CA cohorts. FIG. 44B is a table of SA and UNK (disease unknown) cohorts. FIG. 44C is a table of UNK cohorts. FIG. 44D is a table of UNK cohorts.

FIGS. 45A and 45B illustrate tables results of crystal analysis according to one or more aspect of a method of evaluating synovial fluid samples. FIG. 45A is a table of NSA and RA cohorts. FIG. 45B is a table of RA cohorts.

FIGS. 46A-46O illustrate tables results of sample integrity and infection analysis according to one or more aspects of method of evaluating synovial fluid samples. FIG. 46A is a table of a CA cohorts. FIG. 46B is a table of CA cohorts. FIG. 46C is a table of SA cohorts. FIG. 46D is a table of SA and UNK cohorts. FIG. 46E is a table of UNK cohorts. FIG. 46F is a table of UNK and OA cohorts. FIG. 46G is a table of OA cohorts. FIG. 46H is a table of OA and UNK cohorts. FIG. 46I is a table of UNK cohorts. FIG. 46J is a table of UNK and OA cohorts. FIG. 46K is a table of OA cohorts. FIG. 46L is a table of RA cohorts. FIG. 46M is a table of RA cohorts. FIG. 46N is a table of RA cohorts. FIG. 46O is a table of RA cohorts.

FIGS. 47A-47E illustrate examples of reports of the results from the methods shown in FIGS. 37A-37G. FIG. 47A illustrates an example report for a synovial fluid sample COMP/IL-8 ratio (+) (>4.3 ng/pg). FIG. 47B illustrates an example report for a synovial fluid sample having elevated WBCs and PMN %. FIG. 47C illustrates an example report for a synovial fluid sample having an elevated COMP and elevated IL-8. FIG. 47D illustrates an example report for a synovial fluid sample having an elevated COMP and elevated IL-8 according to another aspect. FIG. 47E illustrates an example report for a synovial fluid sample having elevated COMP:IL-8 (≥4.3 ng/pg).

FIGS. 48A-48E illustrate tables of screening results for biomarkers. FIG. 48A is screening results OA samples. FIG. 48B is a continuation of the table of FIG. 48A. FIG. 48C is a table of screening results for RA samples. FIG. 48D is a table of screening results for T/I samples. FIG. 48E is a continuation of the table of FIG. 48D.

FIG. 49 illustrates a table of ROC analysis of various biomarkers that can discriminate OA from RA, T/I, or RA and T/I combined. AUC=area under the curve.

FIGS. 50A-50G illustrate tables of various biomarkers in the primary screenings of pooled synovial fluid samples from OA, RA, T/I, Aseptic, and PJI. FIG. 50A is screening results for various cytokine/chemokine biomarkers. FIG. 50B is screening results for various cytokine/chemokine biomarkers. FIG. 50C is screening results for cytokine/chemokine biomarkers. FIG. 50D is screening results for cytokine/chemokines and soluble cytokine/chemokine receptor biomarkers. FIG. 50E is screening results for soluble cytokine/chemokine biomarkers and matrix metalloproteinases. FIG. 50F is screening results for matrix metalloproteinases, inhibitors of MMPs and bone metabolism biomarkers. FIG. 50G is screening results for bone metabolism biomarkers, MMP-9 complexes with other biomarkers, and COMP. OR=out of range; *=extrapolated below low standard; ND=not done.

DETAILED DESCRIPTION

Figure 1A:
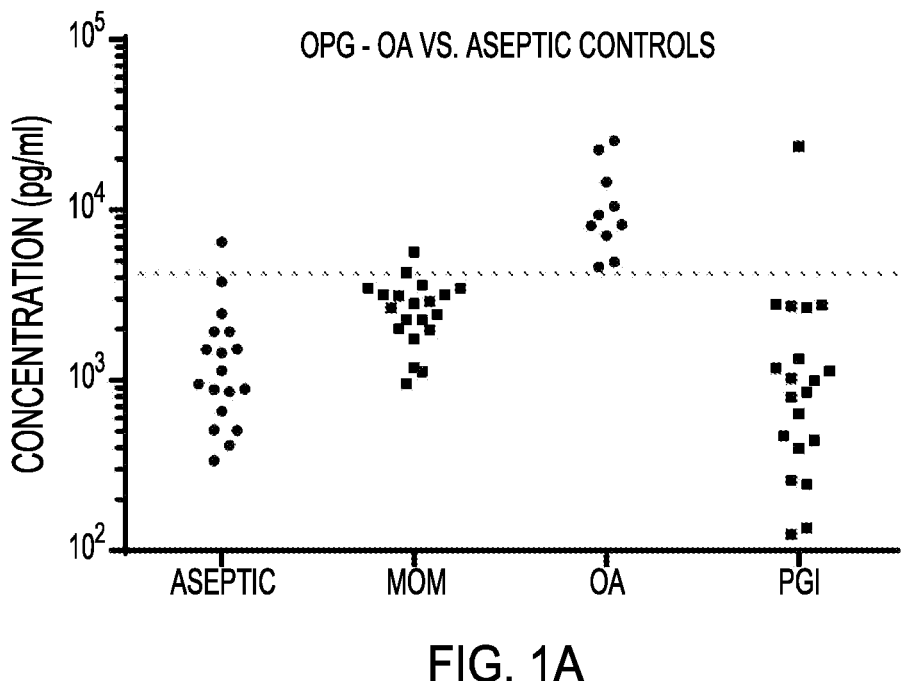
FIGS. 1A and 1B illustrate plots biomarker (OPG) levels in synovial fluid samples.
Figure 1B:
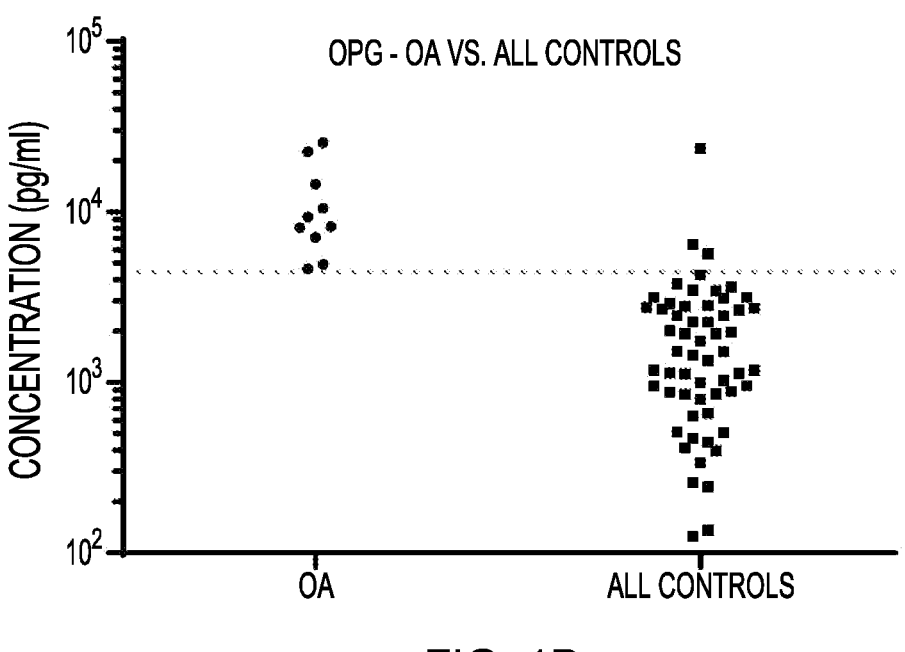
Figure 2A:
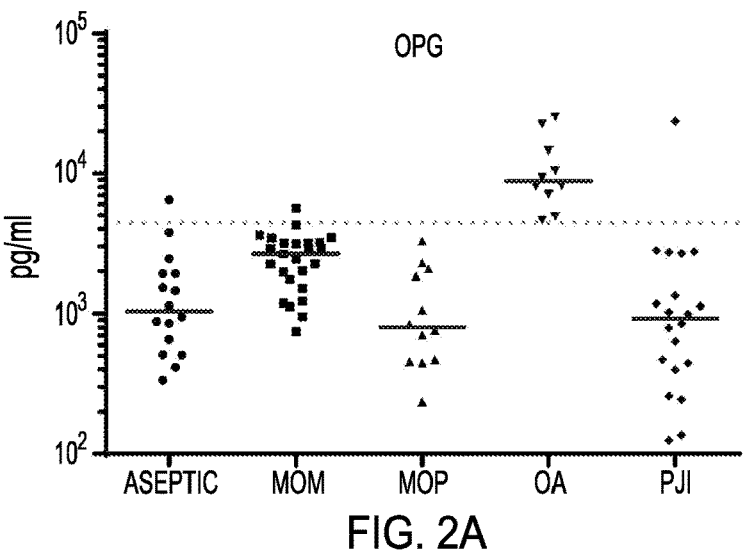
FIGS. 2A and 2B illustrate plots of the biomarker (OPG) levels in synovial fluid samples.
Figure 2B:
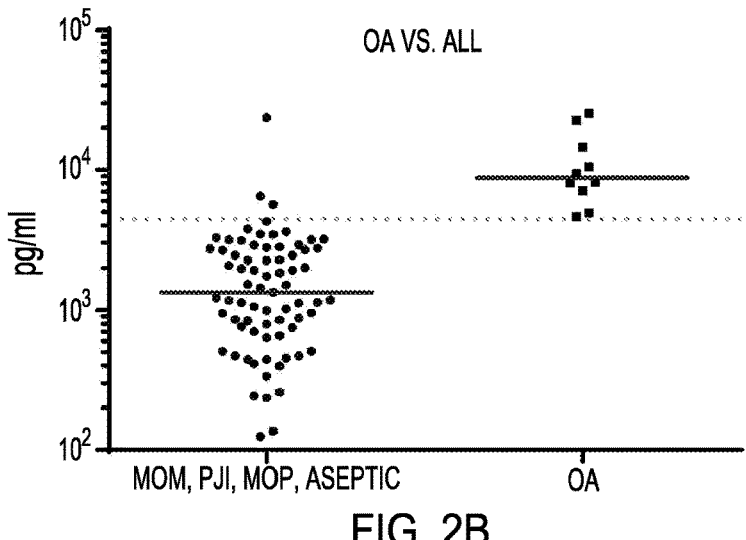

Osteoarthritis (OA) is prevalent and results in a significant socio-economic burden. Osteoarthritis is a progressive degenerative disease characterized by progressive destruction and loss of articular cartilage, changes to underlying bone and formation of new bone leading to pain and limitation or ultimately loss of function. Osteoarthritis is a whole joint disease affecting the subchondral bone, synovium, meniscus, ligaments, and periarticular muscles and nerves, in addition to the cartilage. Common signs and symptoms of knee OA include inflammation, swelling, deformity, tenderness, crepitus (joint cracking or popping), and pain. Osteoarthritis occurs in stages. Once the disease has progressed to more severe stages the only recourse is to remove the damaged joint and replace it with an artificial joint. Diagnosis of OA in earlier stages of the disease would enable treatment, e.g., with hyaluronic acid, autologous protein solution, platelet-rich plasma, stem cells, or disease modifying drugs, before further or irreparable damage is done to the joint.

Knee OA is primarily diagnosed based on clinical signs and symptoms. Radiographs can be used to confirm a diagnosis of OA but is only used in late stage of disease. Laboratory testing can improve the specificity of diagnosis, although blood testing is generally not considered to be useful in diagnosing knee OA and synovial fluid analysis is infrequently used to rule out other conditions in a differential diagnosis.

TABLE 1

Diagnosis of Knee Osteoarthritis

| Clinical Criteria | Laboratory Criteria | Radiography |
|---|---|---|
| Age > 50 years | Erythrocyte sedimentation < 40 mm/hr | Presence of osteophytes |
| Bony enlargement | Rheumatoid factor < 1:40 | |
| Bony tenderness | Synovial fluid: clear, viscous WBCs < $2 \times 10^9$/L | |
| Crepitus | | |
| No palpable warmth | | |
| Stiffness for < 30 minutes | | |

TABLE 2

Diagnostic Accuracy of Knee Osteoarthritis

| Criteria | Sensitivity | Specificity |
|---|---|---|
| Knee pain plus at least three clinical criteria | 95% | 69% |
| Knee pain plus at least five clinical criterial or laboratory criteria | 92% | 75% |
| Knee pain plus at least five clinical criterial or laboratory criteria, plus osteophytes present | 91% | 86% |

Film radiography remains the gold standard for assessment of OA, with key features including joint space narrowing and osteophytes. The Kellgren-Lawrence classification or grading scheme is the most common tool used to classify the severity of OA. This subjective score of 0 to 4, as shown in Table 3, is assigned based on the examination of the radiograph by a trained physician. Although research has shown that patients with more severe evidence of OA on X-ray are more likely to have worse clinical scores, there is evidence of a poor correlation of x-ray evidence of OA with clinical symptoms.

TABLE 3

Kellgren-Lawrence (KL) Classification Scale of Osteoarthritis

| Grade | Severity | Description |
|---|---|---|
| 0 | Normal | No features |
| 1 | Doubtful | Doubtful narrowing of joint space and possible osteophytes |
| 2 | Mild | Definite osteophytes, definite narrowing of joint |
| 3 | Moderate | Moderate multiple osteophytes, definite narrowing of joint space, some sclerosis and possibly deformity of bone contour |
| 4 | Severe | Large osteophytes, marked narrowing of joint space, severe Kr and definite deformity of bone contour. |

Film radiography does not directly measure changes in cartilage, is limited to late stages of OA, and evaluation of film radiographs can be subjective. Disease rating or classification systems, e.g., the Kellgren-Lawrence (KL) classification, can also be subjective thereby limiting the utility of such rating or classification systems. Current OA detection and classification or staging methods also do not allow for early detection and intervention in the disease process.

A simplified approach to evaluating a patient with unspecified knee pain or inflammation is: 1) the physician first determines whether the pain is associated with an acute traumatic event; 2) if an acute traumatic event is not identified, the physician determines whether an effusion is present; 3) in cases where an effusion is present, the physician then attempts to discern whether the pain increases with physical activity or is not related to activity; 4) the patient is asked to point with one finger to the precise location of the pain to help inform the differential diagnosis and inform the potential utility of imaging. Occasionally, it may be unclear whether the pain increases with physical activity or is independent of activity level, particularly in the elderly, less physically active population. In other cases, the clinical signs are not well-aligned with the symptoms described by the patient. Also, small effusions (5 to 10 mL) can be clinically significant but difficult to detect by physical examination alone, particularly in obese or muscular patients, and so the presence or absence of an effusion may be unclear when musculoskeletal ultrasound is unavailable. In these circumstances, a differential diagnosis including, but not limited to, osteoarthritis, rheumatoid arthritis, septic arthritis, and crystalline arthritis may be necessary.

The high prevalence of OA makes it an obvious leading hypothesis for causes of unspecified knee pain, particularly when paired with an atypical clinical presentation of an alternative hypothesis and/or x-ray evidence of joint space narrowing and osteophytes. Under these circumstances, a patient may be misdiagnosed as having OA when they do not actually have the disease. Alternatively, a patient may be diagnosed with and treated for primary OA when, in fact, the OA is either secondary to another type of arthritis or OA is the primary disease but another type of arthritis is also affecting the joint and should be treated. Rheumatoid arthritis, crystalline arthritis (presence of monosodium urate crystals and/or calcium pyrophosphate dihydrate crystals), injury/trauma, and/or septic arthritis (joint infection) can contribute to an inaccurate or incomplete diagnosis of knee pain/inflammation as being due to OA.

Rheumatoid arthritis (RA) is the most common inflammatory arthropathy. Published data indicates a prevalence of secondary OA in 71% of patients with rheumatoid arthritis (RA). Notably, to conclusively determine that an OA diagnosis is secondary to RA, the RA diagnosis must have been previously confirmed by presence of anti-cyclic citrullinated peptide (anti-CCP) and/or rheumatoid factor (RF). Secondary OA has been diagnosed predominantly (68.6%) in patients that are seropositive for anti-CPP. The prevalence of seronegative (anti-CCP and RF) RA at initial presentation is as high as 50%. In cases of seronegative RA or early RA prior to seropositive (anti-CCP and RF) test results, it is possible that OA secondary to undiagnosed RA could be misdiagnosed and treated as primary OA, particularly when the symptoms and clinical presentation are atypical of the symmetric, inflammatory, peripheral polyarthritis generally observed in RA patients. One study found that one fifth of the patients diagnosed with RA had been misdiagnosed, and nearly two thirds of these misdiagnosed patients had OA. These misdiagnosed OA patients had been treated with disease modifying antirheumatic drugs, which has substantial clinical health and economic implications.

Gout is a crystal-induced arthritis caused by deposition of the monosodium uric acid (MSU) crystal related to long standing hyperuricemia. It is a common inflammatory arthritis affecting around 5% of the middle-aged and elderly population worldwide. Published data indicates a possible link between gout and OA pathogenesis. Acute attacks of gout at individual joints has been associated with the presence of clinically assessed OA, and the knee joint was identified as a joint where a highly significant association was observed. It is unknown whether OA causes a predisposition to localized deposition of monosodium urate (MSU) crystals or if acute attacks of gout and increased inflammatory mediators in the synovial tissues trigger the pathogenesis of OA. In addition to the known association between MSU crystal deposition and osteoarthritis, where both conditions exist and must be treated, the ability to differentiate between an acute attack of gout and an inflammatory episode of osteoarthritis is necessary to inform treatment decisions. The inflammatory properties which propagate an inflammatory episode of OA may be indicative of an underlying inflammatory arthritis that has not yet been diagnosed.

Calcium pyrophosphate dihydrate (CPP or CPPD) crystal deposition disease is the most common cause of articular cartilage chondrocalcinosis (CC). The classification of CPPD includes asymptomatic CPPD, OA with CPPD (formerly known as pseudo-OA), acute CPP crystal arthritis (formerly known as pseudogout), and chronic CPP crystal inflammatory arthritis (formerly known as pseudo-RA). CPPD has been reported to be the fourth most prevalent rheumatic condition after OA, rheumatoid arthritis, and gout. There is a clear association between OA and CPPD, with studies demonstrating calcium crystals in the synovial fluid of 30-60% of unselected OA patients. Unfortunately, the causal relationship between OA and CPPD, the impact of calcium crystal deposition on OA disease progression and treatment effects, and the role of calcium crystals in the synovial inflammation often observed in OA joints remain unanswered. It has been noted that grade of synovial fluid effusion is increased in patients with CPPD with OA versus OA alone, indicating a more inflammatory state for joints affected by both conditions. This difference in the inflammatory status may very well impact the natural progression rate of the disease and effectiveness of an OA treatment, and so the identification of calcium pyrophosphate crystals in an OA joint is important when making treatment decisions.

The incidence of septic arthritis (SA), also known as infectious arthritis, varies from 2 to 10 per 100,000 in the general population to 30-70 per 100,000 in patients with rheumatoid arthritis and patients with joint prostheses. Clinical signs of SA include joint pain, swelling, warmth, and restricted movement. Concomitant septic arthritis in osteoarthritis, rheumatoid arthritis, and crystalline arthritis cases is uncommon but is not rare. A history of rheumatoid arthritis and previous intraarticular corticosteroid injections are both risk factors for septic arthritis. Furthermore, an examination of synovial fluid aspirates found concomitant infection in 5% of samples with crystalline arthritis. Early diagnosis of septic arthritis, as well as prompt and effective treatment, is essential to avoid irreversible joint destruction or even death. The emergent nature of native septic arthritis gives rise to medical guidelines recommending arthrocentesis with synovial fluid analysis in all patients who have a joint effusion or signs suggestive of inflammation within the joint, without a known cause.

The biomarkers, compositions, algorithm, and methods disclosed herein provide a valid differential diagnosis of OA, including osteoarthritis, rheumatoid arthritis, crystalline arthritis (gout and pseudogout), and native septic arthritis, aid in the early detection of knee OA following traumatic joint/ligament injury, determine OA progression prognosis, and, ultimately, can aid in optimizing the treatment pathway for OA patients by predicting the likelihood of treatment success.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used in this specification and the appended claims, the singular forms "a," "an," and "the" include plural references unless the context clearly dictates otherwise. By way of example, "an element" means one element or more than one element. Similarly, references to "the method" includes one or more methods, and/or steps of the type described herein and/or which will become apparent to those persons skilled in the art upon reading this disclosure and so forth. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" means acceptable variations within 20%, of the stated value, such as within 19%, 18%, 17%, 16%, 15%, 14%, 13%, 12%, 11%, 10%, 9%, 8%, 7%, 6%, 5%, 4%, 3%, 2% or 1% of the stated value.

As used herein, the term "antibody" refers to a protein consisting of one or more polypeptides, substantially encoded by immunoglobulin genes or fragments of immunoglobulin genes, that specifically binds to an antigen. Antibody encompasses polyclonal antibodies, monoclonal antibodies, and fragments thereof, as well as molecules engineered from immunoglobulin gene sequences. Antibodies include intact immunoglobulins as well as antigen-binding fragments thereof, which may be produced by digestion with various peptidases, or synthesized de novo either chemically or using recombinant DNA expression technology. Such fragments include, for example, F(ab)2 dimers and Fab monomers. Useful antibodies include single chain antibodies (antibodies that exist as a single polypeptide chain), e.g., single chain Fv antibodies (scFv) in which a VH and a VL chain are joined together (directly or through a peptide linker) to form a continuous polypeptide. Antibodies also include variants, chimeric antibodies and humanized antibodies.

The terms "biomarker" and "marker" can be used interchangeably herein and refer to generally refer to a protein or polypeptide, nucleic acid molecule, clinical indicator, physiological indicator, a blood cell count (red blood cell (RBC), white blood cell (WBC), polymorphonuclear cell count (PMN)), or other evidence of a physical or physiological condition or state of a subject that is associated with a disease and that can be used as a target for analyzing samples obtained from subjects. Biomarker can encompass proteins or polypeptides themselves as well as antibodies against same that may be present in a test sample. Proteins or polypeptides used as a marker include any variants and fragments thereof and, immunologically detectable fragments. Proteins or fragments thereof can also occur as part of a complex. Proteins or polypeptides used as biomarkers according to the present disclosure also include such complexes. The terms "biomarker" and "marker" also encompass nucleic acid molecules comprising a nucleotide sequence that codes for a marker protein, and polynucleotides that can hybridize under stringent conditions with a part of such nucleic acid molecules. The terms "biomarker" and "marker" also include "biomarker(s) of osteoarthritis," "OA biomarker," and "biomarker of OA" as defined herein.

As used herein a "biomarker(s) of osteoarthritis," an "OA biomarker(s)" and "biomarker(s) of OA" can be used interchangeably and refer to a protein or polypeptide (used interchangeably and together referred to as proteins), antibodies against such proteins and any fragment thereof, and any nucleic acid molecule comprising a nucleotide sequence that codes for an OA biomarker protein. Biomarkers of OA include the following identified by UniProtKB Accession No. (*Homo sapien*): P49747 cartilage oligomeric matrix protein (COMP); P10145 interleukin-8 (IL-8); P41159 leptin (Leptin); P10451 osteopontin (OPN); 000300 osteoprotegerin (OPG); P02818 osteocalcin (OC); P09038 fibroblast growth factor-2 (FGF-2); P01033 tissue inhibitor of metalloproteinase 1 (TIMP1); P16035 tissue inhibitor of metalloproteinase 2 (TIMP2); P35625 tissue inhibitor of metalloproteinase 3 (TIMP3); Q99727 tissue inhibitor of metalloproteinase 4 (TIMP4); P05452 tetranectin (Tetranectin; CLEC3B); Q9NQ79 cartilage acidic protein 1 (CRTAC1); P43652 afamin (Afamin); P51884 lumican (Lumican); Q08380 galectin 3 binding protein (Galectin 3BP); P59665 alpha defensin (AD); P08246 neutrophil elastase (HNE); P05231 interleukin-6 (IL-6); P0274 C-reactive protein (CRP); P14780 matrix metalloproteinase-9 (MMP-9); P08254 matrix metalloproteinase-3 (MMP-3); P80188 neutrophil gelatinase-associated lipocaln (NGAL); P04085 platelet-derived growth factor-AA (PDGF-A; PDGF-AA); P01127 platelet-derived growth factor-B (PDGF-B; PDDGF-BB); platelet-derived growth factor-AB (PDGF-AB); Q9Y653 adhesion G-protein coupled receptor G1 (ADGRG1); P09341 growth regulated alpha protein (GRO; CXCL1); P12104 fatty acid-binding protein (FABP2); Q96LA6 Fc receptor-like protein 1 (FCRL1); Q6IA17 single Ig IL-1-related receptor (SIGIRR); P78333 glypican-5 (GPC5); P22894 neutrophil collagenase (MMP-8); P41273 tumor necrosis factor super family member 9 (TNFSF9); P01019 angiotensinogen (AGT); P02768 albumin (ALB); 075888 tumor necrosis factor ligand superfamily member 13 (APRIL); Q9Y275 tumor necrosis factor ligand superfamily member 13B (BAFF); Q13145 BMP and activin membrane-bound inhibitor homolog (BAMBI); O00626 C-C motif chemokine 22 (CCL22); Q99062 granulocyte colony-stimulating factor receptor (CSF3R); Q16663 C-C motif chemokine 15 (CCL15); P42081 T-lymphocyte activation antigen CD86 (CD86); Q9NPF0 CD320 antigen (CD320); P10909 clusterin (Clusterin); Q92765 secreted frizzled-related protein 3 (FRZB); P19883 follistatin (FST); P12034 fibroblast growth factor 5 (FGF5); Q15768 ephrin-B3 (EFNB3); P14207 folate receptor beta (FOLR2); P29460 interleukin-12p (IL-12p); Q14005 pro-interleukin-16 (IL-16); Q8WWZ1 interleukin-1 family member 10 (IL1F10); Q9UBHO interleukin-36 receptor antagonist protein (IL36RN); Q6GTX8 leukocyte-associated immunoglobulin-like receptor 1 (LAIR1); P11279 lysosome-associated membrane glycoprotein 1 (LAMP1); 095944 natural cytotoxicity triggering receptor 2 (NCR2); Q9HDB5 neurexin-3-beta (NRXN3); Q9NZQ7 programmed cell death 1 ligand 1

(PDCD1); P26022 pentraxin-related protein (PTX3); P01374 tumor necrosis factor superfamily 1 (TNFSF1B); P48307 tissue factor pathway inhibitor 2 (TFPI2); A0A024R7F8 tartrate-resistant acid phosphatase 5a (TRACP5a); P35442 thrombospondin-2 (THBS2); P40189 soluble glycoprotein 130 (sgp130); Q15109 soluble receptor for advanced glycation end-product specific receptor (sRAGE); 014788 tumor necrosis factor ligand superfamily 11 (RANKL); Q01718 adrenocorticotropic hormone (ATCH); 094907 Dickkopf-related protein 1 (DKK1); P51671 eotaxin; P01133 epidermal growth factor (EGF); Q9GZV9 fibroblast growth factor 23 (FGF23); P36888 FMS-like tyrosine kinase 3 ligand (Flt-3L); P78423 fractalkine (Fractalkine); P01215 glyprotein hormones, alpha chain (CGA); P09919 granulocyte colony stimulating factor (G-CSF); P04141 granulocyte macrophage colony stimulating factor (GM-CSF); P02778 interferon-γ inducible protein-10 (IP-10, CXCL10); P01308 insulin (Insulin); P01579 interferon-γ (IFN-γ); P01563 interferon-α2 (IFN-α2); P01583 interleukin-1α (IL-1α); P01584 interleukin-1β (IL-1β); P60568 interleukin-2 (IL-2); P08700 interleukin-3 (IL-3); P05112 interleukin-4 (IL-4); P05113 interleukin-5 (IL-5); P13232 interleukin-7 (IL-7); P15248 interleukin-9 (IL-9); P22301 interleukin-10 (IL-10); P29460 interleukin-12 P40 (IL-12P40); P29459 interleukin-12 P70 (IL-12P70); P35225 interleukin-13 (IL-13); P40933 interleukin-15 (IL-15); Q16552 interleukin-17A (IL-17A); P18510 interleukin-1 receptor antagonist (IL-1RA); P26927 hepatocyte growth factor-like protein (MST1); P03956 interstitial collagenase (MMP-1); P08253 72 kDa type IV collagenase (MMP-2); Q9NPA2 matrix metalloproteinase-6 (MMP-6); P09237 matrilysin (MMP-7); P09238 stromelysin-2 (MMP-10); P39900 macrophage metalloelastase (MMP-12); P45452 collagenase 3 (MMP-13); P13500 C-C motif chemokine 2 (MCP-1); P10147 C-C motif chemokine 3 (MIP-la); P13236 C-C motif chemokine 4 (MIP-1β); P13501 C-C motif chemokine 5 (RANTES); P80098 C-C motif chemokine 7 (MCP-3); 075078 Disintegrin and metalloproteinase domain-containing protein 11 (MDC); 014931 natural cytotoxicity triggering receptor 3 (NKp30). Q03431 parathyroid hormone (PTH); Q9BQB4 sclerostin (SOST); P28908 soluble tumor necrosis factor receptor superfamily member 8 (sCD30); P29965 soluble CD40 ligand (sCD40L); P00533 soluble epidermal growth factor receptor (sEGFR); P14778 soluble interleukin-1 receptor I (sIL-1RI); P27930 soluble interleukin-1 receptor II (sIL-1RII); P24394 soluble interleukin-4 receptor alpha (sIL-4R); P08887 soluble interleukin-6 receptor alpha (sIL-6R); P19438 soluble tumor necrosis factor receptor superfamily member 1A (sTNF-RI); P20333 soluble tumor necrosis factor receptor superfamily member 1B (sTNF-RII); P17948 soluble vascular endothelial growth factor receptor 1 (sVEGFR1); P35968 soluble vascular endothelial growth factor receptor 2 (sVEGFR2); P35916 soluble vascular endothelial growth factor receptor 3 (sVEGFR3); P0113 transforming growth factor-α (TGF-α); P01375 tumor necrosis factor-α (TNF-α); P01374 tumor necrosis factor-β (TNF-β); P01374 vascular endothelial growth factor (VEGF); complexes of MMP-9/NGAL; complexes of MMP-9/TIMP1; rheumatoid factors (RFs); anti-cyclic citrullinated peptide (anti-CCP); monosodium urate crystals (MSU); and calcium pyrophosphate dihydrate crystals (CPP). For purposes of this disclosure, PDGF-AA, PDGF-BB and PDGF-AB can be individually referred to as PDGF or collectively referred to as PDGF and, unless otherwise specifically provided, when PDGF is used the term refers to and includes PDGF-AA, PDGF-BB and PDGF-AB.

In some instances, the names and abbreviations of biomarkers of osteoarthritis can be referred to herein using a name or abbreviation that is not the official name and/or abbreviation in UniProtKB; in some cases the name and/or abbreviation used herein is identified in UniProtKB as an alternative name or abbreviation for the biomarker. The differential expression in a synovial fluid sample of one or a combination of the foregoing biomarkers of osteoarthritis can be useful in characterizing a subject as having or being at risk of developing osteoarthritis, for determining the stage of osteoarthritis, for determining the prognosis of the subject, for assessing therapeutic benefit or efficacy, or for selecting a treatment regimen.

As used herein, the terms "assessing", "assaying", "measuring", "evaluating", and "detecting" refer to both quantitative and qualitative determinations, and as such, can be used interchangeably. Where a quantitative meaning is intended, the terms assessing, assaying, measuring and detecting can be used together with terms such as "an amount" of an analyte or "a level" of an analyte or "a concentration" of an analyte, and the like.

As used herein "determining" refers to learning or discerning information, e.g., "determining" a level of a biomarker can include learning qualitative or quantitative information related to a biomarker in a subject or a reference. Determining can include learning such information from a viewing a display, a slide, a plate, a gel, or other device indicating quantitative and/or qualitative information regarding a biomarker, or viewing a report (hard copy/paper or electronic format) disclosing the qualitative and/or quantitative information regarding a biomarker, such as from the result of an assay or other procedure to detect the biomarker. "Determining" when referencing a biomarker can also mean evaluating, assessing, measuring, assaying, or detecting, e.g., a biomarker presence or biomarker level.

As used herein the term "expression" refers to the conversion of the DNA sequence information into messenger RNA (mRNA) or mRNA sequence information into protein or polypeptide. Expression can be detected by measuring the levels of mRNA, mRNA fragments, protein or polypeptide, or protein or polypeptide fragments (proteins and polypeptides are referred to herein interchangeably). As used herein the terms "differential expression" or "differentially expressed" mean a biomarker is expressed in a disease state at a level that is greater than or at a level that is less than the level of expression in reference. For example, a protein can be differentially expressed in a non-inflammatory arthropathy, such as osteoarthritis, relative to expression of the protein in an inflammatory arthropathy, such as rheumatoid arthritis, septic arthritis, crystalline arthritis, or trauma/injury. Differential expression an also be referred to herein as "differentially increased" when the biomarker is expressed at a higher level in a sample relative to a reference, or "differentially decreased" when the biomarker is expressed at a lower level relative to a reference. A biomarker can be differentially expressed by at least 10% or more, for example, 20%, 30%, 40%, or 50%, 60%, 70%, 80%, 90% or more higher or lower than a reference and any and all whole or partial increments therebetween, and/or 1.1 fold, 1.2 fold, 1.3 fold, 1.4 fold, 1.5 fold, 1.6 fold, 1.7 fold, 1.8 fold, 1.9 fold, 2.0 fold or more different than the reference, e.g., higher or lower, and any and all whole or partial increments therebetween.

As used herein the terms "normal" and "healthy" can be used interchangeably to refer to an individual or individuals who do not display the clinical symptoms of osteoarthritis, rheumatoid arthritis, crystalline arthritis, septic arthritis or joint trauma/injury.

As used herein "inflammatory arthropathy" means any one or more of: rheumatoid arthritis (RA); crystalline arthritis e.g., gout (MSU crystals) or pseudogout (CPPD crystals), collectively referred to as CA; native septic arthritis (NSA) or periprosthetic joint infection (PJI), collectively NSA and PJI can be referred to as septic arthritis (SA); and joint pain or inflammation and arthritis symptoms related to trauma or injury (T/I) to a joint.

As used herein a "reference" or "control" refers to a source or standard for comparison. A reference can be blood, urine, plasma, serum, synovial fluid, or other bodily fluid or tissue obtained from a healthy individual or obtained from an individual that has known isolated, idiopathic osteoarthritis (i.e., the reference does not have any other arthropathy), or a reference can be from an individual that has a joint disease or disorder other than osteoarthritis (e.g., RA, CA, septic arthritis, trauma/injury to the joint, or other inflammatory arthropathy). For purposes of disease staging, a reference can also mean an individual that has a confirmed or known to have a particular stage of a disease (e.g., stage 1, 2, 3, or 4 of isolated, idiopathic osteoarthritis). For purposes of monitoring disease progression in a subject and/or monitoring response to a therapeutic treatment in the subject, a reference can also mean a bodily fluid or tissue obtained from the subject at an earlier time, e.g., prior to therapeutic treatment or at an earlier stage of a disease in the subject. For use in conjunction with the term "reference" or "control," an "individual" can mean the reference fluid or tissue is obtained from one person or more than one person. A "reference level", e.g., of a biomarker, can be the level present in a reference body fluid or tissue obtained from the reference individual(s). A difference in the level of a biomarker (or differential expression of a biomarker) in sample from a subject does not need to be a statistically significant difference in the level or in the expression of the biomarker relative to the reference to be used in the compositions, systems, methods and algorithms disclosed herein. A reference level can include a cutoff (C/O) value or level that discriminates between one disease state and another disease state or that discriminates between a normal reference and a disease state.

As used herein, "specifically binds" refers to a compound (e.g., antibody) that recognizes and binds a molecule (e.g., polypeptide), but which does not substantially recognize and bind other molecules in a sample, e.g., a synovial fluid sample.

As used herein, the terms "subject" and "subjects" refer to any mammal of interest from which a bodily fluid or tissue sample has been extracted or which is the being evaluated and/or treated.

As used herein the terms "treat," "treating," and "treatment," mean therapeutic or preventative measures such as those described herein. The methods of "treatment" employ administration to a patient of a treatment regimen in order to prevent, cure, delay, reduce the severity of, or ameliorate one or more symptoms of the disease or disorder or recurring disease or disorder. Treatments for osteoarthritis can include, without limitation, one or more of: lifestyle modifications (e.g., weight-loss, exercise to increase muscle strength at the affected joints); physical therapy; analgesics, e.g., aspirin, acetaminophen, opioids; oral or injectable non-steroidal anti-inflammatory drugs (NSAIDs), e.g., indomethacin, ibuprofen, naproxen, ketoprofen, piroxicam or diclofenac, celecoxib, rofecoxib, valdecoxib, corticosteroids, disease-modifying osteoarthritis drugs (DMODs), viscosupplementation e.g., hyaluronic acid or hyaluronan (HA), platelet-rich plasma (PRP), cartilage transplant, and total or partial joint replacement surgery. Treatments for RA can include, without limitation: physical and/or occupational therapy for affected joints; nonsteroidal anti-inflammatory drugs (NSAIDs); corticosteroid medications (oral or injectable) e.g., dexamethasone, betamethasone, prednisone; disease-modifying antirheumatic drugs (DMARDs), e.g., methotrexate, leflunomide, hydroxychloroquine and sulfasalazine; biologic response modifying drugs, e.g., abatacept, adalimumab, anakinra, baricitinib, certolizumab, etanercept, golimumab, infliximab, rituximab, sarilumab, tocilizumab and tofacitinib; and surgery to repair damaged joints, e.g., synovectomy to remove the inflamed lining of the joint (synovium), tendon repair, joint fusion and/or joint replacement. Treatments for monosodium urate crystalline arthritis (gout) can include, without limitation: dietary modifications (gout); oral or injectable NSAIDs; colchicine; corticoids; xanthene oxidase inhibitors (XOIs), including allopurinol and febuxostat; uricosuric agents, e.g., probenecid, fenofibrate, losartan, azapropazone, and calcium channel blockers; pegloticase, rasburicase, lesinurad. Treatments for calcium pyrophosphate dihydrate disease (CPPD, pseudogout) can include, without limitation; NSAIDs; corticosteroid (oral or injection); colchicine; phosphocitrate; polyphosphate; magnesium carbonate; viscosupplementation (e.g., HA); hydroxychloroquine; methotrexate; biologic response modifying drugs, e.g., as listed above: synovectomy; surgery. Treatments for septic arthritis (native septic arthritis and periprosthetic joint infection) can include, without limitation: analgesics; NSAIDs; antibiotics, antifungals and antiviral drugs, as appropriate to the nature of the infectious agent. Treatments for trauma/injury can include, without limitation; ice and/or heat; analgesics; NSAIDs; corticosteroids (oral or injection); viscosupplementation (e.g., hyaluronon); PRP: physical therapy, exercise; and surgery.

As used herein the term "comprising," "having" and "including" and the like are used in reference to compositions, systems, methods, and algorithms, and respective component(s) and feature(s) thereof, that are present in a given aspect, yet open to the inclusion of one more or more unspecified elements. The term "including" is used herein to mean, and is used interchangeably with, the phrase "including but not limited to."

As used herein the term "consisting essentially of" refers to those elements required for a given aspect. The term permits the presence of additional elements that do not materially affect the basic and novel or functional characteristic(s) of that aspect of the invention. The term "consisting of" refers to compositions, systems, methods, algorithms, and respective components thereof as described herein, which are exclusive of any element not recited in that description of the aspect.

Other terms used in the fields of recombinant nucleic acid technology, microbiology, immunology, antibody engineering and molecular and cell biology as used herein will be generally understood by one of ordinary skill in the applicable arts. For example, conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, Molecular Cloning: A Laboratory Manual, 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

Detecting Biomarkers

Provided herein are biomarker expression profiles or expression signatures in which one or more biomarkers of osteoarthritis can be used to evaluate a bodily fluid or tissue sample to detect, diagnose, stage, monitor disease progression, treat, or monitor the treatment of osteoarthritis. A biomarker expression profile can be obtained from assessment of a sample from a subject or a reference. A sample or reference sample of whole blood, blood plasma, serum, urine, saliva, synovial fluid, synovial tissue, cartilage, muscle, tendon, ligament, and/or other bodily fluid or tissue can be used to develop an biomarker expression profile for a subject or a reference. In a one aspect a biomarker expression profile can be obtained from analysis of OA biomarkers in synovial fluid. By analyzing samples of a bodily fluid or tissue obtained from normal individuals (such as a normal reference) and from individuals with isolated, idiopathic OA (e.g., early-stage OA (KL 0, 1, 2), mid-stage OA (KL 2, 3), and late-stage OA (KL 4), the present inventors have developed biomarker profiles (e.g. levels of various combinations of biomarkers) that can discriminate between normal individuals and subjects with OA. Biomarker profiles of the present disclosure can also discriminate between subjects with differing stages of severity of OA (KL 0, 1, 2=early stage; KL 2, 3=mid-stage OA; KL 4=late stage OA) and, thus, can be used to determine the stage of OA disease severity in a subject and/or to monitor OA disease progression in a subject. By analyzing fluid or tissue obtained from a individuals with isolated, idiopathic OA (e.g., KL 1, 2, 3, or 4) and comparing to the biomarker profile and or biomarker level to a reference fluid or tissue from individuals with an inflammatory arthropathy (e.g., RA, CA, septic arthritis, or trauma/injury to a joint) the present inventors have developed OA biomarker expression profiles that can discriminate between subjects having isolated, idiopathic OA, subjects having an inflammatory arthropathy, e.g., RA, CA, septic arthritis, trauma/injury to a joint, and subjects having OA secondary to an inflammatory arthropathy. The biomarkers and biomarker profiles disclosed herein, and the methods, compositions, systems and algorithms using such biomarkers and biomarker profiles can also be used to exclude OA from a differential diagnosis of a biological fluid or tissue sample from a subject experiencing joint pain or joint inflammation.

In one aspect biomarkers can be measured in a fluid or tissue, e.g., synovial fluid from a reference individual or from a subject experiencing joint pain or joint inflammation. In an aspect a biomarker expression profile or biomarker level can be of one or a combination of biomarker polypeptides or proteins (which shall be used herein interchangeably, and the term protein shall include polypeptides). In a preferred aspect, biomarkers can be proteins in a synovial fluid sample from a subject experiencing joint pain or inflammation. In one aspect, the biomarkers comprise proteins that are differentially expressed in osteoarthritis. In an aspect an OA biomarker can be differentially expressed in the varying stages of osteoarthritis. In one aspect biomarkers can be differentially increased in OA, i.e., the level of the OA biomarker is increased relative to a reference, such as normal individual without OA, or an individual with a particular stage of OA, or an individual with an inflammatory arthropathy such as RA, CA, septic arthritis, or trauma/injury to a joint, or a reference from the subject at an earlier time. In other aspects OA biomarkers can be differentially decreased, i.e., decreased level relative to a reference, such as normal individual without OA, an individual with a particular stage of OA, or an individual with an inflammatory arthropathy such as RA, CA, septic arthritis, or trauma/injury to a joint, or a reference from the subject at an earlier time. In one aspect an expression profile of OA biomarkers can comprise at least one OA biomarker that is differentially increased in OA and at least one OA biomarker that is differentially increased in an inflammatory arthropathy. In one aspect an expression profile of OA biomarkers can comprise at least one OA biomarker that is differentially increased in OA and at least one OA biomarker that is differentially decreased in OA or in a particular stage of OA.

In an aspect an expression profile of OA biomarkers can comprise 2, 3, 4, 5, 6, or more OA biomarkers that are each differentially increased in OA relative to a reference. In one aspect an expression profile of OA biomarkers can comprise 2, 3, 4, 5, 6, or more OA biomarkers that are each differentially decreased in OA relative to a reference. In another aspect an expression profile of OA biomarkers can comprise 2, 3, 4, 5, 6, or more biomarkers of OA, some of which are differentially increased in OA (or in a particular stage of OA) and some of which are differentially decreased in OA (or in a particular stage of OA). In another aspect an expression profile of OA biomarkers can comprise 2, 3, 4, 5, 6, or more biomarkers of OA, some of which are differentially increased in OA and some of which are differentially increased in an inflammatory arthropathy. In an aspect an expression profile of OA biomarkers can comprise 2, 3, 4, 5, 6, or more biomarkers of OA, some of which are differentially increased in OA and some of which are differentially decreased in an inflammatory arthropathy.

Osteoarthritis can be detected, diagnosed (including differential diagnosis), staged, monitored, and/or treated by determining the presence and/or level of one or more OA biomarkers in a subject sample. Assessing or detecting the presence and/or level (e.g. a concentration) of expression of any one or a plurality of biomarkers can be performed by any one or any combination of a variety of techniques that are known in the art. Detection methods that can be employed for detection of biomarkers include, without limitation, optical methods, electrochemical methods (voltammetry and amperometry techniques), atomic force microscopy, and radio frequency methods, e.g., multipolar resonance spectroscopy. In one aspect assessing or detecting an OA biomarker can be performed using a combination of known techniques to provide more accurate detection of the biomarker (e.g., biochip in combination with mass spectrometry, immunoassay in combination with mass spectrometry, 2-D DIGE in combination with mass spectrometry, and any other combination of known techniques for detecting and/or assessing a level of a nucleic acid, a polypeptide or protein). Expression of a biomarker can be assessed in vitro or in vivo in a subject or a reference. Known methods and techniques for isolating DNA, RNA and protein, and performing the methods and techniques disclosed herein can be found and described more detail in standard molecular biology reference publications, such as: Ausubel et al., (2003) CURRENT PROTOCOLS IN MOLECULAR BIOLOGY, John Wiley & Sons, New York, N.Y., CURRENT PROTOCOLS IN MOLECULAR BIOLOGY, John Wiley & Sons, Online ISDN: 1934-3647; Sambrook et al. (1989) MOLECULAR CLONING: A LABORATORY MANUAL, Cold Spring Harbor Press, Cold Spring Harbor, N.Y.; PROTOCOLS USED IN MOLECULAR BIOLOGY (eds. Singh, S. K., and Kumar, D., 2020), Benthan Science ISBN: 9789811439292 (available at researchgate.net).

In an aspect a biomarker can be a protein that can be assessed or detected using several known techniques that can be antibody-based. In one aspect the level of one or more biomarkers can be detected and/or measured by immunoassay. Immunoassay can typically utilize an antibody (or other agent that specifically binds the biomarker or interest) to detect the presence or level of a biomarker in a sample. Antibodies can be produced by methods well known in the art, e.g., by immunizing animals with the biomarkers, such as biomarker proteins. Biomarkers can be isolated from samples based on their binding characteristics. Alternatively, if the amino acid sequence of a polypeptide or protein biomarker is known, the polypeptide or protein can be synthesized and used to generate antibodies by methods well known in the art. Further, antibodies are commercially available for biomarkers from many sources (R&D Systems, RayBiotech, EMD Millipore, et.c.). Suitable immunoassay detection methods for use in the methods and systems disclosed herein include, without limitation, Western blot, sandwich immunoassays including enzyme-linked immunosorbent assay (ELISA) and other enzyme immunoassays, fluorescence-based immunoassays, and chemiluminescence. Other forms of immunoassay include magnetic immunoassay, radioimmunoassay, and real-time immunoquantitative PCR (iqPCR).

In one aspect an ELISA can be used to detect and quantify biomarker protein levels. This method can include preparing the antigen (i.e., biomarker protein of interest), coating the wells of a microtiter plate with the antigen, incubating the antigen with an antibody that recognizes the antigen, washing away the unbound antibody, and detecting the antibody-antigen complex. The antibody can generally be conjugated to an enzyme, such as horseradish peroxidase or alkaline phosphatase, which can generate colorimetric, fluorescent, or chemiluminescent products. In another aspect an ELISA can use two antibodies, one of which is specific to the biomarker protein of interest and the other of which recognizes the first antibody and is coupled to an enzyme for detection. In still other aspects the antibody can be coated on the well and a second antibody conjugated to a detectable compound is added to the well following the addition of the antigen to the biomarker protein of interest.

In another aspect an antibody array platform, e.g., Luminex (Luminex Corp., Austin, TX) can be used to detect and quantify biomarker protein levels using multiplexed assays based on a capture bead system in which microsphere beads are color-coded with dyes. Each color-coded bead set is coated with a specific binding reagent such as an antibody specific to a selected biomarker protein, allowing the capture and detection of specific protein analytes from a very small amount of fluid, e.g. a drop of fluid from plasma, serum, urine, cells lysates or synovial fluid. Depending upon the analyte(s) being screened, at least one or several bead sets may be incubated with a sample to capture the analytes. In one aspect lasers can be used to excite the dyes that identify each microsphere bead and any reporter dye captured during the assay. Exemplary multiplex immunoassay platforms that can be used in the present methods, systems and algorithms include the xMAP platform (Qiagen, Inc.).

In an aspect a biomarker protein level can be assessed using a protein microarray or an antibody microarray. In these methods, the proteins or antibodies are covalently attached to the surface of the microarray or biochip. The biomarker protein of interest can be detected by interaction with an antibody, and the antibody/antigen complexes are generally detected through fluorescent tags on the antibody. An exemplary microarray that can be used in the methods, systems and algorithms disclosed herein includes the Quantibody™ platform (RayBiotech, Inc.).

In another aspect biomarker protein levels can be assessed by immunohistochemistry in which a protein is localized in cells of a tissue section by its interaction with a specific antibody. The antigen/antibody complex may be visualized by a variety of methods. One or two antibodies may be used, as described above for ELISA. The detection antibody may be tagged with a fluorophore, or it may be conjugated to an enzyme that catalyzes the production of a detectable product. The labeled complex is typically visualized under a microscope.

In yet another aspect a biomarker protein level can be measured by Western blotting. Western blotting generally comprises preparing protein samples, using gel electrophoresis to separate the denatured proteins by mass, and probing the blot with antibodies specific to the biomarker protein of interest. Detection can be accomplished using two antibodies, the second of which is conjugated to an enzyme for detection or another reporter molecule. Methods used to detect differences in protein levels include colorimetric detection, chemiluminescent detection, fluorescent detection, and radioactive detection.

In one aspect a biomarker protein profile can be assessed by Two-dimensional difference gel electrophoresis (2D-DIGE). 2D-DIGE is a modified form of 2D electrophoresis (2DE) that allows the comparison of two or three protein samples simultaneously on the same gel. The proteins in each sample can be covalently tagged with different colored fluorescent dyes that are designed to have no effect on the relative migration of proteins during electrophoresis. The proteins in the sample are separated in 2 dimensions using electrophoresis (molecular weight in one dimension; isoelectric point (or net charge) in the second dimension). When illuminated with appropriate wavelengths of light, the color contribution and intensity of individual protein spots indicates which sample (disease group) the protein came from. Protein spots of interest are cut from the gel and the identity of the protein is determined by mass spectrometry.

In one aspect the level of biomarkers can be detected by mass spectrometry (MS). Mass spectrometry is a well-known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer and hybrids of these. The method may be performed in an automated (Villanueva, et al., Nature Protocols (2006) 1(2):880-891) or semi-automated format. This can be accomplished, for example with the mass spectrometer operably linked to a liquid chromatography device (LC-MS/MS or LC-MS) or gas chromatography device (GC-MS or GC-MS/MS).

In certain aspects OA biomarkers, e.g., MSU and/or CPP crystals, RBCs, WBCs, can be detected using various forms of microscopy, such as light polarizing microscopy and phase contrast microscopy. In one aspect biomarkers comprising whole cells can be detected and quantified by well-known manual counting methods and/or automated counting methods using automated devices.

Diagnosing Joint Pain and/or Inflammation

In one aspect a biomarker expression profile can be used to diagnose joint pain and/or joint inflammation, diagnose OA, stage OA, monitor OA disease progression, treat OA and/or monitor OA treatment. In one aspect a subject sample, e.g., a synovial fluid sample extracted from a painful or inflamed joint of a subject, can be assessed by determining a biomarker profile comprising any one or any combination of OA biomarkers. In one aspect a biomarker profile can comprise a first OA biomarker known to evidence cartilage degradation, e.g., without limitation, COMP. In one aspect a first OA biomarker evidencing cartilage degradation is differentially increased in OA relative to a reference, e.g. a normal individual. In an aspect an OA biomarker profile can comprise a first OA biomarker known to evidence cartilage degradation and a second OA biomarker known to be expressed in low levels in OA relative to an inflammatory arthropathy, i.e. differentially decreased in OA (e.g., without limitation, IL-8, IL-6, CRP, MMP-9, MMP-3, NGAL). In an aspect an OA biomarker profile can comprise a first OA biomarker known to evidence cartilage degradation and a second OA biomarker that is differentially increased in an inflammatory arthropathy (RA, CA, septic arthritis) relative to a normal reference and/or relative to a reference known to have OA. In an aspect an OA biomarker profile can comprise a first OA biomarker known to evidence cartilage degradation and a second OA biomarker known to be a biomarker of inflammation that is expressed in reduced levels in OA (differentially decreased in OA relative to an inflammatory arthropathy) or that is known to be expressed in greater levels in an inflammatory arthropathy (differentially increased relative to OA).

In one aspect an biomarker profile can comprise at least two OA biomarkers selected from: AD; HNE; COMP; IL-8; OPN; OPG; OC; Leptin; CRTAC1; Tetranectin; FGF2; TIMP1; TIMP2; IL-8; IL-6; CRP; MMP-3; MMP-9; RANTES; PDGF; and NGAL. In a preferred aspect the biomarker profile is a polypeptide or protein profile. In another aspect, a method for evaluating a synovial fluid sample obtained from a subject experiencing joint pain or joint inflammation can include determining a level (e.g., a concentration or a total amount) of one or more biomarkers in a synovial fluid sample. In one aspect a OA biomarker protein can comprise one or more of COMP, OPN, OPG, OC, Leptin, CRTAC1, Tetranectin, IL-8, CRP, AD, HNE, MMP-3, MMP-9, IL-6, RANTES, NGAL, and PDGF. In an aspect the protein level of COMP, OPN, OPG, OC, Leptin, CRTAC1, Tetranectin, IL-8, CRP, AD, HNE, MMP-3, MMP-9, IL-6, RANTES, NGAL, or PDGF can be detected by immunoassay, e.g., ELISA, Luminex, multiplex-ELISA. In an aspect a biomarker profile can comprise a first biomarker and a second biomarker that are each differentially increased in osteoarthritis. In another aspect a first OA biomarker and a second OA biomarker can be each differentially decreased in OA. In yet another aspect one of a first OA biomarker and a second OA biomarker and can be differentially increased in OA and the other one of the first OA biomarker and the second OA biomarker can be differentially decreased in OA. In still another aspect a first OA biomarker can be differentially increased in OA and a second OA biomarker can be differentially increased in an inflammatory arthropathy.

In one aspect, a synovial fluid sample can be assessed for the level of a first OA biomarker and the level of a second OA biomarker, the levels of the first and second OA biomarkers in the sample can together diagnose or discriminate whether the subject has osteoarthritis, whether the subject has an inflammatory arthropathy (e.g., RA, CA, septic arthritis, trauma/injury to a joint), or whether the subject has osteoarthritis in conjunction with (e.g., OA secondary to) an inflammatory arthropathy. In an aspect a first OA biomarker and a second OA biomarker can be differentially expressed in osteoarthritis relative to a reference. In one aspect biomarkers that can be differentially increased in OA relative to a reference (e.g., relative to a normal subject or relative to a subject with an inflammatory arthropathy) can include COMP, OPN, OPG, OC, Leptin, CRTAC1, Tetranectin, FGF2, TIMP1, TIMP2, TNFSF9, CGA, MST1, ADGRG1, THBS2, LAMP1, SIGIRR, PTX3, FABP2, CD320, IL36RN, CXCL1, LAIR1, FST, ILIF10, NRXN3, FCRL1, PDCD1, and BAMBI. In other aspects biomarkers that can be differentially decreased in OA relative to a reference (e.g., relative to a normal subject or relative to a subject with an inflammatory arthropathy) can include IL-8, IL-6, CRP, AD, HNE, MMP-3, MMP-9, NGAL, RANTES, and PDGF. In one aspect a synovial fluid sample from a subject can be assessed for the level of a first OA biomarker and a second OA biomarker that are each differentially increased in OA relative to a reference. In another aspect a first OA biomarker and a second OA biomarker can each be differentially decreased in OA relative to a reference. In still other aspects a first OA biomarker can be differentially increased in OA relative to a reference and a second OA biomarker can be differentially decreased in OA relative to a reference. In another aspect a first OA biomarker can be differentially increased in Oa relative to a reference and a second OA biomarker can be differentially increased in an inflammatory arthropathy relative to a reference.

In an aspect a synovial fluid sample can be assessed for a level of a first OA biomarker comprising COMP, OPN, OPG, OC, Leptin, CRTAC1, Tetranectin, FGF2, TIMP1, or TIMP2, and a assessed for a level of a second OA biomarker comprising IL-8, IL-6, CRP, AD, HNE, MMP-3, MMP-9, NGAL, RANTES, or PDGF. In one aspect a synovial fluid sample can be assessed for a level of COMP and a level of a second OA biomarker selected from OPN, OPG, OC, Leptin, CRTAC1, Tetranectin, FGF2, TIMP1, TIMP2, IL-8, IL-6, CRP, AD, HNE, MMP-3, MMP-9, NGAL, RANTES and PDGF. Exemplary combinations of a first OA biomarker and a second OA biomarker can include, without limitation: COMP and IL-8; COMP and CRP; COMP and MMP-9; COMP and MMP-3; COMP and NGAL; COMP and PDGF; COMP and AD; COMP and HNE; COMP and OPN; COMP and OPG; and COMP and OC.

In one aspect the level of a first OA biomarker and the level of a second OA biomarker relative to one another can be used to diagnose OA or discriminate between OA and an inflammatory arthropathy in a subject. In an aspect a level of a first OA biomarker and a level of a second OA biomarker relative to one another in a reference can be used to as a reference for diagnosing OA or discriminating between OA and an inflammatory arthropathy. In one aspect a biomarker ratio of the level of a first OA biomarker to the level of a second OA biomarker in a synovial fluid sample from a subject can diagnose OA or discriminate between OA and an inflammatory arthropathy in the subject. In another aspect a reference ratio of the level of a first OA biomarker to the level of a second OA biomarker in a reference synovial fluid can be used as a reference for diagnosing OA or discriminating between OA and an inflammatory arthropathy. In one aspect a biomarker ratio of a first OA biomarker and a second OA biomarker can be compared to a reference ratio of the first OA biomarker and the second OA biomarker. In an aspect a biomarker ratio or a reference ratio can be based on quantities (e.g., concentrations) that are adjusted to have like units, such that the level of each biomarker is expressed in the ratio as pg/mL, ng/mL, pg/mL, mg/mL, or mg/dl, or the like such that the units cancel each other. For example, a synovial fluid sample can have a first OA biomarker level of 100 ng/mL and a second OA biomarker level of 100 pg/mL (or 0.01 ng/mL), providing a biomarker ratio of 100/0.01 or 10,000. In another aspect a biomarker ratio or a reference ratio can be based on quantities (e.g., concentrations) that are not adjusted to have like units, such that a first OA biomarker can have a level expressed in units that differ from the units of the level of the second OA biomarker. For example, a first OA biomarker can have a level of 1000 ng/mL and the second OA biomarker can have a level of 100 pg/mL providing a biomarker ratio of 1000/100 or 10. In one aspect a biomarker ratio can be the ratio of a first OA biomarker that is differentially increased in OA and a second OA biomarker that is differentially increased in an inflammatory arthropathy, e.g., differentially decreased in OA. In an aspect the first OA biomarker can be selected from COMP, OPN, OPG, OC, Leptin, CRTAC1, Tetranectin, FGF2, TIMP1, and TIMP2, and a second OA biomarker can be selected from IL-8, IL-6, CRP, AD, HNE, MMP-3, MMP-9, NGAL, RANTES or PDGF. In an aspect a biomarker ratio greater than or equal to 2.0 can diagnose OA or discriminate between OA and an inflammatory arthropathy, e.g., 2.1, 2.2, 2.3, 2.4, 2.5, 2.6, 2.7, 2.8, 2.9 and any number therebetween. In an aspect the biomarker ratio can comprise a ratio of COMP:IL-8 and a COMP:IL-8 ratio greater than or equal to 2.0 can diagnose idiopathic OA in a subject.

Staging and Monitoring Progression of OA

In one aspect the level of one or more OA biomarkers can be assessed to determine the stage of OA the severity of OA disease. In an aspect a synovial fluid sample extracted from an inflamed or painful joint in a subject can be evaluated for the level of one or more OA biomarkers and compared to a reference level of the one or more OA biomarkers to stage OA or to assess the severity of OA in a subject. In an aspect a reference for staging OA can be synovial fluid from an individual that has a known stage or a known severity of OA. In another aspect a reference for staging OA in a subject can be a synovial fluid from the subject at an earlier time, e.g., an earlier stage of OA such that a change in the level of one or more OA biomarkers in the synovial fluid sample from the reference (subject synovial fluid at an earlier time) and a later synovial fluid sample indicate a change in the OA stage or severity of OA in the subject. In one aspect the synovial fluid level of one or more OA biomarkers can be assessed on two, three, four, five, six or more occasions over a period of time and compared to a reference to determine a stage of OA or OA disease severity in a subject. In an aspect the synovial fluid level of one or more OA biomarkers can be assessed over a period of time or interval of time and compared to a reference, the period or time or interval of time being 1, 2, 3, 4 or more weeks or any time therebetween, or 1, 2, 3, 4, 5, 6, 7, 8, 9, 10, 11, or 12 months or more or any time therebetween, or 1, 2, 3, 4, 5, 6, 7, 8, 9, 10, 11, or 12 years or more or any time therebetween.

In an aspect biomarkers for staging OA or determining OA disease severity can comprise any one or more OA biomarker selected from: COMP; IL-8; Leptin; OPN; OPG; OC; FGF-2; TIMP1; TIMP2; TIMP3; TIMP4; Tetranectin or CLEC3B; CRTAC1; Afamin; Lumican; Galectin 3BP; TNFSF9; CGA; MST1; ADGRG1; THBS2; LAMP1; SIGIRR; PTX3; FABP2; CD320; IL36RN; CXCL1; LAIR1; FST; IL1F10; NRXN3; FCRL1; PDCD1; BAMBI; FGF5; TFP12; GPC5; FRZB; CCL22; IL16; EFNB3; NCR2; TNFSF1B; IL-1B: CD86; MMP-8; AGT; CSF3R; CCL15; and IL-12B. In one aspect the level of one or more OA biomarkers in a synovial fluid sample of a subject can increase as the stage of OA disease progresses and/or severity of osteoarthritis increase or worsens, i.e., from early stage (KL 0/1/2) to mid-stage (KL 2/3) to late stage (KL 4). In other aspects the level of one or more OA biomarkers in the synovial fluid sample of a subject can decrease as the stage and/or severity of OA increases or worsens, i.e., from early stage (KL 0/1/2) to mid-stage (KL 2/3) to late stage (KL 4). In one aspect OA biomarkers that can increase as the stage of OA progresses or OA disease severity increases can include one or more of: TNFSF9; CGA; MST1; ADGRG1; THBS2; LAMP1; SIGIRR; PTX3; FABP2; CD320; IL36RN; CXCL; LAIR1; FST; ILIF10; NRXN3; FCRL1; PDCD1; and BAMBI. In an aspect biomarkers that can decrease as the stage of OA progresses or OA disease severity increases can include one or more of: FGF5; TFP12; GPC5; FRZB; CCL22; IL16; EFNB3; NCR2; TNFSF1B; IL-1B; CD86; MMP-8; AGT; CSF3R; CCL15; and IL-12B.

In yet another aspect the synovial fluid level of one or more of TNFSF9, CGA, MST1, ADGRG1, THBS2, LAMP1, SIGIRR, PTX3, FABP2, CD320, IL36RN, CXCL1, LAIR1, FST, ILIF10, NRXN3, FCRL1, PDCD1, and BAMBI can be assessed and monitored over time to determine whether the biomarker level increases to reflect progression of OA and/or an increasing severity or worsening of OA, e.g., from early stage (KL 0/1/2) to mid-stage (KL 2/3) to late stage (KL 4). In other aspects the synovial fluid level of one or more of FGF5, TFP12, GPC5, FRZB, CCL22, IL16, EFNB3, NCR2, TNFSF1B, IL-1B, CD86, MMP-8, AGT, CSF3R, CCL15, and IL-12B can be assessed and monitored over time to determine whether the biomarker level decreases to reflect progression of OA and/or an increasing severity or worsening of OA, e.g., from early stage (KL 0/1/2) to mid-stage (KL 2/3) to late stage (KL 4).

Monitoring Treatment of OA

In one aspect the level of one or more OA biomarkers can be assessed and monitored at one or more times during treatment of subject diagnosed with OA to assess whether treatment is having a beneficial effect. In an aspect a reference for monitoring a treatment of OA can be synovial fluid from the subject at an earlier time, e.g., before treatment begin, or within a period after treatment has begun. In one aspect the synovial fluid level of one or more biomarkers can be assessed on two, three, four, five, six or more occasions over a period of time and compared to a reference to determine the efficacy of a treatment in a subject. In an aspect the synovial fluid level of one or more OA biomarkers can be assessed over a period of time or interval of time and compared to a reference (e.g., an earlier level of the OA biomarker in the subject's synovial fluid), the period or time or interval of time being 1, 2, 3, 4 or more weeks or any time therebetween, or 1, 2, 3, 4, 5, 6, 7, 8, 9, 10, 11, or 12 months or more or any time therebetween, or 1, 2, 3, 4, 5, 6, 7, 8, 9, 10, 11, or 12 years or more or any time therebetween.

In one aspect OA biomarkers for monitoring treatment of OA can comprise one or more of: TNFSF9; CGA; MST1; ADGRG1; THBS2; LAMP1; SIGIRR; PTX3; FABP2; CD320; IL36RN; CXCL1; LAIR1; FST; IL1F10; NRXN3; FCRL1; PDCD1; BAMBI; FGF5; TFP12; GPC5; FRZB; CCL22; IL16; EFNB3; NCR2; TNFSF1B; IL-1B; CD86;

MMP-8; AGT; CSF3R; CCL15; and IL-12B. In one aspect the level of one or more OA biomarkers in a synovial fluid sample of a subject can increase with improvement in OA disease severity (lessening of severity) in response to the treatment. In other aspects the level of one or more OA biomarkers in the synovial fluid sample of a subject can decrease with improvement in OA disease severity (lessening of severity). In an aspect one or more OA biomarkers can remain unchanged indicating lack of benefit from the treatment. In another aspect one or more OA biomarkers measured after treatment can evidence progression of OA stage or an increase in OA severity (as described above) indicating lack of benefit from a treatment. In one aspect one or more biomarkers that can decrease to indicate benefit of treatment can include one or more of: TNFSF9; CGA; MST1; ADGRG1; THBS2; LAMP1; SIGIRR; PTX3; FABP2; CD320; IL36RN; CXCL1; LAIR1; FST; IL1F10; NRXN3; FCRL1; PDCD1; and BAMBI. In an aspect biomarkers that can increase to indicate benefit of treatment can include one or more of; FGF5; TFP12; GPC5; FRZB; CCL22; IL16; EFNB3; NCR2; TNFSF1B; IL-1B; CD86; MMP-8; AGT; CSF3R; CCL15; and IL-12B.

Methods of Diagnosing and Treating Inflamed or Painful Joints

In one aspect one or more OA biomarkers can be useful in methods of treating a painful joint or an inflamed joint in a subject and methods of diagnosing osteoarthritis in a subject. In one aspect one or more biomarkers can be used for differentially diagnosing osteoarthritis in a subject. The methods of treating an inflamed joint or a painful joint can include methods of assessing or evaluating a synovial fluid sample from a subject according to any one or any combination of aspects disclosed above. The methods of treating an inflamed joint or a painful joint can include assessing or evaluating one or more OA biomarkers in a synovial fluid sample from a subject and/or monitoring OA disease progression by assessing one or more biomarkers in a synovial fluid sample according to any one or any combination of aspects disclosed above. The methods of treating an inflamed joint or a painful joint can also include assessing or evaluating a synovial fluid sample from a subject and monitoring treatment efficacy according to any one or any combination of aspects disclosed above.

Figure 37A:
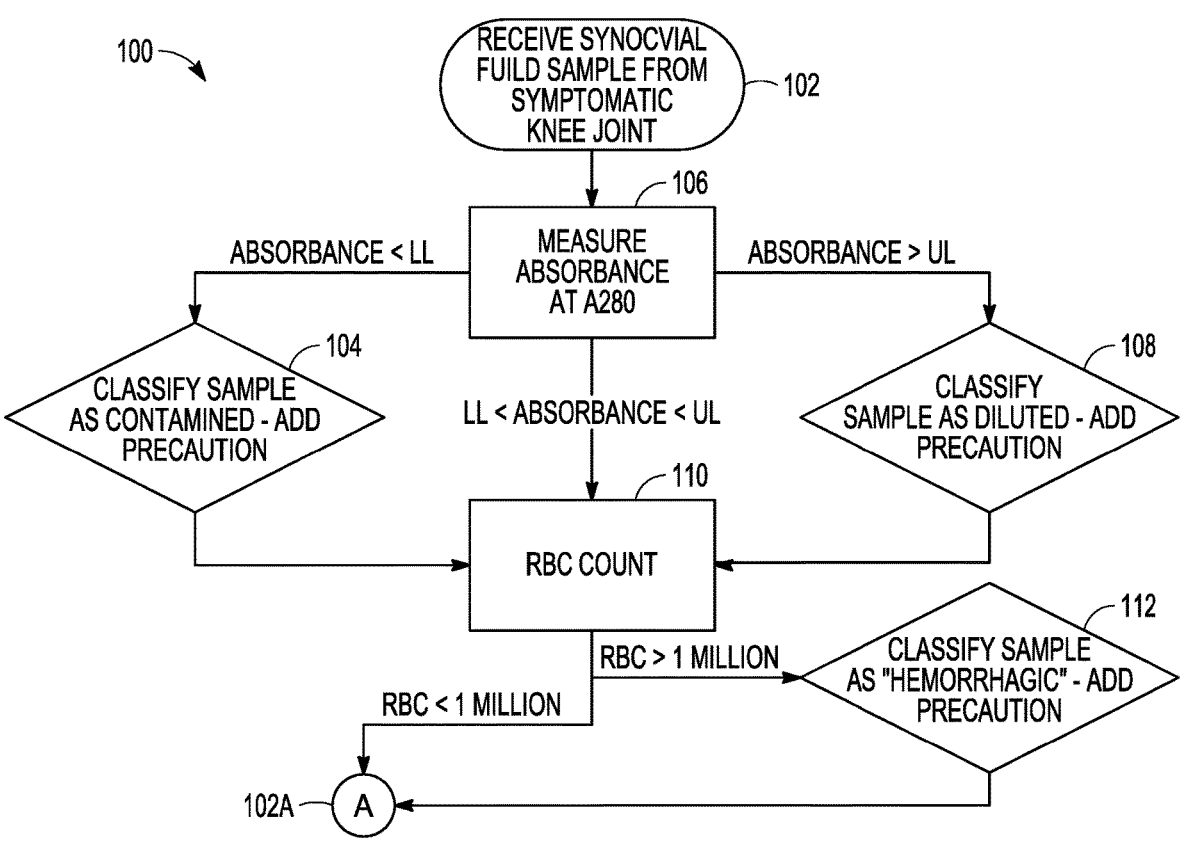
FIGS. 37A-37G illustrate various methods of evaluating a synovial fluid sample.

As illustrated in FIGS. 37A-37G and as described in one or more of the Examples, in an aspect a painful joint or an inflamed joint of a subject can be treated by determining a level of a first biomarker in a tissue or a fluid sample from the subject, e.g., a synovial fluid sample from the joint, and treating the subject for OA when the level of the first biomarker indicates the subject has osteoarthritis according to one or more aspects disclosed above or treating the subject for an inflammatory arthropathy according to the results of a differential analysis of the synovial fluid sample. In one aspect, as shown in FIG. 37A, a subject sample 102 can be assessed to determine sample integrity. In an aspect a subject sample can be assessed to determine whether the sample has been diluted 104 during extraction of the sample from the subject, e.g., by saline or bodily fluid that is not synovial fluid. In an aspect a subject sample 102 can be assessed to determine whether the subject sample is contaminated 104 during extraction of the sample from the subject, e.g., with a contrast agent or other agent used during the extraction procedure. In one aspect a subject sample 102 can be assessed using a spectroscopic measurement of the sample absorbance 106. In one aspect the spectroscopic absorbance 106 of a sample can be measured at 280 nm (A280). In an aspect a subject sample 102 absorbance can be compared to a reference absorbance, e.g., a reference synovial fluid sample that is not diluted and is not contaminated. In one aspect a reference synovial fluid can have an A280 within a range of 0.342 to 1.190 (a normal range) and absorbance outside of the normal range can indicate the sample is diluted or is contaminated. In one aspect a subject sample A280 absorbance 106 less than 0.342 can indicate a subject sample has been contaminated during extraction 104. In another aspect an A280 absorbance 106 greater than 1.190 can indicate the subject sample has been diluted during extraction 108. In one aspect an A280 for a subject sample 102 can be determined by reviewing a report of the subject sample assessment 106 as shown in FIGS. 47A-47E. The results of a sample assessment 106 can be provided in a report or a report can be automatically generated to indicate the results of the assessment. In one aspect a report can indicate a subject sample is contaminated 104 and provide a cautionary statement that the results of a biomarker assay of the sample should be interpreted with caution due to the contaminated status. In another aspect a report can indicate a subject sample is diluted 108 and include a cautionary statement that the results of a biomarker assay of the sample should be interpreted with caution due to the diluted status.

Figure 37B:
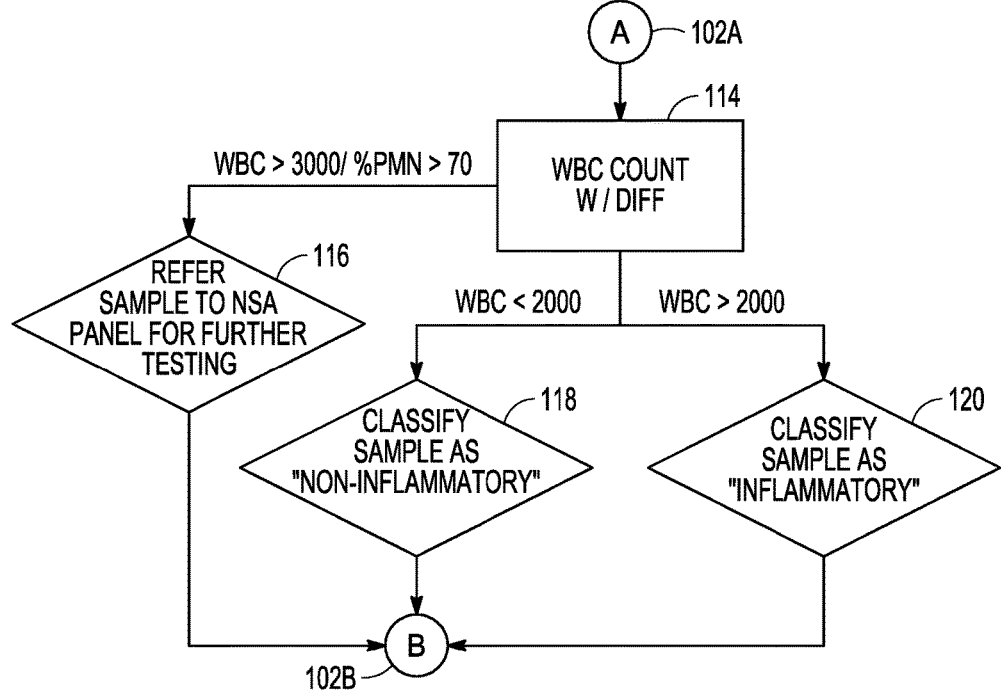

In an aspect, as shown in FIG. 37B, a subject sample integrity can be assessed to determine whether the subject sample is hemorrhagic, e.g., includes an excessive quantity (concentration) of red blood cells (RBCs) or is diluted by blood. In one aspect a subject sample can be assessed for the quantity or RBCs (RBC count) 110 relative to a reference level. Methods of quantifying RBCs are well known in the art and can include manual counting and automated counting methods. In one aspect a reference synovial fluid sample can have less than 1,000,000 RBCs per microliter, i.e., is not hemorrhagic. In an aspect a subject synovial fluid sample having greater than 1,000,000 RBCs per microliter can be considered hemorrhagic 112. In one aspect a subject sample having an A280 within the range of 0.342 to 1.190 (within normal range, not diluted or contaminated) can be assessed 110 to determine whether the sample has greater than 1,000,000 RBCs per microliter (hemorrhagic) 112. In another aspect a subject sample that has been determined to be contaminated 104 can be assessed to determine whether the sample has greater than 1,000,000 RBCs per microliter (hemorrhagic). In still another aspect a subject sample that has been determined to be diluted 108 can be assessed to determine whether the sample has greater than 1,000,000 RBCs per microliter. In one aspect an RBC count 110 for a subject sample can be determined by reviewing a report for an assay of the subject sample as shown in FIGS. 47A-47E. The results of a sample assessment 110 can be provided in a report or a report can be automatically generated to indicate the results of the assessment. In one aspect a report can indicate a subject sample is classified as hemorrhagic 112 and provide a cautionary statement that the results of a biomarker assay of the sample should be interpreted with caution due to the hemorrhagic status.

Figure 37C:
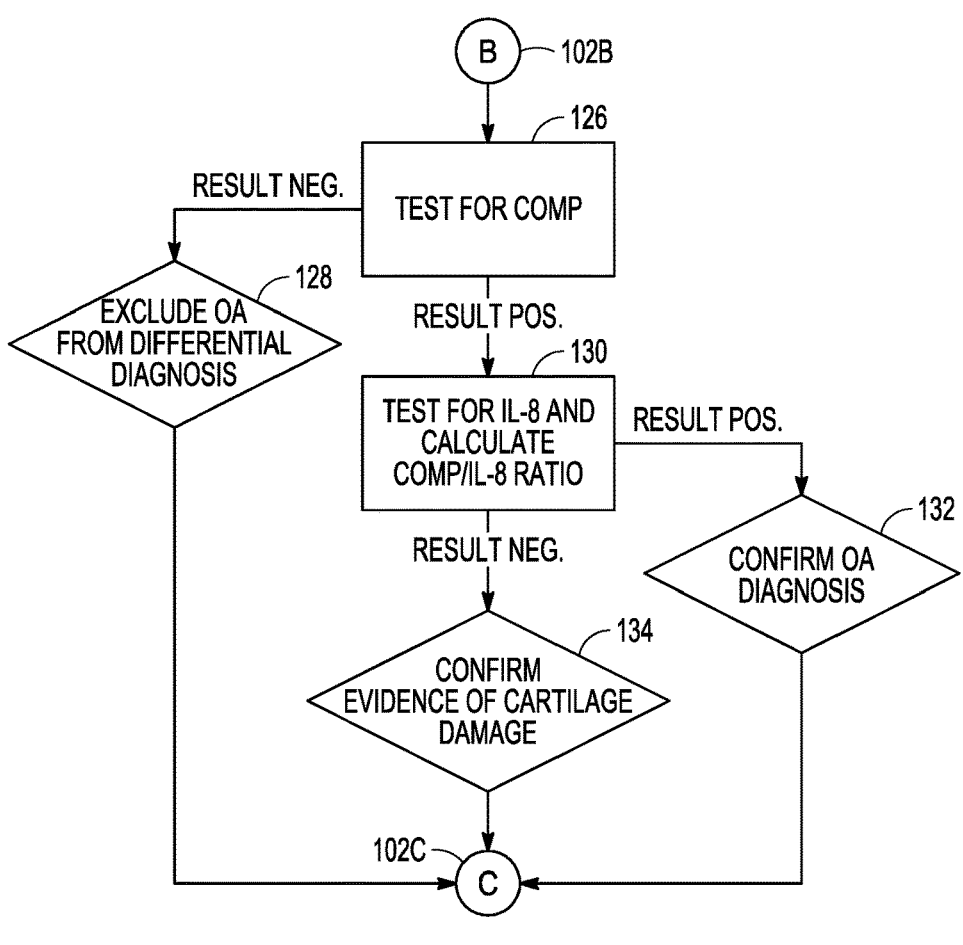

As shown in FIG. 37C, in an aspect a quantity of white blood cells (WBC), i.e., a WBC count 114, can be determined for a subject sample 102, 102A. In one aspect a WBC count can be a differential WBC count. Methods of quantifying WBCs are well known in the art and can include manual quantification and automated quantification. In an aspect a differential WBC count can include the total number of WBCs per volume (WBC concentration), and the proportion (percentage) of one or more WBC types (e.g., % neutrophils (PMN); % mononuclear cells) relative to the total WBC quantity. In an aspect a subject sample 102, 102A can be compared to a reference e.g., a synovial fluid sample for a subject that is known to not have a joint infection or inflammatory arthropathy. In an aspect a reference synovial fluid can have a WBC count with less than or equal to 3,000 WBCs per microliter and/or can have fewer than 70% PMN. In one aspect a subject sample can have a WBC count 114 greater than 3,000 cells per microliter 116 suggesting infection, e.g., native joint septic/infection or periprosthetic joint infection, and the subject sample 101, 102B can be further assessed to determine whether infection is present, e.g., culture of the sample and/or assessing biomarkers HNE, AD and/or lactate (NSA Panel) as described below. In an aspect a subject sample 102, 102A can have a greater than 70% PMN 116 suggesting infection, e.g., native septic joint or periprosthetic joint infection, and the subject sample can be further assessed to determine whether infection is present, e.g., culture of the sample, assessing biomarkers HNE, AD and/or lactate (NSA Panel). In one aspect a WBC count 114 can be determined by reviewing a report for the subject sample analysis as shown in FIGS. 47A-47E. The results of a sample assessment 114 can be provided in a report or a report can be automatically generated to indicate the results of the assessment. In one aspect a report can include a WBC differential count. In one aspect a report for a subject sample that has greater than 3,000 WBC per microliter or greater than 70% PMN can include a statement that the subject and/or subject sample should receive further assessment to determine whether infection is present, which can include sample culture and/or additional biomarker assessment (e.g., biomarker assessment for HNE, AD and/or lactate). In one aspect a report for a subject sample that has fewer than 2,000 WBC per microliter can be classified as a non-inflammatory sample 118 suggesting that infection or an inflammatory arthropathy are unlikely to be present in the subject's joint. In another aspect a report for a subject sample that has greater than 2,000 WBC per microliter but less than 3,000 WBC per microliter can be classified as an inflammatory sample 120 suggesting the likelihood that an inflammatory arthropathy may be present (either as a primary disease or a secondary disease) in the subject's joint and indicating a need for further assessment, (e.g., additional biomarkers assessment for AD, lactate, assessment or for RA and/or CA).

In one aspect a method of treating an inflamed or a painful joint can comprise assessing a synovial fluid sample for one or more biomarkers and treating the subject for OA when the one or more biomarkers indicates OA is present in the subject. In one aspect a method of differentially diagnosing a painful or inflamed joint can include determining a level of one or more biomarkers in a synovial fluid sample and treating the subject for OA when the one or more biomarkers indicates the subject has OA. In an aspect, a first biomarker level comprising a WBC count can indicate the subject sample 102A has an inflammatory status 116, 120 according to one or more aspects disclosed above. In another aspect a first biomarker level comprising a WBC count can indicate the subject sample has a non-inflammatory status 118. In aspects when the first biomarker level comprising a WBC count indicates an a possible infection 116 or an inflammatory status 120 the subject sample 102B can be further assessed to determine whether the subject has an OA and/or an inflammatory arthropathy, e.g., CA, RA. as shown in FIGS. 37D-37G.

In one aspect a subject sample 102, 102A, 102B having a possible infection 116, a sample classified as non-inflammatory 118, or an sample classified as inflammatory 120 can be further assessed for biomarkers HNE, AD and/or lactate (NSA Panel) to determine whether the synovial fluid sample was obtained from an infected joint, i.e., the subject has septic arthritis. In an aspect a synovial fluid sample that is negative for AD can be confirmed to not have septic arthritis. In one aspect a synovial fluid sample that is negative for lactate can be confirmed to not have septic arthritis. In another aspect a synovial fluid sample that is positive for AD and that is positive for lactate can be confirmed to have septic arthritis. In an aspect a synovial fluid sample that is positive for AD and that is negative for lactate or has a lactate level less than 70 mg/dL can be considered indeterminate or inconclusive for diagnosis of septic arthritis. In one aspect presence of AD or a lactate in a synovial fluid sample can be determined by reviewing a report for the subject sample analysis as shown in FIGS. 47B and 47E. The results of a sample assessment AD and/or lactate can be provided in a report or a report can be automatically generated to indicate the results of the assessment.

Figure 37D:
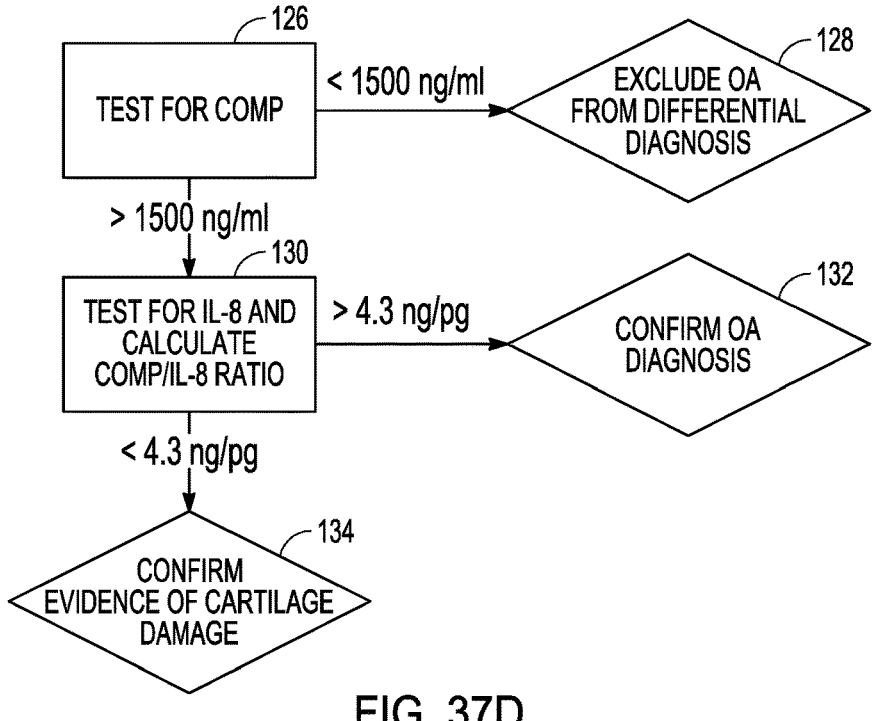

In an aspect one or more OA biomarkers in a synovial fluid sample can be compared to a reference to determine whether the subject has OA. In one aspect a reference level of an OA biomarker can be a level in a synovial fluid sample from one of a normal individual, an individual confirmed to have OA, or an individual confirmed to have an inflammatory arthropathy, e.g., RA, CA, septic arthritis, trauma or injury to a joint. As illustrated in FIGS. 37C and 37D, in one aspect subject sample 102, 102A, 102B can be assessed to determine a level of a first OA biomarker 126. The one or more OA biomarkers can be assessed and the results of the assessment can be used to diagnose joint pain or inflammation in a subject (e.g., as OA, RA, CA, SA or a combination thereof) and to administer one or more treatments to a subject according to one or more aspects described above. In one aspect an OA biomarker level can be determined by reviewing a report for the subject sample analysis as shown in FIGS. 47A-47E. The result of an assessment of one or more OA biomarkers, e.g. a biomarker level or a biomarker ratio as described below, can be provided in a report or a report can be automatically generated to indicate the results of the assessment.

Figures 37E, 37F:
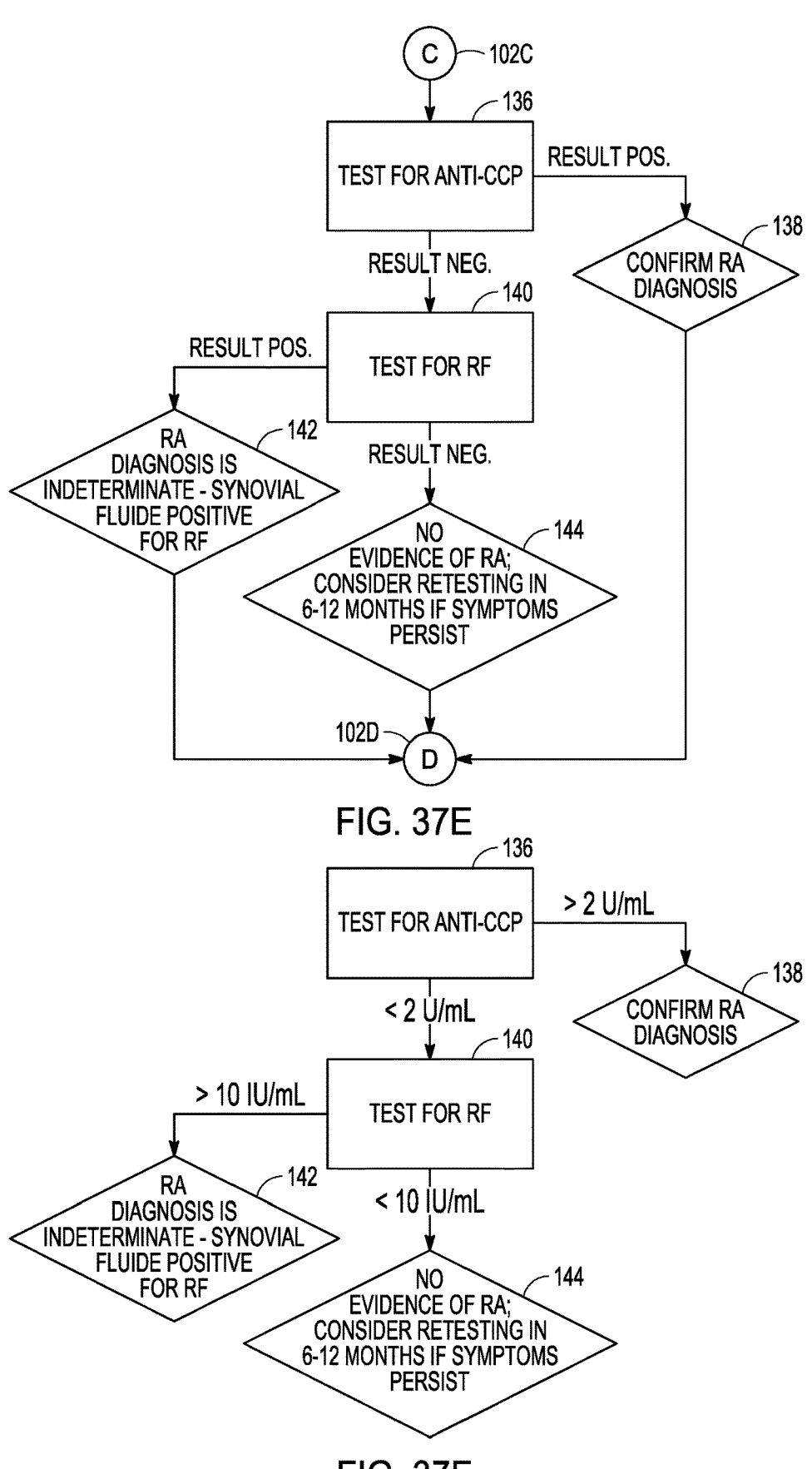

As shown in FIGS. 37C and 37D, in one aspect a first biomarker level can be assessed 126 (COMP is used only as a representative biomarker in FIGS. 37C and 37D and use of COMP in the figures is not intended to exclude any other biomarker from used in such methods). In an aspect a level of a first OA biomarker compared to a reference level of the first OA biomarker can indicate the subject does not have osteoarthritis 128 according to one or more aspects disclosed above, e.g., OA can be excluded from the diagnosis. In an aspect a first OA biomarker level can indicate the subject does not have osteoarthritis 128 according to one or more aspects disclosed above and the subject sample 102C can be further evaluated as shown in FIGS. 37E, 37F and/or 37G to determine whether one or more inflammatory arthropathies are present. In one aspect when the level of the first OA biomarker indicates that the subject does not have osteoarthritis 128 the subject sample 102C can be further assessed to diagnose an inflammatory arthropathy according to one or more aspects disclosed herein, e.g., as shown in FIGS. 37E, 37F and/or 37G. In an aspect when the level of the first OA biomarker indicates that the subject does not have osteoarthritis 128 the subject can be administered a treatment for an inflammatory arthropathy.

In one aspect an OA biomarker that can be assessed 126 to exclude OA from a diagnosis can comprise one or more biomarkers that are differentially increased in OA. In an aspect OA biomarkers that are differentially increased in OA (i.e., increased relative to a normal individual and/or to an individual having an inflammatory arthropathy) include, without limitation, one or more of: COMP; IL-8; Leptin; OPN; OPG; OC; FGF-2; TIMP1; TIMP2; TIMP3; TIMP4; Tetranectin or CLEC3B; CRTAC1; Afamin; Lumican; Galectin 3BP; TNFSF9; CGA; MST1; ADGRG1; THBS2; LAMP1; SIGIRR; PTX3; FABP2; CD320; IL36RN; CXCL1; LAIR1; FST; IL1F10; NRXN3; FCRL1; PDCD1; BAMBI. When the OA biomarker level is less than a reference (i.e., an OA synovial fluid reference), osteoarthritis can be excluded from a diagnosis 128. In one aspect the first OA biomarker can be differentially increased by at least 2-fold. In an aspect an OA biomarker that is differentially increased in OA can be used to diagnose a subject as having osteoarthritis, e.g., a synovial fluid sample has a level that is greater than or equal to the OA reference the subject may have osteoarthritis. In an aspect, a biomarker that is differentially increased in OA may not conclusively diagnose OA and a second OA biomarker level may be considered in combination with a first OA biomarker to diagnose and/or treat the subject.

In one aspect a first OA biomarker that is differentially increased in OA can comprise COMP and a synovial fluid level of COMP less than or equal to a reference level of COMP can exclude OA from a diagnosis 128. In one aspect a COMP level less than or equal to 4,500 ng/mL can exclude OA from a diagnosis. In an aspect a synovial fluid level of COMP less than 4,000 ng/mL can exclude OA from a diagnosis. In another aspect a synovial fluid level of COMP less than 3,500 ng/mL can exclude OA from a diagnosis. In one aspect a synovial fluid level of COMP less than 3,000 ng/mL can exclude OA from a diagnosis. In one aspect a synovial fluid level of COMP less than 2,500 ng/mL can exclude OA from a diagnosis. In one aspect a synovial fluid level of COMP less than 2,000 ng/mL can exclude OA from a diagnosis. In one aspect a synovial fluid level of COMP less than or equal to 1,500 ng/mL can exclude OA from a diagnosis. In another aspect a synovial fluid level of COMP less than or equal to 1,000 ng/mL can exclude OA from a diagnosis.

An aspect of diagnosing and/or treating a subject can include determining a level of a first OA biomarker and a level of a second OA biomarker 130 in a synovial fluid sample. In one aspect a first OA biomarker and a second OA biomarker can be differentially increased in OA and a synovial fluid sample level of the first OA biomarker and/or second OA biomarker that is greater than or equal to a reference level of the first OA biomarker can indicate the subject has osteoarthritis. Biomarkers that can be differentially increased in OA can comprise, without limitation, any one or more of: COMP; IL-8; Leptin; OPN; OPG; OC; FGF-2; TIMP1; TIMP2; TIMP3; TIMP4; Tetranectin or CLEC3B; CRTAC1; Afamin; Lumican; Galectin 3BP; TNFSF9; CGA; MST1; ADGRG1; THBS2; LAMP1; SIGIRR; PTX3; FABP2; CD320; IL36RN; CXCL1; LAIR1; FST; IL1F10; NRXN3; FCRL1; PDCD1; BAMBI.

In another aspect a first OA biomarker and a second OA biomarker can be differentially decreased in OA and a synovial fluid sample level of the first OA biomarker and the second OA biomarker can indicate the subject has osteoarthritis. In an aspect a synovial fluid sample having a first OA biomarker and a second OA biomarker level that are less than or equal to a reference level can indicate the subject has OA. Biomarkers that can be differentially decreased in OA can comprise, without limitation, one or more of: IL-8; IL-6; CRP; AD; HNE; MMP-3; MMP-9; NGAL; RANTES;

PDGF; FGF5; TFP12; GPC5; FRZB; CCL22; IL16; EFNB3; NCR2; TNFSF1B; IL-1B; CD86; MMP-8; AGT; CSF3R; CCL15; IL-12B.

In one aspect a first OA biomarker can be a biomarker that is differentially increased in OA (e.g., without limitation, those biomarkers identified above) and a second OA biomarker can be a biomarker that is differentially decreased in OA or differentially increased in an inflammatory arthropathy. In one aspect a first OA biomarker and a second OA biomarker can be selected from COMP, OPG, OPN, OC, Leptin, CRTAC1, Tetranectin, AD, HNE, IL-8, IL-6, CRP, MMP-9, MMP-3, NGAL, PDGF-AA, PDGF-BB, and PDGF-AB. In one aspect a first OA biomarker can be selected from COMP, OPG, OPN, OC, Leptin, Tetranectin, and CTRAC1. In an aspect a second OA biomarker can be selected from AD, HNE, IL-8, IL-6, CRP, MMP-9, MMP-3, NGAL, PDGF-AA, PDGF-BB, and PDGF-AB. In one aspect COMP can be selected as the first OA biomarker and a second OA biomarker can be selected from IL-8, CRP, MMP-9, MMP-3, NGAL, IL-6, PDGF-AA, PDGF-BB, or PDGF-AB. In one aspect a first Oa biomarker can comprise COMP and a second OA biomarker can comprise IL-8 130 and subject synovial fluid sample level of COMP greater than 1,500 ng/mL and a subject synovial fluid sample level of IL-8 less than or equal to 150 pg/mL can confirm a subject has osteoarthritis 132.

In an aspect a synovial fluid level of first OA biomarker can be compared to a reference level of the first OA biomarker and a second OA biomarker in the synovial fluid can be compared to the level of the second OA biomarker in a reference. In one aspect the reference for comparing the first OA biomarker level can be the same as the reference for comparing the second OA biomarker level. In another aspect the reference for comparing the first OA biomarker level can be different from the reference for comparing the second OA biomarker level. In one aspect a reference level for COMP can be greater than or equal to 1,000 ng/mL. In one aspect a reference level for COMP can be greater than or equal to 1,500 ng/mL. In another aspect a reference level for COMP can be greater than or equal to 2,000 ng/mL. In an aspect a reference level for COMP can be greater than or equal to 2,500 ng/mL. In one aspect a reference level for COMP can be greater than or equal to 3,000 ng/mL. In one aspect a reference level for COMP can be greater than or equal to 4,000 ng/mL. In one aspect a reference level for OPG can be greater than or equal to 3,000 pg/mL. In an aspect a reference level for OPN can be greater than or equal to 10,000 pg/mL. In one aspect a reference level for OC can be greater than or equal to 3,000 pg/mL. In an aspect a reference level for Leptin can be greater than or equal to 2,000 pg/mL. In an aspect a reference level for Tetranectin (CLEC3B) can be greater than or equal to $2.5 \times 10^6$ pg/mL. In one aspect a reference level for CTRAC1 can be greater than or equal to $3.5 \times 10^6$ pg/mL. In an aspect a reference level for IL-8 can be less than or equal to 1000 pg/mL. In an aspect a reference level for IL-8 can be less than or equal to 800 pg/mL. In an aspect a reference level for IL-8 can be less than or equal to 600 pg/mL. In one aspect a reference level for IL-8 can be less than or equal to 400 pg/mL. In an aspect a reference level for IL-8 can be less than or equal to 300 pg/mL. In an aspect a reference level for IL-8 can be less than or equal to 200 pg/mL. In one aspect a reference level of IL-8 can be less than or equal to 150 pg/mL. In an aspect a reference level for NGAL can be less than or equal to $1.5 \times 10^5$ pg/mL. In one aspect a reference level for CRP can be less than or equal to 3.0 mg/dl. In an aspect a reference level for MMP-9 can be less than or equal to 25,000 pg/mL.

In one aspect a reference level for PDGF-AA, PDGF-BB or PDGF-AB can be less than or equal to 500 pg/mL. I an aspect a reference level for MMP-3 can be less than or equal to $3.0 \times 10^6$ pg/mL. In one aspect a reference level for IL-6 can be less than or equal to 3,000 pg/mL.

In one aspect a first OA biomarker level and a second OA biomarker level can be used to calculate a biomarker ratio 130. In an aspect a first OA biomarker level can be differentially increased in OA and a second OA biomarker level can be differentially decreased in OA and the first and second OA biomarker levels can be used to calculate a biomarker ratio. In an aspect a first OA biomarker can be differentially increased in OA and a second OA biomarker can be differentially increased in an inflammatory arthropathy, e.g., RA, CA, SA, trauma/injury, can be used to calculate a biomarker ratio. In one aspect a biomarker ratio of a first OA biomarker differentially increased in OA and a second OA biomarker differentially decreased in OA can be greater than or equal to 2.0 and can diagnose a subject as having OA. In an aspect a biomarker ratio can be 2.0, 2.5, 3.0, 3.5, 4.0, 4.5 or greater, and any whole or fractional number greater than 2.0. In another aspect a biomarker ratio of a first OA biomarker differentially increased in OA and a second OA biomarker differentially increased in an inflammatory arthropathy can be 2.0 and can diagnose a subject as having OA, e.g., a ratio of 2.0, 2.5, 3.0, 3.5, 4.0, 4.5 or greater, and any whole or fractional number greater than 2.0. For example, without limitation, in an aspect a biomarker ratio of COMP:IL-8 130 greater than or equal to 3.0 in a synovial fluid sample of a subject can diagnose osteoarthritis in a subject 132. In an aspect when the biomarker ratio a first OA biomarker differentially increased in OA and a second OA biomarker differentially decreased in OA or differentially increased in RA confirm the subject has OA 132 the subject can be administered a treatment for OA according to one or more aspect disclosed herein.

In one aspect synovial fluid levels of a first OA biomarker and a second OA biomarker 130 compared to respective reference levels can be inconclusive 134 as to a diagnosis of OA or can indicate OA may be present in conjunction with an inflammatory arthropathy, e.g., RA, CA, SA. In an aspect, an inconclusive result 134 can be a level of a first OA biomarker that is differentially increased in OA indicates OA is present while the second OA biomarker that is differentially increased in OA does not indicate OA is present in the subject. In another aspect an inconclusive result 134 can be a level of a first OA biomarker that is differentially increased in OA indicates OA is present while a second OA biomarker that is differentially decreased in OA does not indicate OA is present. In an aspect an inconclusive result 134 can be a level of a first OA biomarker that is differentially increased in OA indicates OA is present while a second OA biomarker that is differentially increased in an inflammatory arthropathy indicates an inflammatory arthropathy is present. In one aspect an inconclusive result 134 can be an inconclusive biomarker ratio of synovial fluid levels of a first OA biomarker and a second OA biomarker that is inconclusive as to a diagnosis of OA or can indicate OA may be present in conjunction with an inflammatory arthropathy, e.g., RA, CA, SA. In an aspect an inconclusive biomarker ratio can be a biomarker ratio less than a reference ratio for OA and can be inconclusive as to the presence of OA 134.

In instances where the levels of a first OA biomarker and a second OA biomarker are inconclusive as to the presence of OA, a subject sample 102C can be further assessed according to one or more aspects disclosed herein to determine if there is an inflammatory arthropathy as shown in FIGS. 37E, 37F and/or 37G. In another aspect in instances where the levels of a first OA biomarker and a second OA biomarker are inconclusive as to the presence of OA the subject sample can be further evaluated for cartilage damage, e.g., repeating an assessment 130 of one or more OA biomarkers different from the first OA biomarker and the second OA biomarker, or imaging by x-ray, ultrasound, computerized tomography (CT), magnetic resonance imaging (MRI), or by endoscopic examination of the joint for cartilage damage.

In an aspect of diagnosing OA and/or treating OA, as shown in FIGS. 37E and 37F, in a synovial fluid sample 102, 102A, 102B, 102C a synovial fluid sample can be assessed for one or more OA biomarkers that are differentially increased or present in an inflammatory arthropathy. In one aspect the presence of anti-CCP 136 can be determined for the synovial fluid sample. In an aspect the level of anti-CCP 136 can be determined for the synovial fluid sample. In one aspect the presence of RFs 140 can be determined for a synovial fluid sample. In an aspect the level of RFs 140 can be determined for a synovial fluid sample. In one aspect the presence of anti-CCP can be conclusive as to the presence of RA in the subject 138. In an aspect a level of anti-CCP can be conclusive as to the presence of RA in the subject 138. In one aspect an anti-CCP level determined for the synovial fluid sample and can be compared to a reference anti-CCP level. In one aspect a reference level of anti-CCP can be greater than or equal to 2 U per milliliter. In another aspect a level of anti-CCP greater than or equal to 2 U per milliliter can confirm rheumatoid arthritis is present in the subject 138 and a subject can be administered a treatment for RA.

In an aspect a synovial fluid sample 102, 102A, 102B, 102C that is negative for presence of anti-CCP can be further assessed for RFs 140. In an aspect a synovial fluid level of anti-CCP level less a reference, e.g., less than 2 U per milliliter, can be assessed for the presence of RFs. In an aspect a synovial fluid sample RF level can be determined 140 and can be compared to a reference level. In one aspect a reference level of RF can be 10 IU per milliliter. In an aspect a synovial fluid sample RF level greater than or equal to 10 IU per milliliter can indicate the subject may have RA, i.e., the assessment is indeterminate 142. Subjects having an RF greater than or equal to 10 IU per milliliter can be administered a treatment for RA. In one aspect a synovial fluid RF level less than 10 IU per milliliter can indicate that RA is not then present in the subject 144 and the subject can be referred for re-assessment if clinical symptoms persist and/or the subject can be administered a treatment for the symptoms (pain, inflammation). In an aspect a synovial fluid sample 102D confirmed to have RA can be further assessed for biomarkers to determine whether other inflammatory arthropathies are present, e.g., CA or SA. In another aspect a synovial fluid sample 102D with an indeterminate diagnosis of RA 142 can be further assessed for biomarkers to determine whether other inflammatory arthropathies are present, e.g., CA or SA. In yet another aspect a synovial fluid sample 102D determined to not have RA 144 can be further assessed for biomarkers to determine whether other inflammatory arthropathies are present, e.g., CA or SA. In one aspect the presence of anti-CCP and/or the presence of RF can be determined by reviewing a report for the subject sample analysis as shown in FIGS. 47A-47E. The results of a sample assessment can be provided in a report or a report can be automatically generated to indicate the results of the assessment.

Figure 37G:
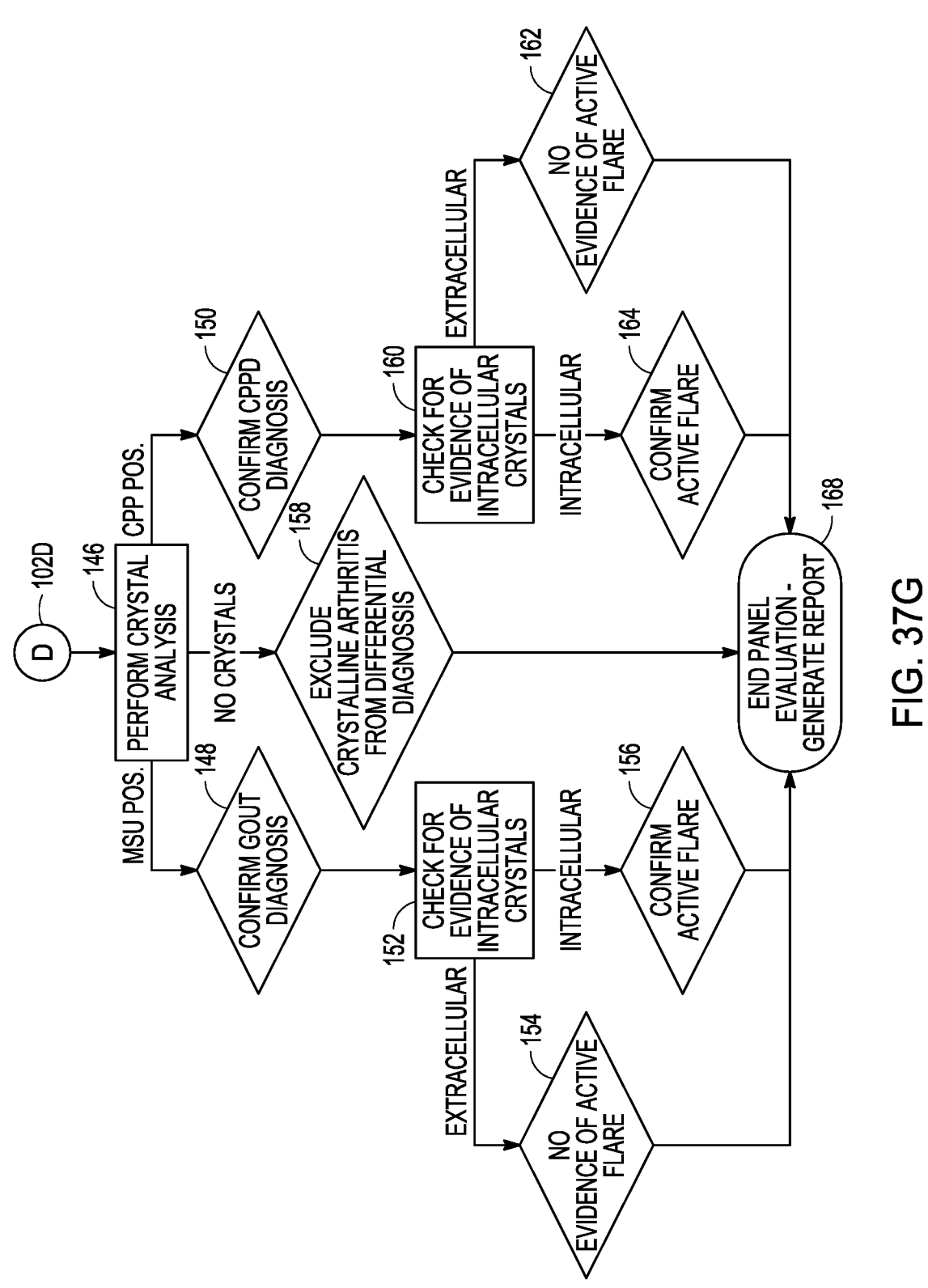

As shown in FIG. 37G, in one aspect a synovial fluid sample 102, 102A, 102B, 102C, 102D can be assessed for the presence of crystalline arthritis (CA) 146. Crystals in a synovial fluid sample can be extracellular or intracellular. In one aspect the crystals can be MSU crystals. In another aspect the crystals can be CPP crystals. In an aspect the absence of crystals in a synovial fluid sample can exclude CA from a diagnosis 158. In one aspect the presence of MSU crystals in synovial fluid sample can confirm the presence of gout in a subject 148. In one aspect assessing a synovial fluid sample can include determining the presence of MSU crystals that are intracellular 152. In an aspect the presence of intracellular MSU crystals indicates an active flare-up of gout 156. In another aspect the presence of extracellular MSU crystals and the absence of intracellular MSU crystals in a synovial fluid sample indicates there is not an active flare-up of gout 154. In one aspect a synovial fluid sample 102, 102A, 102B, 102C, 102D can be assessed for CPP crystals 146. In an aspect the presence of CPP crystals can confirm a diagnosis of CPP disease in the subject 150. In an aspect the presence of intracellular CPP crystals indicates an active flare-up of CPP disease 164. In another aspect the presence of extracellular CPP crystals and an absence of intracellular CPP crystals in a synovial fluid sample indicates there is not an active flare-up of CPP disease 162. In an aspect the presence or absence of crystals (and crystal type) in a synovial fluid sample can be determined by reviewing a report for the subject sample analysis as shown in FIGS. 47A-47E. The results of a sample assessment can be provided in a report or a report can be automatically generated to indicate the results of the assessment, e.g., the absence of crystals, type of crystals present (MSU or CPP), whether the crystals present are intracellular, extracellular, and/or whether there is/is not an active-flare up of CA.

It will be readily understood by those of skill in the art the above described assessments of synovial fluid samples as shown in FIGS. 37A-37G, or any of steps 102 through 168 shown in the figures can be performed in any order and in any combination.

Compositions, Combinations and Systems

Compositions, combinations, and systems for detecting OA biomarkers and thus, evaluating synovial fluid samples, diagnosing OA, monitoring OA and/or treating OA are also provided. In one aspect a composition, a combination and/or a system can include one or more agents configured to recognize a corresponding one or more OA biomarkers. In an aspect the composition can include a synovial fluid sample, e.g., a synovial fluid sample from a subject or a reference synovial fluid.

In an aspect the compositions, combinations and systems of the present disclosure can include one or more agents comprising antibodies, or antigen binding fragments thereof, for use in connection with an immunoassay such as ELISA, multiplex immunoassay, immunohistochemistry, Western blot, or 2-D DIGE. Alternatively, the composition, combination or system can include specific primers and/or probes for use in connection with qRT-PCR (e.g., using primers of 10-30 bp designed to target one or more OA biomarkers) or Northern blot (e.g., using probes of 30-300 bp designed to target one or more OA biomarkers). The combination or system can also include a microarray for detecting one or more OA biomarkers (nucleic acid or protein microarray).

In one aspect the combination or system comprises a solid support, such as a chip, a microtiter plate, a slide, a bead or resin, a membrane, or other device or substance having capture reagents attached thereon. Any method available to an art worker to attached capture agents (e.g., the biomarkers disclosed herein) can be used. In an aspect the combination or system can also comprise a washing solution or instructions for making a washing solution, in which the combination of the capture reagent and the washing solution allows capture of one or more biomarkers on the solid support for subsequent detection by, e.g., mass spectrometry or immunoassay. In an aspect the combination or system can include one or more biomarkers each present on a different solid support. In another aspect the combination of system can include a combination of biomarkers on the same solid support.

In one aspect a combination or system can comprise instructions for use in any of the methods described herein. In embodiments, the instructions provide suitable operational parameters in the form of a label or separate insert. For example, the instructions may inform a user how to collect a sample, e.g., a synovial fluid sample, how to prepare a sample for one or more of the assessments disclosed herein for the biomarkers to be detected.

Example 1

Primary Biomarker Screening

Pooled synovial fluid samples obtained from individuals previously diagnosed and confirmed to have osteoarthritis (e.g., OA having KL 1, 2, 3, or 4), rheumatoid arthritis (RA), injury/trauma (T/1), crystalline arthritis (MSU or CPP crystals; collectively referred to as CA), native septic arthritis (NSA), aseptic (confirmed to not have infection), periprosthetic joint infection (PJI), and normal individuals (controls), at multiple dilutions, were screened on quantitative assays run on Luminex® (Luminex Corp.) or by ELISA. Primary screening is shown in FIGS. 50A-50G. Samples were pooled to detect biomarkers that might be present at low concentrations in individual samples, such as cytokines. Luminex® (Luminex Corp.) assays were typically multiplexed assays allowing large panels of markers to be screened in a short amount of time with only small amounts of sample, with sensitivities typically in picograms ($10^{-12}$ grams) per milliliter. Once biomarkers were identified in the primary screening, a large number individual samples (rather than pools) were screened to identify biomarkers, or combinations of biomarkers, for discrimination of early from late stage osteoarthritis.

One of the key aspects to successful completion of a project to distinguish late stage osteoarthritis from early stage (stages 0/1) is the acquisition of a set of well characterized samples. Individuals with late stage (stage 4) osteoarthritis tend to be much older and control age matched samples, with no disease at all, are rare. We addressed that by using approximate age matched samples with conditions other than osteoarthritis as the primary complaint. Synovial fluid samples were obtained from individuals with osteoarthritis undergoing surgical procedures, typically total knee arthroplasty and synovial fluid from individuals diagnosed with rheumatoid arthritis (RA) or individuals presumed normal but suffering from joint trauma or injury. Screening studies were initially conducted on pooled samples of synovial fluid. Pools were made of 14 samples of known OA, 10 samples of known RA, and 15 samples of known trauma/injury. These same pools were used both for identification of proteins of relative abundance by 2D-DIGE, followed by mass spectroscopy, as well as screening in multiplexed and single assays. In all 52 samples from late stage OA (mean age 69); 22 samples from rheumatoid arthritis (mean age 72); and 35 samples from trauma/injury (mean age 60) were analysed. Given the age of the donors, it is quite likely that many of the individuals in the RA and trauma/injury may have early (or even late stage) osteoarthritis as a comorbidity. It should be apparent that using these groups as controls will tend to make the selection of biomarkers and cutoffs significantly more stringent than using controls from young adults. All samples were stored frozen (−80° C.) prior to analysis. For immune-biomarker studies, but not the 2-D gels, thawed samples were treated with hyaluronidase to reduce the viscosity of the synovial fluid, filtered through a 0.2 µm membrane and diluted in an appropriate assay buffer prior to testing.

Markers selected for screening by Luminex® were ones that were anticipated to be present at concentrations below 1 microgram per milliliter (mL) (i.e., low abundance). These were markers, often signaling molecules, that could be related to the disease process including proinflammatory and anti-inflammatory cytokines, soluble cytokine receptors, factors involved in bone remodeling and metabolism, enzymes related to the breakdown of the extracellular matrix (matrix metalloproteinases), inhibitors of these enzymes, and complexes of these enzymes with other molecules. Luminex® assays are typically multiplexed, that is many markers can be run simultaneously on the same sample with very sensitive results. This is a critical feature as well characterized samples are often quite precious. Samples for primary screening were pools from OA, RA, and trauma/ injury, all from native joints. Additionally, we ran the periprosthetic joint infection (infection of a prosthetic joint or PJI) and aseptic pools as a reference. A total of 85 different biomarkers were run on these pools and those distinguishing OA are:

Cytokine Panel (Source: EMD Human Cytokine 41): EGF, FGF-2, eotaxin, TGF-α, G-CSF, Flt-3L, GM-CSF, fractalkine, IFNα2, (IFNγ, GRO, IL-10, MCP-3, IL-12 P40, MDC, IL-12 P70, IL-13, IL-15, sCD40L, IL-17A, IL-1RA, IL-1α, IL-9, IL-1β, IL-2, IL-3, IL-4, IL-5, IL-6, IL-7, IL-8, IP-10, MCP-1, MIP-1α, MIP-1β, TNFα, TNFβ, VEGF, PDGF-AA, PGGF-AB/BB, RANTES Soluble cytokine receptors (Source EMD: Soluble Cytokine Receptor): sCD30, sEGFR, sgp130, sIL-1R1, sIL-1RII, sIL-4R, sIL-6R, sRAGE, sTNFR1, sTNF-RII, sVEGFR1, sVEGFR2, sVEGFR3

Bone Metabolism Panel (Source: EMD Bone Metabolism: ACTH, DKK1, IL-6, insulin, leptin, TNFα, OPG, OC, OPN, SOST, IL-1β, PTH, FGF23

RANKL (bone metabolism) (Source: EMD RANKL)

Matrix metalloproteinase panel 1 (Source: EMD Human MMP Panels 1 and 2): MMP-3, MMP-12, MMP-13, MMP-1, MMP-2, MMP-7, MMP-9, MMP10

Tissue inhibitors of Metalloproteinases (Source: EMD TIMP Panel): TIMP1, TIMP2, TIMP3, TIMP4

NGAL (metalloproteinase enhancement) (Source: EMD NGAL)

Complexes of metalloproteinase 9 with other molecules (Source: R&D Systems ELISAs): MMP-9/NGAL; MMP9/TIMP1; and COMP.

In primary screening, pools were run in duplicate at three different dilutions to establish which markers might distinguish OA from other diseases (RA, trauma/injury, NSA, PJI) as well as to establish the working range of the assay for native synovial fluids. While pools offer a way to quickly screen large numbers of biomarkers, there are disadvantages. Pools may contain outliers, which may skew the values, although with pools of ten or more this should be limited. Pools may also show apparent differences between groups, when individual analysis will show great amounts of overlap between the groups. We used criteria that the separation between OA and the other groups (RA, injury/trauma, PJI, aseptic, controls) should be at least several fold, e.g., 2-fold and typically greater than 5-fold, to have the potential for individual analyses to show good sensitivity and specificity. Primary screening identified both the biomarkers to take forward into secondary screening as well as the dilutions to use for each assay in secondary screening to be within the range of the assay.

OA pools from late or end stage OA (stage KL 4) patients consistently showed no elevations in inflammatory cytokines and soluble cytokine receptors. Indeed, the values were typically the same as the other native joint groups. OA showed values lower than RA and/or trauma/injury for 17 cytokines, values roughly equal to the other native joint groups for 13 markers and undetectable levels for all groups for 11 of the markers. Values for individual assays are shown in FIGS. 50A-50G.

For soluble cytokine receptors, which typically serve as surrogate markers for cytokine activity, 11 markers showed somewhat (typically 2-fold) lower values for OA than for RA and/or trauma/injury, with 2 markers showing approximately equal values. Results for selected markers IL-6, IL-8, PDGF AB/BB, and RANTES and soluble cytokine markers TNFRII and VEGFR2 are shown in FIGS. 8A-8F. Matrix metalloproteinases (MMPs) are zinc dependent proteases response for the breakdown of extracellular matrix. There are over 25 MMPs known, with Luminex®-based immunoassays available for 8 MMPs, along with assays for 5 other molecules that can complex with the metalloproteinases (e.g., tissue inhibitors of metalloproteinases (TIMPs) and neutrophil gelatinase associated lipocalin (NGAL)). Additionally, ELISAs using commercially available antibodies (e.g., from R&D Systems, Minneapolis, MN) were run to detect complexes of MMP-9 with either TIMP or NGAL. Elevated levels of MMPs are often seen in inflammatory conditions and elevations can be driven by several factors, including inflammatory cytokines.

Figure 19A:
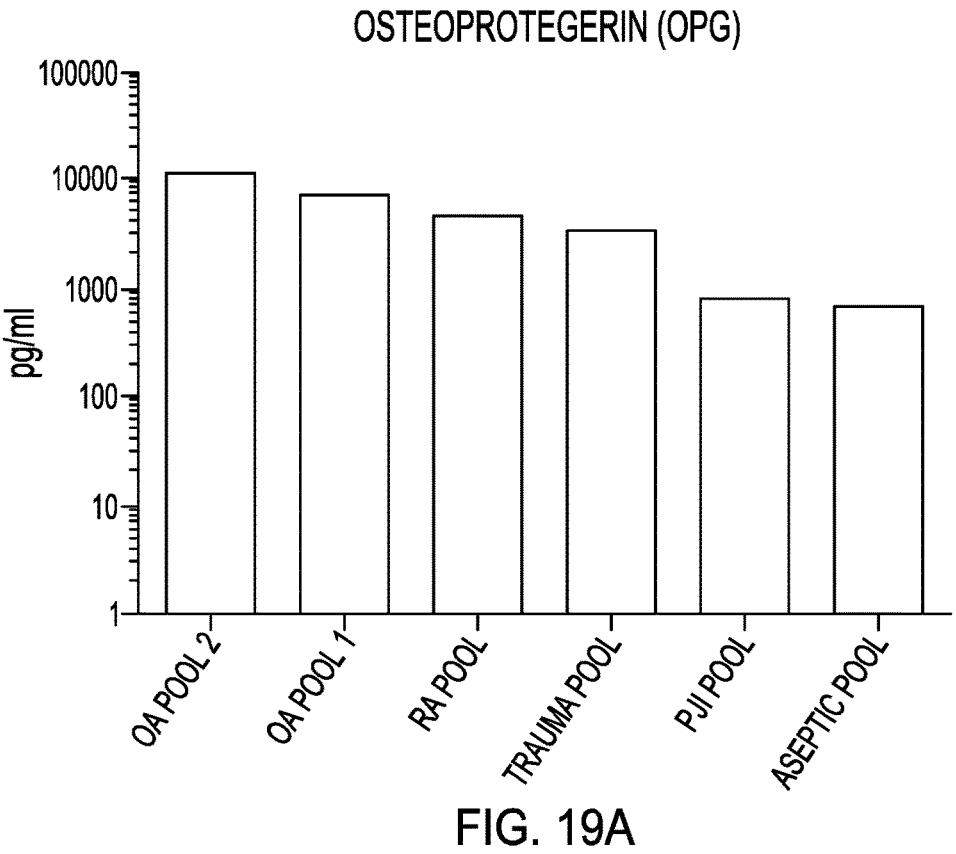
FIGS. 19A-19C illustrate bar graphs of biomarkers in pooled synovial fluid samples.
Figure 19B:
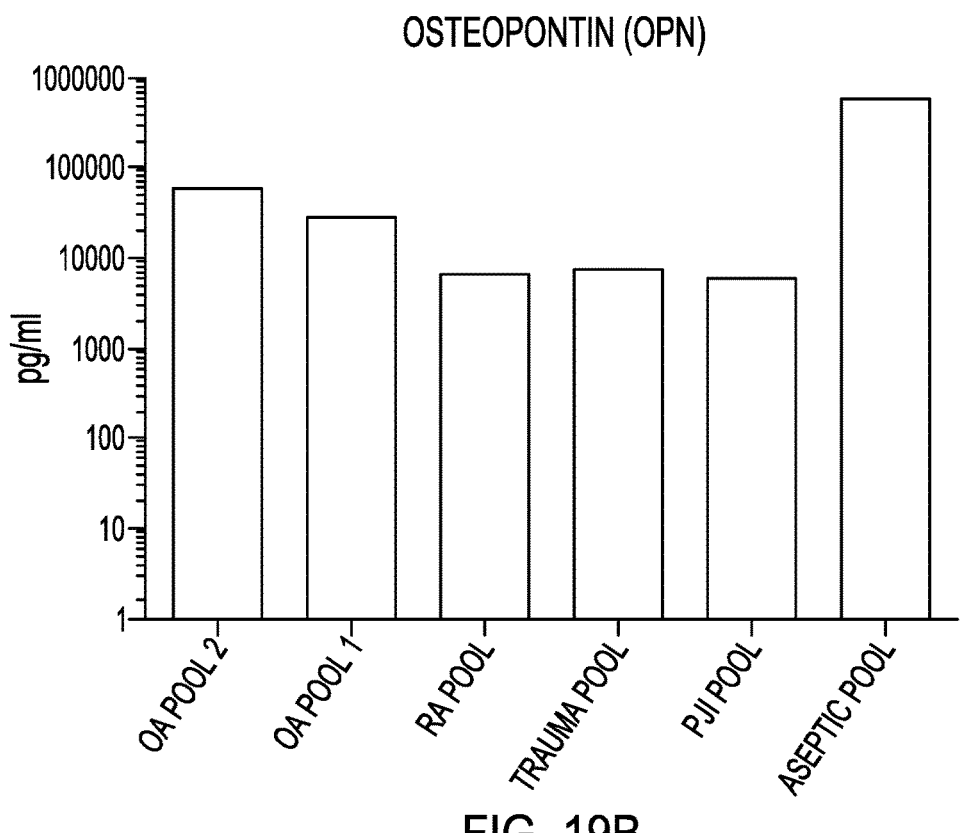
Figure 19C:
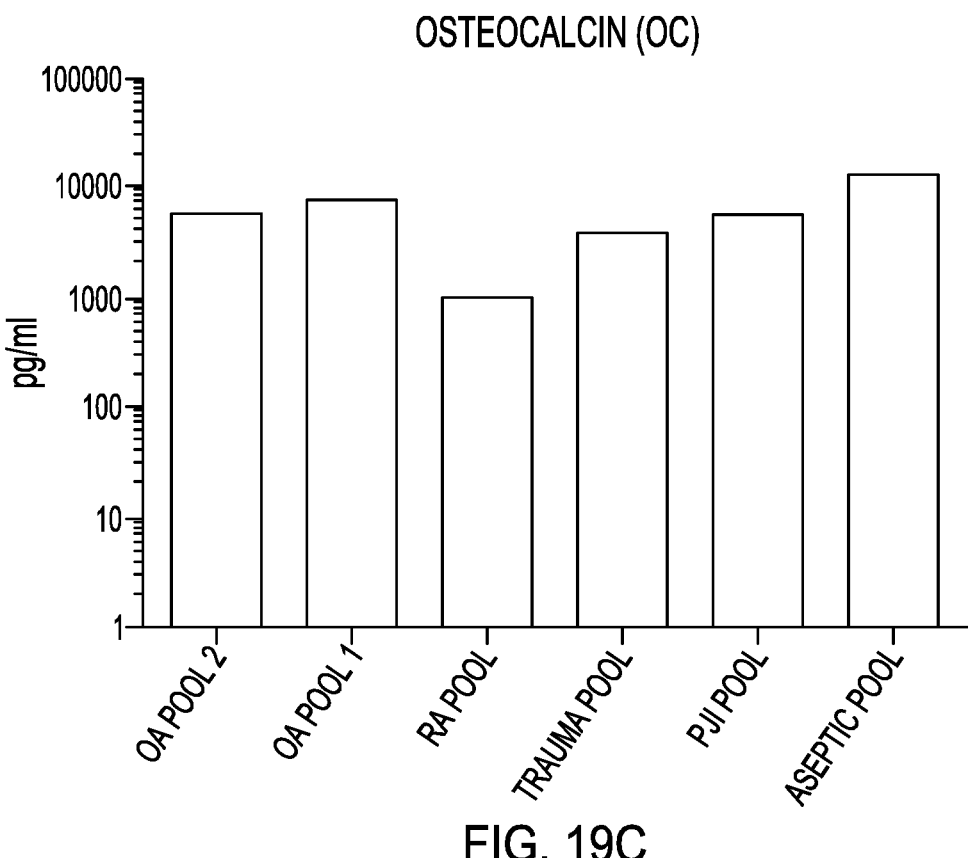

As shown in FIGS. 12A-12F and 18A-18F, synovial fluid sample pools consistently showed equal or lower values for the tested matrix metalloproteinases than the RA or trauma/injury pool. OA synovial fluid sample pools showed a slight increase in TIMP1. Biomarkers of bone metabolism might be expected to be altered in OA. Osteoprotegerin (OPG), produced by osteoblasts, B lymphocytes, stromal cells, and articular chondrocytes functions as a decoy receptor for the signaling molecule RANKL, which stimulates differentiation and growth of osteoclasts. Consistent with observations in the scientific literature, OPG is somewhat elevated in OA synovial fluid. It should be noted that while OPG is described in the literature as a biomarker for osteoarthritis, both in serum and synovial fluid, OPG also shows an increase with increasing age. The ligand for OPG, RANKL is not elevated. Osteocalcin (OC), a non-collagenous bone matrix protein produced by osteoblasts and frequently used as a biomarker of bone formation showed slight elevations as does Osteopontin (OPN), an extracellular highly negatively charged structural protein of bone, involved in bone mineralization. Values for these and other biomarkers of bone metabolism are found in FIGS. 50A-50G. Graphs for OPG, OPN, and OC are shown in FIGS. 19A-19C.

Other biomarkers suitable for distinguishing OA from inflammatory arthropathies (RA, NSA, PJI, CA, trauma/injury), include APRIL, BAFF, TRACP5a. Generally, as shown in Table 4 below, levels of APRI, BAFF and TRACP5a in pooled synovial fluid samples from inflammatory arthropathies (e.g., PJI, metal on metal (MOM), and aseptic) are at least 2-fold greater than levels of each of APRIL, BAFF and TRACP5a in synovial fluid levels of OA subjects.

TABLE 4

| Biomarkers Discriminate OA from Inflammatory Arthropathies | | | |
|---|---|---|---|
| Group ID | APRIL (pg/mL) | BAFF (pg/mL | TRACP5a (pg/mL) |
| OA Pool | 313 | 1051 | 2396 |
| Aseptic Pool | 682 | 1683 | 12906 |
| PJI Pool | 806 | 4516 | 7126 |
| MOM 20 | 777 | 2678 | 13993 |
| MOM 681 | 651 | 3560 | 5735 |
| MOM 1298 | 4322 | 4255 | 32676 |
| MOM 1145 | 2123 | 6509 | 35556 |
| MOM 842 | 1528 | 2633 | 35773 |

Nine biomarkers from this primary screening group showed sufficient distinction between the OA and other groups to take to a secondary screening of individual samples. Along with those biomarkers, levels of alpha defensin (AD), C-reactive protein (CRP), and Human neutrophil elastase (HNE) were tested in these individual samples. Alpha defensin and HNE are both performed as qualitative tests.

Example 2

Secondary Biomarker Screening

Figure 11A:
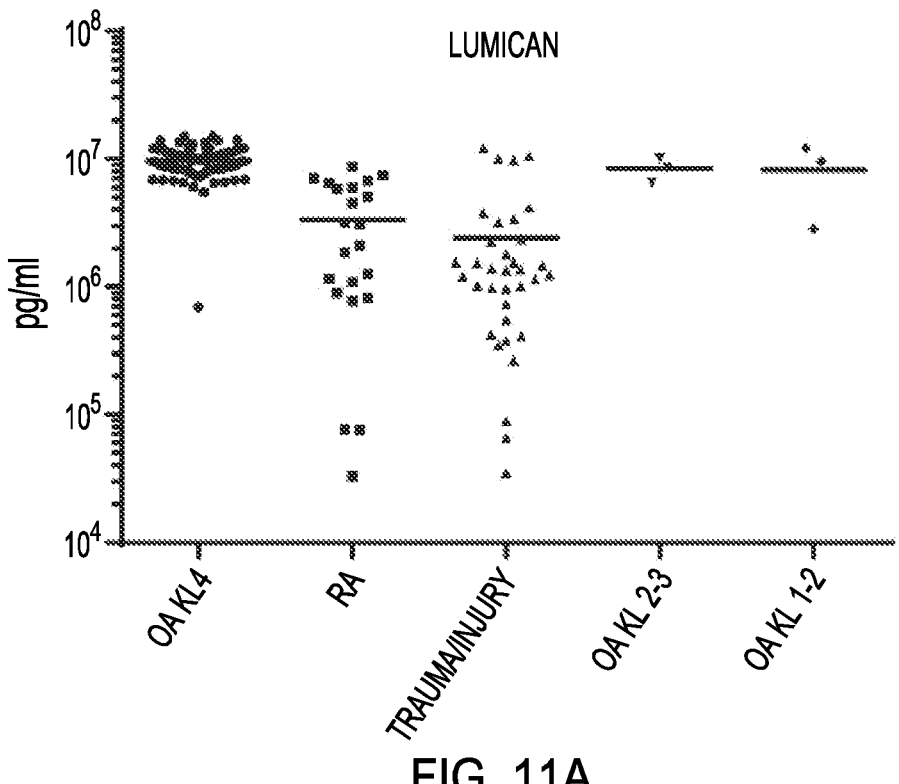
FIGS. 11A-11C illustrate plots of biomarkers in individual synovial fluid samples.
Figure 11B:
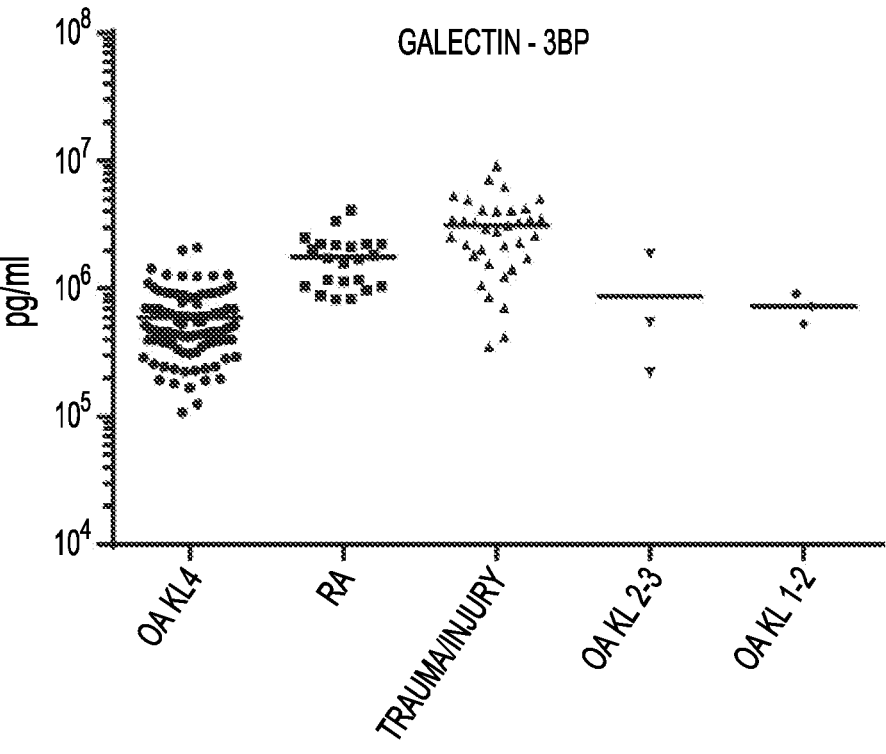
Figure 11C:
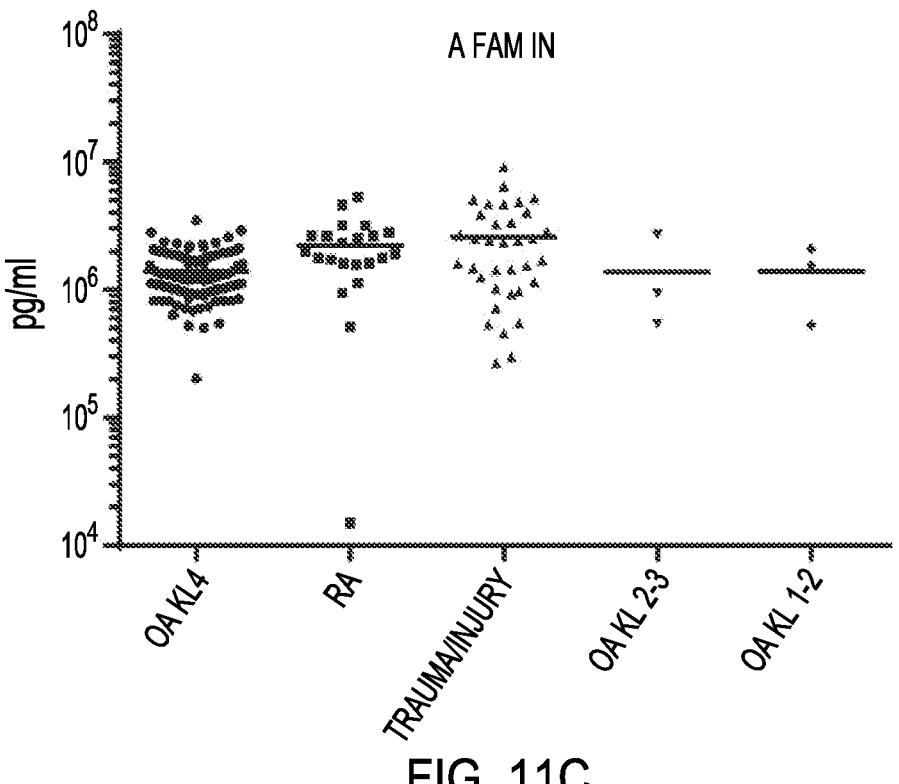
Figure 12A:
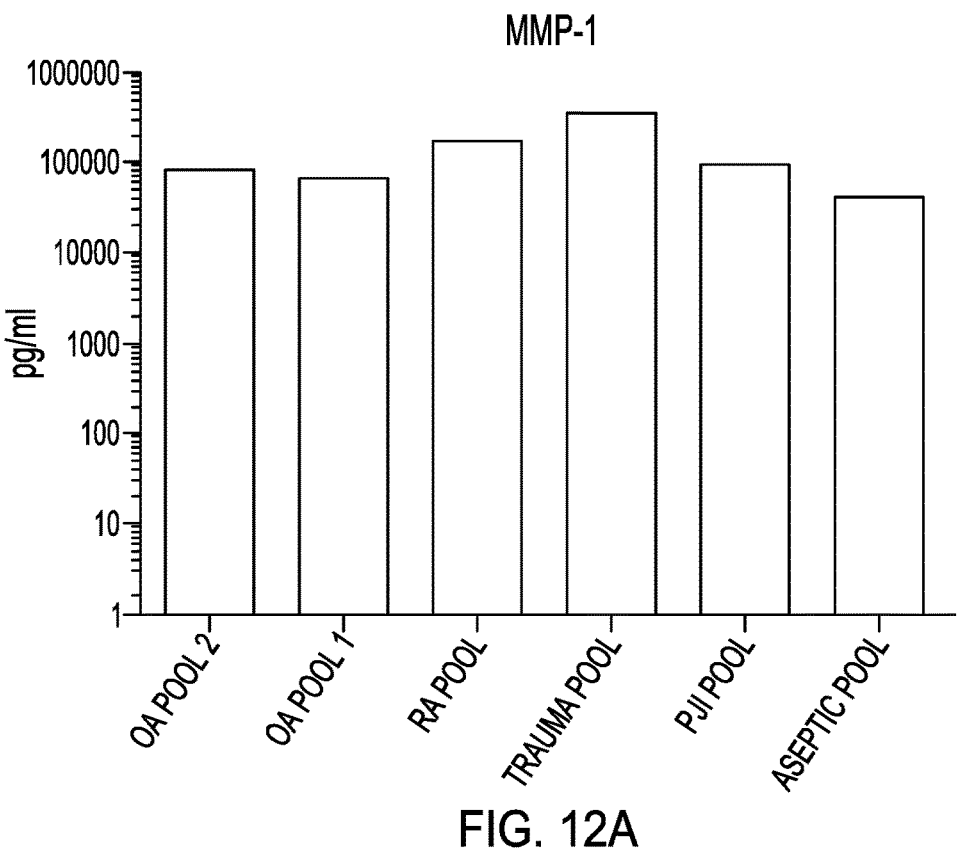
FIG. 12A-12F illustrate bar graphs of various biomarker in pooled synovial fluid samples.
Figure 12B:
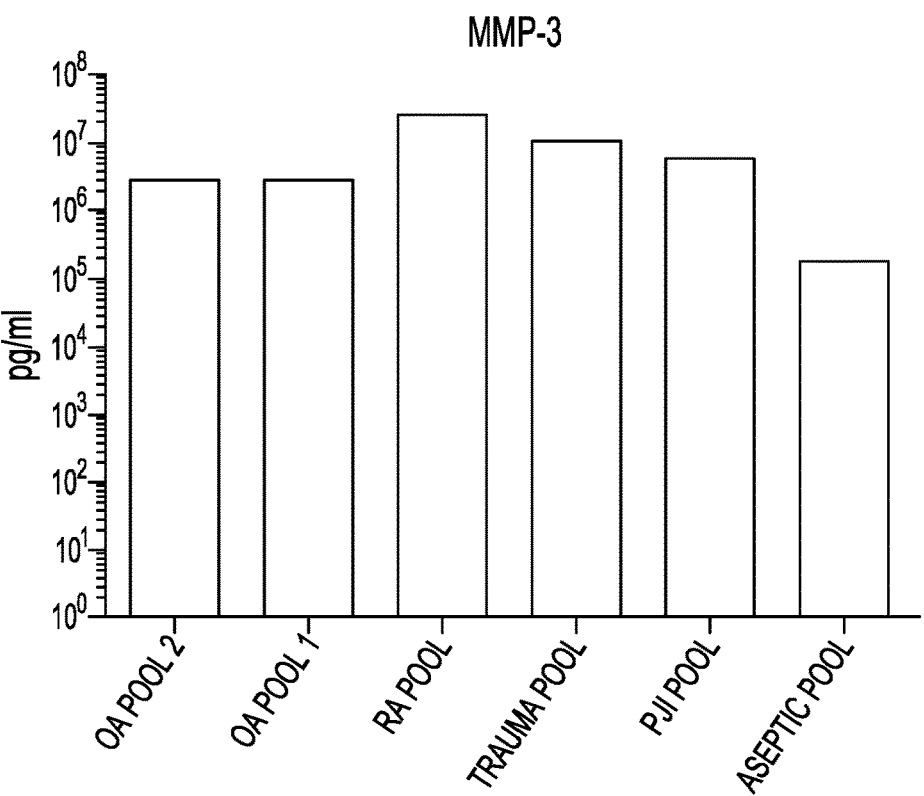
Figure 12C:
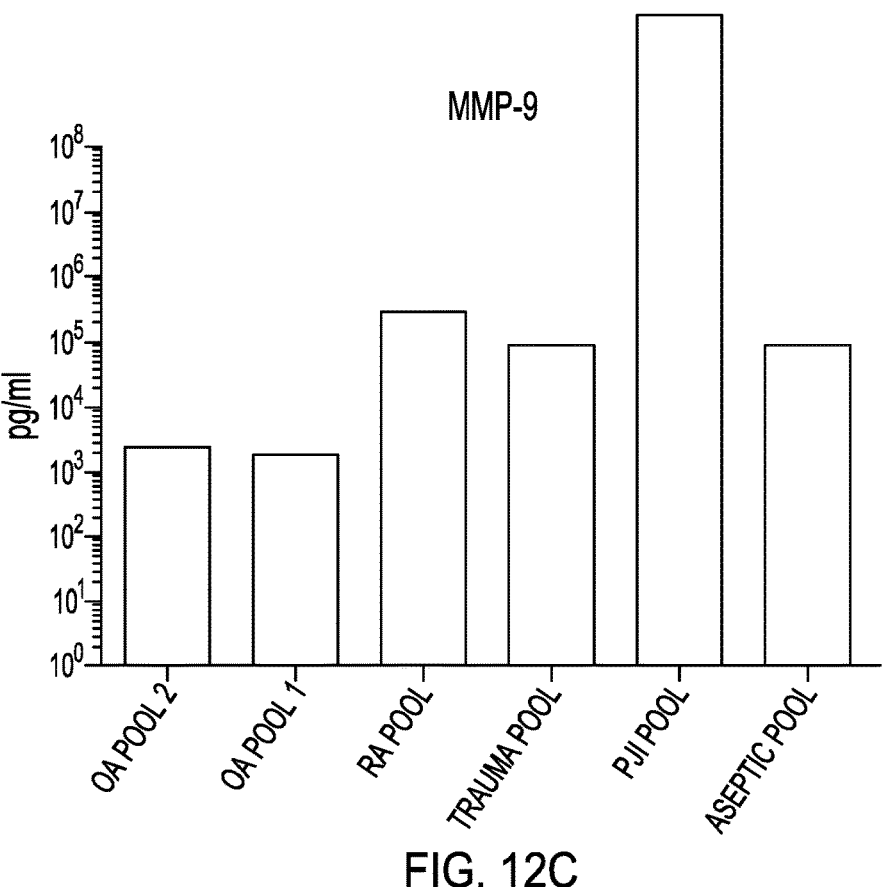
Figure 12D:
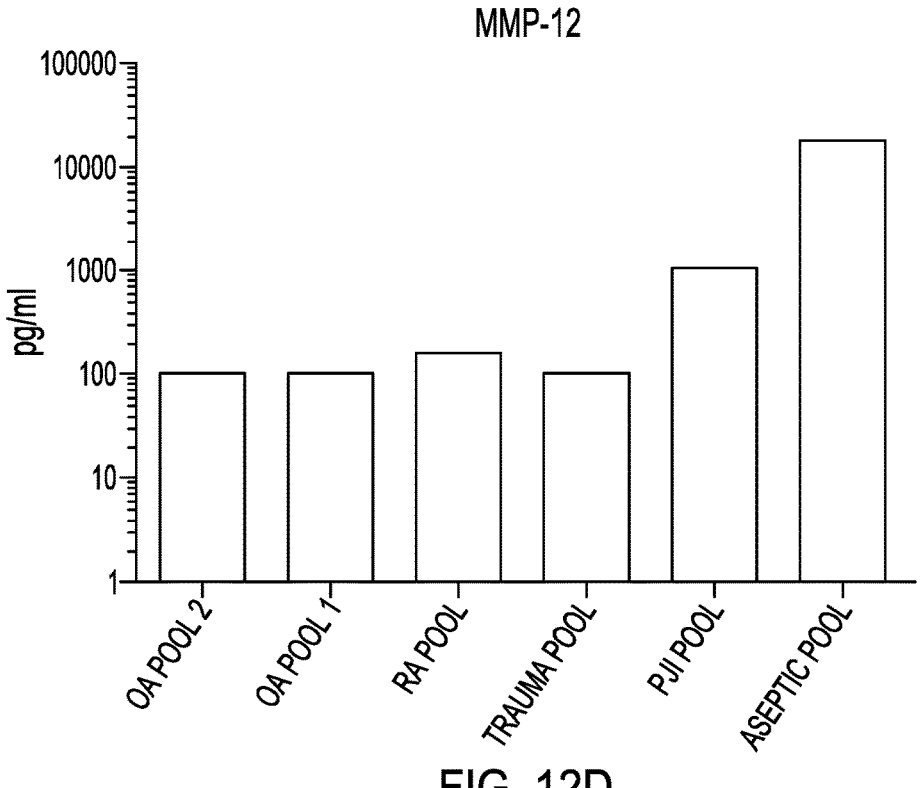
Figure 12E:
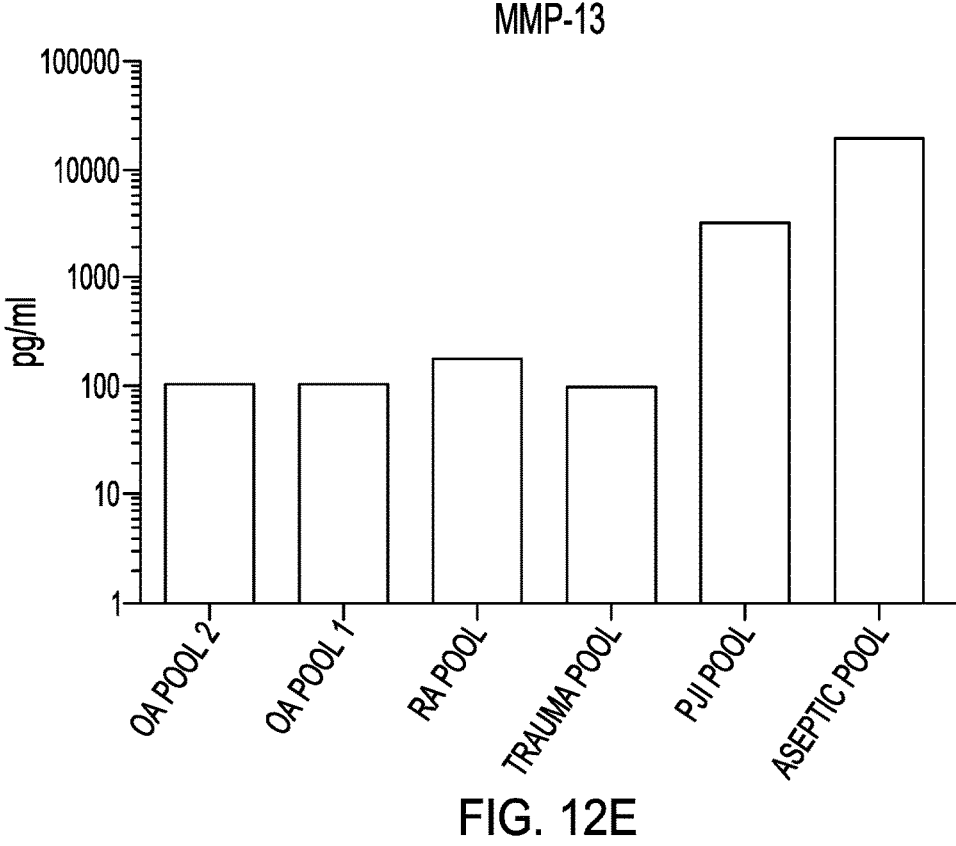
Figure 12F:
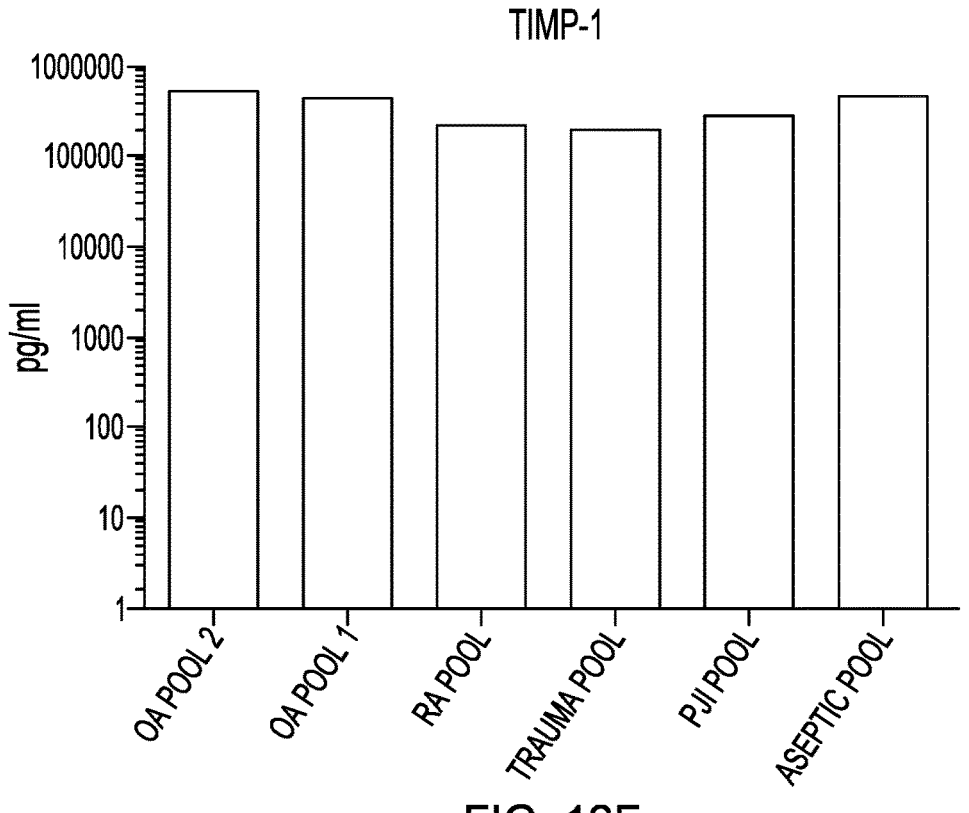
Figure 13A:
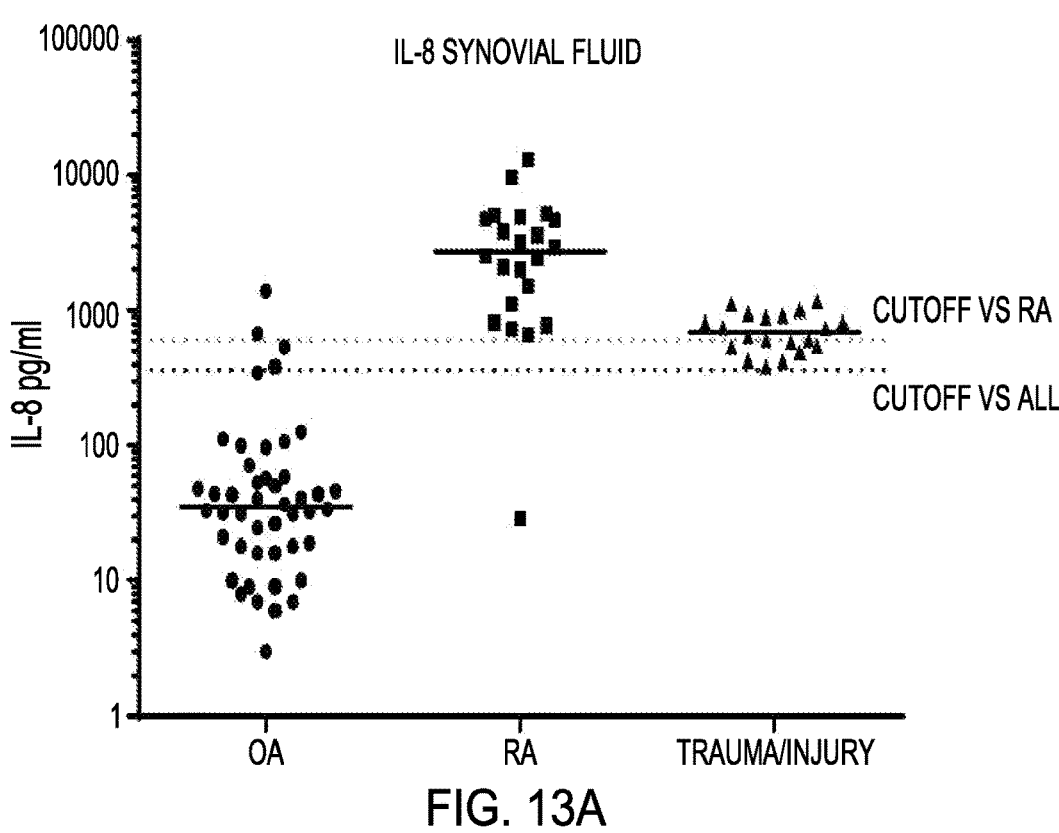
FIGS. 13A-13F illustrate plots of the level of various biomarkers in individual synovial fluid samples.
Figure 13B:
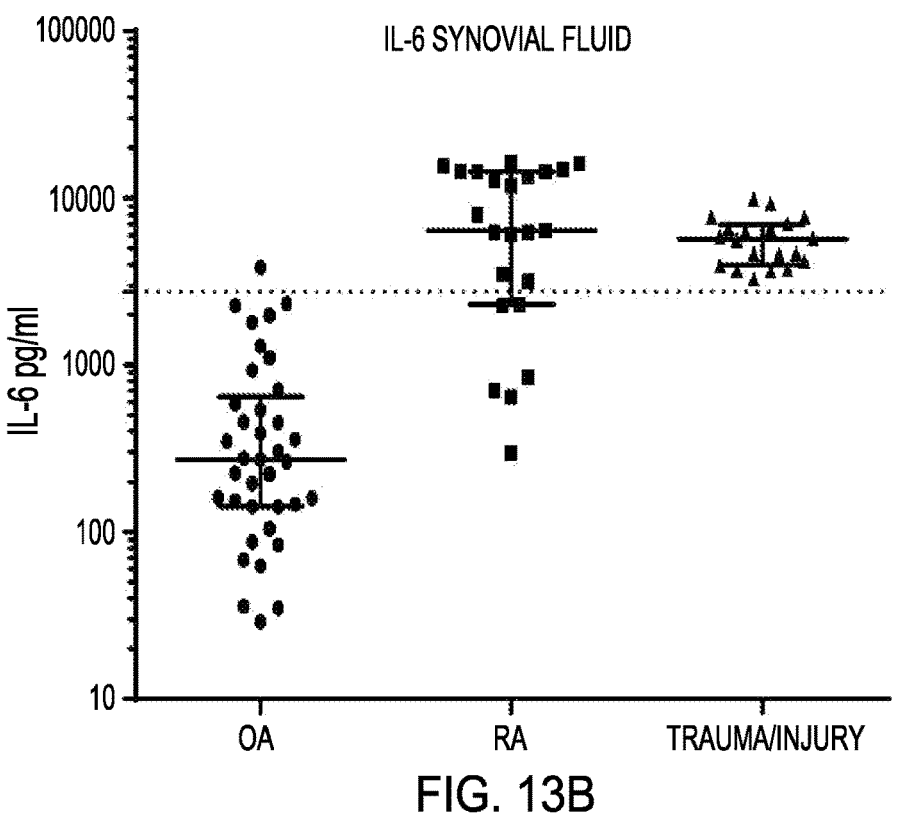
Figure 13C:
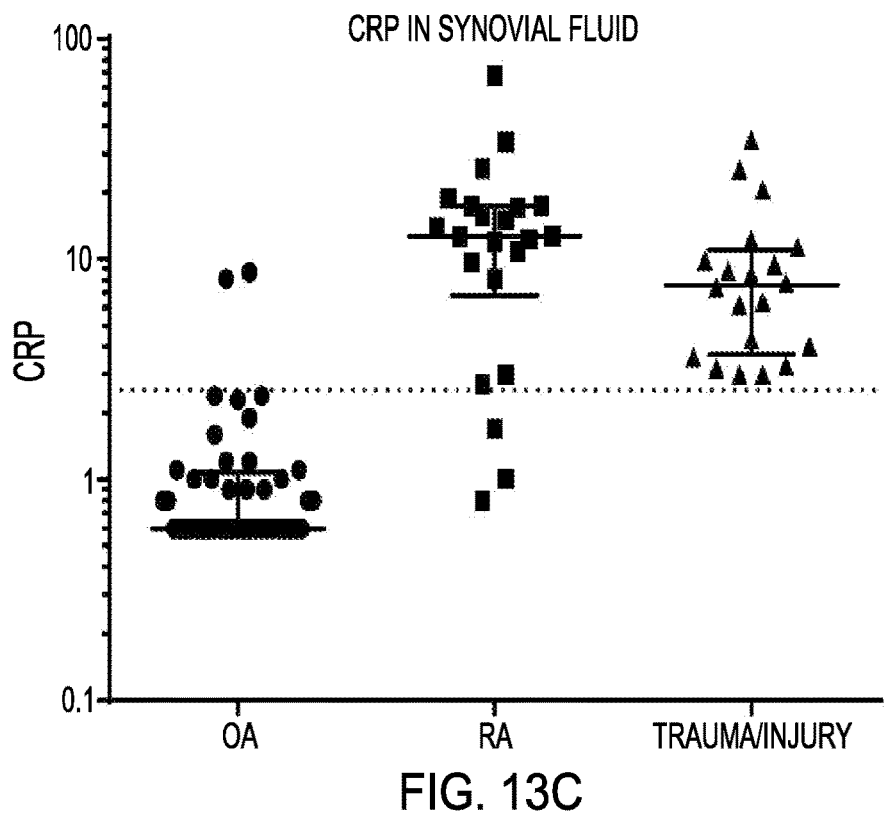
Figure 13D:
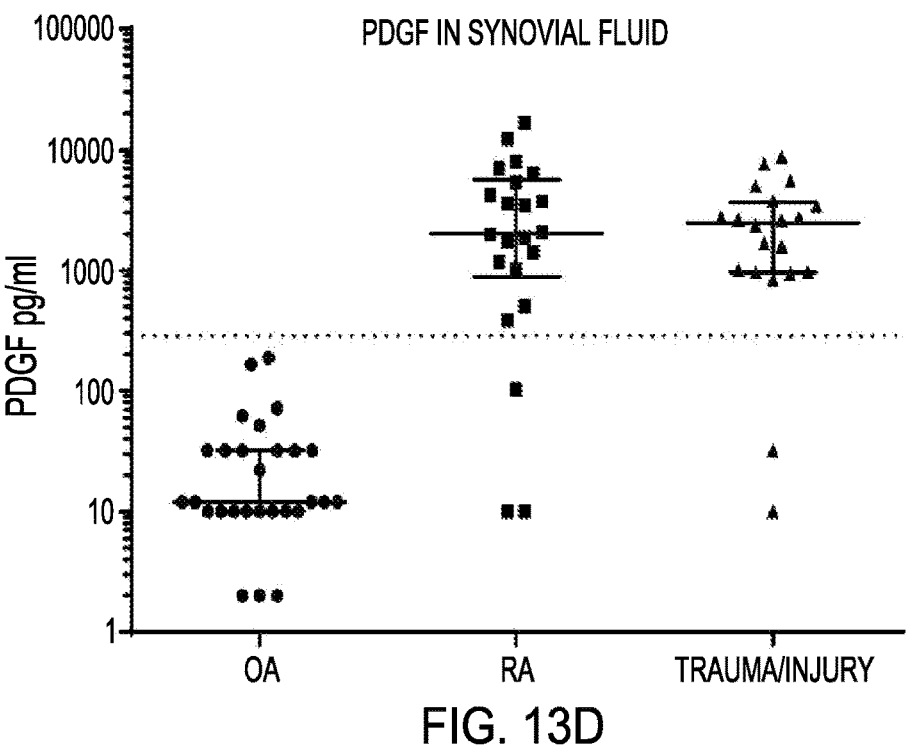
Figure 13E:
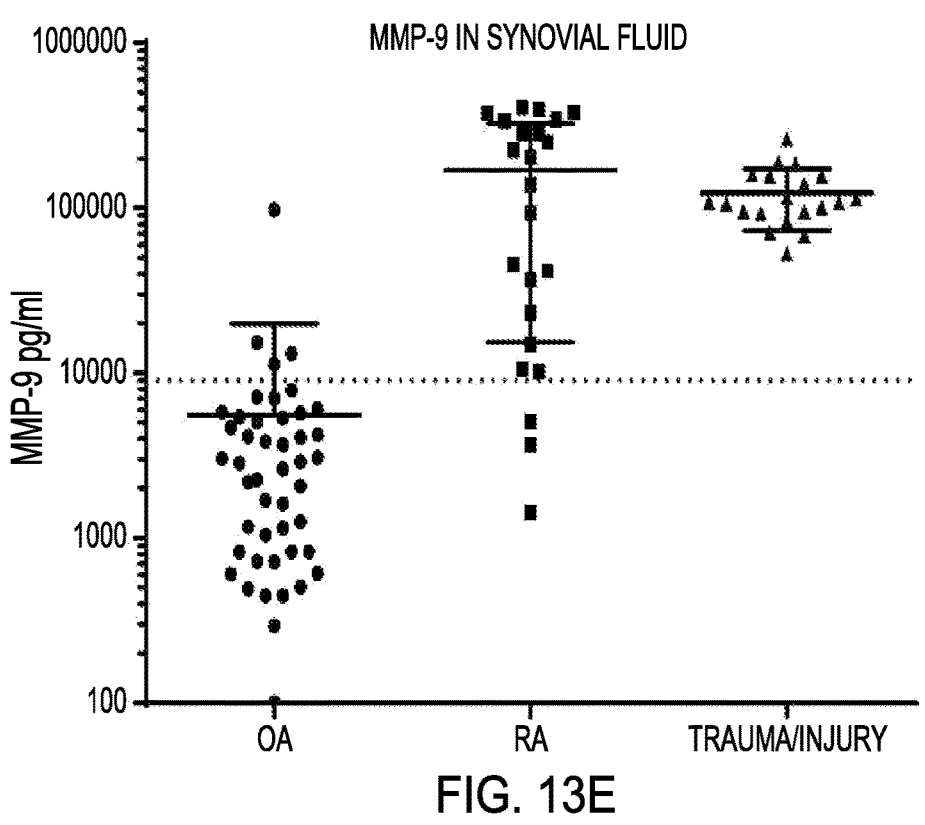
Figure 13F:
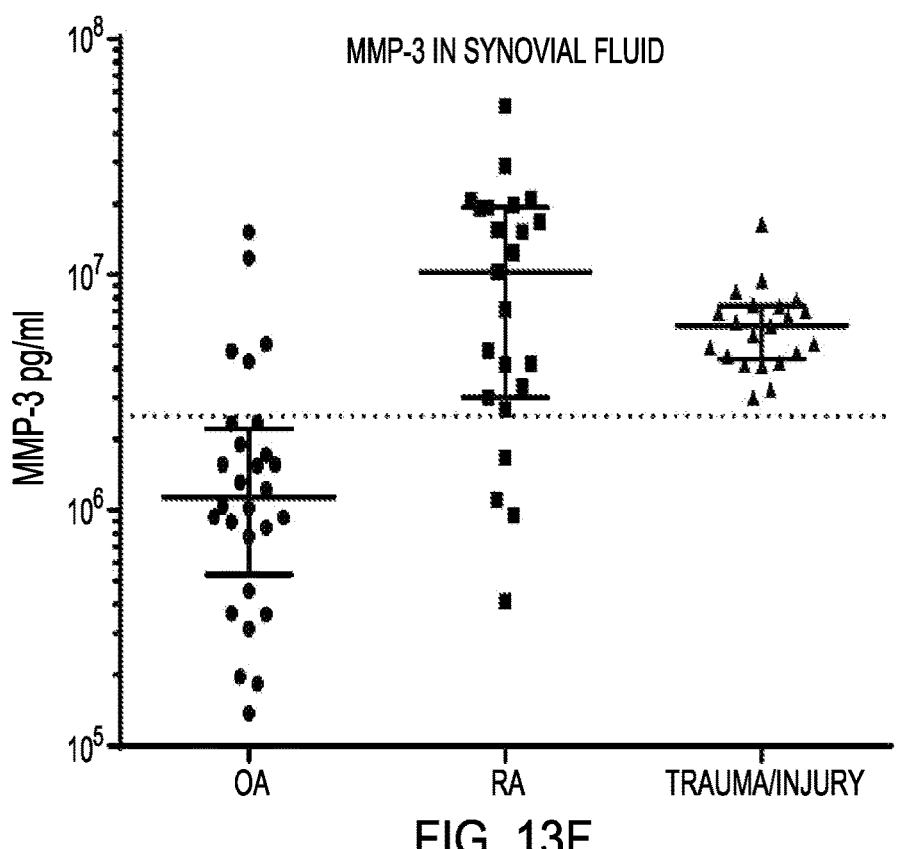
Figure 14A:
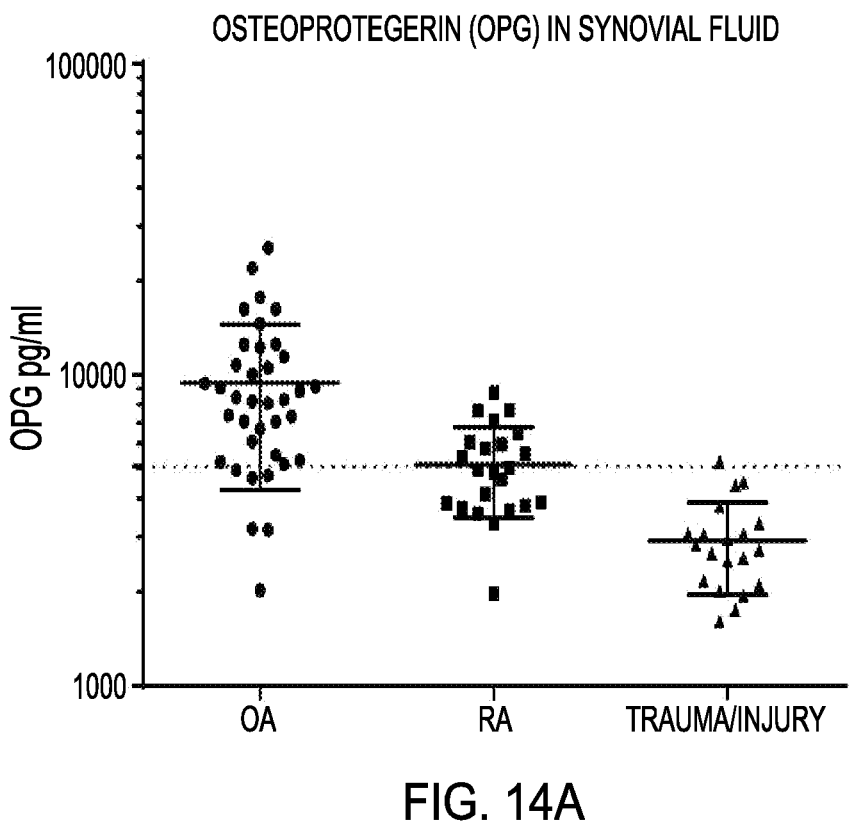
FIGS. 14A-14C illustrate plots biomarkers in individual synovial fluid samples.
Figure 14B:
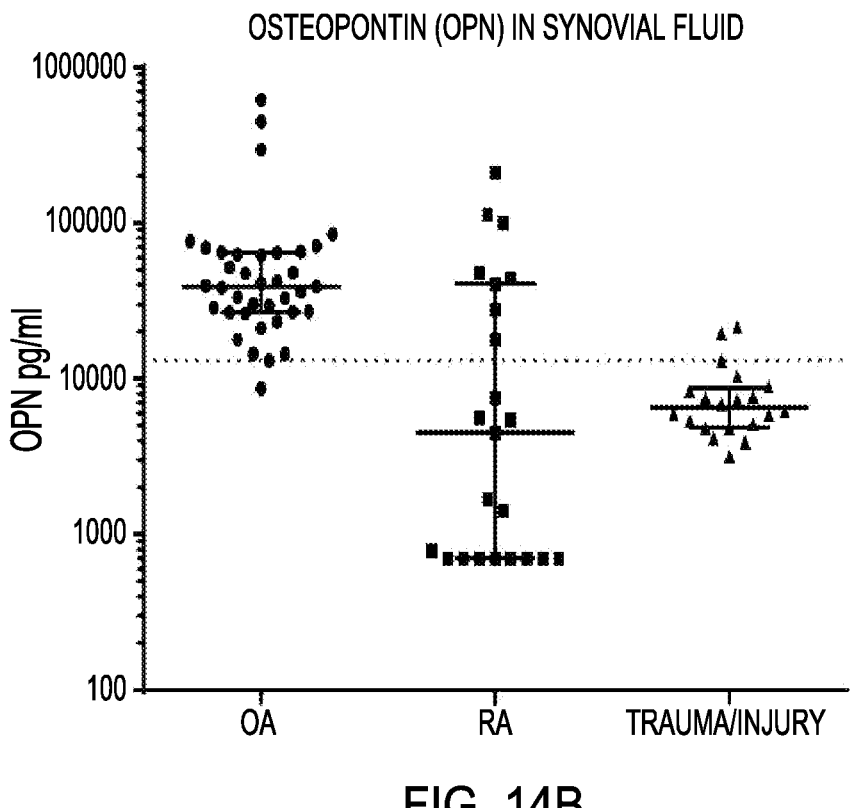
Figure 14C:
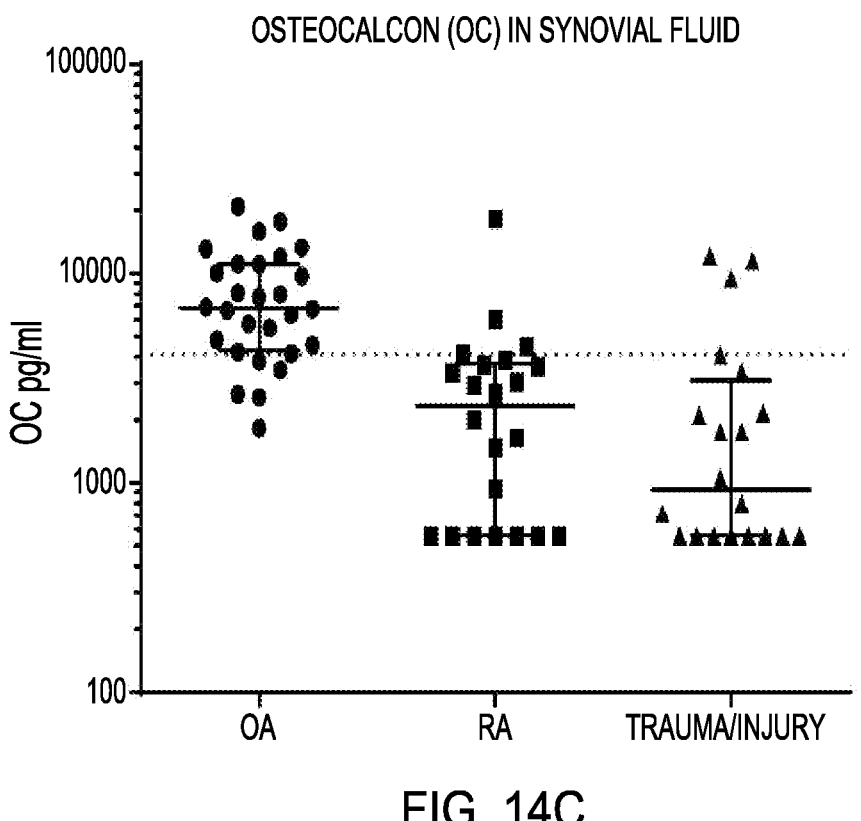
Figure 15A:
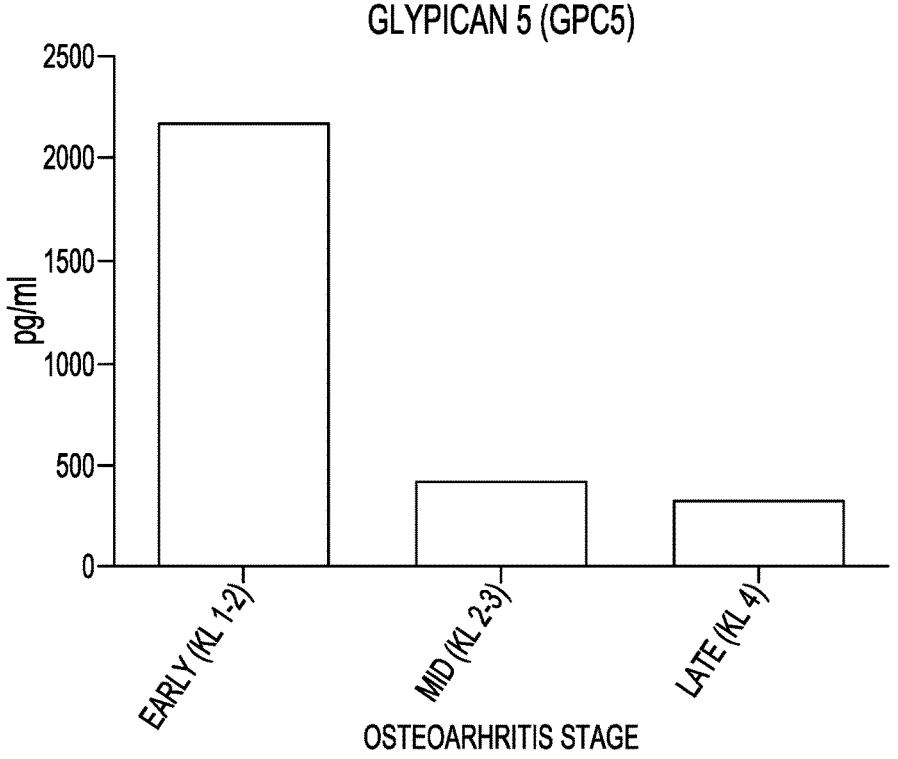
FIGS. 15A-15D illustrate bar graphs of biomarker in pooled synovial fluid samples with various stages of OA.
Figure 15B:
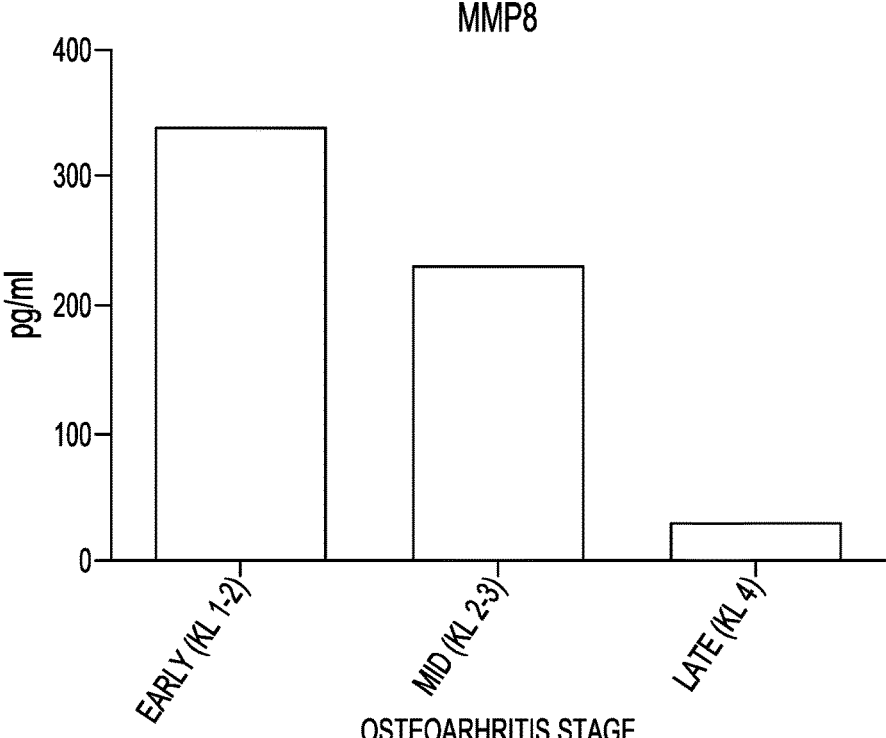
Figure 15C:
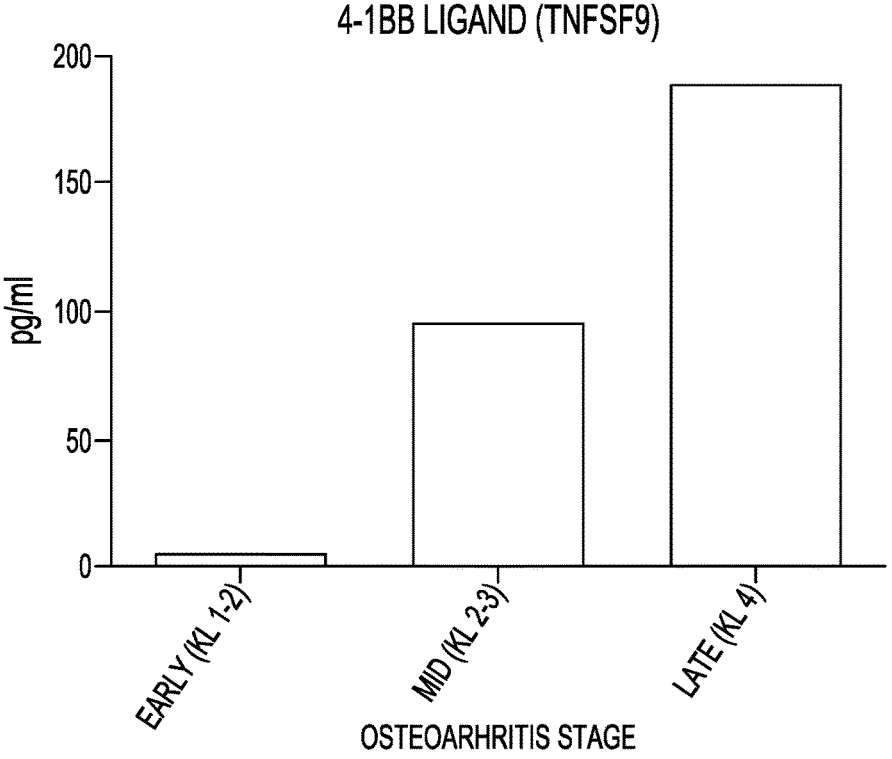
Figure 15D:
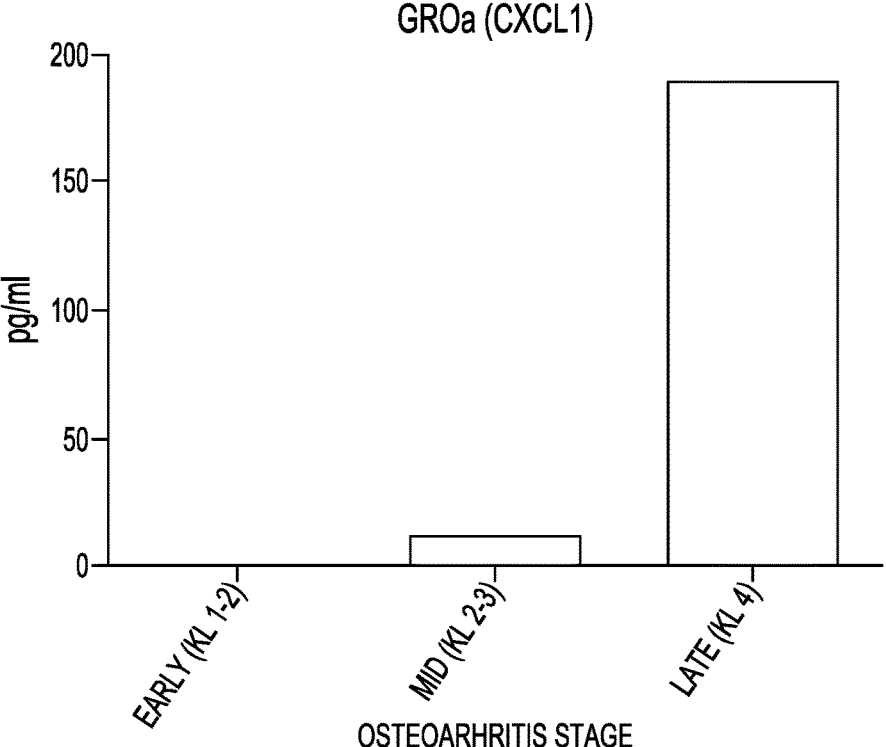
Figure 16A:
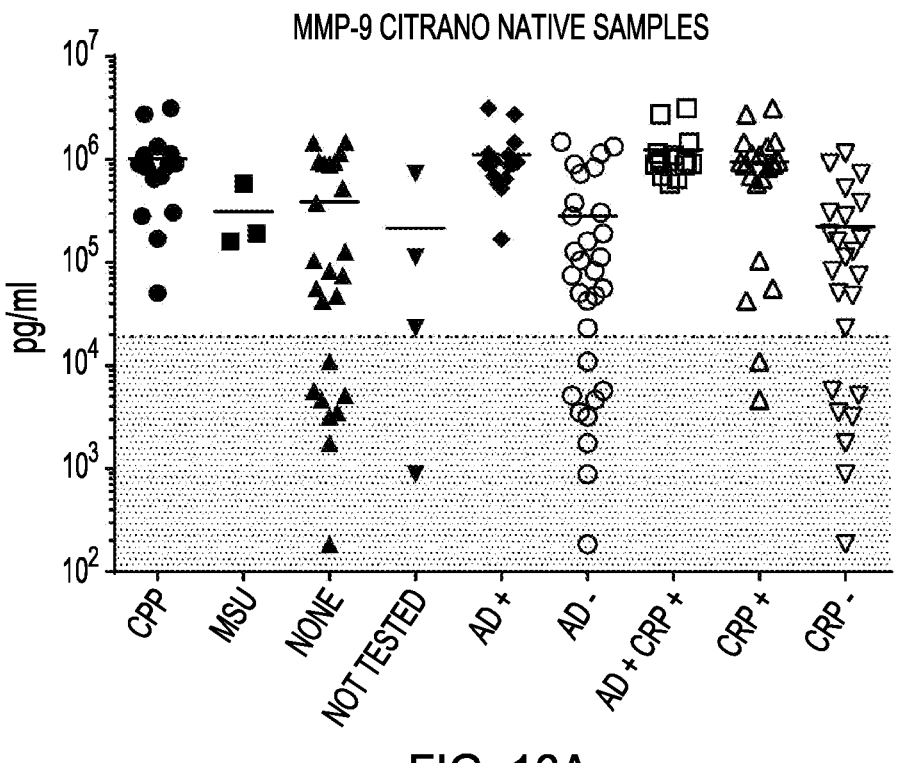
FIGS. 16A-16C illustrate plots of biomarkers in individual synovial fluid samples from native joints.
Figure 16B:
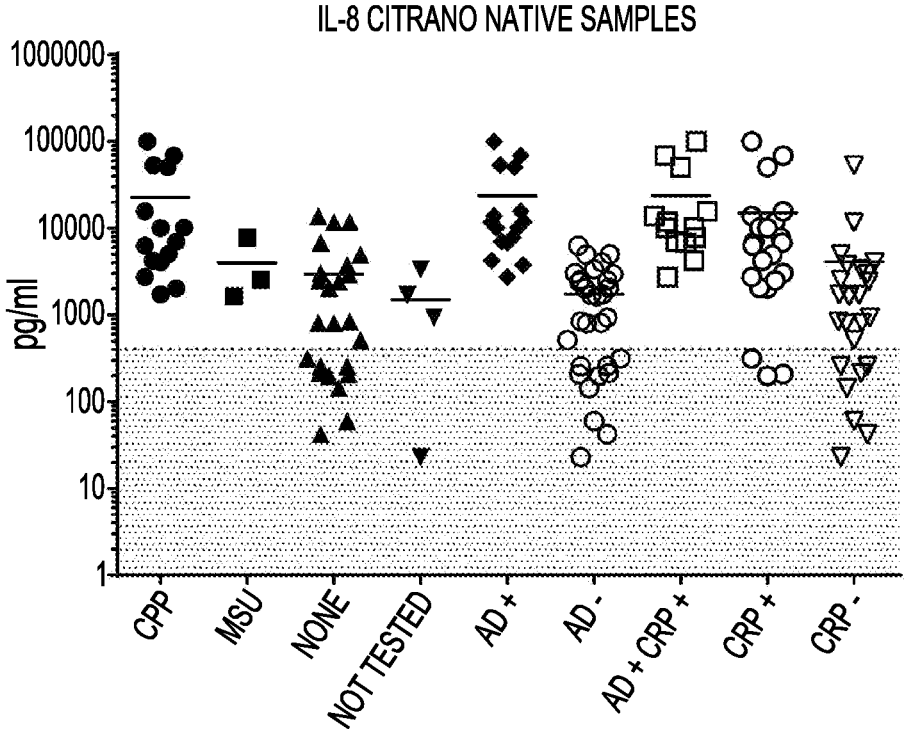
Figure 16C:
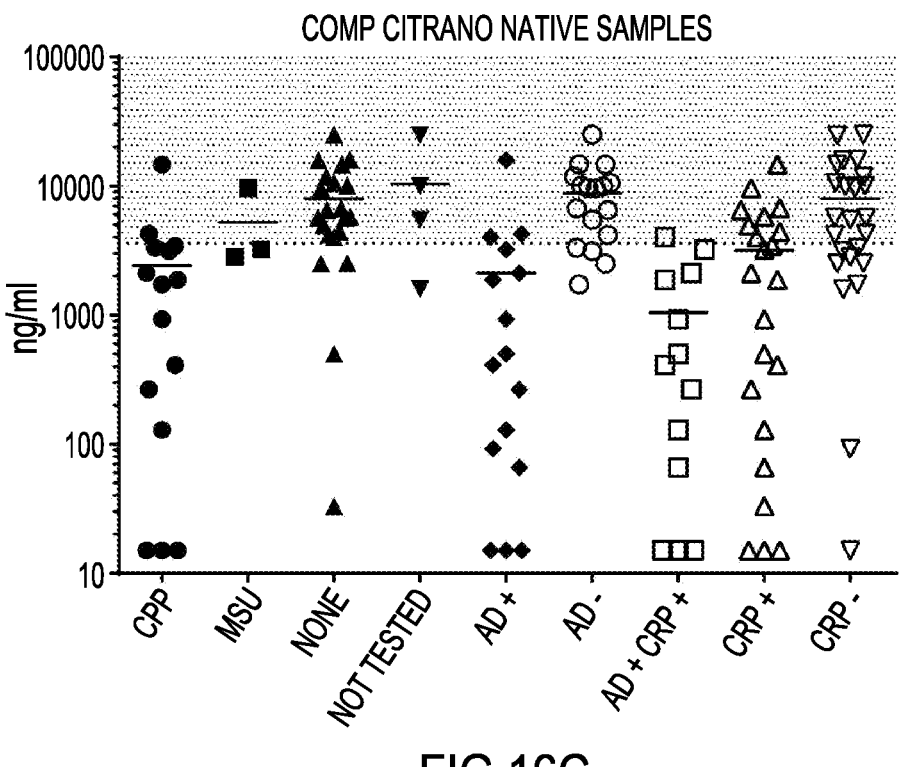
Figure 17A:
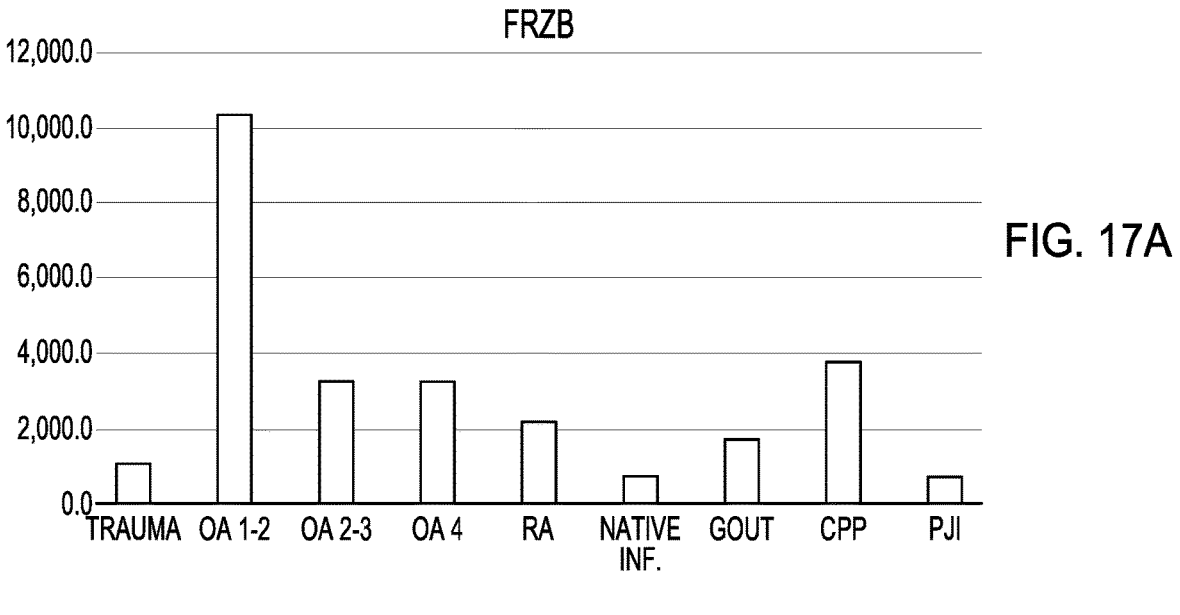
FIGS. 17A-17H illustrate plots of various biomarkers in pooled synovial fluid samples of RA, NSA, CA, and various stages of OA.
Figure 17B:
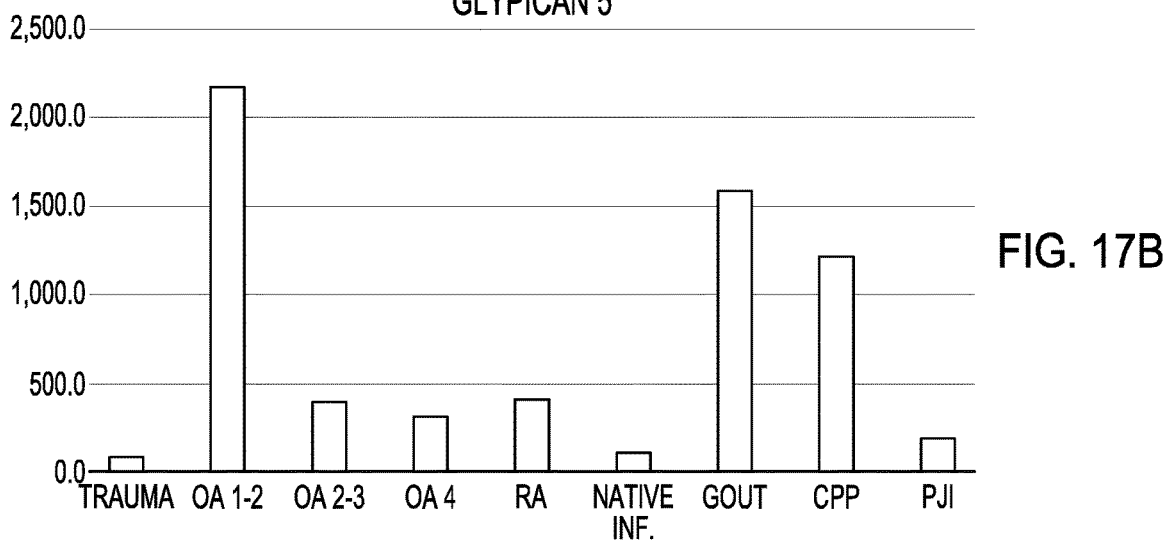
Figure 17C:
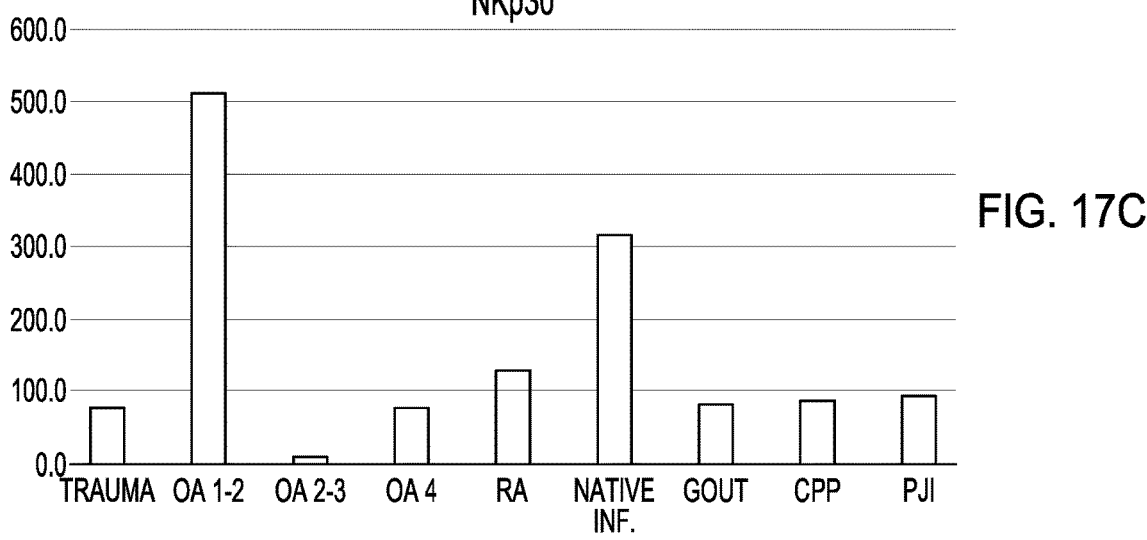
Figure 17D:
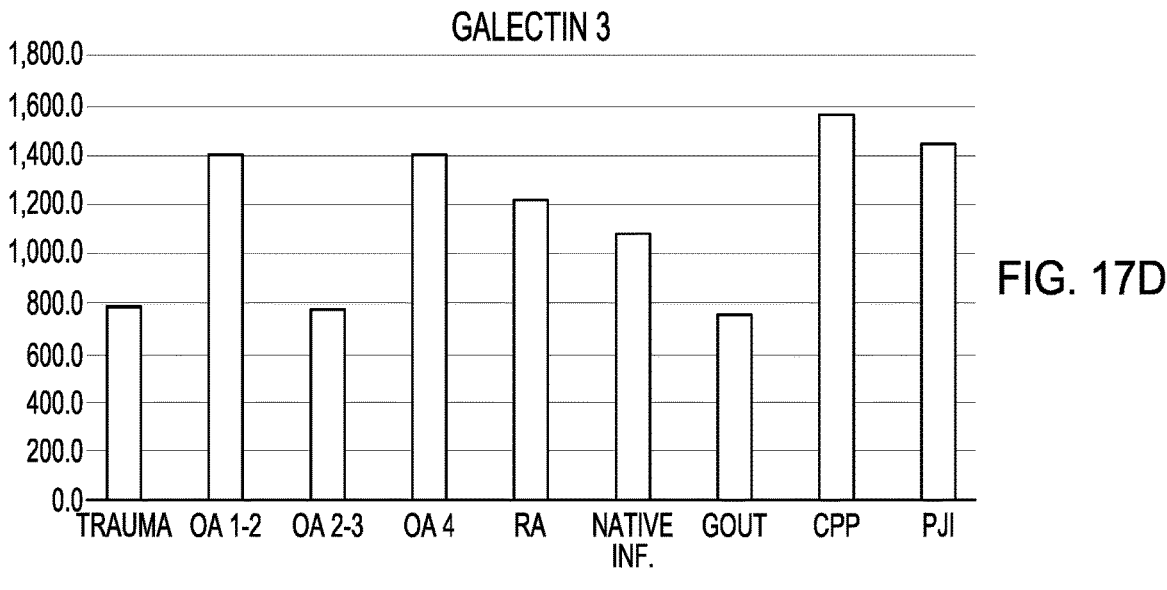
Figure 17E:
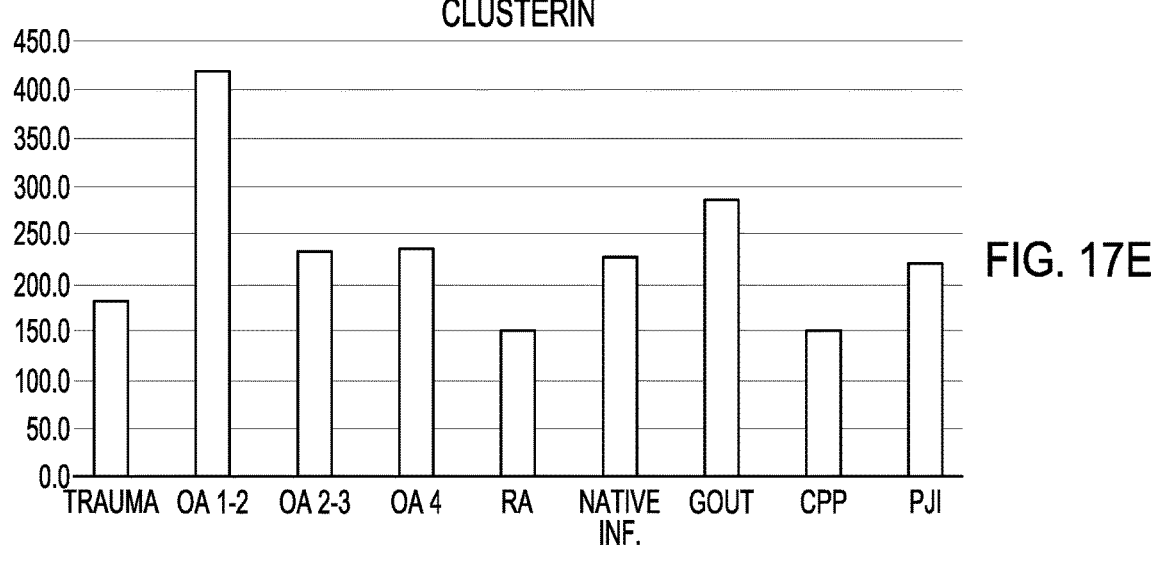
Figure 17F:
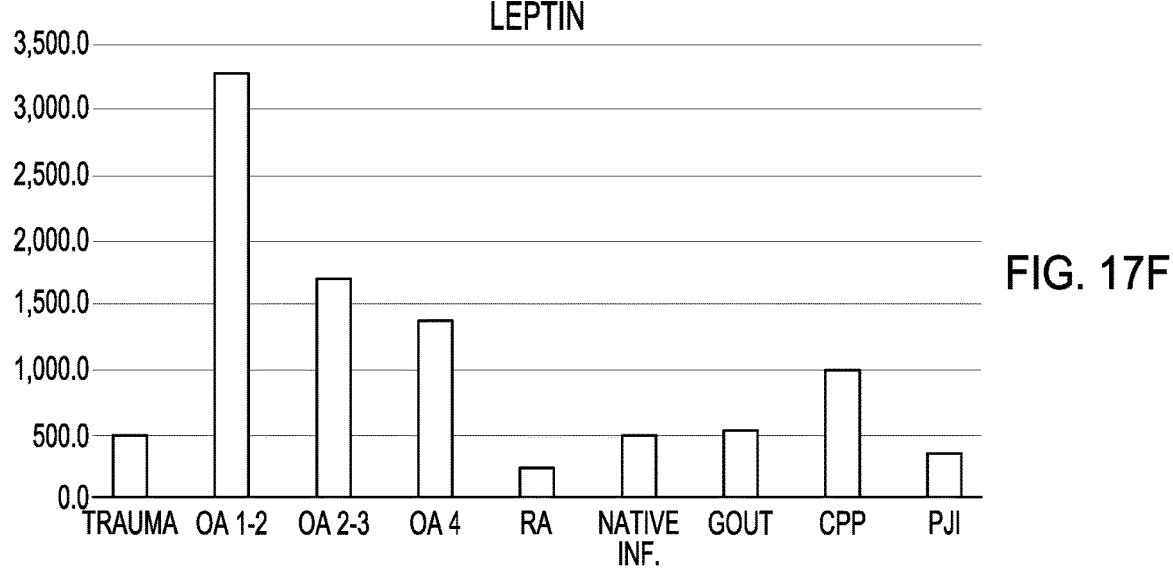
Figure 17G:
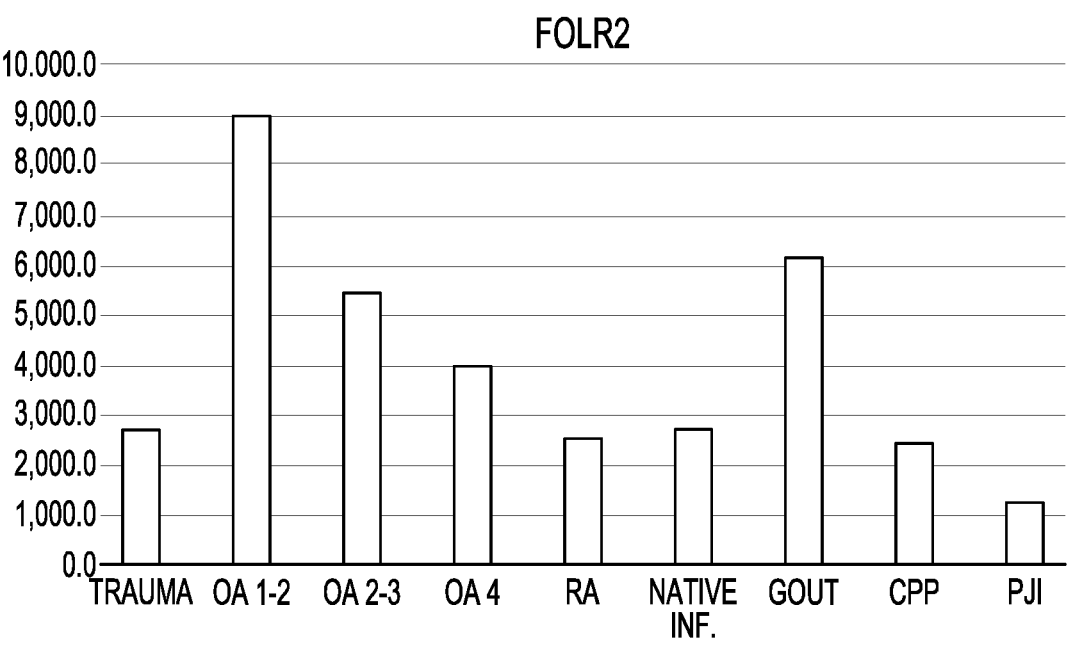
Figure 17H:
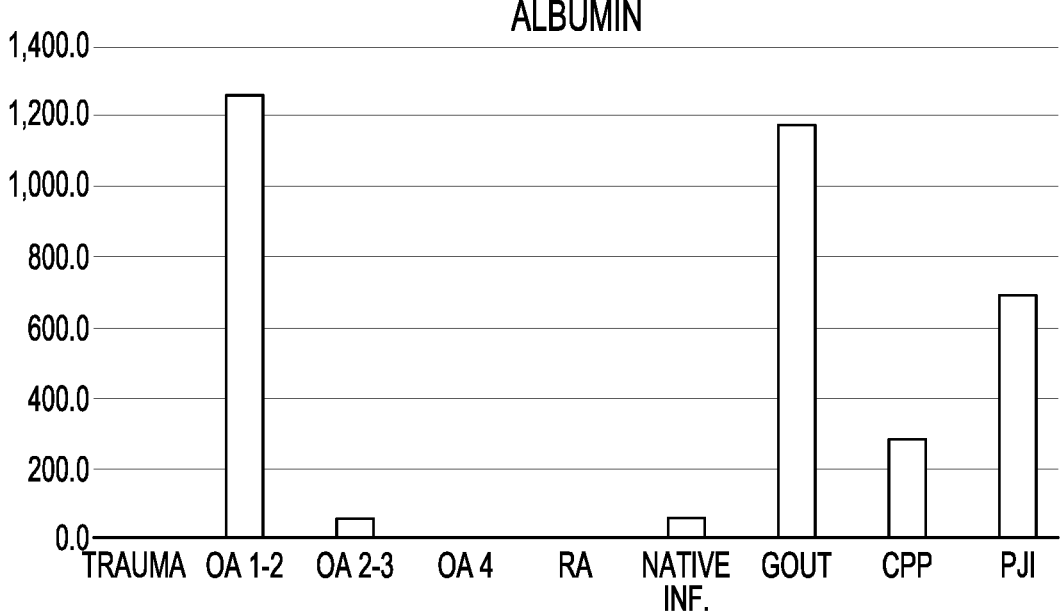
Figure 18A:
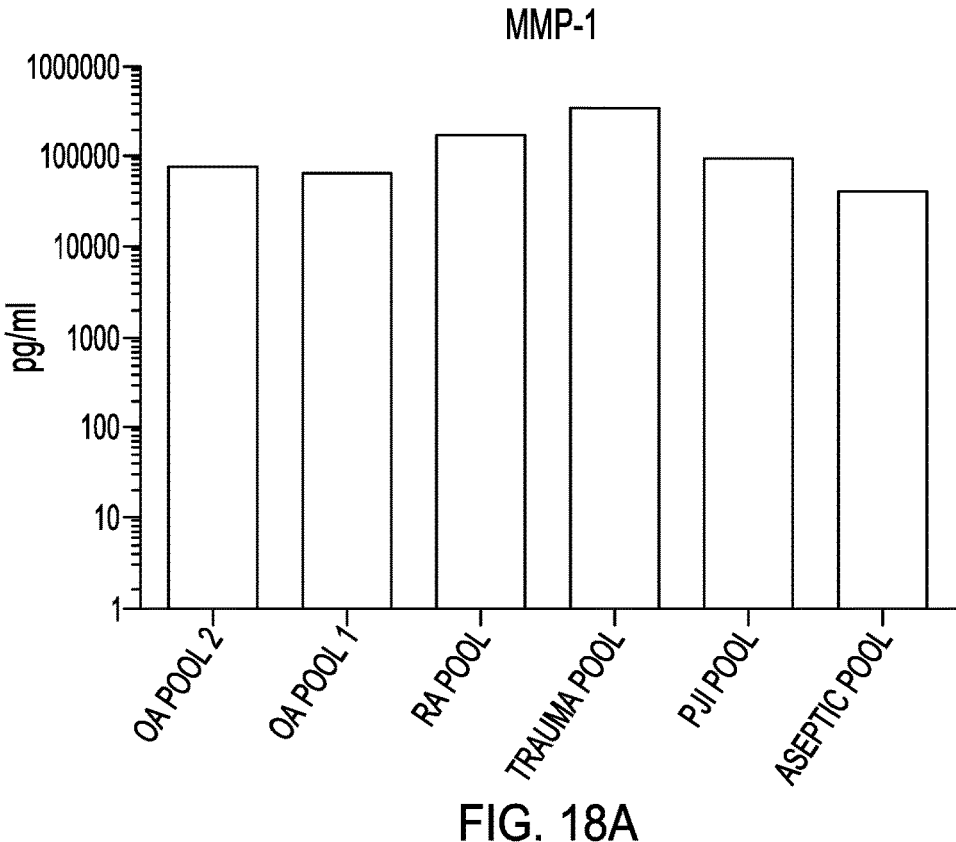
FIGS. 18A-18F illustrate bar graphs of various biomarkers in pooled synovial fluid sample.
Figure 18B:
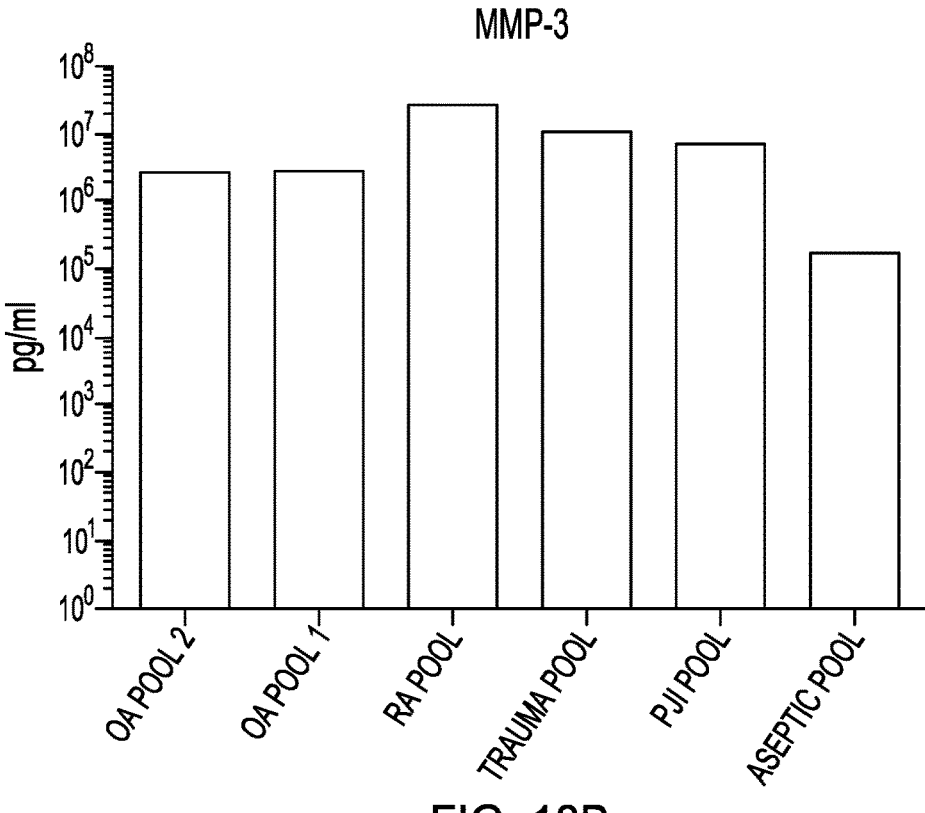
Figure 18C:
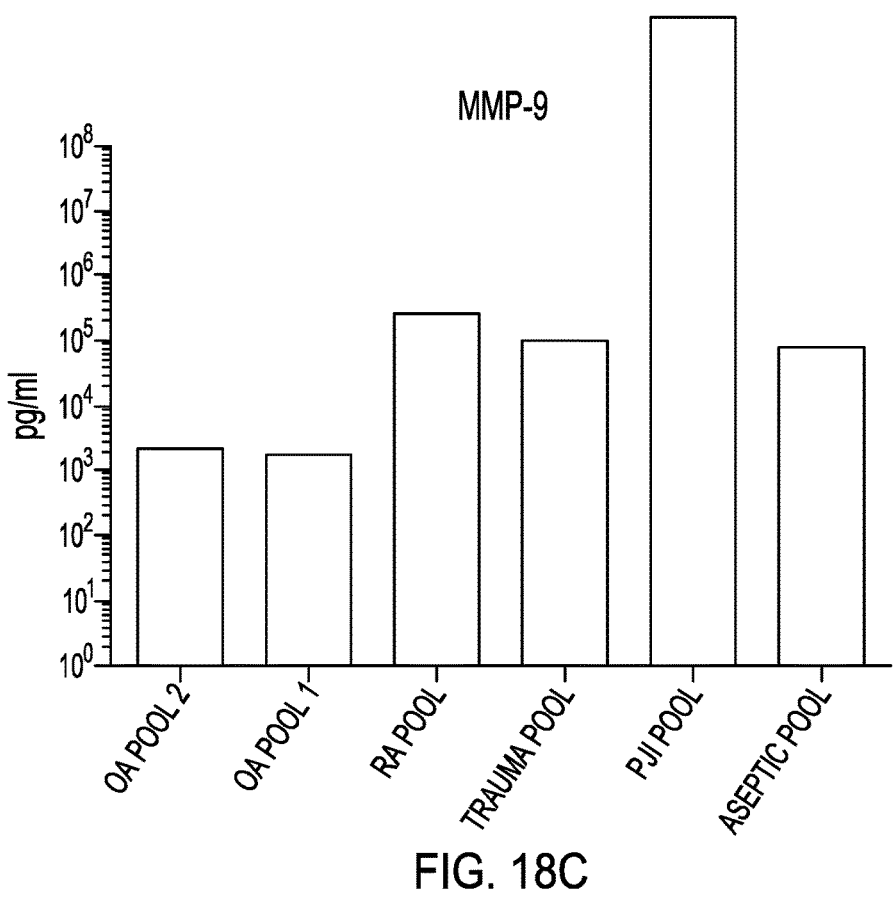
Figure 18D:
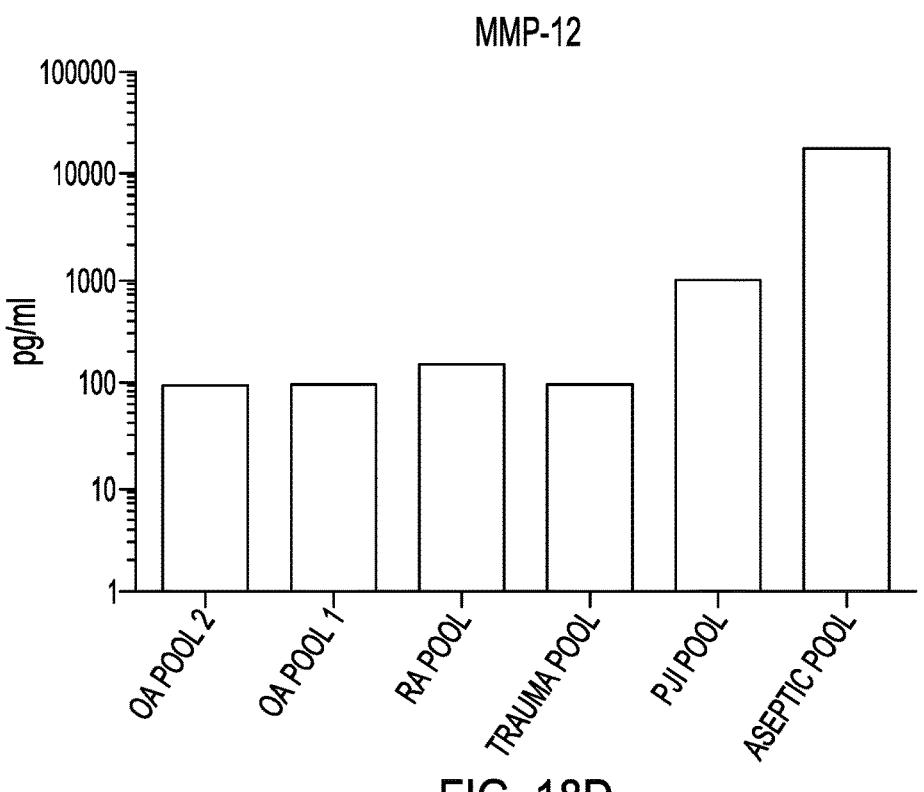
Figure 18E:
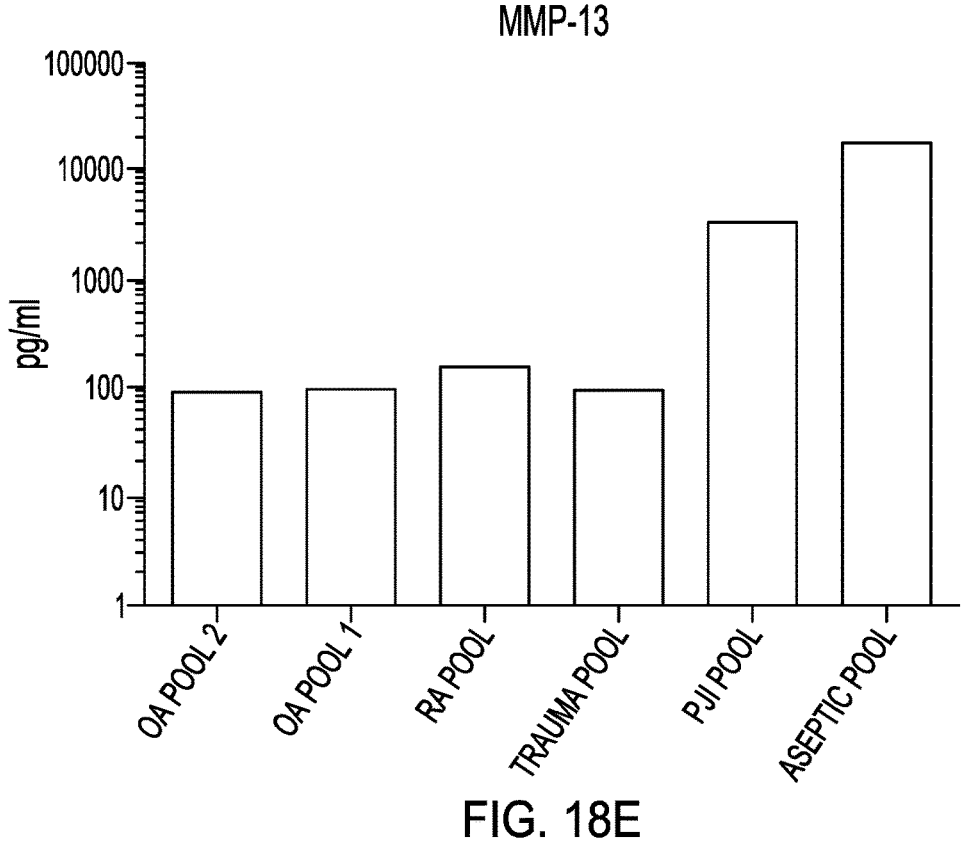
Figure 18F:
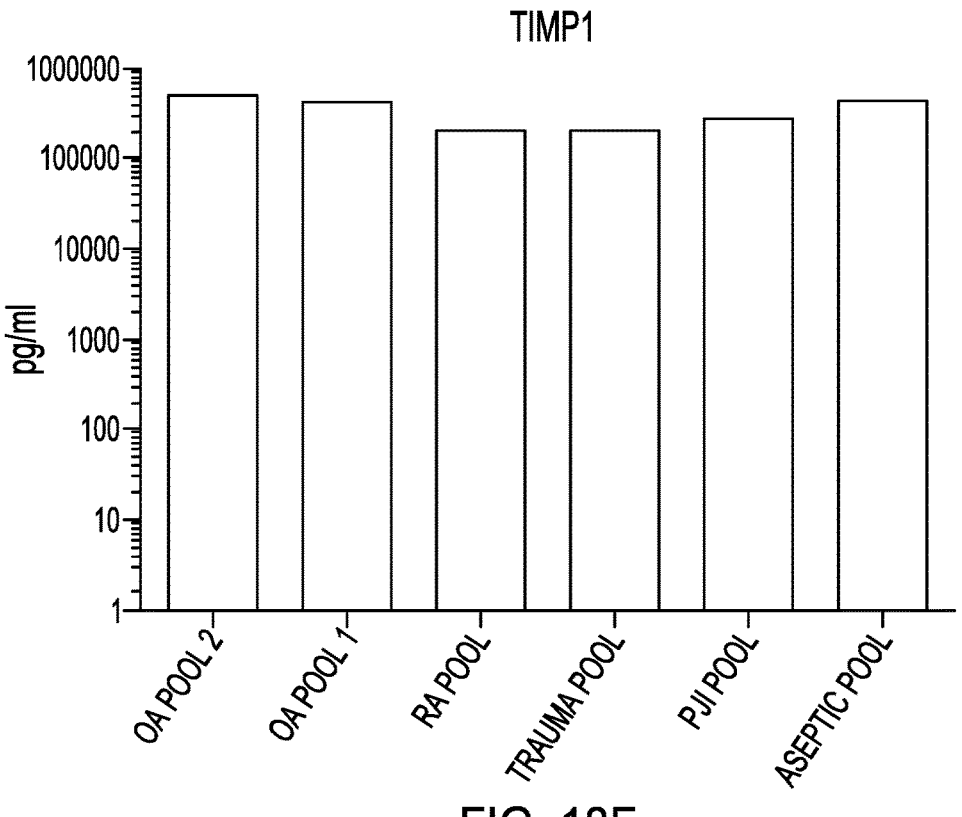

In a second approach to distinguishing osteoarthritis from other arthropathies, we used 2-dimensional difference in gel electrophoresis (2-D DIGE) followed by mass spectroscopy to evaluate each pooled synovial fluid sample type (OA, RA and trauma/injury) for proteins that may be more abundant in these same disease pools, to identify biomarkers that might distinguish OA from RA, CA, and trauma/injury. Protein spots of interest were cut from the gel and the identity of the protein was determined by mass spectrometry. Spots from 2D-DIGE were picked on the basis of computer algorithms analysing color to assess the relative contribution of each disease group pool to that spot, as well as avoiding portions of the gel where high abundance proteins were known to migrate and confound the analysis. See, e.g., FIGS. 11A-11C. Of 23 spots selected for analysis in two rounds of selection, 3 spots of particular interest were identified: Tetranectin (CLEC3B, reportedly decreased in RA), cartilage acidic protein 1 (CRTAC1), and cartilage oligomeric matrix protein (COMP). Both CRTAC1 and COMP could be products of the degradative process of cartilage in osteoarthritis. Results from testing synovial fluid samples are shown in FIGS. 9 and 10A-10C. Although there are commercially available immunoassays for CLEC3B and CRTAC1 they are not very reliable. Antibodies and immunoassays were commercially available for COMP and much research over the years has been devoted to using COMP as a marker for osteoarthritis, particularly in serum. COMP is a pentameric protein that binds types 1, II, and IX collagen along with fibronectin and aggrecan and composes approximately 1% weight of cartilage. In the destruction of cartilage and the extracellular matrix seen in joint disease, one would expect the release of COMP or fragments.

Figure 20:
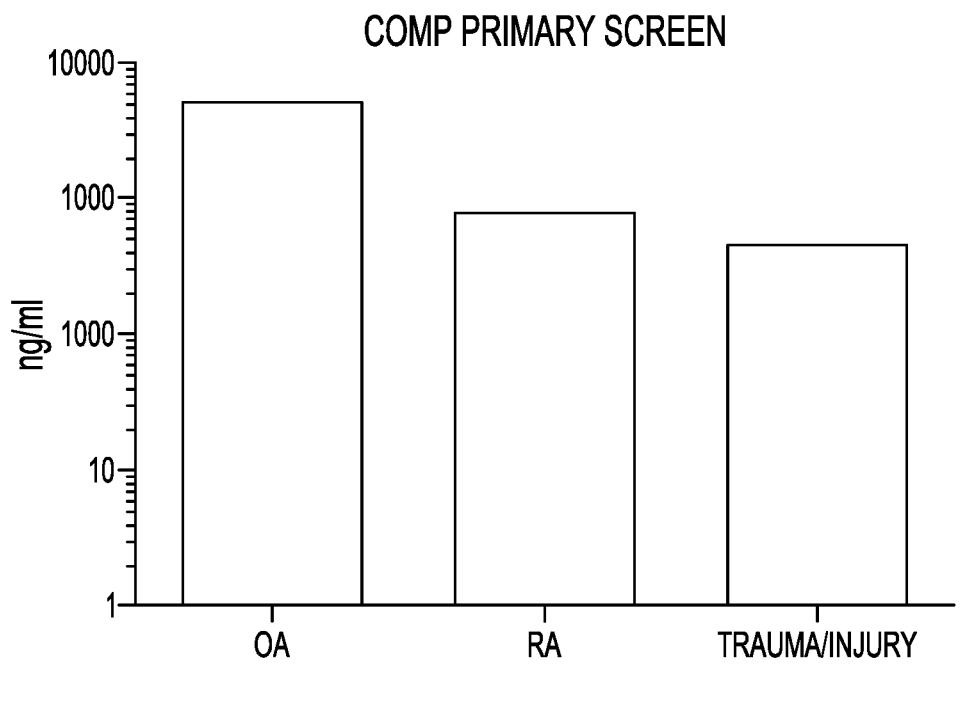
FIG. 20 illustrates a bar graph of COMP in pooled synovial fluid samples.

We used a commercial kit to measure COMP (Source: Quantikine COMP ELISA Kit). Several commercial kits are available and depending on the antibodies as well as the forms of COMP (whole, monomeric, or fragmented) used in such kits one might well expect different results from different kits. Our pooled OA samples showed COMP values higher than those from RA (7-fold) or those from trauma/injury (11-fold), as shown in FIG. 20 making COMP a potential marker to evaluate in secondary screening.

Secondary screening involved many fewer biomarkers and much larger numbers of samples using the same assays as used in the primary screen (Example 1), with recommended dilutions defined during the primary screen. Testing larger numbers of individual samples from each disease group (OA, RA, trauma/injury) enabled receiver operating characteristic (ROC) curve analysis of the data to establish cutoff concentrations between disease groups and to establish clinical sensitivity and specificity. For each biomarker, some of the 111 samples contained concentrations within the working range of the assay and some contained concentrations that were outside the range, either high or low. Samples that were out of range were assigned a concentration equal to the sample dilution factor multiplied by the concentration of the low standard or the high standard depending on whether the sample concentration was out of range low or high respectively. Cutoff concentrations were calculated by ROC curve analysis comparing both the RA group as controls, the trauma/injury group as controls, as well as both RA and trauma injury samples combined as controls.

Figure 3:
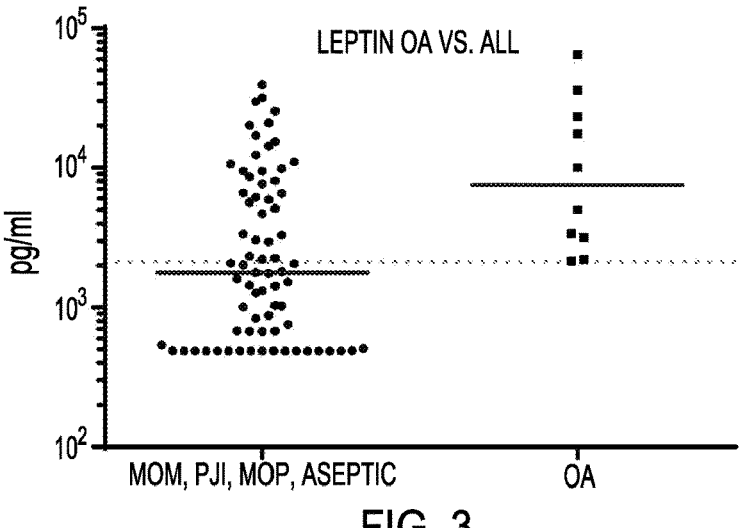
FIG. 3 illustrates a plot of the biomarker (Leptin) levels in synovial fluid samples. C/O>2130 pg/mL, Sensitivity 1.0 Specificity 0.56.
Figure 4A:
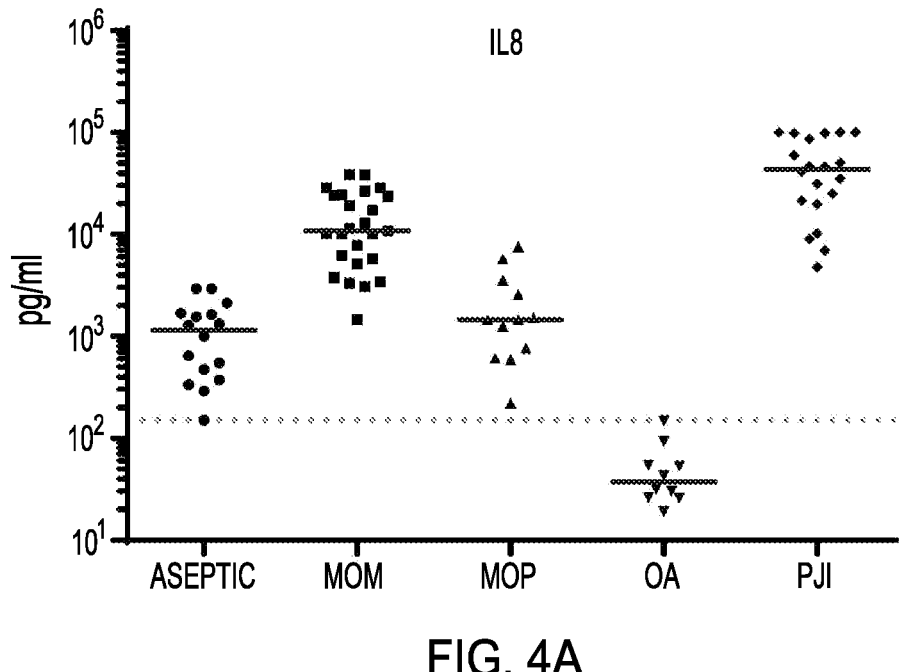
FIGS. 4A and 4B illustrate plots of the biomarker (IL-8) levels in synovial fluid samples.
Figure 4B:
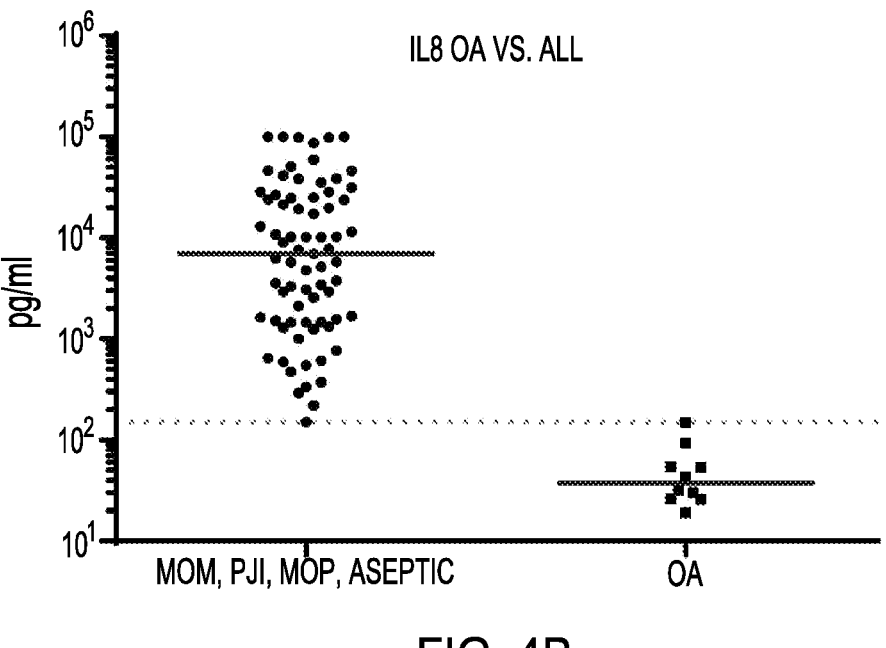
Figures 5A, 5B, 5C:
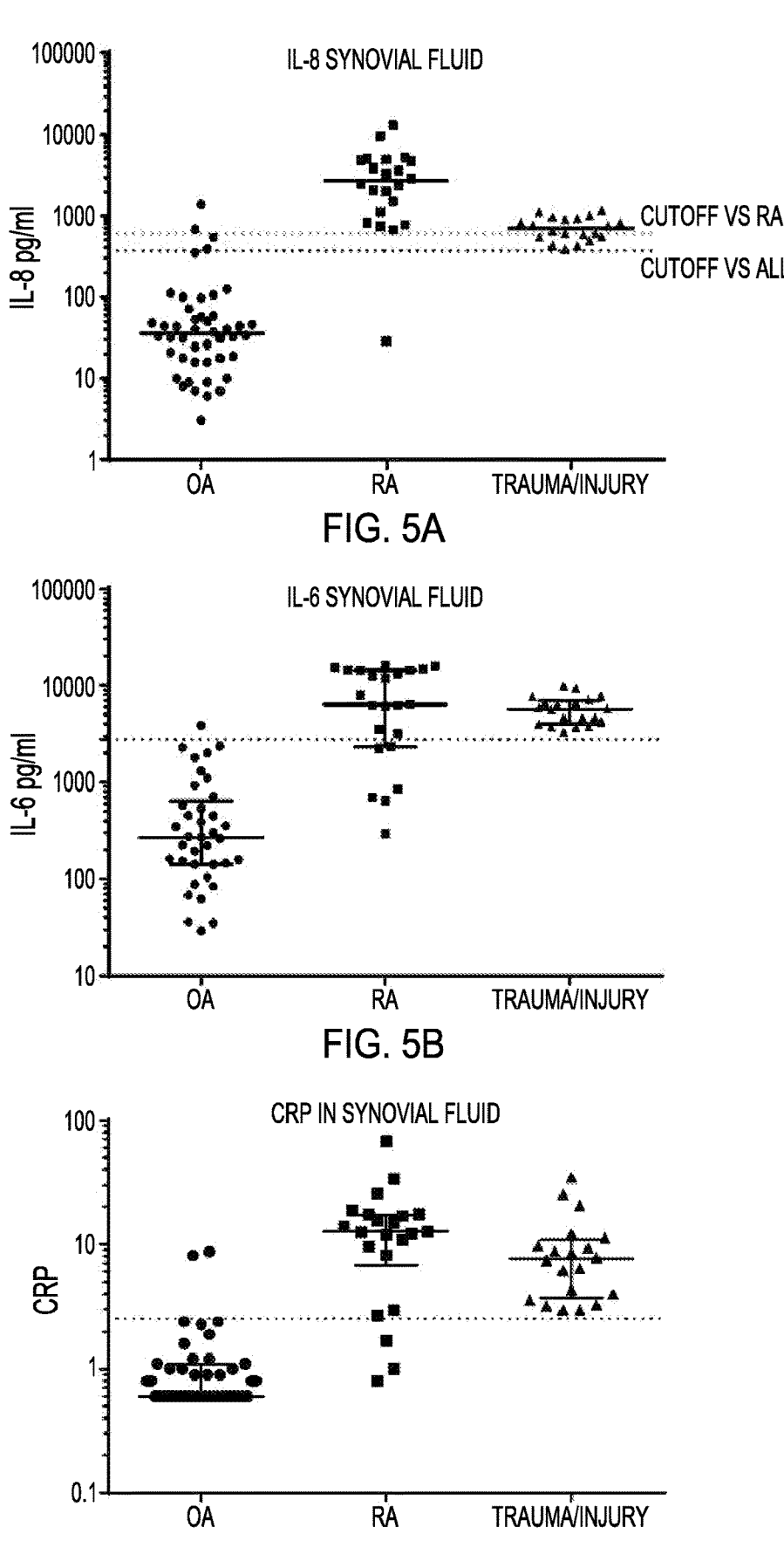
FIGS. 5A-5I illustrate plots of the level of various biomarkers in synovial fluid samples.
Figure 5D:
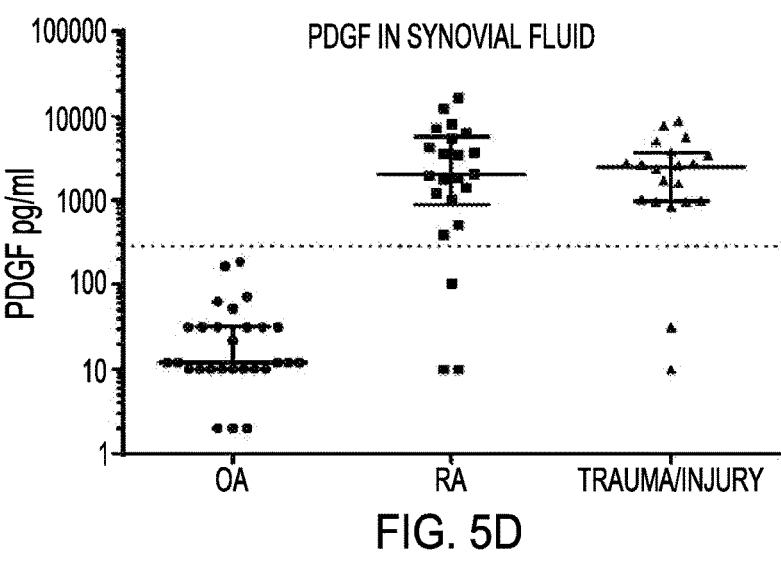
Figure 5E:
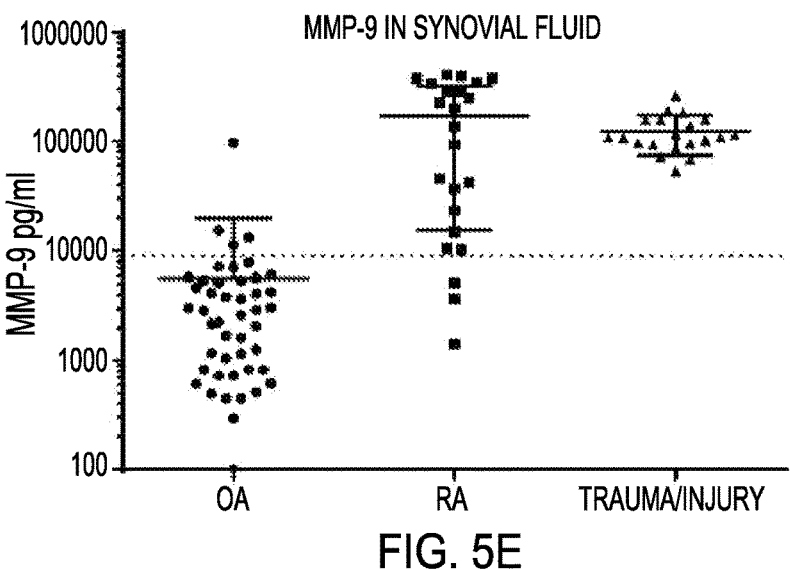
Figure 5F:
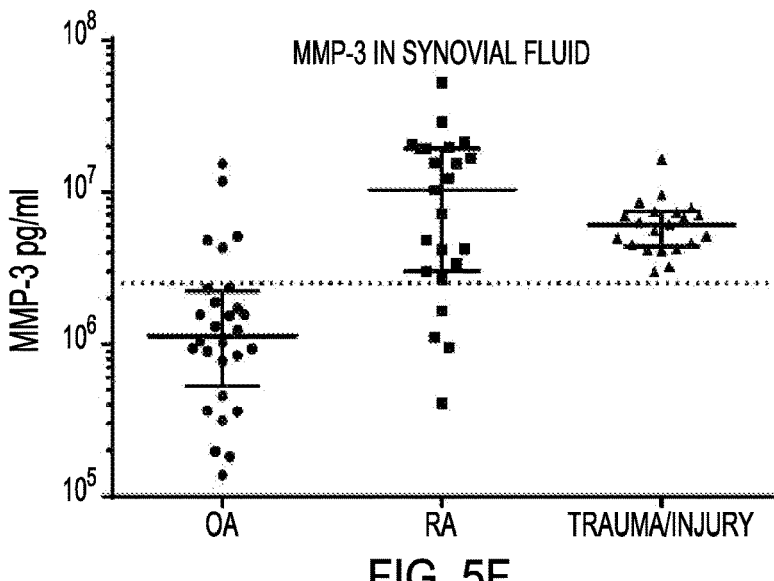
Figure 5G:
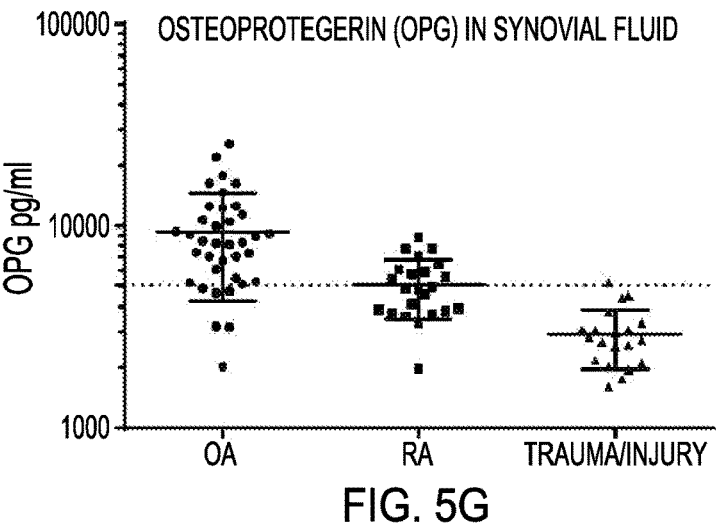
Figure 5H:
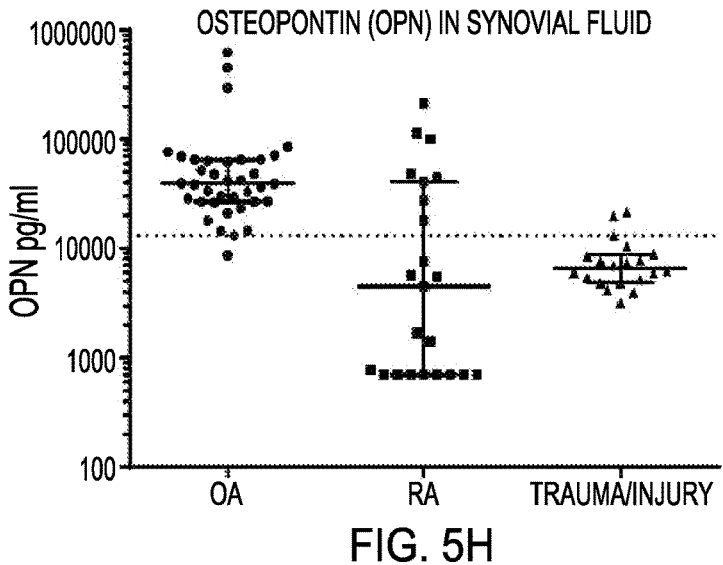
Figure 5I:
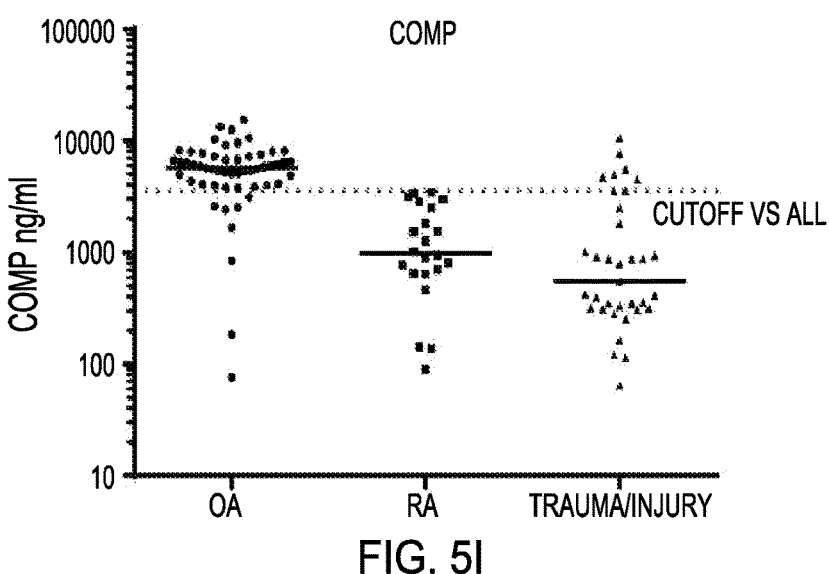
Figure 6A:
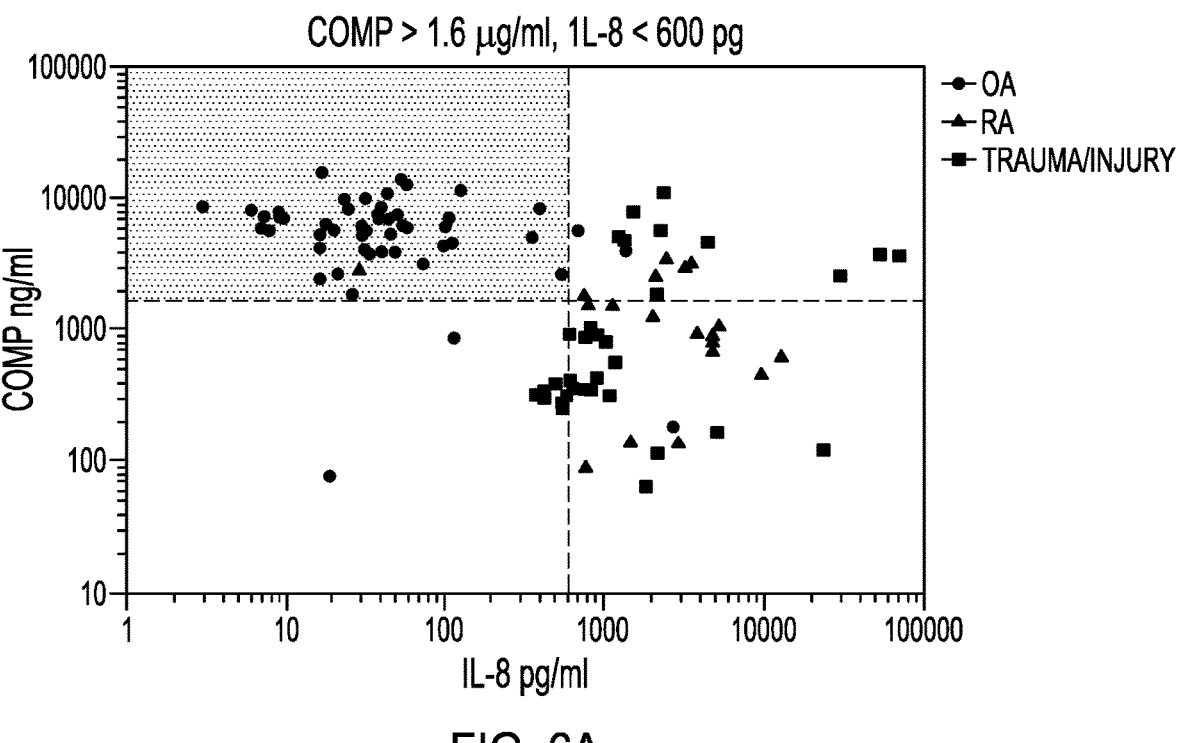
FIGS. 6A-6D illustrate scatter plots of an OA biomarker combinations in synovial fluid samples.
Figure 6B:
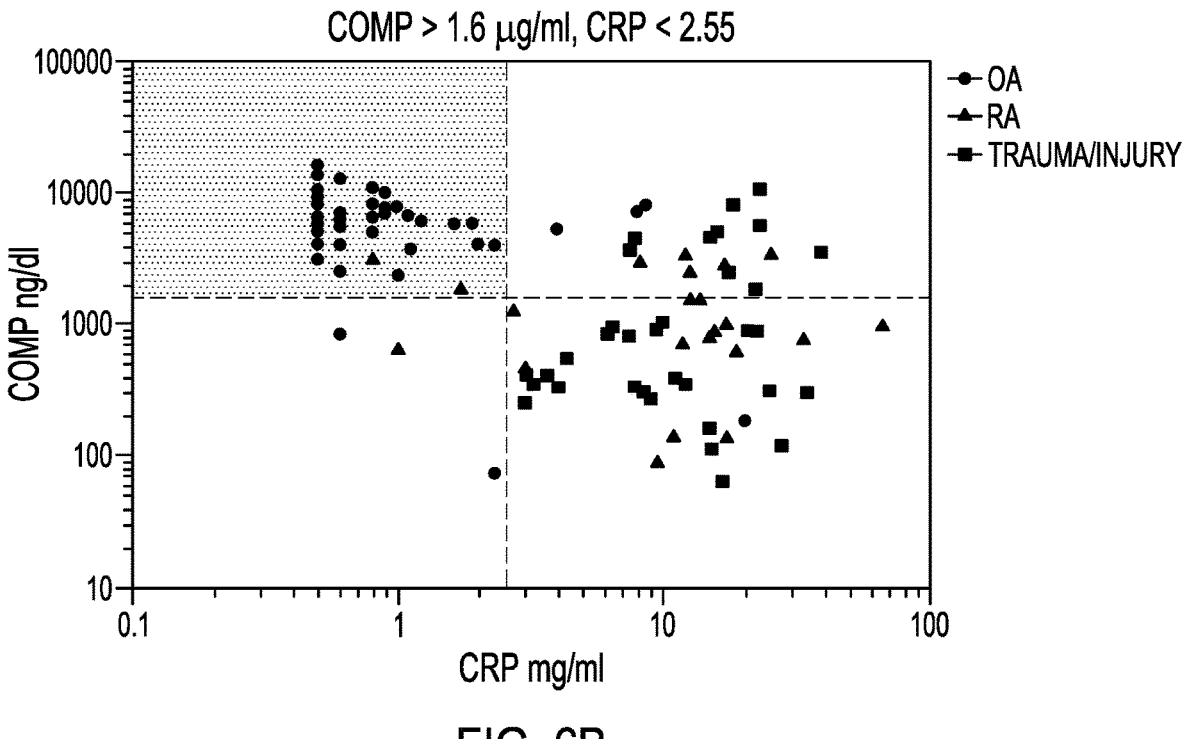
Figure 6C:
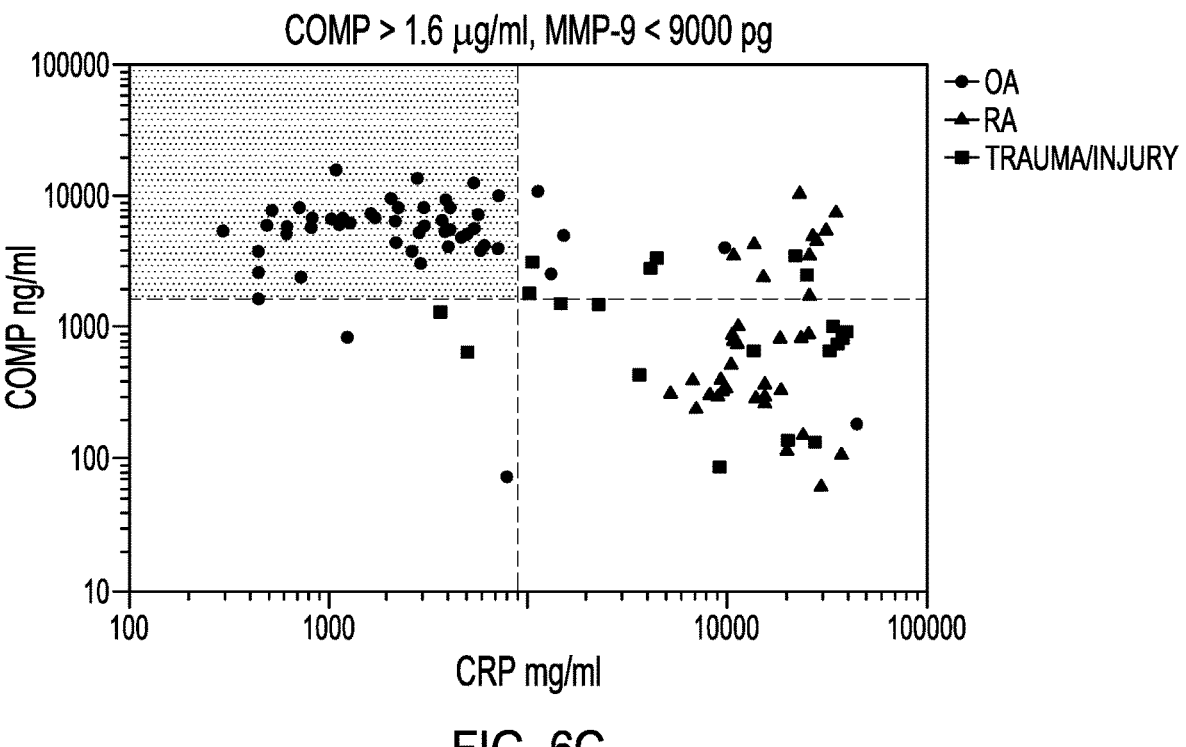
Figure 6D:
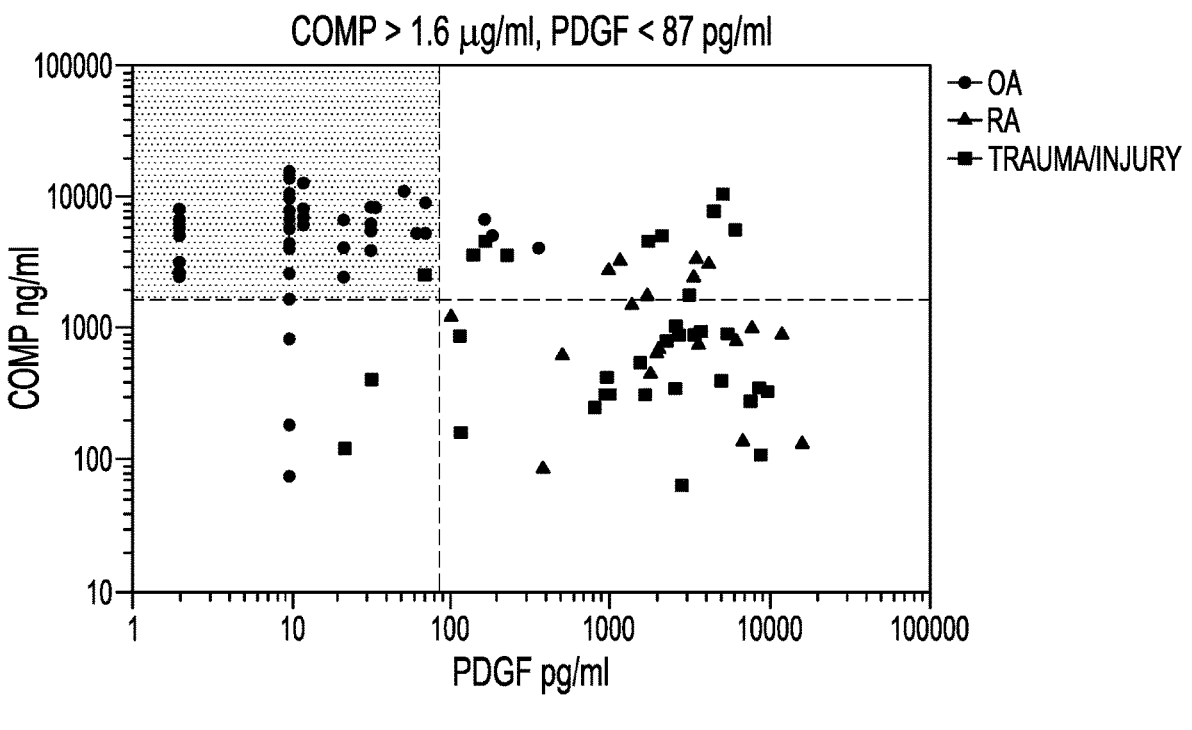
Figures 7A, 7B:
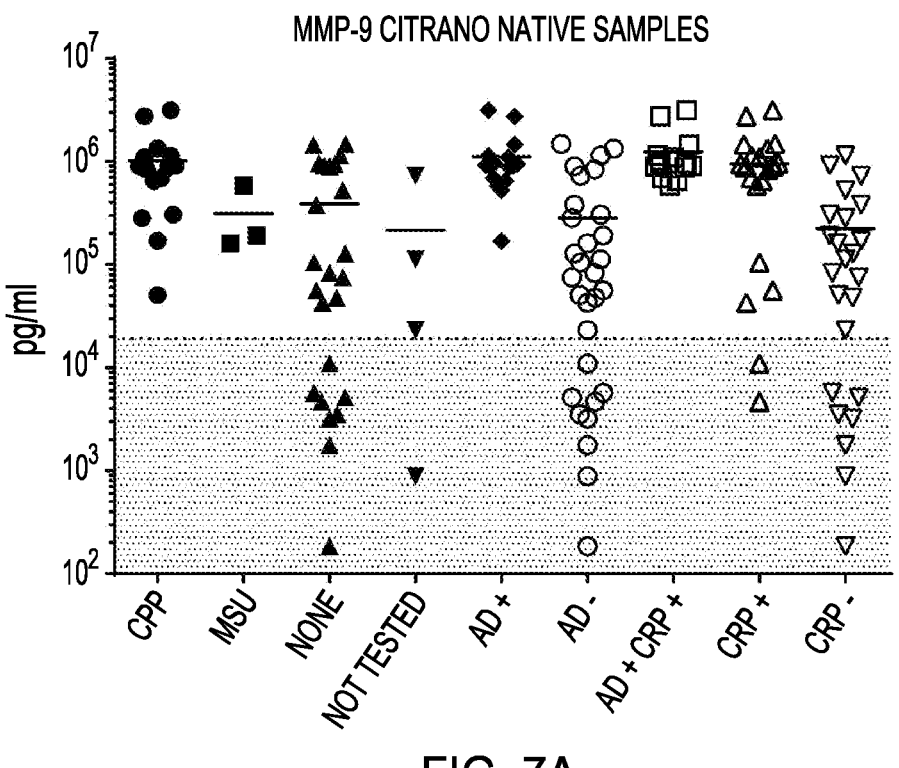
FIGS. 7A-7C illustrate plots of biomarker levels in synovial fluid samples with known crystal disease biomarker profiles.
Figure 7C:
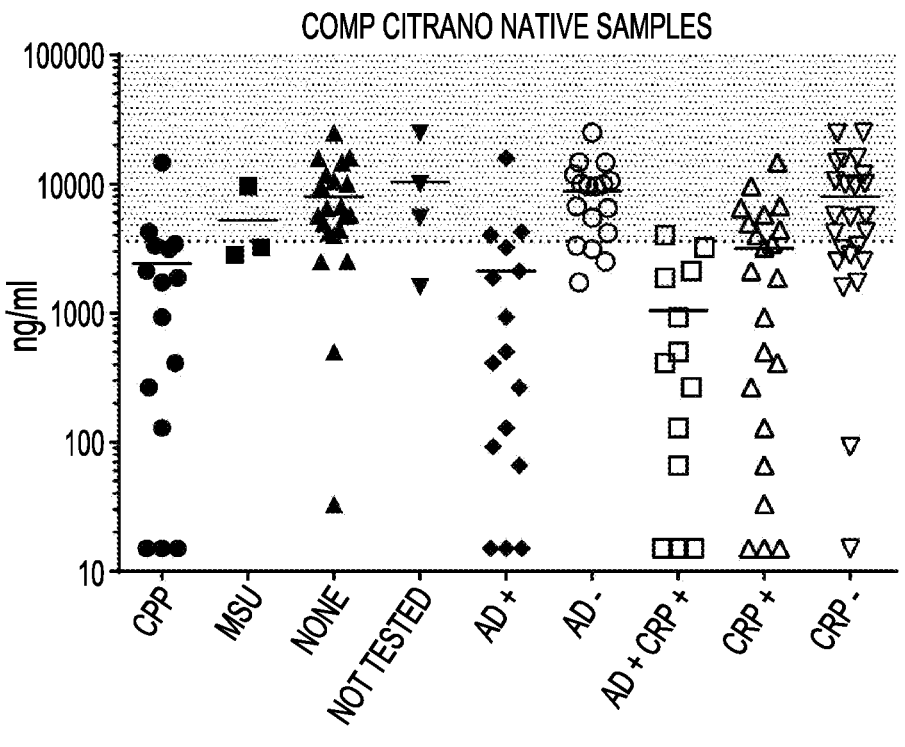
Figure 8A:
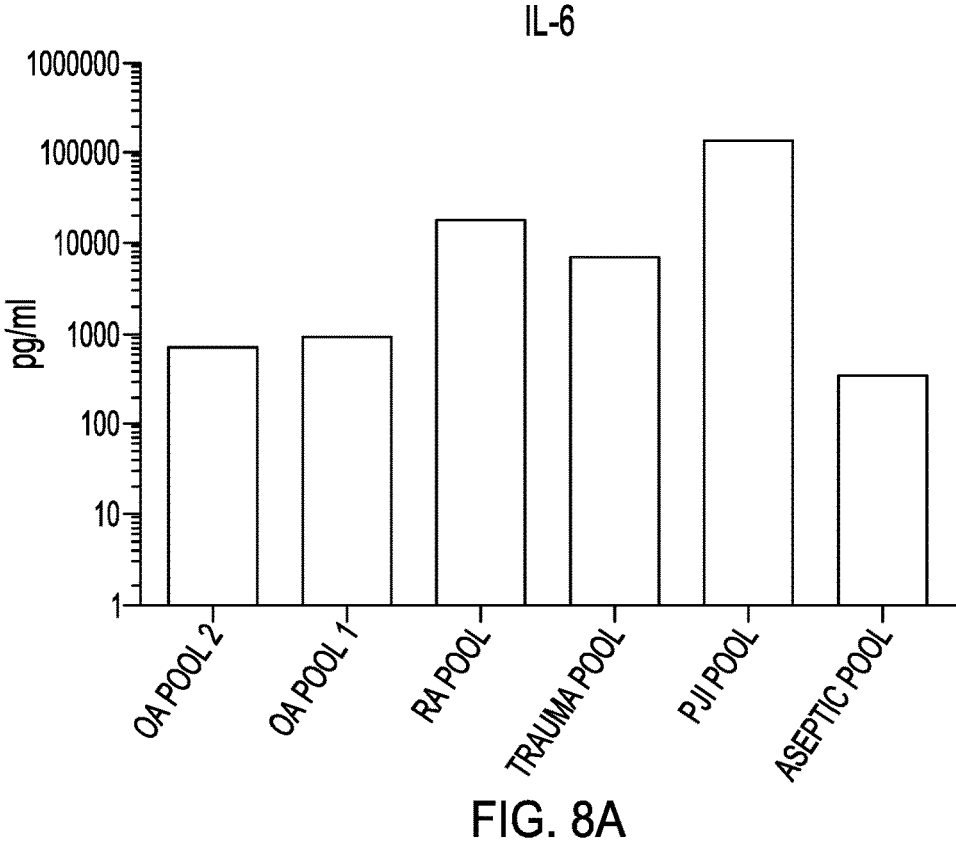
FIGS. 8A-8F illustrate bar graphs of various biomarker in pooled synovial fluid samples.
Figure 8B:
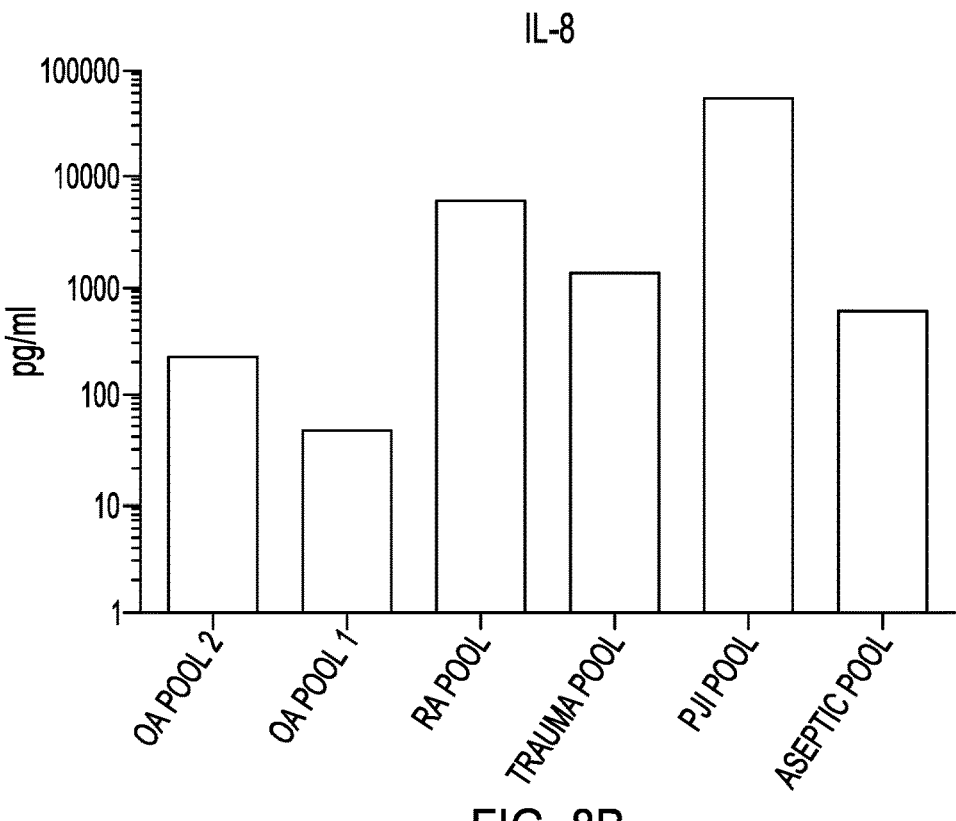
Figure 8C:
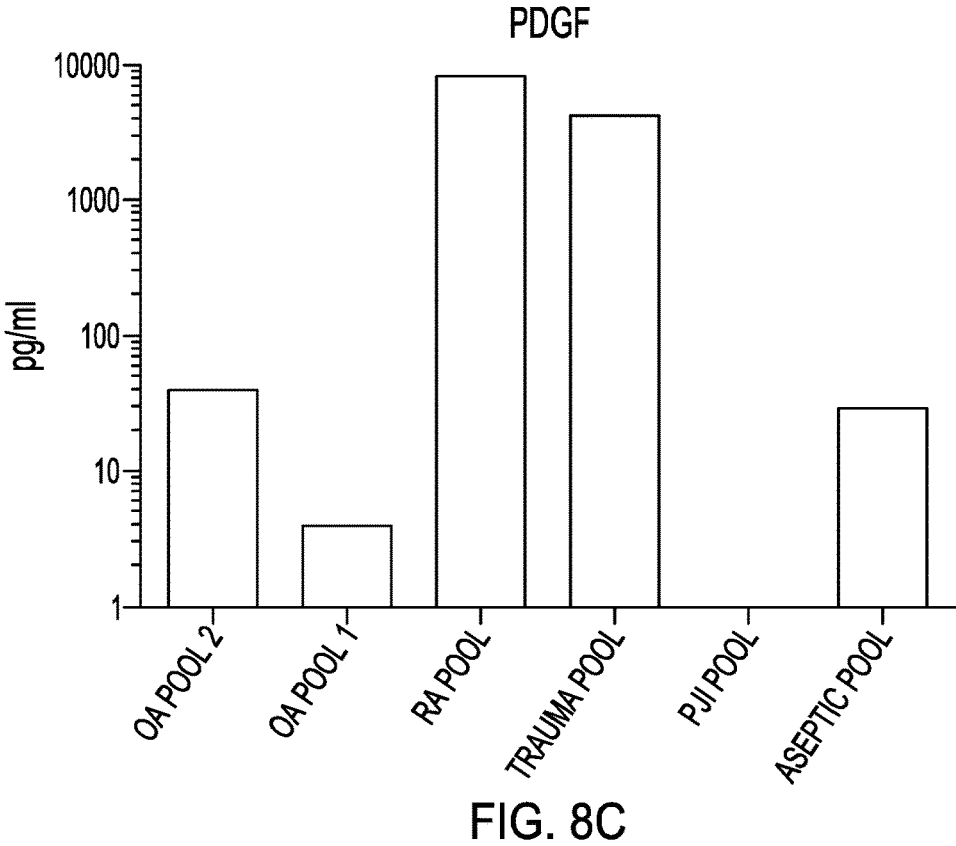
Figure 8D:
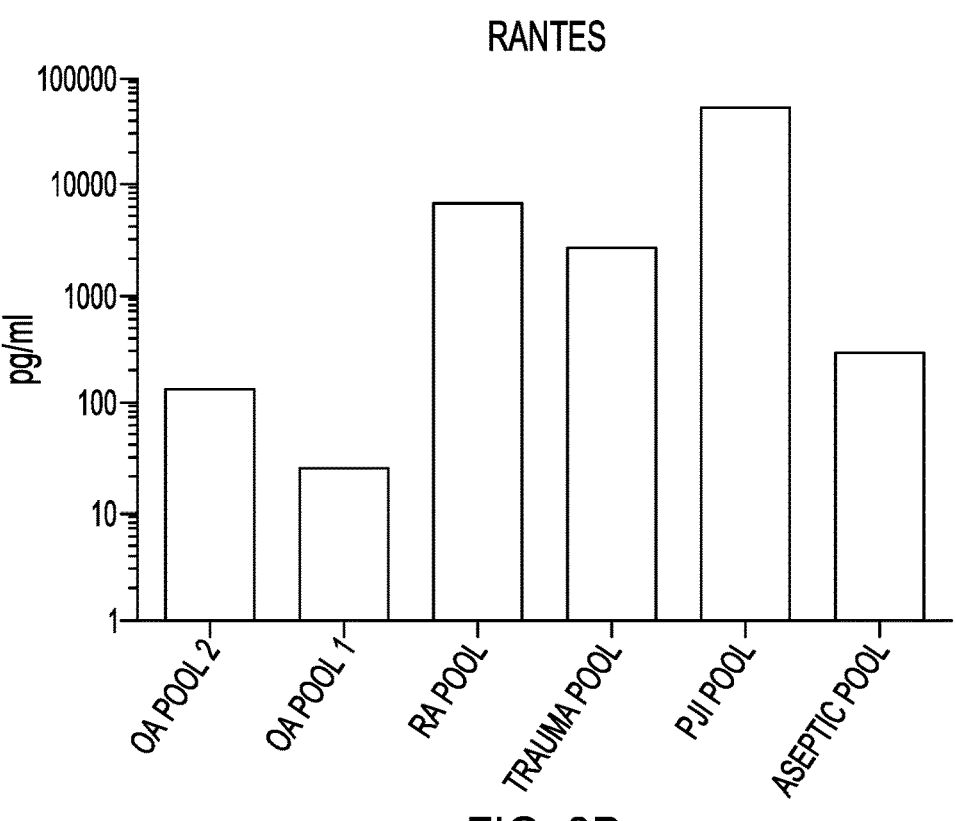
Figure 8E:
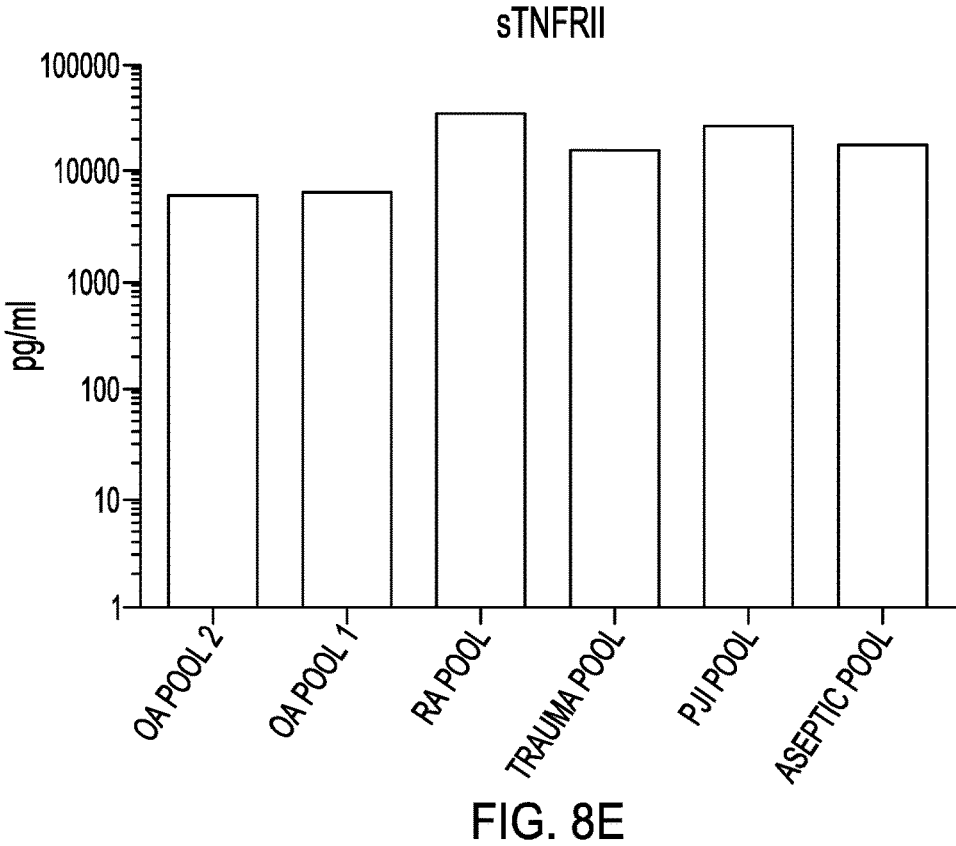
Figure 8F:
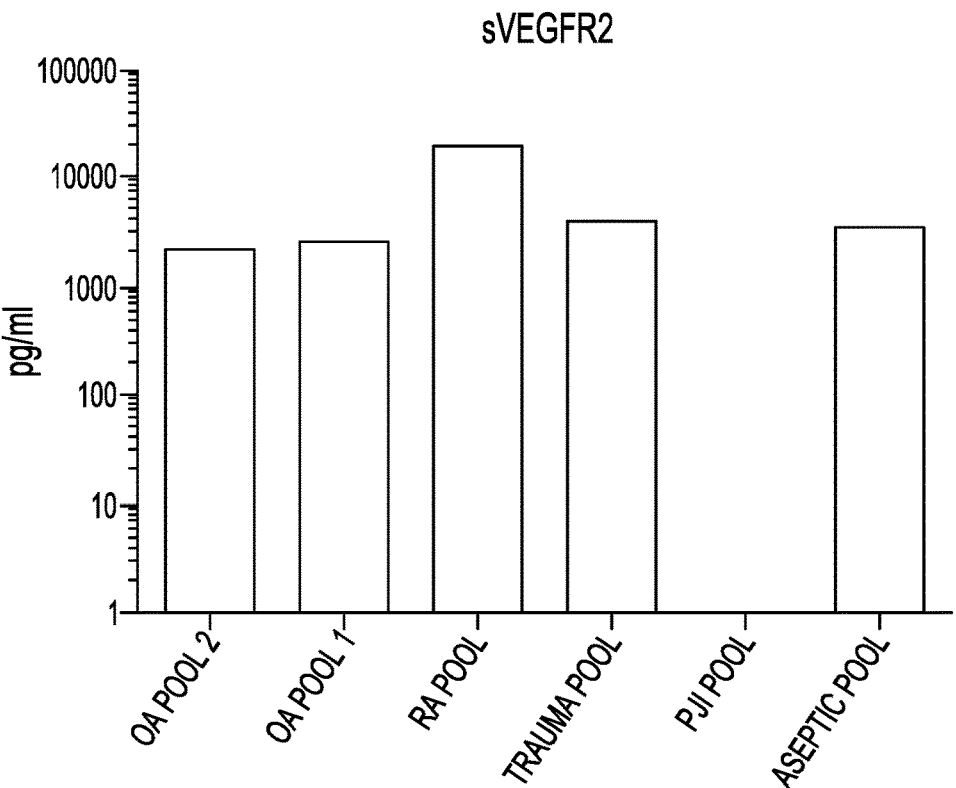
Figure 9:
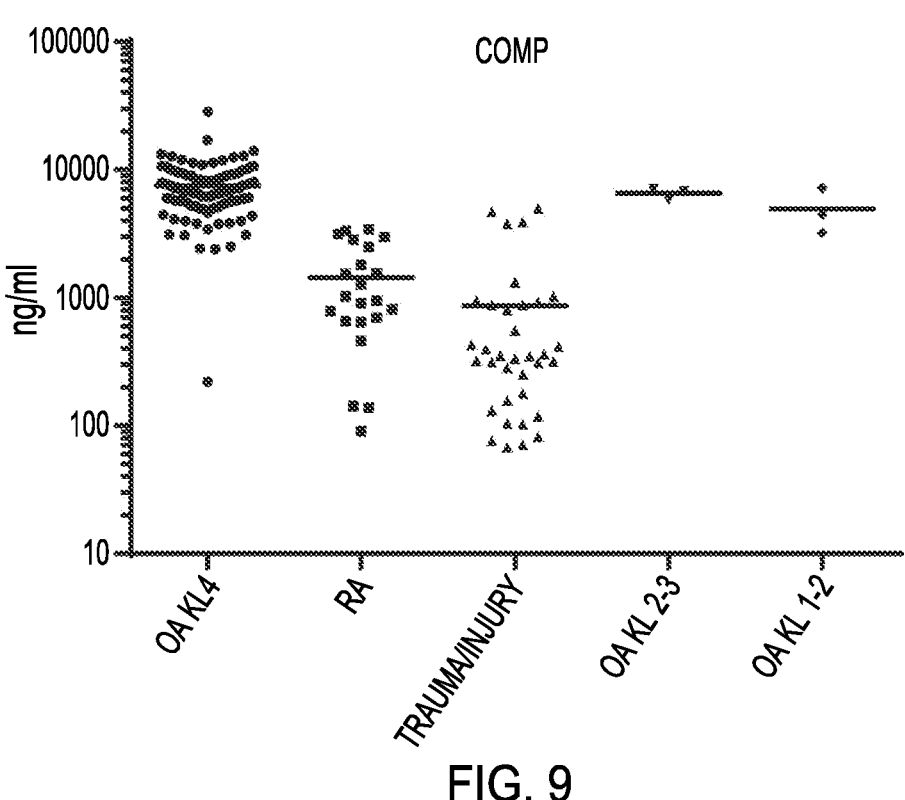
FIG. 9 illustrates a plot of COMP in individual synovial fluid samples with RA, Trauma/Injury and various stages of OA.
Figure 10A:
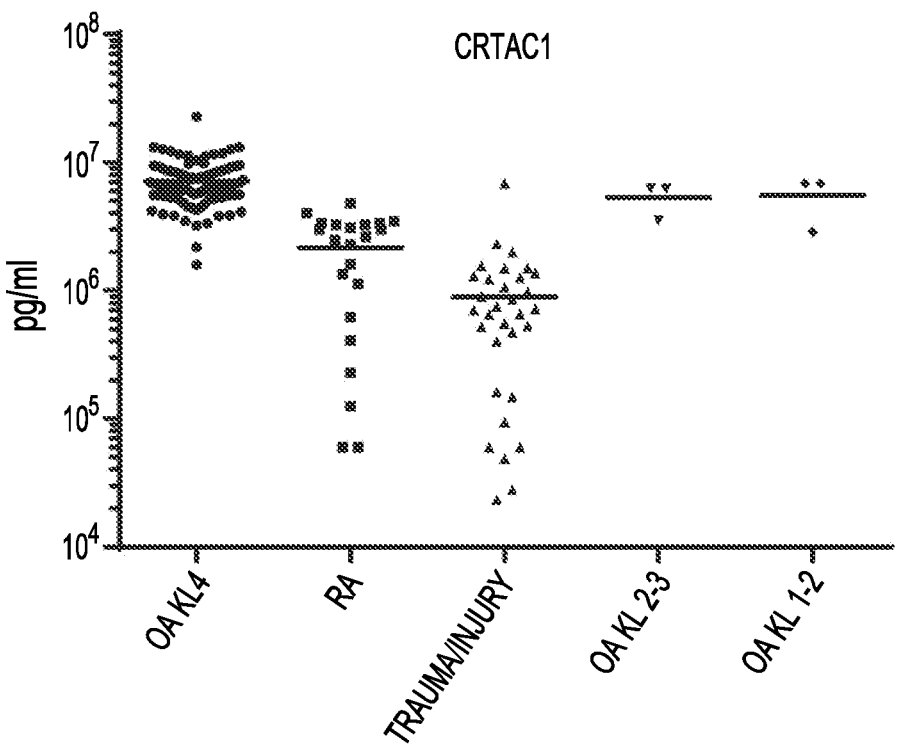
FIGS. 10A-10C illustrates levels of biomarkers in individual synovial fluid samples with RA, Trauma/Injury and various stages of OA.
Figure 10B:
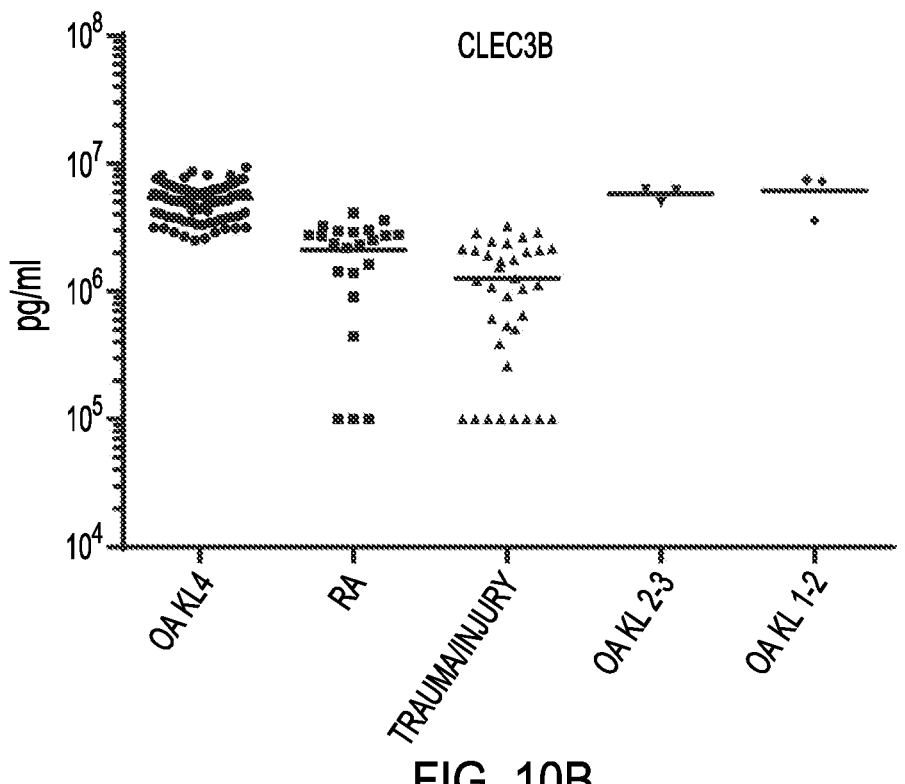
Figure 10C:
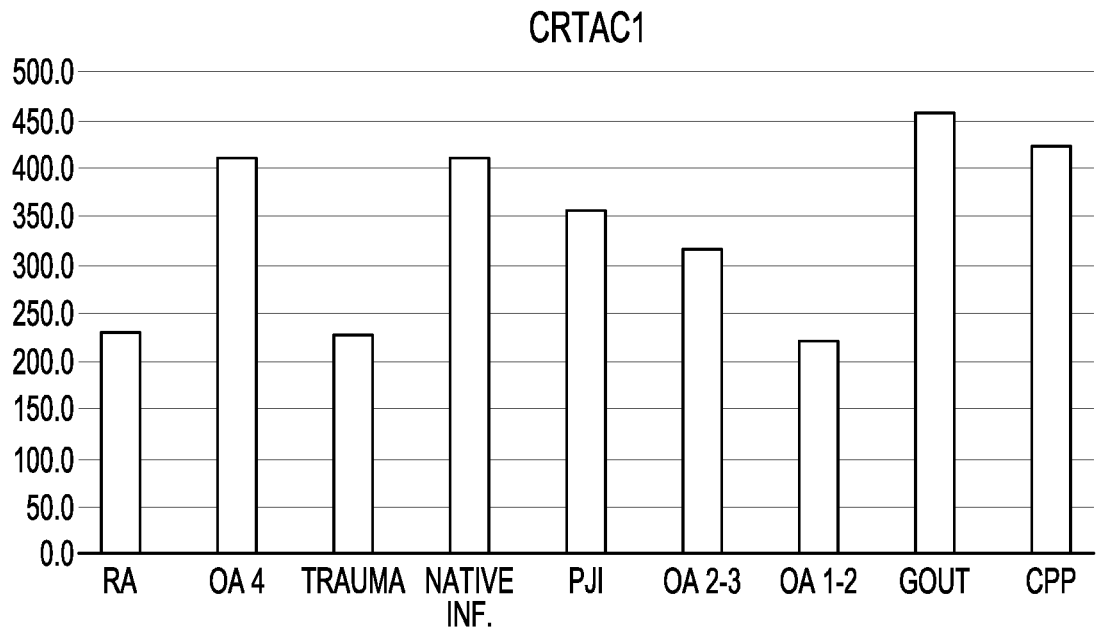

In the secondary analysis, individual synovial fluid samples were analysed for 13 human biomarkers: AD; CRP; HNE; CRP; MMP-9; MMP-3; OPG; OPN; IL-6; IL-8; PDGF; NGAL; OC; and COMP. Not all samples were analysed for all 13 biomarkers as we continued to acquire new samples and to narrow the list and focus on biomarkers that showed the greatest utility. Synovial fluid samples from native joints (no. 111) were run as follows: 54 from individuals with late stage (3/4) OA undergoing joint replacement, 22 individuals with RA, and 35 individuals who had suffered trauma/injury to the joint. The values for individual samples from OA, RA and trauma/injury are shown in FIGS. 48A-48E. Thirteen biomarkers were run on 70 samples (28 OA, 22 RA, and 20 trauma/injury). Values are noted when there is a positive response for cutoffs (C/O) for each biomarker consistent with the ROC curve for OA determined for the biomarker. Biomarker plots for individual samples from various disease states are shown as follows: OPG (FIGS. 1A-2B, and 5G); Leptin (FIG. 3); IL-8 (FIGS. 4A-5A); IL-6 (FIG. 5B); CRP (FIG. 5C); PDGF (FIG. 5D); MMP-9 (FIG. 5E); MMP-3 (FIG. 5F); OPN (FIG. 5H); and COMP (FIG. 5I). Results for COMP, IL-8 and MMP-9 in synovial fluid samples from NSA and CA are shown in FIGS. 7A-7C and 16A-16C.

Figure 21A:
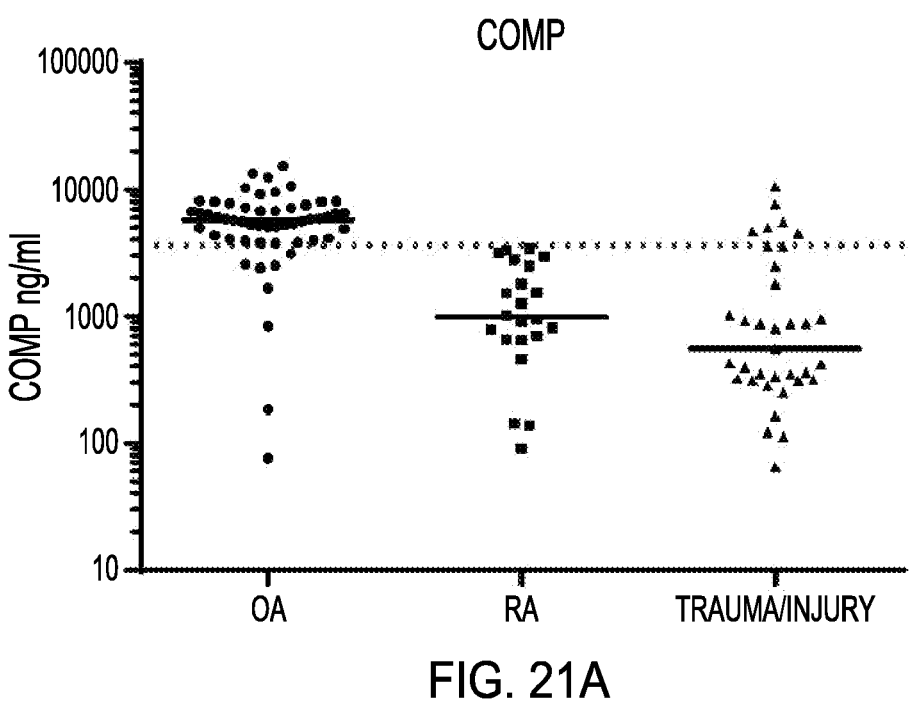
FIGS. 21A and 21B illustrate graphs of COMP for discriminating OA from inflammatory arthropathies.
Figure 21B:
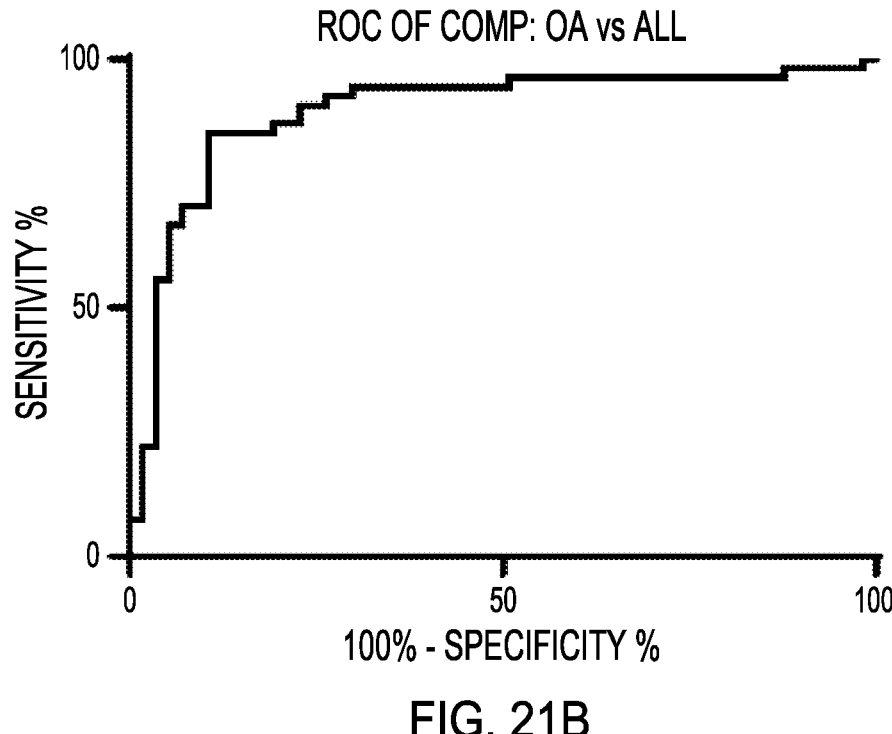

In secondary screening, COMP was able to distinguish most osteoarthritis synovial fluid samples from the controls (either rheumatoid arthritis, trauma/injury, or the combined groups). Primary screen data for COMP is shown in FIG. 20. Secondary screen for COMP is shown in FIG. 21A and demonstrates a cutoff of greater than 3,000 ng/mL can discriminate OA from RA and T/I. Receiver operator characteristic (ROC) curve for COMP is shown in FIG. 21B. COMP vs. RA and TI combined has cutoff of >3,697 ng/mL with sensitivity of 85.19% and a specificity of 89.47%. COMP vs. RA has a cutoff of >3609 ng/mL with sensitivity of 85.19% and specificity of 100%. COMP vs. T/I has a cutoff of >3697 ng/mL with sensitivity of 85.19% and specificity of 82.86%.

It should be noted that all Trauma/Injury samples above the cutoff for COMP showed high levels of multiple markers of inflammation (including IL-8, MMP-9, and CRP), whereas osteoarthritis samples typically showed low levels. The data demonstrate that COMP in synovial fluid can be a valuable biomarker for osteoarthritis because it is a direct measure of cartilage destruction in the affected joint. Further the high levels of COMP observed in synovial fluid samples make it amenable to a rapid point of care device, as well as a laboratory assay. Significant sample dilutions (typically 1/1,200 in the R&D Systems ELISA) we have identified as the lab-based method show no matrix effect.

Figure 22A:
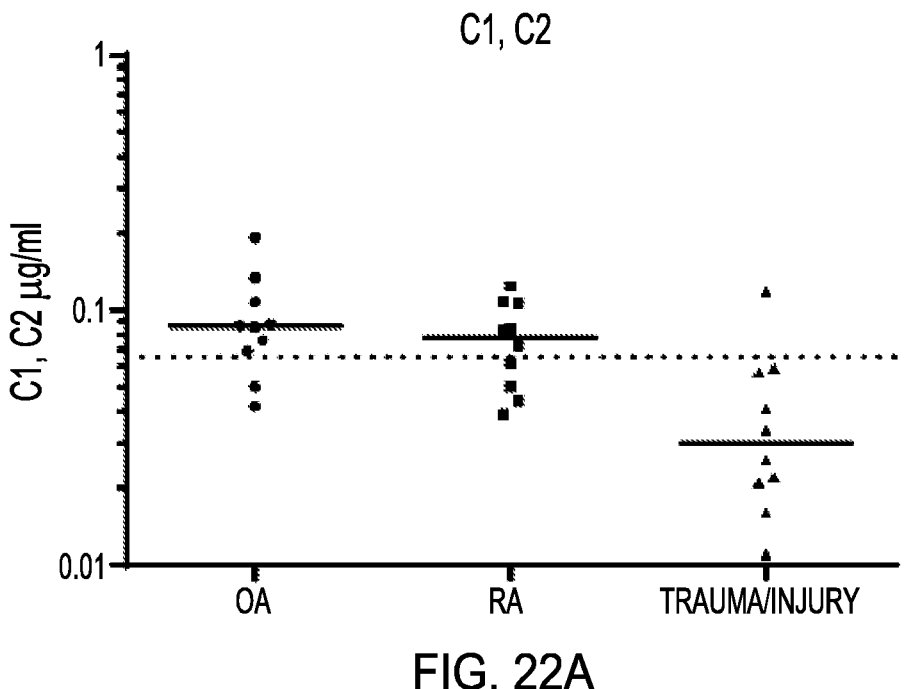
FIG. 22A-22B illustrate plots of biomarkers in synovial fluid samples.
Figure 22B:
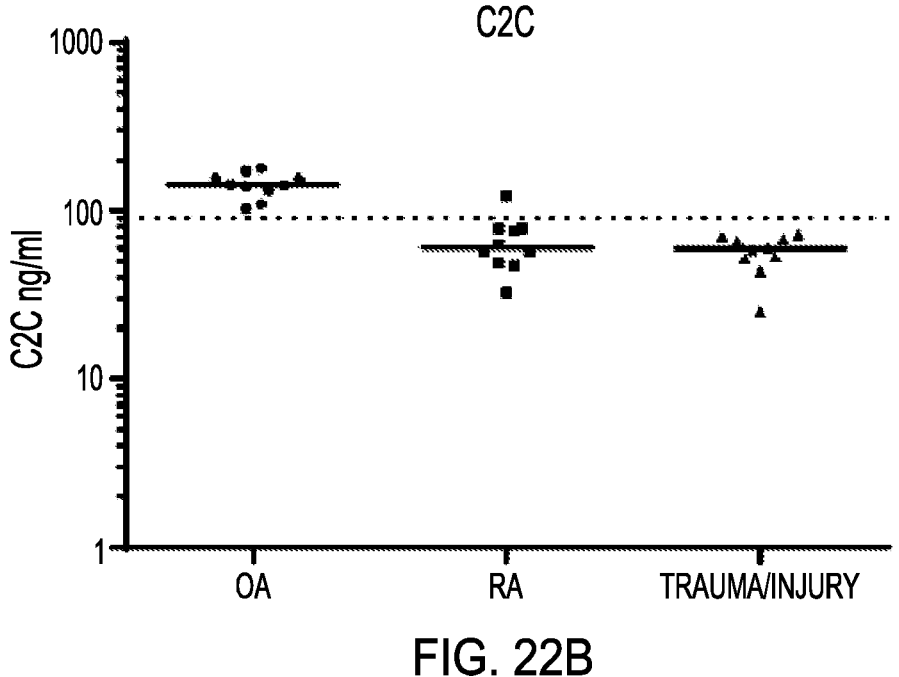
Figure 23A:
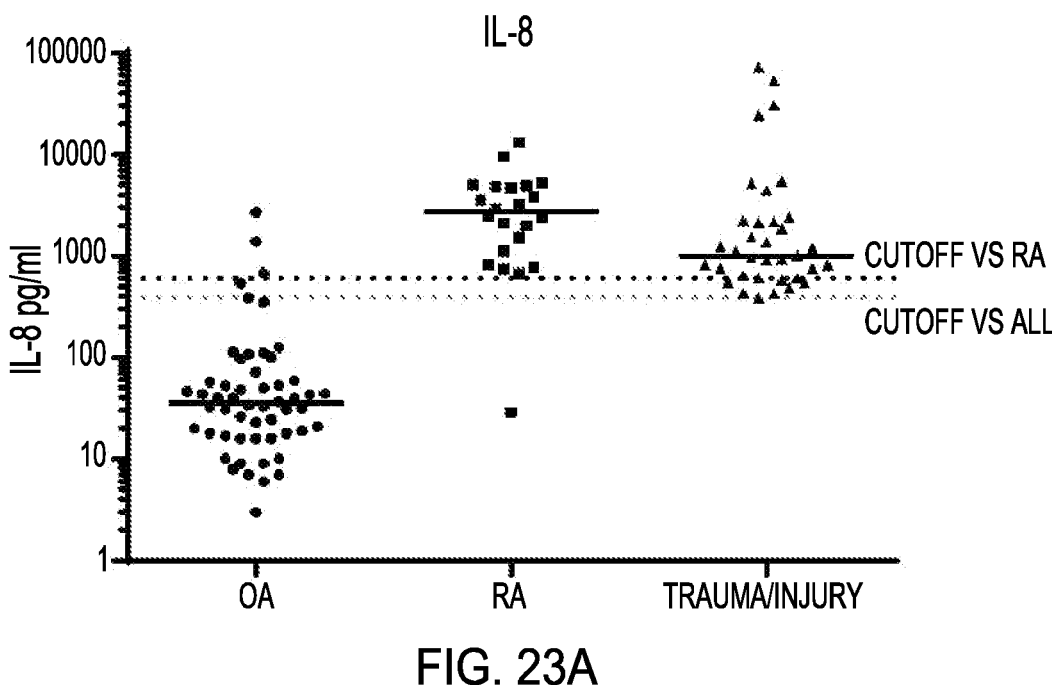
FIGS. 23A-23H illustrate graphs of biomarkers in synovial fluid samples for discriminating OA from inflammatory arthropathies.
Figure 23B:
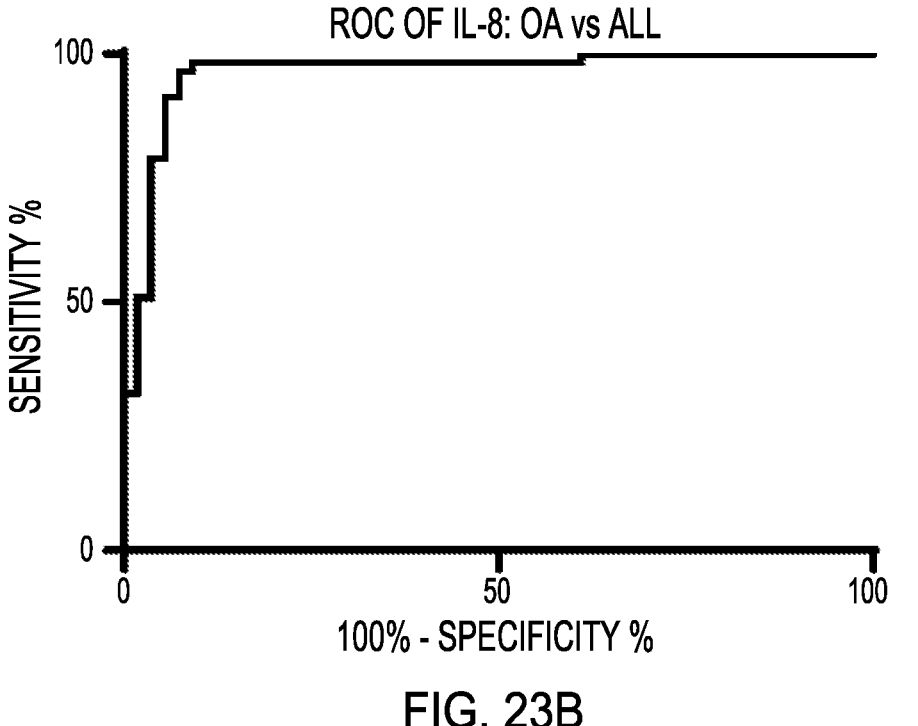
Figure 23C:
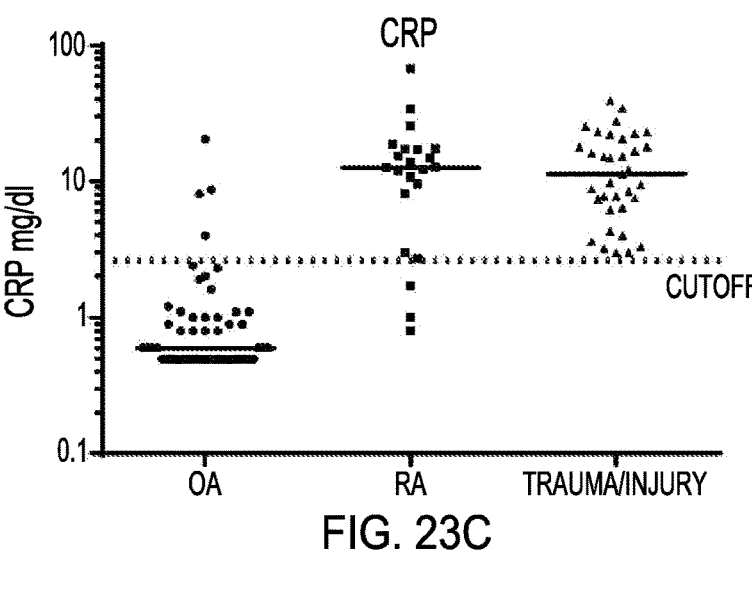
Figure 23D:
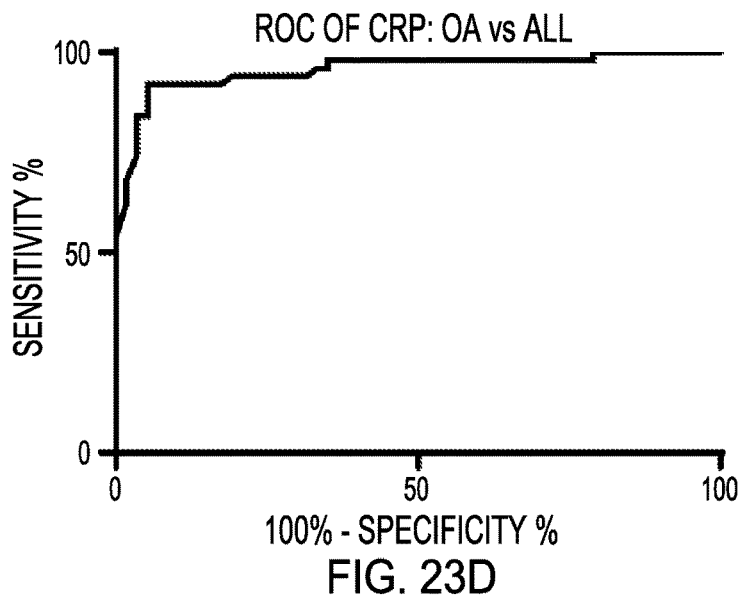
Figure 23E:
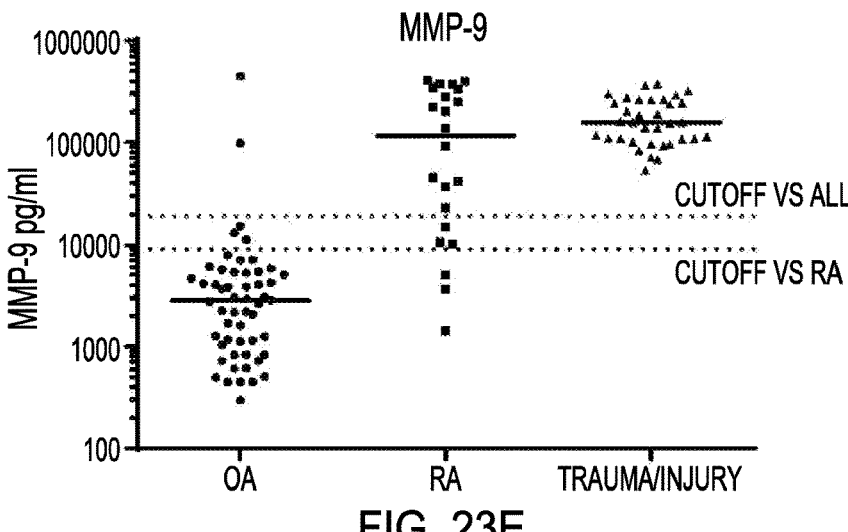
Figure 23F:
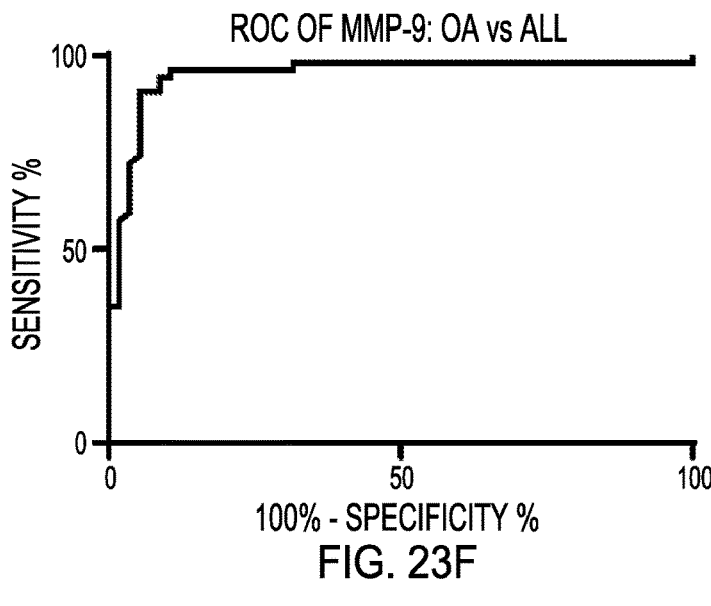
Figure 23G:
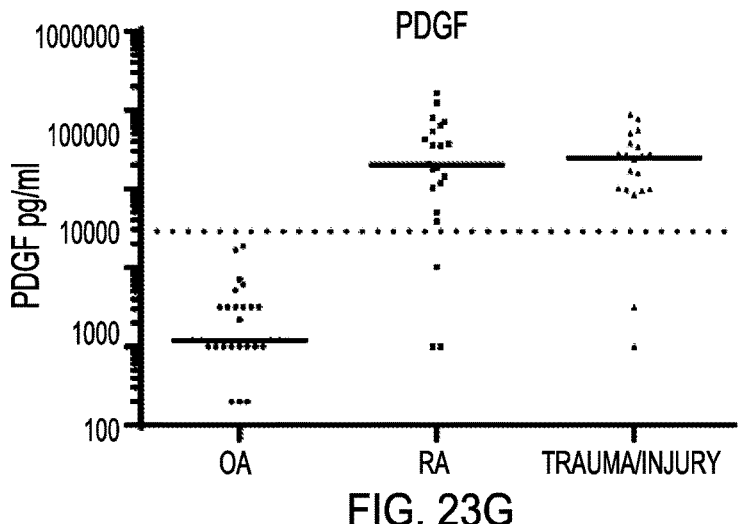
Figure 23H:
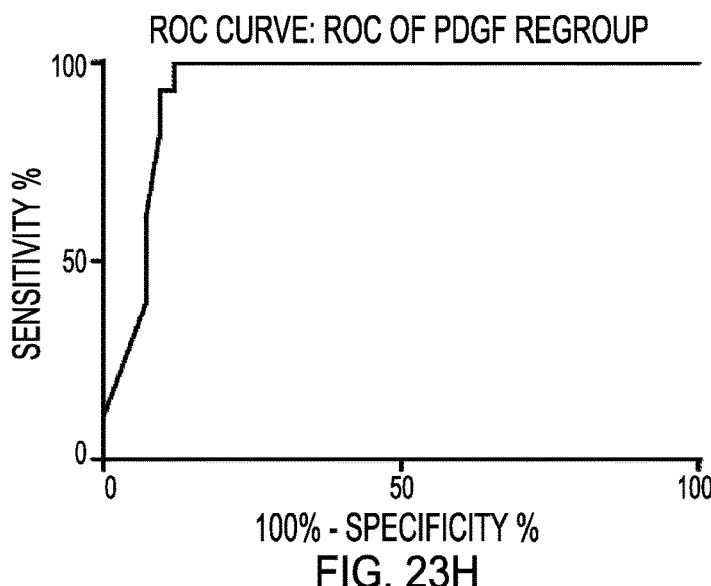
Figures 25A, 25B, 25C:
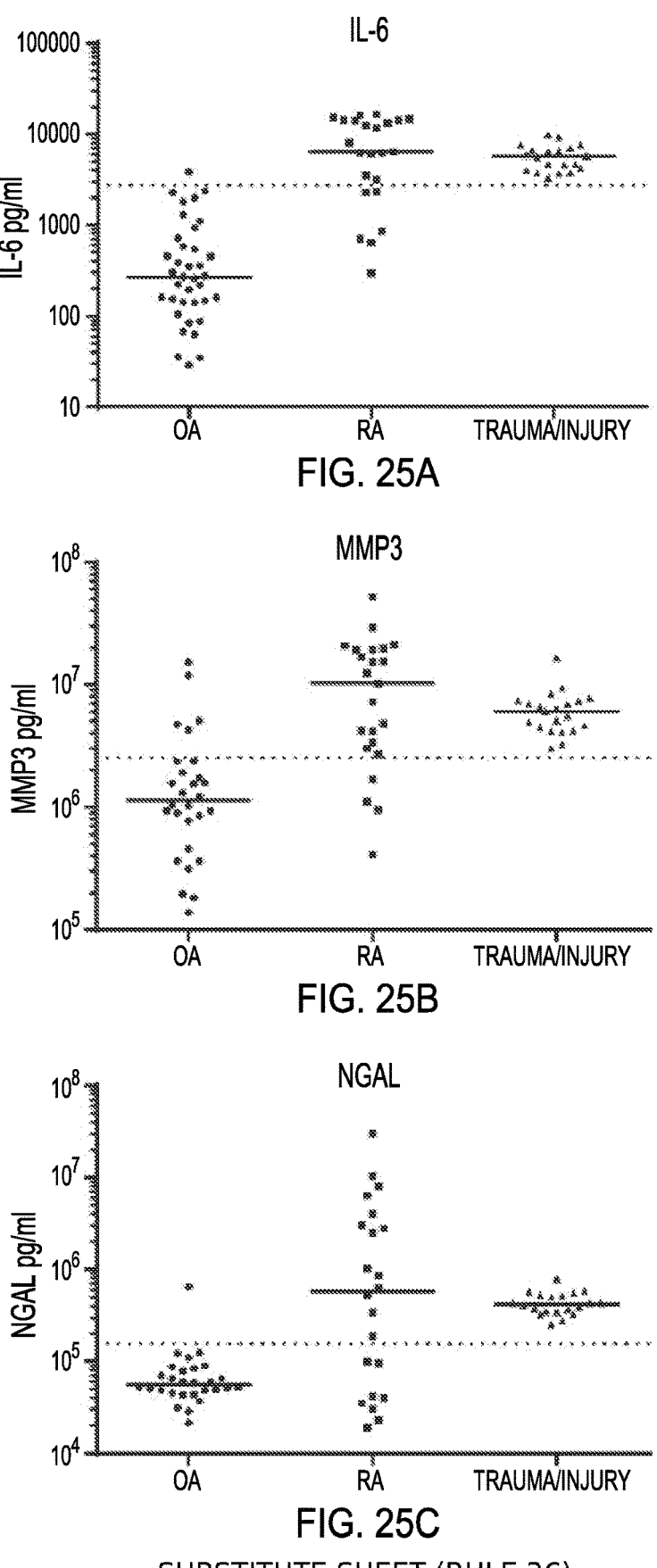
FIG. 25A-25C illustrate plots of various biomarkers in synovial fluid samples.
Figure 26:
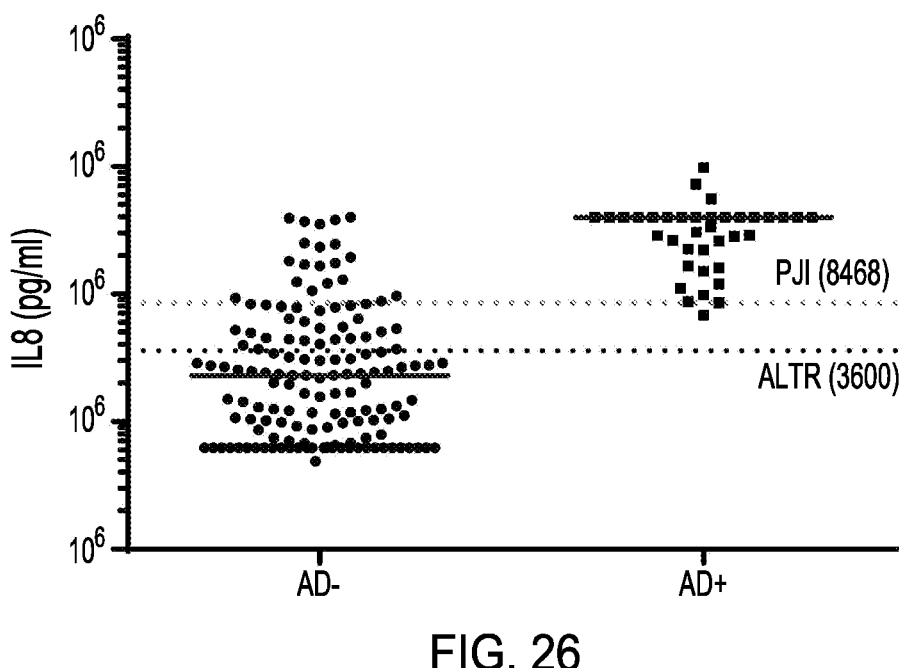
FIG. 26 illustrates a plot of IL-8 in synovial fluid samples to discriminate OA from AD+(PJI) or AD-(ALTR-adverse local tissue reaction). C/O<4×10$^6$ pg/mL (ALTR) and C/O<1×10' (PJI).

As shown in FIGS. 22A and 22B, two additional biomarkers of cartilage degradation, C1, C2 (ELISA assay) and C2C (ELISA source: IBEX Pharmaceuticals, Inc, Toronto CA), both for degradation of type 2 collagen, were run on a limited sample set. While C2C showed promising results on a small sample set, a variety of antibodies and kits for this marker are somewhat limited. Additionally, the available ELISA is a competition ELISA, which is less user friendly, produces rather large assay coefficients of variation and requires significant amounts of sample.

As shown in FIGS. 4A-4B, 5A-5F, 13A-13F, FIGS. 23A-23H and FIGS. 25A-25C, secondary screening for IL-6, IL-8, CRP, MMP-9, PDGF, MMP-3 and NGAL (biomarkers of inflammation) all were able to distinguish most osteoarthritis samples from the controls (either rheumatoid arthritis, trauma/injury or the combined groups). As shown in FIGS. 1A-2B, 5G, 5H, and 14A-14C, biomarkers OPG, OPN, and OC were also able to distinguish osteoarthritis samples from the controls.

Results of receiver operating characteristic (ROC) analysis of 11 biomarkers in discriminating OA from RA and Trauma/Injury or a combined group of RA and Trauma/Injury (All) are shown in FIGS. 24 and 49. AUC=area under the curve. Sensitivity and Specificity are in percentages. FIG. 24: values for COMP are in ng/mL; values for CRP are in mg/dL; all other values are in pg/mL.

Example 3

Multiplex Biomarker Analysis

Combining multiple markers can add greater sensitivity and specificity than a single biomarker used alone. In the case of OA, combining a biomarker of cartilage degradation (e.g., COMP) with a biomarker of inflammation that is expressed in lower levels in OA (e.g., IL-6, IL-8, CRP, MMP-3, MMP-9, NGAL, or PDGF), gives superior discrimination of osteoarthritis samples from RA or trauma/injury, e.g., as shown in FIGS. 6A-6D.

Using two markers also allows greater leeway in adjustment of cutoffs, balancing sensitivity and specificity depending on the consequences of false negatives (OA missed) or false positives (incorrect classification of a different disease group). Table 5 below shows sensitivity and specificity of the combined markers (data from FIGS. 24 and 49) for comparing OA with all other groups. We recommend the combination of COMP with IL-8 as the best combination for the determination of late stage osteoarthritis. As disclosed in this patent document other combinations are possible.

Analysis of 111 samples of synovial fluid from osteoarthritis (n=52) compared to age matched groups of rheumatoid arthritis (n=22) and trauma/injury (n=35) have shown that combining a biomarker of cartilage degradation, e.g., cartilage oligomeric matrix protein (COMP), with a biomarker of low inflammation, e.g., low interleukin 8 (IL-8), low MMP-9 or low PDGF, gives superior performance over either biomarker alone. Each of these biomarkers has been reported in the literature as a valuable marker of osteoarthritis, however the combinations we report here are unique.

TABLE 5

Sensitivity and Specificity of a combination of COMP
and other biomarkers (see, e.g., FIG. 24).

| Biomarkers | % Sensitivity | % Specificity |
|---|---|---|
| COMP and IL8 | 90.7 | 98.0 |
| COMP and CRP | 88.9 | 96.0 |
| COMP and MMP-9 | 87.0 | 97.9 |
| COMP and PDGF | 100.0 | 84.8 |
| COMP and OPN | 89.3 | 86.2 |
| COMP and OC | 82.1 | 88.5 |
| COMP and OPG | 64.3 | 85.7 |

Example 4

COMP and IL-8 Combination Discriminates OA from RA and T/I

A sample set consisting of 146 knee synovial fluid samples encompassing a broader number of arthritic conditions (rheumatoid arthritis, septic arthritis, osteoarthritis, and crystalline arthritis) were screened to assess and confirm the relevance of utilizing a COMP and IL-8 as a clinical tool to differentiate osteoarthritis from the other inflammatory arthritic conditions. The concentrations of IL-8 and COMP were determined using two quantitative ELISA kits as described below. The Human IL-8 immunoassay is a 3-hour solid phase ELISA designed (Source: CD Laboratories®) to quantify IL-8 in synovial fluid. A monoclonal antibody raised against the recombinant 72 AA-variant of human IL-8 derived from *E. coli* is coated on the wells of a microtiter plate. The same recombinant protein is used in the standards and quality controls. Samples, including standards of known IL-8 concentrations, control specimens or unknowns are pipetted into these wells. Synovial fluid samples diluted 1:10 are added to a precoated microtiter plate with anti-IL-8 antibody. After a wash step, a biotinylated antibody conjugate (mouse monoclonal anti-IL-8) is added to complex with captured IL-8. Following another wash step, a streptavidin-(horseradish) peroxidase (SA-HRP) conjugate is added to bind to the biotinylated antibody conjugate. Unbound SA-HRP is removed by an additional washing step. The bound SA-HRP conjugate is measured by a colorimetric reaction after the addition of a substrate solution containing Tetramethylbenzidine (TMB) solution. The SA-HRP in the bound conjugate catalyses the oxidation of TMB solution, producing a blue product. The color development is stopped by the addition of acid to the wells that cause the change from blue to yellow. The optical density is read at 450 nm with 570 nm as a reference (450 nm-570 nm). The intensity of the colored product is directly proportional to the concentration of IL-8 in the sample.

The Human COMP ELISA is a 4.5-hour solid phase test (Source: R&D Systems®) to measure COMP concentrations in biological fluids. A monoclonal antibody specific for hCOMP has been pre-coated onto a 96-wells microplate. Standards, controls, and diluted specimens are added into the microplate wells containing assay diluent and any COMP present in the synovial fluid specimen is bound to the immobilized antibody. After washing away any unbound substances, an enzyme-linked monoclonal antibody specific for hCOMP is added to the wells. Following a wash step to remove any unbound antibody-enzyme reagent, a substrate solution is added to the wells and color develops proportionally to the amount of COMP bound in the diluted specimen addition step. The color formation is stopped by addition of sulfuric acid and measured by reading the optical density at 450 nm using a 570 nm correction.

Figure 34A:
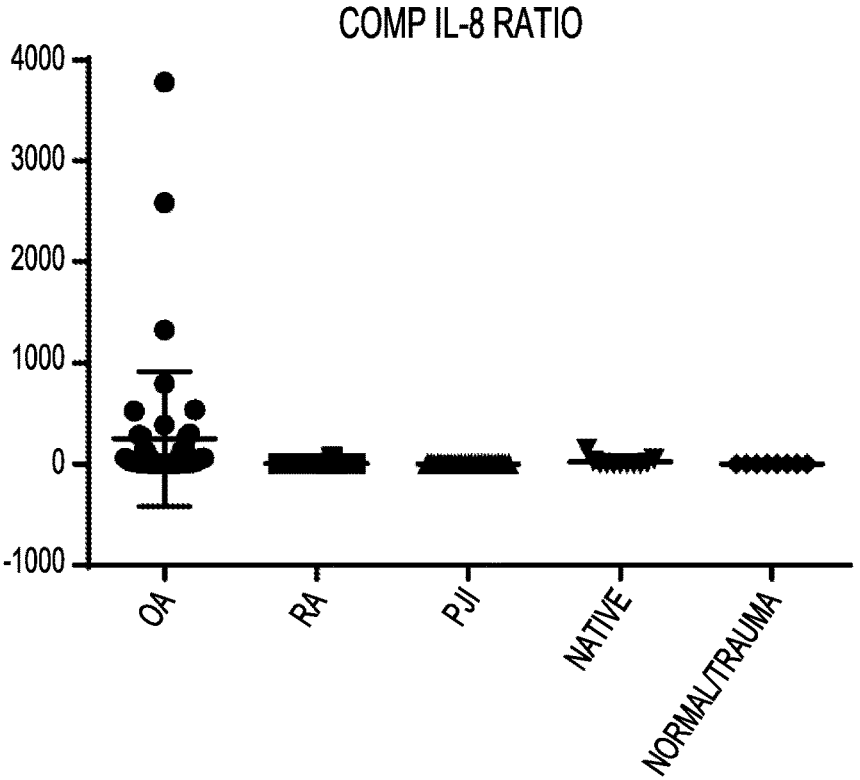
FIGS. 34A and 34B illustrate plots of COMP:IL-8 ratios for synovial fluid samples with various disease states.
Figure 34B:
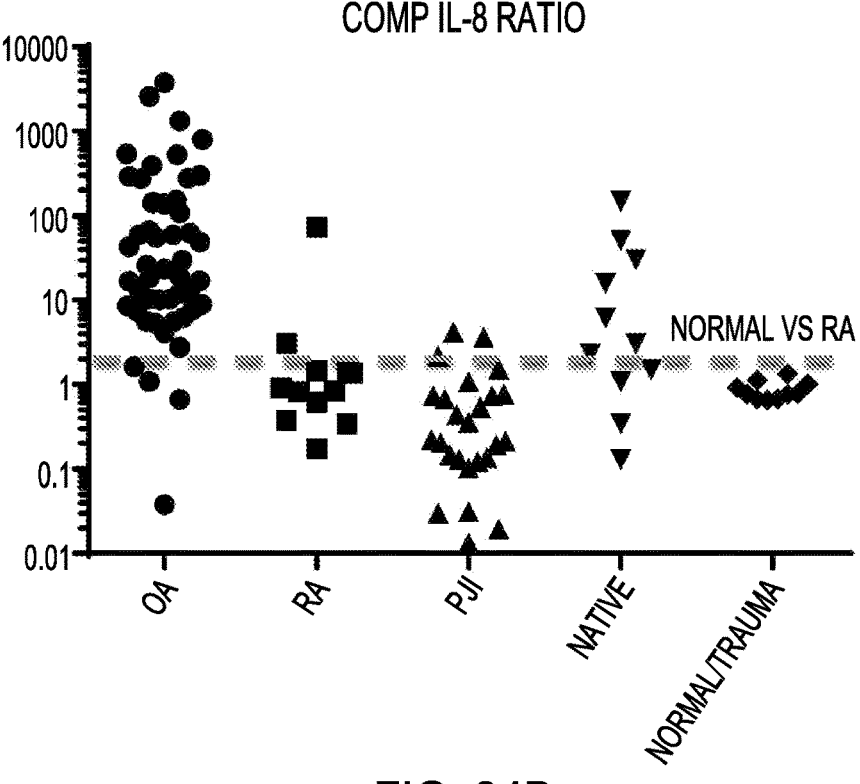

The results of this study confirmed the utility of COMP and IL-8 as a dual biomarker combination in differentiating osteoarthritis from other arthritic arthropathies (e.g. rheumatoid arthritis, periprosthetic infection, crystalline arthritis, and trauma/injury) and broaden the inflammatory arthritides that could be differentiated from osteoarthritis over the initial studies (Examples 1-3). The COMP/IL-8 combination to discriminate between osteoarthritis and other arthritic conditions at a ROC-determined cutoff of 3.96 ng/pg (Table 6 below). At the established COMP/IL-8 cutoff, the clinical sensitivity and specificity of the diagnostic test was 90% and 85%, respectively, and represents a substantial improvement in diagnostic accuracy over each biomarker alone considering that OA samples (8) with indications of inflammation (e.g. high levels of IL-8) were not removed from the data analysis. When these samples are omitted from the analysis, the sensitivity of the COMP/IL-8 algorithm improves to 100% while specificity remain unchanged. Assay results are shown in FIGS. 26, 27, 28A, 29, 30, 31-33B. Plots of COMP:IL-8 ratios are shown in FIGS. 28B, 34A, 34B.

One hundred and forty-six synovial fluid samples representative of various arthropathies were screened for COMP/IL-8 dual biomarker combination. As shown in FIG. 28B, a scatterplot of 89 synovial fluid samples from inflammatory RA (12), NSA (3), and CA (25), and OA (49). A cutoff ratio between COMP/IL-8 of >3.96 is derived from response operator characteristic (ROC) analysis. Native synovial fluid samples with low CRP levels (little or no inflammation) (8), PJI (39), and trauma/injury (10) are excluded from FIG. 28B.

This study is evidence that the ratiometric combination of COMP to IL-8 is a significantly better alternative than the standalone COMP and IL-8 levels at differentiating OA (non-inflammatory) from other inflammatory arthritic types e.g. rheumatoid, native septic, periprosthetic joint infection, and crystalline arthritis.

TABLE 6

Diagnostic accuracy of COMP and IL-8 biomarkers for the
differentiation of noninflammatory and inflammatory
arthrosis for data set depicted in FIG. 28B.

| Biomarker | Cutoff | Sensitivity | Specificity |
|---|---|---|---|
| COMP | >2185 ng/mL | 92% | 55% |
| IL-8 | <751 pg/mL | 88% | 78% |
| COMP/IL-8 Ratio | >3.96 | 90% | 85% |

This preliminary study suggests that the ratio of COMP to IL-8 is a significantly better than the individual measurements of COMP and IL-8 at differentiating OA (non-inflammatory) from other inflammatory arthritic types e.g. rheumatoid, native septic, and crystalline arthritis.

Example 5

Figure 36:
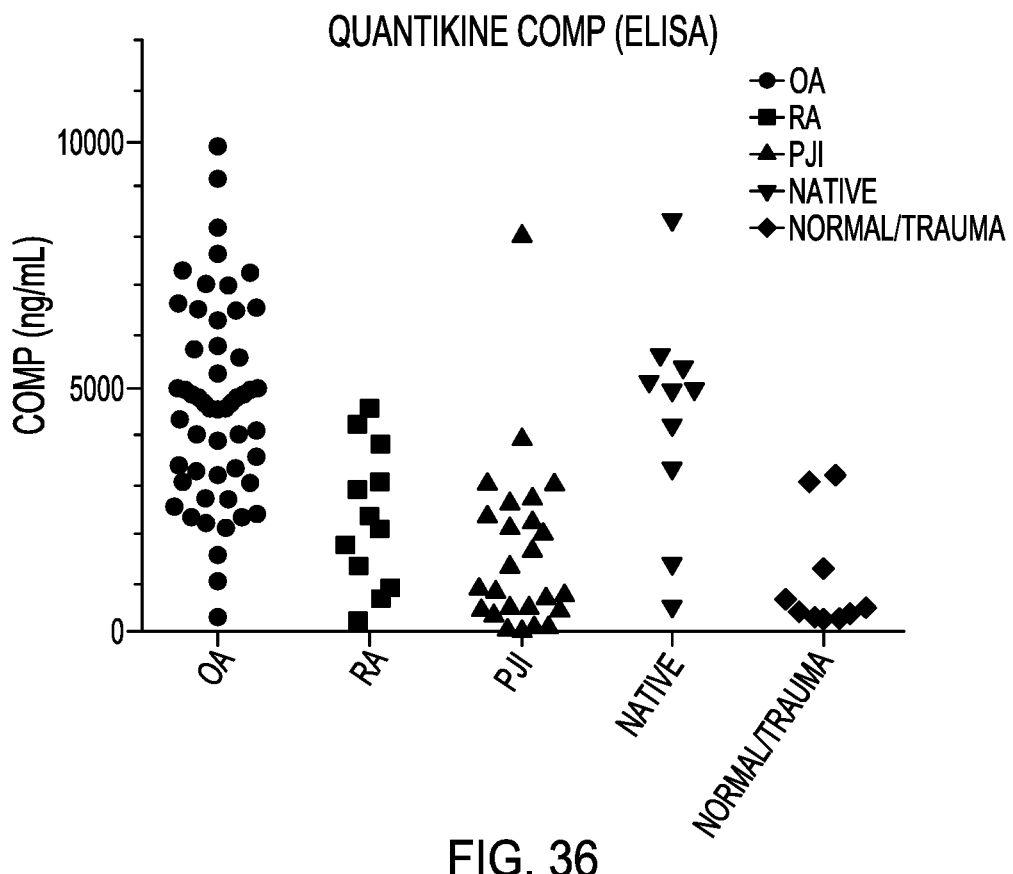
FIG. 36 illustrates a plot of COMP (measured by ELISA) in synovial fluid samples from various disease states.

Cutoff Interrogation for Independent Biomarkers (COMP and IL-8) and Biomarker Ratio of COMP/IL-8 Using Algorithms One hundred and twenty-two (122) synovial fluid samples representative of various arthropathies were screened using ELISA (Source: Quantikine) for COMP/IL-8 dual biomarker combination, as shown in FIG. 36. A scatterplot was prepared using the inflammatory population (11 RA and 2 native samples with alpha defensin (AD) test positive, and

Figure 35:
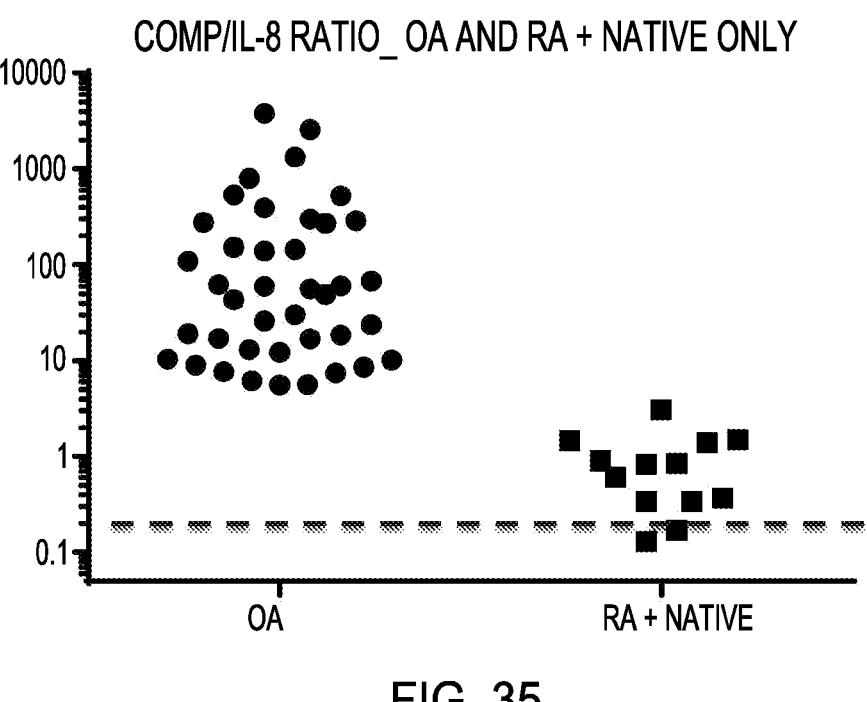
FIG. 35 illustrates COMP:IL-8 ratios for synovial fluid sample with various disease states. COMP:IL-8 C/O>0.2. Units of COMP and IL-8 are the same for calculating ratios.

45 the non-inflammatory OA population (40 samples). As shown in FIG. 35, the dotted line denotes a cutoff ratio for COMP/IL-8 of 4.3 ng/pg (or 4.3*1000 pg/pg=4300), derived by the ROC analysis. Excluded from FIG. 35 were native samples that were AD negative (little or no inflammation) (8); periprosthetic joint samples (39), non-idiopathic isolated OA samples (8), and trauma/injury (10), as they do not represent the intended population for the OA algorithm (FIGS. 37A-37G).

TABLE 7

Diagnostic Accuracy of Individual Biomarkers and Ratio

| Biomarker | Cutoff (C/O) | Population Used in C/O Calculation | % Sensitivity | % Specificity |
|---|---|---|---|---|
| COMP | >1452 ng/mL | Normal, OA | 95.9 | 80 |
| IL-8 | >673.1 pg/mL | OA, RA | 91.7 | 83.7 |
| COMP/IL-8 | >4300 ng/pg | OA, RA, and AD+ (native) | 100 | 100 |

The following algorithm was developed for using COMP and IL8 in diagnosing OA with Sensitivity 87.04% and Specificity 88.3%:

(1) Is COMP>1500 ng/mL? (A) Yes—evidence of cartilage damage, calculate COMP:IL-8 ratio, (B) No—no evidence of OA.

(2) Is COMP/IL-8>4.3 ng/pg? (A) Yes—POSITIVE OA; (B) No—evidence of cartilage damage and high inflammation.

The accuracy of the algorithm is shown in Tables 8 and 9 below.

TABLE 8

Samples Tested using Algorithm

| Test | Disease Present | Sample No. | Disease Absent | Sample No. | Total No. |
|---|---|---|---|---|---|
| Positive | True Pos. | a = 47 | False Pos. | c = 14 | a + c = 61 |
| Negative | False Neg. | b = 7 | True Neg. | d = 106 | b + d = 113 |
| Total | | a + b = 54 | | c + d = 120 | |

TABLE 9

COMP/IL-8 Algorithm Accuracy;

| Statistic | Value | 95% CI |
|---|---|---|
| Sensitivity | 87.04% | 75.10% to 94.63% |
| Specificity | 88.3% | 81.20% to 93.47% |
| Positive Likelihood Ratio | 7.46 | 4.51 to 12.34 |
| Negative Likelihood Ratio | 0.15 | 0.07 to 0.29 |
| Disease Prevalence (*) | 31.03% | 24.25 to 38.48% |
| Positive Predictive Value (*) | 77.05% | 67.00% to 84.74% |
| Negative Predictive Value (*) | 93.81% | 88.32% to 96.81% |
| Accuracy (*) | 87.93% | 82.14% to 92.37% |

(*) = no adjustment for prevalence

The diagnostic accuracy of using COMP alone with a cutoff>1500 ng/mL is shown in Table 10 and 11 below.

TABLE 10

COMP > 1500 ng/mL

| Test | Disease Present | Sample No. | Disease Absent | Sample No. | Total No. |
|---|---|---|---|---|---|
| Positive | True Pos. | a = 53 | False Pos. | c = 55 | a + c = 108 |
| Negative | False Neg. | b = 1 | True Neg. | d = 65 | b + d = 66 |
| Total | | a + b = 54 | | c + d = 120 | |

TABLE 11

COMP > 1500 ng/mL;

| Statistic | Value | 95% CI |
|---|---|---|
| Sensitivity | 98.15% | 90.11% to 99.95% |
| Specificity | 54.17% | 44.83% to 63.29% |
| Positive Likelihood Ratio | 2.14 | 1.76 to 2.61 |
| Negative Likelihood Ratio | 0.03 | 0.00 to 0.24 |
| Disease Prevalence (*) | 31.03% | 24.25 to 38.48% |
| Positive Predictive Value (*) | 49.07% | 44.15% to 54.01% |
| Negative Predictive Value (*) | 98.48% | 90.25% to 99.78% |
| Accuracy (*) | 67.82% | 60.33% to 74.69% |

(*) = no adjustment made for prevalence or specimen integrity

The diagnostic accuracy of using COMP alone with a cutoff>5451 ng/mL to achieve equivalent specificity to COMP/IL-8 ratio is shown in Tables 12 and 13.

TABLE 12

COMP cutoff > 5451 ng/mL

| Test | Disease Present | Sample No. | Disease Absent | Sample No. | Total No. |
|---|---|---|---|---|---|
| Positive | True Pos. | a = 5 | False Pos. | c = 14 | a + c = 19 |
| Negative | False Neg. | b = 49 | True Neg. | d = 106 | b + d = 155 |
| Total | | a + b = 54 | | c + d = 120 | |

TABLE 13

COMP cutoff > 5451 ng/mL.

| Statistic | Value | 95% CI |
|---|---|---|
| Sensitivity | 9.26% | 3.08% to 20.30% |
| Specificity | 88.33% | 81.20% to 93.47% |
| Positive Likelihood Ratio | 0.79 | 0.30 to 2.09 |
| Negative Likelihood Ratio | 1.03 | 0.92 to 1.14 |
| Disease Prevalence (*) | 31.03% | 24/24% to 38.48% |
| Positive Predictive Value (*) | 26.32% | 11.93% to 48.49% |
| Negative Predictive Value (*) | 68.39% | 66.03% to 70.66% |
| Accuracy (*) | 63.79% | 56/18% to 70.93% |

(*) = no adjustment made for prevalence or specimen integrity.

The diagnostic accuracy of using COMP alone with a cutoff>2200 ng/mL to achieve equivalent sensitivity to COMP/IL-8 ratio is shown in Tables 14 and 15.

TABLE 14

| COMP with a cutoff > 2200 ng/mL | | | | |
|---|---|---|---|---|
| Test | Disease Present | Sample No. | Disease Absent | Sample No. | Total No. |
| Positive | True Pos. | a = 47 | False Pos. | c = 45 | a + c = 92 |
| Negative | False Neg. | b = 7 | True Neg. | d = 75 | b + d = 82 |
| Total | | a + b = 54 | | c + d = 120 | |

TABLE 15

| COMP with a cutoff > 2200 ng/mL; | | |
|---|---|---|
| Statistic | Value | 95% CI |
| Sensitivity | 87.04% | 75.10% to 94.63% |
| Specificity | 62.50% | 53.20% to 71.17% |
| Positive Likelihood Ratio | 2.32 | 1.80 to 2.99 |
| Negative Likelihood Ratio | 0.21 | 0.10 to 0.42 |
| Disease Prevalence (*) | 31.03% | 2.24% to 38.48% |
| Positive Predictive Value (*) | 51.09% | 44.78% to 57.36% |
| Negative Predictive Value (*) | 91.46% | 84.11% to 95.59% |
| Accuracy (*) | 70.11% | 62.72% to 76.81% |

(*) = no adjustment made for prevalence or specimen integrity

Diagnostic accuracy of using IL-8 alone with a cutoff set to BQL to achieve best possible specificity results in diagnostic is shown in Tables 16 and 17. An equivalent specificity to COMP/IL-8 with IL-8 alone cannot be achieved due to the number of inflammatory specimens BQL; Set cutoff to BQL.

TABLE 16

| IL-8 cutoff set to BQL | | | | |
|---|---|---|---|---|
| Test | Disease Present | Sample No. | Disease Absent | Sample No. | Total No. |
| Positive | True Pos. | a = 28 | False Pos. | c = 24 | a + c = 52 |
| Negative | False Neg. | b = 26 | True Neg. | d = 96 | b + d = 122 |
| Total | | a + b = 54 | | c + d = 120 | |

TABLE 17

| IL-8 cutoff set to BQL; | | |
|---|---|---|
| Statistic | Value | 95% CI |
| Sensitivity | 51.85% | 37.84% to 65.66% |
| Specificity | 80.00% | 71.72% to 86.75% |
| Positive Likelihood Ratio | 2.59 | 1.67 to 4.03 |
| Negative Likelihood Ratio | 0.60 | 0.45 to 0.81 |
| Disease Prevalence (*) | 31.03% | 24.25% to 38.48% |
| Positive Predictive Value (*) | 53.85% | 42.89% to 64.45% |
| Negative Predictive Value (*) | 78.69% | 73.41% to 83.16% |
| Accuracy (*) | 71/26% | 63.93% to 77.86% |

(*) = no adjustment made for prevalence or specimen integrity

Diagnostic accuracy of using IL-8 alone with a cutoff set to 750 pg/mL to achieve equivalent sensitivity to COMP/IL-8 ratio is shown in Tables 18 and 19.

TABLE 18

| IL-8 cutoff 750 pg/mL | | | | |
|---|---|---|---|---|
| Test | Disease Present | Sample No. | Disease Absent | Sample No. | Total No. |
| Positive | True Pos. | a = 47 | False Pos. | c = 43 | a + c = 90 |
| Negative | False Neg. | b = 7 | True Neg. | d = 77 | b + d = 84 |
| Total | | a + b = 54 | | c + d = 120 | |

TABLE 19

| IL-8 cutoff 750 pg/mL; | | |
|---|---|---|
| Statistic | Value | 95% CI |
| Sensitivity | 87.04% | 75.10% to 94/.63% |
| Specificity | 64.17% | 54.90% to 72.71% |
| Positive Likelihood Ratio | 2.43 | 1.87 to 3.15 |
| Negative Likelihood Ratio | 0.20 | 0.10 to 0.41 |
| Disease Prevalence (*) | 31.03% | 24.25% to 38.48% |
| Positive Predictive Value (*) | 52.22% | 45.72% to 58.65% |
| Negative Predictive Value (*) | 91.67% | 84.47% to 95.70% |
| Accuracy (*) | 71.26% | 63.93% to 77.86% |

(*) = no adjustment made for prevalence or specimen integrity

The diagnostic accuracy of using COMP and IL-8 as a dual biomarker algorithm is shown in Tables 20 and 21. The diagnostic algorithm is: (1) COMP<BQL=OA negative, (2) IL-8>800=OA negative; (3) COMP>BQL and IL-8<800=OA positive.

TABLE 20

| COMP and IL-8 Dual Biomarker Algorithm | | | | |
|---|---|---|---|---|
| Test | Disease Present | Sample No. | Disease Absent | Sample No. | Total No. |
| Positive | True Pos. | a = 48 | False Pos. | c = 13 | a + c = 61 |
| Negative | False Neg. | b = 6 | True Neg. | d = 107 | b + d = 113 |
| Total | | a + b = 54 | | c + d = 120 | |

TABLE 21

| COMP and IL-8 Dual Biomarker Algorithm; | | |
|---|---|---|
| Statistic | Value | 95% CI |
| Sensitivity | 88.89% | 77.37% to 95.81% |
| Specificity | 89.17% | 82.19% to 94.10% |
| Positive Likelihood Ratio | 8.21 | 4/87 to 13.83 |
| Negative Likelihood Ratio | 0.12 | 0.06 to 0.27 |
| Disease Prevalence (*) | 31.03% | 24.25% to 38.48% |
| Positive Predictive Value (*) | 78.69% | 68.66% to 86.15% |
| Negative Predictive Value (*) | 94.69% | 89.32% to 97.44% |
| Accuracy (*) | 89/08% | 83.47% to 93.30% |

(*) = no adjustment made for prevalence or specimen integrity

The diagnostic accuracy of using COMP alone with a cutoff of >5450 ng/mL (CA samples excluded from the data) is shown in Tables 22 and 23.

TABLE 22

| COMP > 5450 ng/mL (CA samples excluded) | | | | |
|---|---|---|---|---|
| Test | Disease Present | Sample No. | Disease Absent | Sample No. | Total No. |
| Positive | True Pos. | a = 13 | False Pos. | c = 0 | a + c = 13 |
| Negative | False Neg. | b = 27 | True Neg. | d = 13 | b + d = 40 |
| Total | | a + b = 40 | | c + d = 13 | |

TABLE 23

| COMP > 5450 ng/mL (CA samples excluded) | | |
|---|---|---|
| Statistic | Value | 95% CI |
| Sensitivity | 32.50% | 18.57% to 49.13% |
| Specificity | 100.00% | 75.29% to 100.00% |
| Positive Likelihood Ratio | | |
| Negative Likelihood Ratio | 0.68 | 0.54 to 0.84 |
| Disease Prevalence (*) | 75.47% | 61.72% to 86.24% |
| Positive Predictive Value (*) | 100.00% | |
| Negative Predictive Value (*) | 32.50% | 27.97% to 37.38% |
| Accuracy (*) | 49.06% | 35.06% to 63.16% |

The diagnostic accuracy of COMP alone using a cutoff of >2200 ng/mL (CA samples excluded from the data) to achieve equivalent sensitivity of COMP/IL-8 ratio is shown in Tables 24 and 25.

TABLE 24

| COMP >2200 ng/mL (CA samples excluded) | | | | |
|---|---|---|---|---|
| Test | Disease Present | Sample No. | Disease Absent | Sample No. | Total No. |
| Positive | True Pos. | a = 47 | False Pos. | c = 45 | a + c = 92 |
| Negative | False Neg. | b = 7 | True Neg. | d = 75 | b + d = 82 |
| Total | | a + b = 54 | | c + d = 120 | |

TABLE 25

| COMP >2200 ng/mL (CA samples excluded) | | |
|---|---|---|
| Statistic | Value | 95% CI |
| Sensitivity | 87.04% | 75.10% to 94.63% |
| Specificity | 62.50% | 53.20% to 71.17% |
| Positive Likelihood Ratio | 2.32 | 1.80 to 2.99 |
| Negative Likelihood Ratio | 0.21 | 0.10 to 0.42 |
| Disease Prevalence (*) | 31.03% | 24.25% to 38.48% |
| Positive Predictive Value (*) | 51.09% | 44.78% to 57.36% |
| Negative Predictive Value (*) | 91.46% | 84.11% to 95.59% |
| Accuracy (*) | 70/11% | 62.72% to 76.81% |

Example 6

Diagnostic Accuracy of Differential Diagnosis Arthritis Panel

The diagnostic algorithm shown in FIGS. 37A-37G was used to analyze two-hundred and thirty-four synovial fluid samples that had been collected and blinded. The study group included samples (cohorts) from patients with OA, RA, CA, and NSA, as well as some samples of unknown diagnosis. Supporting data collected, when possible, for each sample included demographics (age, sex), red blood cell count, hemoglobin concentration, absorbance at 280 nm wavelength, crystal examination, alpha defensin, lactate concentration, white blood cell count, and differential. IL-8, COMP, anti-CCP, and RF tests were performed. Data analysis includes sensitivity, specificity, and predictive value calculations, receiver operating characteristic curves (area under the curve), and likelihood ratios.

COMP is known to be elevated when osteoarthritis is present, and cartilage has degraded. Further, in isolated, idiopathic osteoarthritis, inflammatory chemokine IL-8 is low, and so a high COMP/IL-8 ratio is observed. Conversely, IL-8 is elevated in cases of inflammatory arthritis (RA, NSA, CA) or acute trauma, and so isolated, idiopathic osteoarthritis is unlikely when either COMP is low, or the COMP/IL-8 ratio is low. When COMP is low, osteoarthritis is unlikely due to lacking evidence of cartilage degeneration. When COMP is elevated but the COMP/IL-8 ratio is low, it is likely that the cartilage degradation is due to an inflammatory arthritis or osteoarthritis is comorbid with another inflammatory condition. WBC concentration and % neutrophils are both elevated when infection is present in the joint. The Differential Diagnosis Arthritis Panel provides an option to reflex to the alpha defensin/lactate algorithm for NSA when the decision threshold is met. Presence or absence of crystals of monosodium urate (MSU) or calcium pyrophosphate dihydrate (CPP) crystals was determined by polarization light microscopy. Elevated anti-CCP or elevated RF indicates a high likelihood of RA, although the published specificity of anti-CCP is greater than that of RF. Sensitivities of anti-CCP and RF are low, so a negative test result cannot be used to rule out the disease RA may be classified as indeterminate in cases where anti-CCP is below the decision threshold and RF is above the decision threshold or vice versa. In apparent negative or indeterminate cases, additional RA testing could be considered.

A total of 234 clinical synovial fluid specimens were selected and characterized to confirm the diagnostic accuracy of the components of the Differential Diagnosis Arthritis Panel that had not been previously validated: osteoarthritis (OA) and rheumatoid arthritis (RA). Other panel components consisted of crystalline arthritis (CA), white blood cell count (WBC) and % neutrophils (% PMN) or neutrophil elastase (HNE) and if samples were elevated in any of these test (WBC/% PMN, HNE), they were reflexed to the NSA panel.

Figure 41:
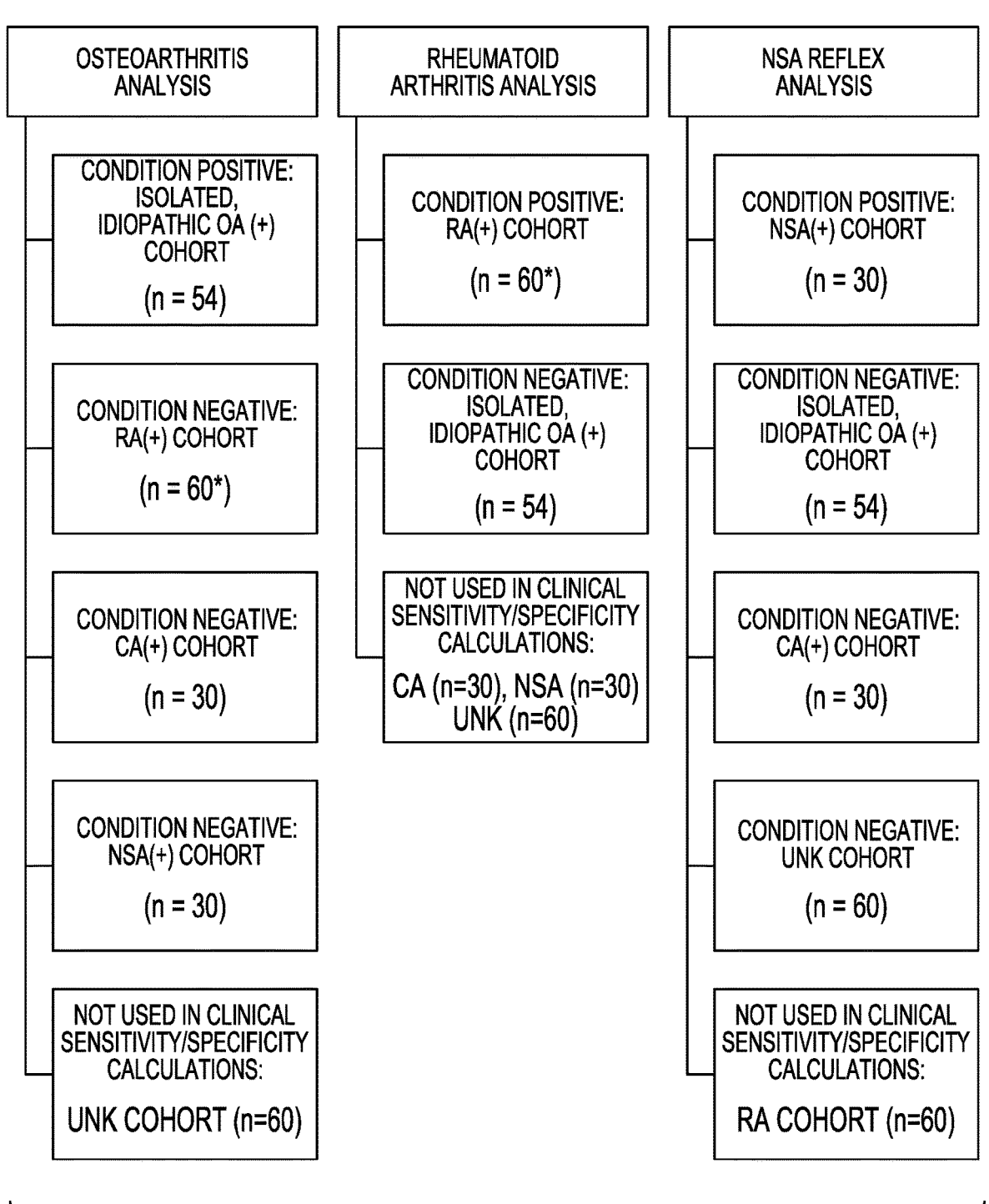
FIG. 41 illustrates a diagram of synovial fluid sample cohorts for methods of evaluating synovial fluid samples according to one aspect.

Acceptance criteria were established based on currently available standard of care diagnostic performance as well as widely accepted performance values for sensitivity and specificity. A statistically valid, representative set of study samples was obtained, and the "true" clinical state of each subject (i.e. sample) was established. The study samples included isolated, idiopathic OA (54), RA (60), NSA (30), CA (30) cohorts, and specimens with representative symptoms of unknown diagnosis (60), as shown in FIG. 41.

For the OA algorithm analysis of OA, RA, CA and NSA cohorts (FIG. 41), performance of 54 isolated, idiopathic OA specimens was compared against 120 inflammatory arthritis specimens (CA+NSA+RA). In the case of RA algorithm, 60 RA specimens were analyzed against 54 non-RA (isolated, idiopathic OA). Specimens from CA, NSA, or UNK groups were excluded from the RA algorithm analysis because RA has not been ruled out from those cases and comorbidities may be present. For the reflex testing, percentages of known positive (NSA cohort) and known negative (OA, CA, UNK cohorts) groups are evaluated.

Immunoassay Sources

Quantikine ELISA human COMP kit components (R&D Systems®); Anti-CCP ELISA kit components (Axis Shield); RF latex reagents R1, R2 (Beckman Coulter), QC1, QC1 (Thermo Scientific); AD (CD Diagnostics).

Arthritis Panel Components

Sample Integrity Assessment: Sample integrity testing consists of measuring absorbance at a wavelength of 280 nm and of measuring the amount of blood contamination in the sample by assessing red blood cell (RBC) concentration. The A280 reading is a nonspecific method to assess protein concentration, which would be expected to be significantly lower in the setting of a saline lavage or significantly higher if a substance with absorbance at A280, such as blood or contrast agent, was added to the synovial fluid prior or during the arthrocentesis. Using synovial fluid samples (n=5858), the optimal absorbance at 280 nm was identified as 0.342 to 1.19. This reference range is now used to verify the quality of the synovial fluid sample, and a note is made on the reported results if the synovial fluid sample absorbance falls outside of this range. Using the same synovial fluid samples (n=5858), an acceptable amount of RBC contamination was established as RBC count<1,000,000 cells/μL, which represents <20% blood contamination. Samples exhibiting RBC count above this range are noted to consist of more than 20% blood, and caution should be used when interpreting results of such highly contaminated samples.

WBC Count/Differential: The Arthritis Panel includes a white blood cell (WBC) count and differential, performed using an automated analyzer. As stated in the medical recommendations, synovial fluid can be categorized as inflammatory or non-inflammatory based on a WBC concentration cutoff of 2000 cells/μL. The % PMNs of the sample also provides an indication of the level of neutrophil infiltration, and a higher percentage is indicative of inflammatory arthritis (i.e. less likely to be a primary OA diagnosis without concomitant inflammatory arthropathy). Additionally, high WBCs and % PMNs in the synovial fluid may be indicative of infection. In order to leverage the existing comprehensive NSA panel, NSA reflex testing is offered for any sample meeting a threshold of >3000 cells/μL or >80% polymorphonuclear cells (PMNs). This threshold was established based on the current criteria established for PJI by the Musculoskeletal Infection Society (MSIS) and is a conservative threshold that is unlikely to fail to refer an infected sample for NSA testing. The comprehensive NSA panel includes a manual confirmation of the automated cell count for cell counts over 3000 cells/μL and the proprietary Synovasure Alpha Defensin Test, which includes alpha defensin, hemoglobin, and lactate. Depending on the available sample volume, Synovasure Neutrophil Elastase, the Synovasure Microbial ID Panel, and fluid culture will be performed and reported as well.

Osteoarthritis: A key component of the Arthritis Panel is the set of biomarkers which informs an OA diagnosis and differentiates primary OA from the inflammatory arthritis types. Feasibility work demonstrated elevated cartilage oligomeric matrix protein (COMP) in synovial fluid samples from patients with a known osteoarthritis diagnosis. Despite the clear association between elevated COMP concentration and osteoarthritis, COMP by itself is not a very useful biomarker because it does not differentiate primary OA patients from patients with cartilage deterioration as well as some inflammatory arthritis type, such as OA secondary to RA or OA with CPPD. To enable clear delineation of primary OA from other, more complicated cases, IL-8 is employed as a second component of the OA algorithm. IL-8 concentration in synovial fluid has been demonstrated to be higher in psoriatic arthritis than in osteoarthritis and is noted to be even higher in rheumatoid arthritis than in psoriatic arthritis.[80] Additionally, IL-8 has been shown to be elevated in synovial fluid in gouty arthritis and is a proposed mediator of crystal-induced inflammation. Synovial fluid concentrations of IL-8 in native septic arthritis samples are not well published, but an internal review of native (i.e. not PJI) samples demonstrates significant elevation of IL-8 in alpha defensin positive samples versus alpha defensin negative samples. Taken together, COMP and IL-8 tests complement each other to form a robust test differentiating primary osteoarthritis from inflammatory arthritis types. First, the COMP concentration is measured to identify cartilage damage indicative of OA. In the case of a positive COMP result, the ratio of COMP concentration to IL-8 concentration can be used to differentiate exclusive primary OA (positive ratio due to high COMP/low IL-8) from inflammatory arthritis with evidence of cartilage damage. It is anticipated that, for some samples with a positive COMP result but a negative COMP/IL-8 ratio (below cutoff), there will be evidence of RA, native septic arthritis, or crystalline arthritis identified in other components of the panel. This would then indicate concomitant disease, such as the common condition of OA with CPPD.

Rheumatoid Arthritis: Current laboratory testing for rheumatoid arthritis is generally limited to serum evaluation of anti-cyclic citrullinated peptide (anti-CCP) and rheumatoid factor (RF), and synovial fluid analysis is suggested for selected patients, but only to aid in the diagnosis or exclusion of crystalline arthritis or septic arthritis.[55] The published specificities of anti-CCP and RF in serum are 95% and 85%, respectively, and so a positive anti-CCP result is considered to be more reliable than a positive rheumatoid factor result for diagnosing RA. Sensitivities of anti-CCP and RF are 66.0% and 71.6%, respectively, and so a negative test result cannot be used to rule out the disease. The presence of either anti-CCP or RF increased testing sensitivity for diagnosis of RA to 81.4%, and the presence of both RF and anti-CCP demonstrated a specificity similar to that of anti-CCP alone. A diagnostic test to measure anti-CCP and RF in synovial fluid is not currently offered by laboratories, presumably because a blood draw is more convenient than a synovial fluid aspiration. Furthermore, many laboratories are set up to process blood, and the introduction of a different specimen type can create logistical challenges. In the case of the Arthritis Panel, however, the joint fluid analysis will provide key insights for several arthritis types, with RA not necessarily being the suspected diagnosis but perhaps has not yet been ruled out. Hence, a key goal of the scientific development of the Arthritis Panel is to validate synovial fluid tests for anti-CCP and RF which have similar (or better) sensitivity and specificity as the serum tests currently performed by other laboratories. Published literature has demonstrated that it is possible to achieve this, with one study demonstrating a synovial fluid anti-CCP test specificity of 95.6% and sensitivity of 83.7%. The same study concluded that it may be possible to detect anti-CCP in synovial fluid earlier in the disease due to local production of the antibody. Based on these data, the approach of measuring local concentrations of anti-CCP and RF in support of an RA diagnosis appears to be scientifically sound and will be further validated prior to launching the panel for clinical diagnostic use.

Crystalline Arthritis: The use of polarized microscopy for examination of synovial fluid and identification of MSU and CPP crystals confirms a diagnosis of gout or calcium pyro-phosphate dehydrate crystal deposition disease (CPPD). Intracellular crystals are diagnostic of an acute flare. Litera-ture has demonstrated that this technique is highly sensitive and specific when executed by trained observers, with a sensitivity and specificity of 95.3% and 97.2% for MSU crystal identification and 92.7% and 92.1% for CPPD crystal identification.

Results

Specimen Integrity: Specimen integrity was performed using A280 and either hemoglobin (in OA and RA samples) or RBC count (NSA, CA, UNK samples). Where RBC counts were available (FIGS. 44A-44D), that data was used for specimen integrity analysis instead of hemoglobin. Samples with acceptable A280 and RBC count ⌑ 1,000,000/ µL (or an equivalent concentration of hemoglobin lower than 20 g/L) were characterized as non-compromised and were included in the diagnostic accuracy analysis. Samples out-side A280 nm range<0.342 or <LL, are classified as diluted while an absorbance of ≥1.190 or >UL are classified as contaminated and were excluded from diagnostic accuracy analyses. Samples with RBC count>1,000,000/µL OR hemoglobin≥20 g/L were characterized as hemorrhagic, diluted with blood and were excluded from diagnostic accuracy analyses. Sample integrity results showed only 3 out of 234 (1.3%) specimens used in this study were flagged as diluted or contaminated per the above criteria. A complete list of A280 nm results for each study sample is found in FIGS. 46A-46O.

WBC, Differential and HNE: The following classification was established for analysis of WBC and % PMN:

Samples with WBC count≤2000/µL were characterized as non-inflammatory. Samples with WBC count>2000/µL were characterized as inflammatory. Samples with WBC count>3000/µL OR % neutrophils (% PMN)>80% were characterized as "recommended for NSA reflex testing." Individual RBC and WBC with differential values for CDL sourced specimens are show in FIGS. 44A-44D.

Twenty-nine out of 30 samples characterized as septic are positive for WBC count or differential criteria. Only one native septic arthritis specimen (031) was classified negative per WBC/PMN (with WBC 2773 cells/µL and 75.6% PMN) but tested positive for alpha defensin NSA algorithm with AD 1.475 and Lactate 71.7 mg/dL. Based on recent adjust-ments to the clinical guidelines which reduced the PMN % threshold for joint infection from 80% to 70%, a re-analysis of the data was performed to include this new % PMN criteria as well. When a 70% PMN decision limit was utilized, the following results were reported:

30 of 30 (100%) septic arthritis samples tested positive for reflex testing and meet acceptance criteria.

36 of 144 (25%) specimens from OA, CA, and RA cohorts were positive for reflex testing, meeting acceptance criteria.

36 of 144 (25%) specimens from OA, CA, and RA cohorts were positive for reflex testing, meeting acceptance criteria.

40 of 144 (27.8%) specimens from CA, OA, and UNK (known non-septic) cohorts were positive for reflex testing: 8 of these were INDETERMINATE for NSA and 1 addi-tional INDETERMINATE specimen from the UNK cohort did not meet criteria for reflex testing. These 9 indeterminate samples were excluded from sensitivity and specificity cal-culations.

Neutrophil elastase (HNE) ELISA was used as a proxy for neutrophil count in synovial fluid from frozen OA and RA cohorts due to the inability to collect cell count data for previously frozen OA and RA SF samples. The purpose of testing HNE was to identify the number of OA and RA samples that would be reflexed for Native Septic Arthritis Panel (NSA) testing (Alpha defensin and lactate tests) according to the following criteria. Results were calculated as a normalized signal, relative to a cutoff value. Samples with HNE≥1.0 were characterized as positive for HNE and "recommended for NSA reflex testing", Sample with HNE<1.0 were characterized as negative for HNE. How-ever, the HNE test was run for all diagnostic accuracy samples regardless of cohort—and the same was done with alpha defensin test and lactate—in order to restrict the number of F/T cycles (FIGS. 46A-46)). Results from AD ELISA in OA and RA cohorts were used to confirm that there was no missed infection diagnosis on these groups.

When HNE test is applied by itself to the entire dataset of 234 samples, 71 (30.3%) were reflexed to the NSA algo-rithm. Of these 71 samples, 40 (56.3%) were categorized as positive with 30 of these 40 originating from the NSA sample set. Other than the NSA sample cohort, the only other sample cohort testing positive by the NSA algorithm was RA with 10 samples. Since the purpose of the HNE test was to serve as a proxy test for neutrophil counts due to the inability to collect cell count data in the OA and RA cohort, the reflex analysis was also performed in these two sample cohorts. Twenty-one samples (18.4%) were reflexed by the HNE test to the NSA algorithm for further analysis.

Using a 70% PMN criteria and considering the NSA cohort (n=30) as clinically positive for infection and the OA, CA, and UNK cohorts as negative for septic (based on AD results for frozen OA specimens), a 2×2 contingency table was constructed to assess WBC and Differential results and to define the number of true positives (TP), false positives (FP), true negatives (TN), and false negatives (FN).

| | Condition Positive | Condition Negative |
|---|---|---|
| Test Positive | 30 | 31 |
| Test Negative | 0 | 135 |

The number of samples in above table were used to calculate diagnostic test results according to the following formulas in MedCalc:

$$\text{Diagnostic (Clinical) Sensitivity} = TP/(TP+FN)$$

$$\text{Diagnostic (Clinical) Specificity} = TN/(TN+FN)$$

Diagnostic accuracy was calculated with no adjustment for disease prevalence (DP), and adjusted for an estimated prevalence of 5% and 10%.

TABLE 26

Diagnostic Accuracy of WBC/PMN tests at Unadjusted and Adjusted
Disease Prevalence (DP); LR = likelihood ratio; PVV = positive
predictive value; NPV = negative predictive value;
(*) = values dependent on DP

| | No DP Adjustment | | DP Adjusted to 10% | | DP Adjusted to 5% | |
|---|---|---|---|---|---|---|
| Statistic | Value | 95% CI | Value | 95% CI | Value | 95% CI |
| Sensitivity | 100.% | 88.4% to 100% | 100% | 88.4% to 100% | 100% | 88.4% to 100% |
| Specificity | 81.3% | 74.6% to 86.9% | 81.3% | 74.6% to 86.9% | 81.3% | 74.6% to 86.9% |
| LR+ | 5.35 | 3.90 to 7.36 | 5.35 | 3.90 to 7.36 | 5.35 | 3.90 to 7.36 |
| LR− | 0.00 | 0.01 to 0.28 | 0.00 | | 0.00 | |
| DP | 15.3% | 10.6% to 21.2% | 10% | | 5.0% | |
| PVV* | 49.2% | 41.3% to 57.1% | 37.3% | 30.2% to 45.0% | 22.0% | 17.0% to 27.9% |
| NVP* | 100% | | 100% | | 100% | |
| Accuracy* | 84.2% | 78.3% to 89.0% | 83.2% | 77.2% to 88.1% | 82.3% | 76.2% to 87.3% |

In summary, the negative predictive value of the reflex algorithm is 100% in all scenarios of disease prevalence. Given the anticipated patient population for which this panel is intended and an estimated disease prevalence of 5%, we estimated that the sensitivity is 100% [95% CI: 88.43% to 100%]. Additionally, the negative likelihood ratio is zero, and any ratio below 0.1 is identified in literature as the threshold of a good "rule-out" test. Furthermore, the number of non-infected samples being reflexed for NSA testing is reasonable at less than 30%. Hence, using the recently updated clinical decision limits of 3000 white blood cells/μL or 70% neutrophils to identify specimens for NSA reflex testing meets acceptance criteria and demonstrates outstanding performance for use as an NSA screening test.

Crystal Examination: The following conditions were considered for analysis of crystal examination during diagnostic accuracy: samples with MSU crystals present were classified as "gout"; samples with CPPD crystals present were classified as "CPPD"; Samples with no crystals present were classified as "no evidence of crystalline arthritis." Crystalline bodies were found most often as singlet types (MSU, CPPD or cholesterol) and rarely in combination (CA cohort, blinded ID 28) for 74 (31.6%) out of the 234 study samples. See FIGS. 45A-45B. Excluding the 4 samples with cholesterol crystals (all in the RA cohort), the rate of MSU and CPPD crystal positivity in this sample study set was 29.9% (70 of 234). MSU was the most predominant crystal encountered in this sample set at 58.6% (41/70). The CA cohort was composed of 30 specimens containing MSU or CPPD crystals and encompassed 30 of 70 (42.9%) samples identified with crystals. The distribution of crystalline arthritis for the remaining of the cohorts was as follows: 29 (41.4%) in RA, 11 (15.7%) in the NSA subset, while no crystals were observed in OA and UNK cohorts. If OA and CA cohorts are omitted from the analysis due to pre-selection for the absence or presence of crystals, respectively, the combined rate of crystal positivity in the UNK, NSA, and RA was 26.6%. For the purposes of clinical data analysis, samples were broadly classified as crystalline arthritis (+) or (−), regardless of which type of crystals were present in the specimen and location (extracellular or intracellular). Cholesterol type of crystal was not taken in account for the positive/negative classification made in this study, however, presence of cholesterol crystals has been previously linked with rheumatoid arthritis.

Osteoarthritis: The OA component of the panel has been designed as an algorithm which suggests isolated, idiopathic OA when COMP meets a decision threshold of >1500 ng/mL AND the COMP/IL-8 ratio meets a decision threshold of 4.3 ng/pg FIGS. 42A-42E. These clinical decision limits were established based on feasibility work (Examples 1-5). In accordance with this algorithm, samples were classified as follows:

Samples with COMP≤1500 ng/mL were classified as "OA negative." Samples with COMP>1500 ng/mL were used to calculate COMP/IL-8. If COMP/IL-8 ratio≤4.3 ng/pg samples were classified as "suggests cartilage damage and elevated inflammatory status." For the purposes of diagnostic accuracy analyses, this outcome was classified as "OA negative", because isolated, idiopathic OA cannot be confirmed. Samples with COMP>1500 ng/mL AND COMP/IL-8 ratio>4.3 ng/pg were classified as "OA positive."

The assessment of clinical validity was performed with 54 condition positive (OA samples) and 117 condition negative (non-OA) distributed across the sample cohorts as follows: 57 RA, 30 NSA, and 30 CA samples. Three RA samples that failed sample integrity test were excluded from consideration. A detailed analysis of COMP/IL-8 ratio in OA cohort showed that 47 out of the 54 specimens reported a ratio>4.3 ng/pg. From the 7 specimens with ratios below the clinical decision limit, six (6) of them reported COMP>1500 ng/mL. A full table of COMP and COMP/IL-8 results in the OA cohort can be found in FIGS. 42A-42E. Of the 13 samples from the OA condition negative group but testing positive for OA, 7 corresponded to the CA cohort, while 6 were in the RA cohort.

A 2×2 contingency table was constructed to evaluate diagnostic accuracy of the OA algorithm and considered the performances of OA (non-inflammatory arthritis) versus RA, CA, and NSA (inflammatory arthritis).

| | Condition Positive | Condition Negative |
|---|---|---|
| Test Positive | 47 | 13 |
| Test Negative | 7 | 104 |

The values displayed in the contingency table were inputted into the diagnostic test calculator (MedCalc₂₂) and analyzed at the unadjusted and 60% disease prevalence (Table 27). Clinical sensitivity was 87.0% (95% CI 75.1% to 94.6%) and specificity was 88.9% (95% CI 81.8% to 94.0%) for an overall accuracy of 88.3% (95% CI 82.5% to 92.7%). The test has a high LR+ of 7.8 suggesting a high probability of an individual with a positive test having the condition relative to one with a positive test without the condition. An individual with osteoarthritis is 7.8× more likely to have a COMP/IL-8 ratio>4.3 (positive) than one with an inflammatory arthritis type (RA, CA, or NSA). Conversely, the LR− of 0.15 is very low indicating a high probability of not having the condition in the presence of a negative test relative to one with a negative test and condition positive. An individual with inflammatory arthritis is about 7×(1/0.15) more likely to have a negative COMP/IL-8 test than someone with OA.

TABLE 27

Diagnostic Accuracy of OA Algorithm Adjusted to 60% Disease Prevalence (DP). *Values dependent on DP.

| Statistic | No Adjustment for DP | | DP Adjusted to 60% | |
|---|---|---|---|---|
| | Value | 95% CI | Value | 95% CI |
| Sensitivity | 87.04% | 75.10% to 84.63% | 87.04% | 75.10% to 94.63% |
| Specificity | 88.89% | 81.75% to 93.95% | 88.89% | 81.75% to 93.95% |
| LR + | 7.83 | 4.64 to 13.21 | 7.83 | 4.64 to 13.21 |
| LR − | 0.15 | 0.07 to 0.29 | 0.15 | 0.07 to 0.29 |
| DP | 31.58% | 24.70% to 39.11% | 60% | |
| PVV* | 78.33% | 68.19% to 85.91% | 92.16% | 87.45% to 95.20% |
| NVP* | 93.69% | 88.13% to 96.75% | 82.05% | 69.55% to 90.15% |
| Accuracy* | 88.30% | 82.52% to 92.71% | 87.78% | 81.91% to 92.28% |

When adjusting for an anticipated prevalence of 60%, the accuracy of the test was 87.8° % (95% CI 81.9% to 92.3%), with positive and negative predictive values of 92.2% (95% CI 87.5% to 95.2%) and 82.1%, (95% CI 69.6% to 90.2%), respectively. As expected, the probability of an individual having the condition in the presence of a COMP/IL-8 ratio result>4.3 ng/pg increased considerably between the unadjusted and adjusted disease prevalence (PPV of 78.3% vs 92.2%). Earlier results of the dual use of this biomarker combination when deployed ratiometrically demonstrated a higher accuracy than the use of each biomarker alone. The ratio COMP/IL-8 is more informative regarding the separation of inflammatory from non-inflammatory arthritis. In summary, the osteoarthritis algorithm can differentiate isolated, idiopathic OA from other inflammatory arthritis types included in the differential diagnosis (crystalline arthritis, septic arthritis, and rheumatoid arthritis) with a high degree of accuracy.

Figure 43:
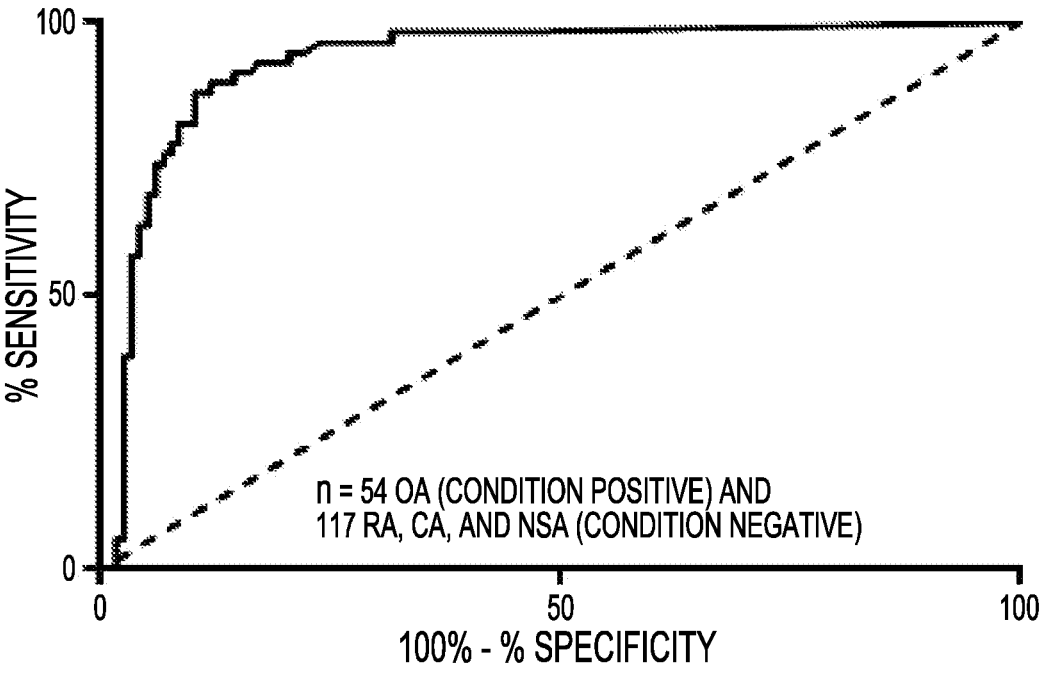
FIG. 43 illustrates a ROC for discriminating OA from RA, CA and NSA according to one method of evaluating a synovial fluid sample.

An analysis of the receiving operating characteristic (ROC) curve (FIG. 43) was derived for COMP/IL-8 ratios calculated on condition positive OA (54) and condition negative from samples cohorts: RA (57), CA (30), and NSA (30).

TABLE 28

Summary statistics for OA COMP/IL-8 ratio test

| Condition Positive/Condition Negative Samples (n) | 54/117 |
|---|---|
| Cutoff (ng/pg) | 4.3 |
| AUC | 0.93 |
| 95% CI for AUC | 0.89 to 0.97 |
| SE | 0.022 |
| p Value | 0.0001 |
| % Sensitivity | 87.0 |
| % Specificity | 88.9 |
| Youden's Index | 0.76 |

As per "rough" guidelines to classify the accuracy of a diagnostic test, an AUC of 0.93 is indicative of a "excellent" test capable of discriminating patients with the condition from condition negative. Similarly, Youden's index (J statistic) of 0.76 (0 to 1 where 0 is a test with no value and 1 is a perfect test) indicates the ability of the diagnostic test to balance detecting the OA condition (sensitivity) versus detecting the condition negative (specificity).

Rheumatoid Arthritis: The RA component of the panel was originally designed as an algorithm which suggests a possible RA diagnosis when anti-CCP meets a decision threshold of 5 U/mL, returns an indeterminate result when the anti-CCP decision threshold is not met but RF meets a decision threshold of 14 IU/mL, and indicates no evidence of RA when neither anti-CCP nor RF meet their respective clinical decision limits. These decision limits were established based on published literature and the manufacturer's recommendations for serum. However, after data collection it became clear in a blinded review that the clinical decision limits may need to be lower for synovial fluid (FIGS. 42A-42E). A "rule of thumb" for circulating biomarkers from serum is that they exist at approximately one-third of the circulating concentration in synovial fluid. Hence, appropriate cutoff for anti-CCP and RF would be to 1.7 U/mL and 4.7 IU/mL, respectively. The lowest non-zero point on the standard curve for each assay is 2 U/mL and 10 IU/mL for anti-CCP and RF, respectively, and the assays are validated for reporting at those limits. Prior to unblinding clinical diagnostic categories, an analysis method was established and included in the protocol to classify the diagnostic status based on these lower thresholds:

Samples with anti-CCP≥2 U/mL AND RF≥10 IU/mL were classified as "RA positive". Samples with anti-CCP≥2 U/mL AND RF<10 IU/mL were classified as "RA indeterminate". Samples with anti-CCP<2 U/mL AND RF≥10 IU/mL were classified as "RA indeterminate". Samples with anti-CCP<2 U/mL AND RF<10 IU/mL were classified as "RA negative".

In the clinical setting, any elevated status of anti-CCP or RF in the joint would be suggestive of RA and for the purposes of diagnostic accuracy, samples reported as "RA indeterminate" were classified as "RA positive". Clinical sensitivity and specificity for RF and anti-CCP, were calculated using the clinical decision limits described above (10 IU/mL and 2 U/mL, respectively). Sensitivity and specificity of both biomarkers were calculated in combination by considering 11 true positives for RF and anti-CCP and 8 indeterminates for anti-CCP as indicated in the 2×2 contingency table below. The number of specimens with condition negative corresponds to the 54 OA specimens that tested negative for RA algorithm.

| | Condition Positive | Condition Negative |
|---|---|---|
| Test Positive | 19 | 0 |
| Test Negative | 38 | 54 |

Diagnostic test calculations in MedCalc were made with either unadjusted disease prevalence or with an anticipated prevalence of 15%, based on a previous estimation suggested by the design team for the target population this Arthritis Panel would serve (Table 29).

TABLE 29

Diagnostic Evaluation of RA Algorithm at Unadjusted Disease Prevalence and at 15% Disease Prevalence (DP).
*values dependent on DP.

| | No Adjustment for DP | | DP Adjusted to 60% | |
|---|---|---|---|---|
| Statistic | Value | 95% CI | Value | 95% CI |
| Sensitivity | 33.33% | 21/40% to 47.06% | 33.33% | 21/40% to 47.06% |
| Specificity | 100.00% | 93.40% to 100.0% | 100.00% | 93.40% to 100.0% |
| LR + | | | | |
| LR − | 0.67 | 0.55 to 0.80 | 0.67 | 0.55 to 0.80 |
| DP* | 51.35% | 41.68% to 63.06% | 15% | |
| PVV* | 100.00% | | 100% | |
| NVP* | 58.70% | 54.19% to 63.06% | 89.47% | 87.62% to 91.08% |
| Accuracy* | 65.77% | 56.16% to 74.51% | 90.00% | 82.85% to 94/88% |

Although acceptance criteria for diagnostic specificity were met, acceptance criteria for RA diagnostic sensitivity were not met. Diagnostic accuracy for the RA algorithm was also evaluated for each biomarker separately by analyzing the AUC in GraphPad. ROC curves were constructed for RF and anti-CCP using the method described above for COMP/IL-8 ratio.

TABLE 30

Summary Statistics for receiver operating characteristic (ROC) analysis for RF and anti-CCP Tests

| Test | AUC | SE | 95% CI for AUC | Hypothesis Test | p Value |
|---|---|---|---|---|---|
| RF | 0.61 | 0.05 | 0.05 – 0.71 | Rejected | 0.0464 |
| Anti-CCP | 0.66 | 0.05 | 0.57 – 0.77 | Rejected | 0.0022 |

AUC results show acceptance criteria for the RA components of the panel are met via this pathway, indicating that the test does have the ability to discriminate between RA and non-RA specimens. As per "rough" guidelines to classify the accuracy of a diagnostic test, the AUCs for the RF and anti-CCP tests were between 0.6-0.7 and the test can be categorized as "sufficiently" capable of discriminating patients with condition positive from condition negative. Even though specificity is 100%, sensitivity is very low (33.33%), and consequently a negative result for the anti-CCP/RF combination of tests should not be used to aid in the exclusion of RA from the differential diagnosis. Given the observed comorbidities in the RA cohort, further evaluation may be considered to better characterize the RA(+), but the existing results from diagnostic accuracy can be used to support results reporting and performance claims at launch.

Diagnostic Accuracy Summary

Clinical performance (sensitivity/specificity) of the OA algorithm consisting of the COMP+, and COMP/IL-8 ratio was tested. Results showed clinical sensitivity of COMP/IL-8 was 87.0% (95% CI 75.1% to 94.6%) and specificity was 88.9% (95% CI 81.8% to 94.0%), for an overall accuracy of 88.3% (95% CI 82.5% to 92.7%). See FIG. 43. When disease prevalence was adjusted to 60%, the OA algorithm shows an overall accuracy at 87.8%, with positive predictive values of 92.2% and negative predictive values of 82.1% for aiding in diagnosis of isolated, idiopathic OA. The COMP/IL-8 test has a high LR+ (7.8) suggesting that an individual with osteoarthritis is 7.8× more likely to have a COMP/IL-8 ratio>4.3 ng/pg (positive) than one without the condition. Conversely, the LR− of 0.15 is very low indicating an individual without OA is about 7× more likely to have a negative COMP/IL-8 test than someone with OA.

Regarding the assessment of RA algorithm (RF/anti-CCP components), the test met acceptance criteria via the AUC pathway with a 0.6 result. This was done by evaluating the diagnostic accuracy of the panel components at pre-determined clinical decision limits. RA algorithm results indicate that RF and anti-CCP tests do have the ability to discriminate between RA and non-RA specimens. Even though specificity is 100%, sensitivity is low (33.3%) (95% CI 21.40% to 47.06%), and so a negative result for the combination of anti-CCP and RF tests should not be used to aid in the exclusion of RA from the differential diagnosis. Given the observed comorbidities in the RA Cohort, further evaluation could be used to review and attempt to better characterize the RA (+) cohort used in this study.

Example 7

Comparison of Earlier and Later COMP/IL-8 Ratio Data

Figure 27:
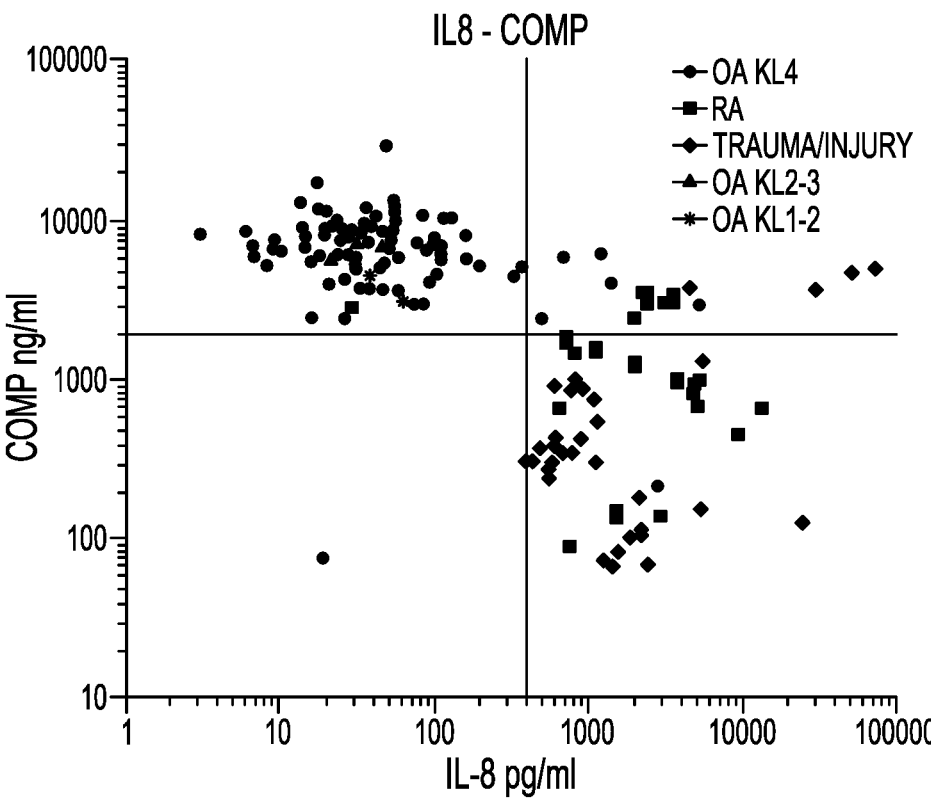
FIG. 27 illustrates a scatter plot of levels of COMP and IL-8 in synovial fluid samples from RA, T/I and various stages of OA. COMP C/O>1100 ng/mL; IL-8 C/O<400 pg/mL.
Figure 28A:
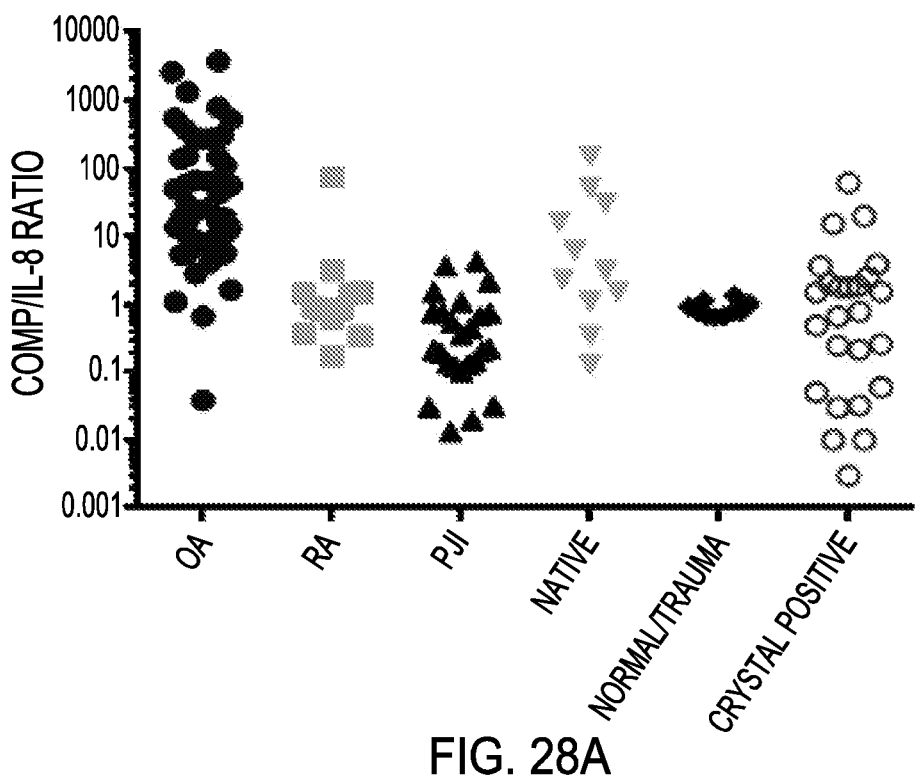
FIGS. 28A and 28B illustrate graphs of COMP:IL-8 ratios for synovial fluid samples.
Figure 28B:
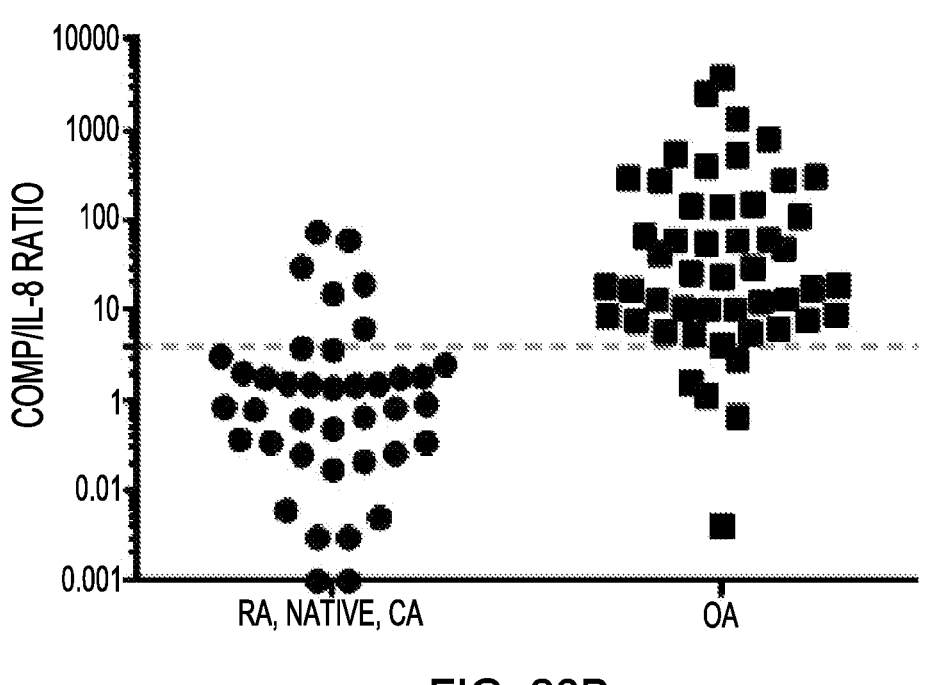
Figure 29:
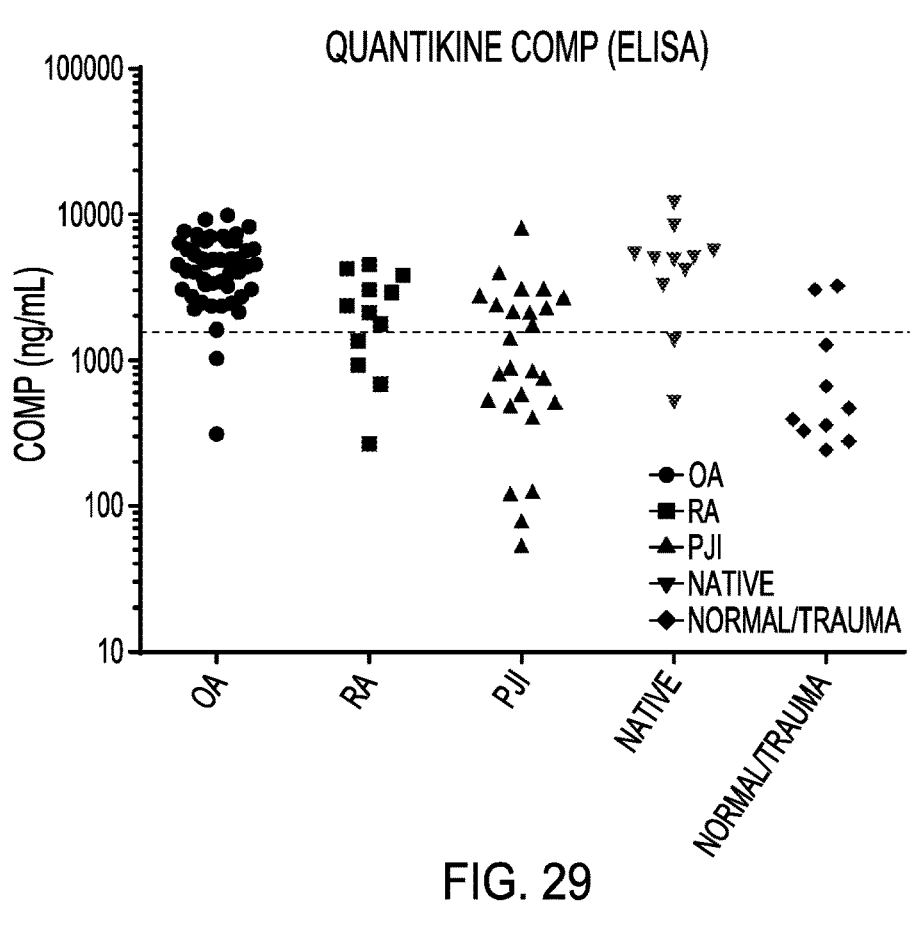
FIG. 29 illustrates a plot of COMP levels (detected by ELISA) in synovial fluid samples. COMP C/O>1000 ng/mL.
Figure 30:
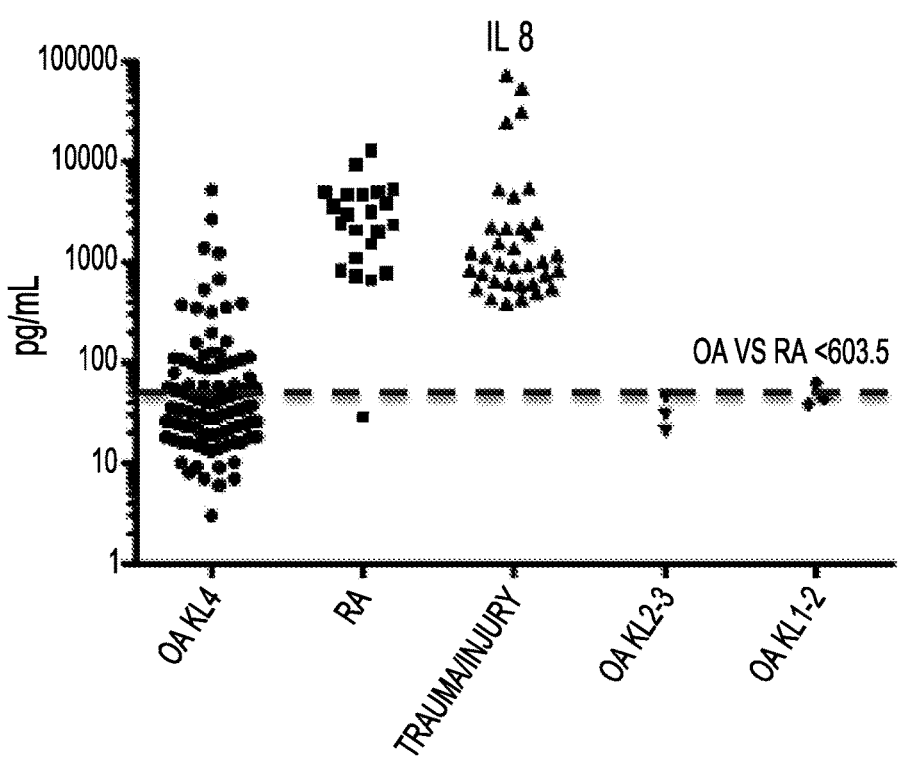
FIG. 30 illustrates a plot of IL-8 levels in synovial fluid samples from RA, T/I and various stages of OA. IL-8 C/O<600 pg/mL (OA vs. RA).
Figure 31:
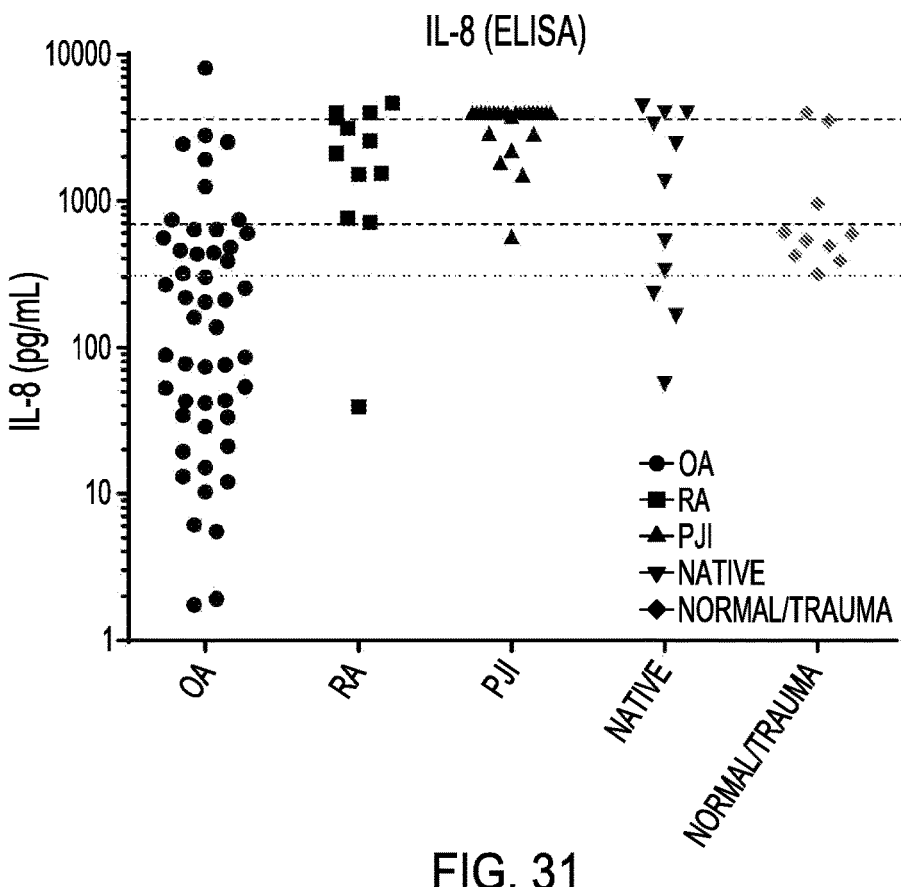
FIG. 31 illustrates a plot of IL-8 levels (detected by ELISA) in synovial fluid samples from various disease states. IL-8 C/O<700 pg/mL (RA, T/I).
Figure 32:
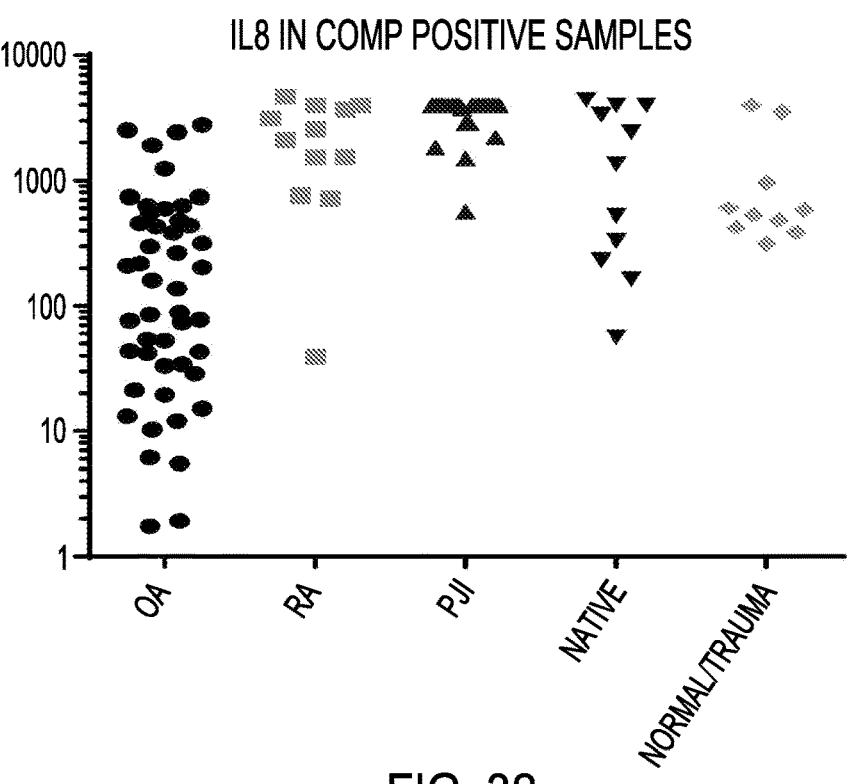
FIG. 32 illustrates a plot of IL-8 in COMP positive synovial fluid samples in various disease states.
Figure 33A:
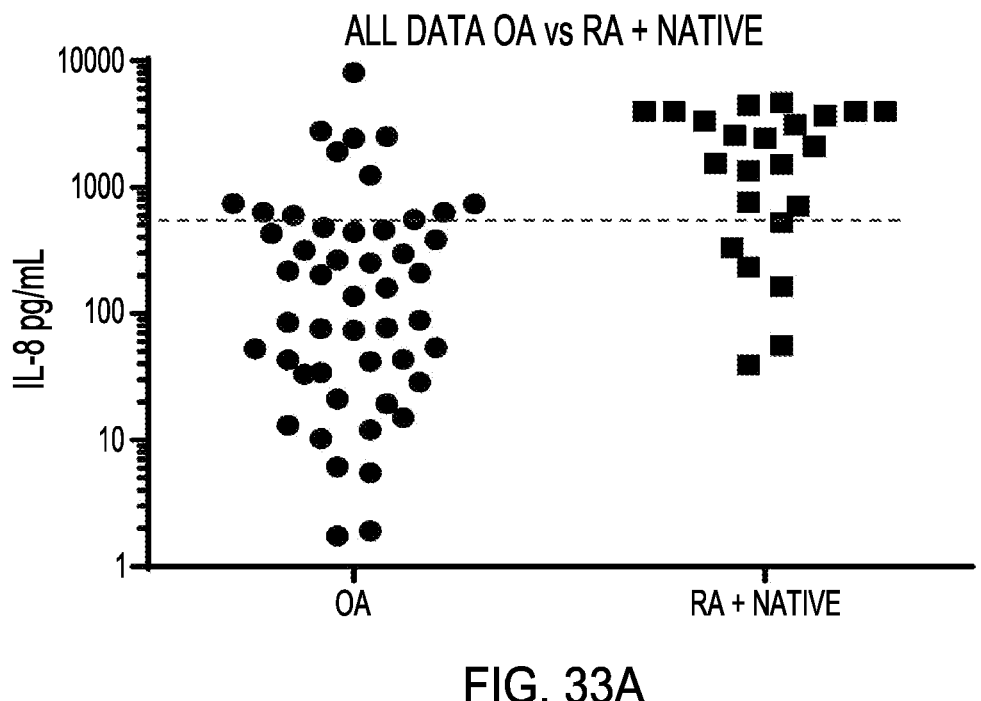
FIGS. 33A and 33B illustrate plots IL-8 in synovial fluid samples.
Figure 33B:
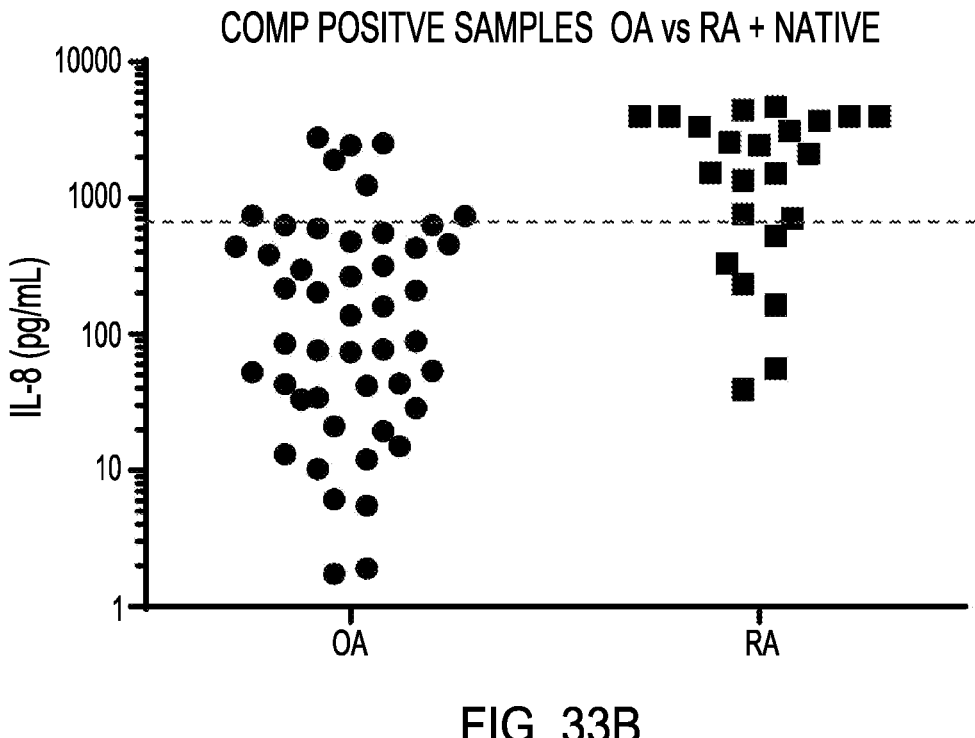

In an earlier study we determined the utility of a dual combination of biomarkers consisting of COMP and IL-8 in discriminating between osteoarthritis from rheumatoid arthritis (RA) and trauma/injury (T/I), as shown in FIG. 27 (Dotted lines denote cutoffs for COMP>1872 ng/mL or IL-8<381 pg/mL).

In a more recent study during February 2019, we utilized a sample set consisting of 108 knee synovial fluid samples encompassing a broader number of conditions (osteoarthritis (n=49) rheumatoid arthritis (n=12), native synovial fluid (n=11), normal/trauma (n=11), and prosthetic joint synovial fluid (n=25)) to assess and confirm the relevance of utilizing a COMP and TL-8 operation as a clinical tool to differentiate osteoarthritis from the other inflammatory arthritic conditions (OA versus RA and NSA samples testing positives for alpha defensin (AD) test which are equivalent to septic arthritis) (FIGS. 34A and 34B). The concentrations of IL-8 and COMP on each sample were determined by using two quantitative ELISA tests described in Example 4.

The results from the early 2019 study confirmed the utility of COMP and IL-8 as a dual biomarker combination in differentiating osteoarthritis from other arthritic arthropathies and broaden the inflammatory arthritides that could be differentiated from osteoarthritis over the initial study. The COMP/IL-8 combination discriminated osteoarthritis from inflammatory and septic arthritic conditions at a ROC-determined cutoff of 4.3 ng/pg (FIG. 35). Eight out of 48 OA specimens were removed from cutoff analysis due to elevated IL-8 (>673.1 pg/mL). The leftover 40 OA specimens with high COMP or COMP positive (>1500 ng/mL) were used on the cutoff calculation. For the RA cohort, one sample with high COMP (>1500 ng/mL) and low IL-8 sample was removed from analysis as it did not represent a typical inflammatory RA specimen and was considered a biological outlier.

Later, in September of 2019, a total of 25 knee synovial fluid specimens positive for crystalline arthritis were screened for COMP and IL-8 and results were combined with the earlier 2019 dataset in order to recalculate cutoff and reassess the effect of crystalline arthritis in the inflammatory arthropathies group (RA+NSA+CA) and versus OA cohort.

TABLE 31

Comparison of diagnostic accuracy of COMP/IL-8 ratio
before and after addition of CA cohort

| | COMP/IL-8 Cutoff | Sensitivity | Specificity |
|---|---|---|---|
| Feb. 2019 | >4.3 ng/pg | 100% | 85% |
| Sept. 2019 | >3.96 ng/pg | 90% | 85% |

At the established COMP/IL-8 cutoff, the clinical sensitivity and specificity of the diagnostic test was 90% and 85%, respectively, and represents a substantial improvement in diagnostic accuracy over each biomarker alone considering that OA samples (8) with indications of inflammation and removed during the first cutoff analysis back in February 2019 (e.g. high levels of IL-8) were kept on this occasion (Table 31). When these samples are omitted from the analysis, the sensitivity of the COMP/IL-8 algorithm improves to 100% while specificity remain unchanged. The addition of 25 crystalline arthritis samples changed the cutoff of OA versus non-OA in 8% from 4.3 ng/pg to 3.96 ng/pg. A comparison of the cutoffs obtained for each biomarker separately versus COMP/IL-8 ratio, showed the highest sensitivity and specificity for the ratio.

TABLE 32

Diagnostic accuracy of COMP and IL-8
biomarkers for the differentiation of
noninflammatory and inflammatory arthrosis.

| | Biomarker | COMP/IL-8 Cutoff | Sensitivity | Specificity |
|---|---|---|---|---|
| Feb. 2019 | COMP | >2185 ng/mL | 92% | 55% |
| | IL-8 | <751 pg/mL | 88% | 78% |
| Sept. 2019 | COMP | >3046 ng/mL | 78% | 75% |
| | IL-8 | <673.1 pg/mL | 92% | 84% |

The results show that the ratiometric combination of COMP to IL-8 is a significantly better alternative than the standalone COMP and IL-8 assessments at differentiating OA (non-inflammatory) from other inflammatory arthritic types e.g. rheumatoid, native septic, and crystalline arthritis. Cutoff was decided to be used at 4.3 ng/pg which shows only 8% difference with the newly determined 3.96 ng/pg ratio.

Example 8

COMP/IL-8 Ratio Decreases with OA Severity

Figure 38:
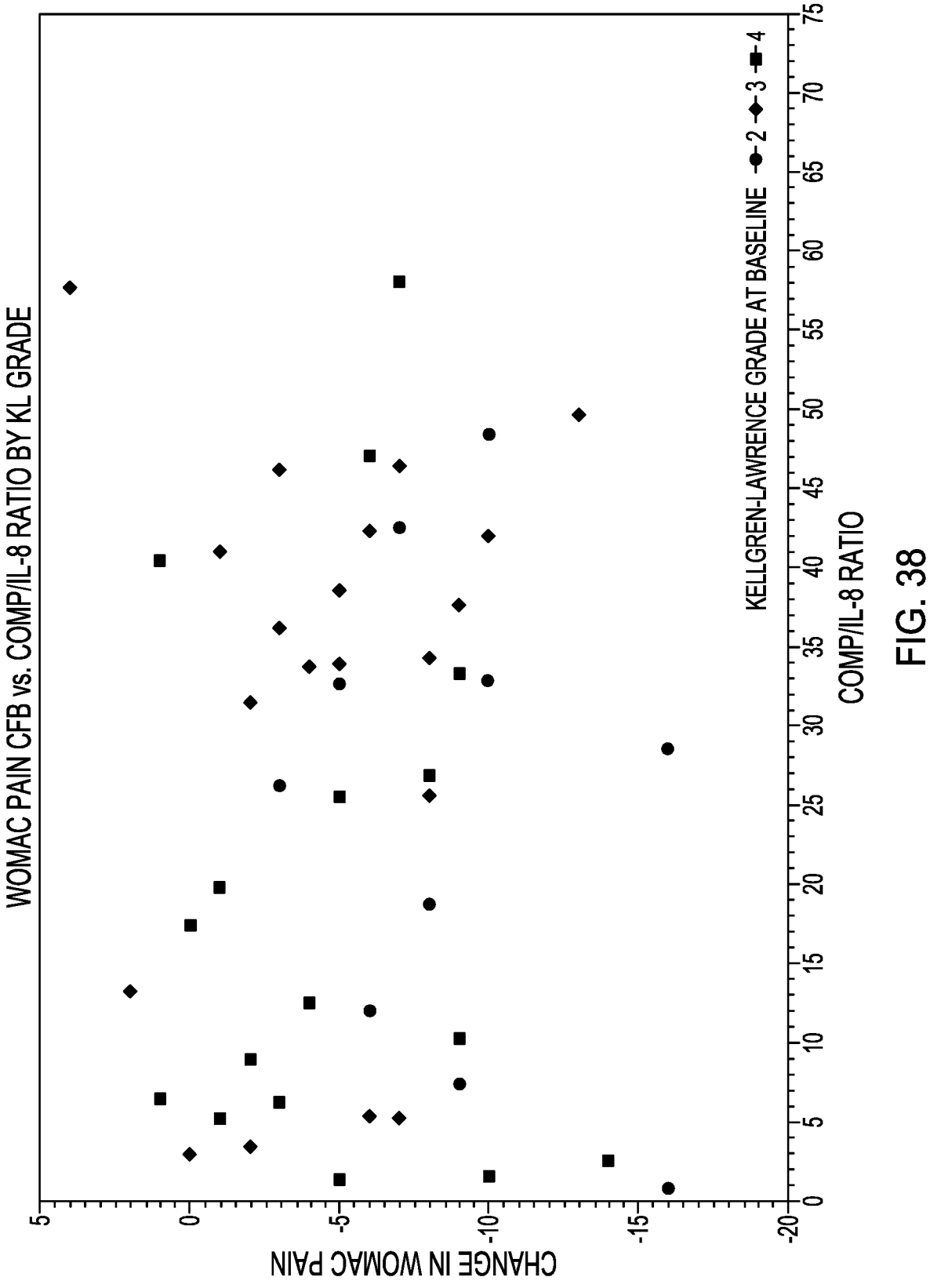
FIG. 38 illustrates a plot of synovial fluid samples by COMP:IL-8 ratio and Western Ontario and McMaster Universities Pain Index ((WOMAC) for various stages of OA.
Figure 39:
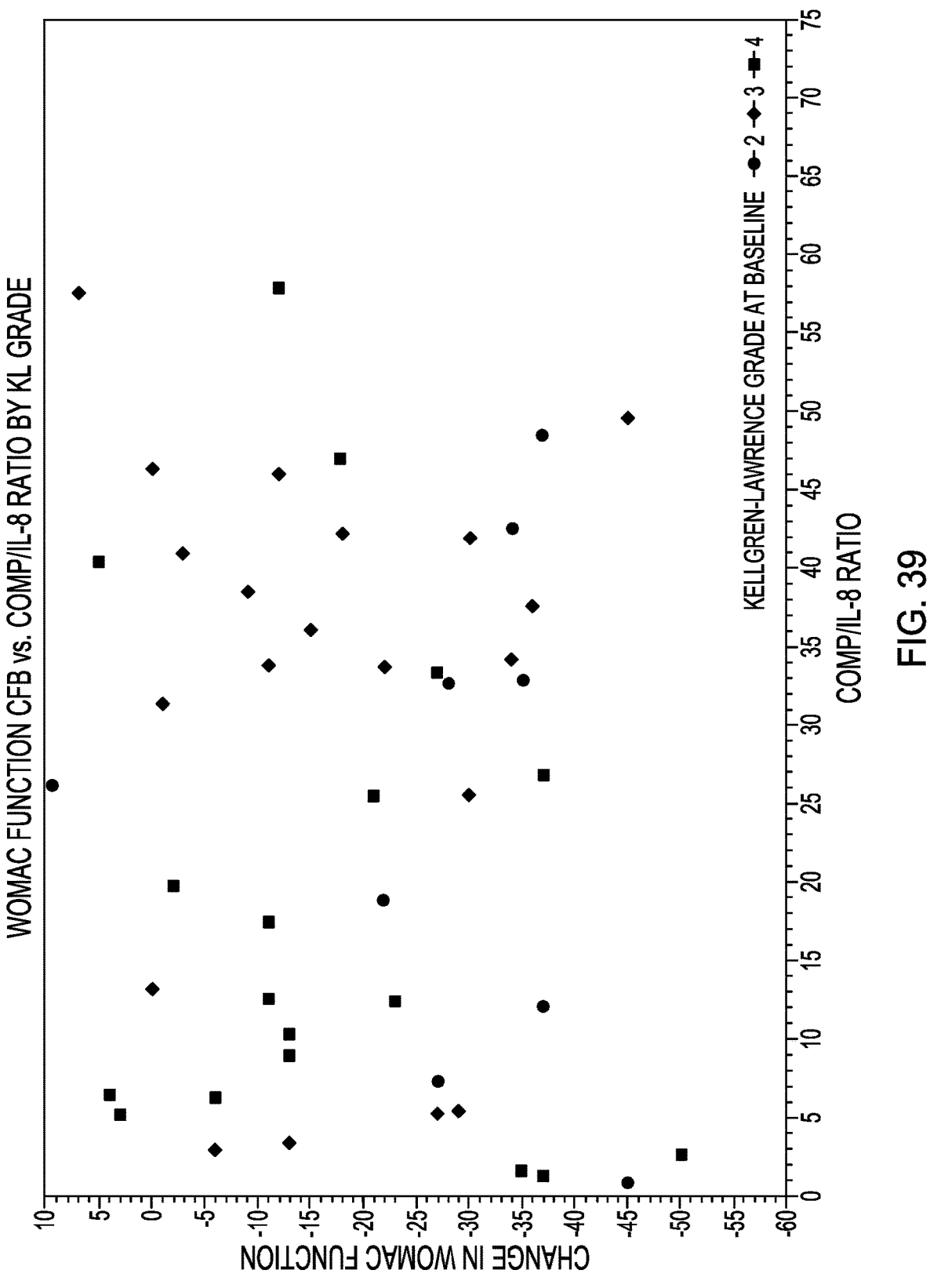
FIG. 39 illustrates a plot of synovial fluid samples by COMP:IL-8 ratio and WOMAC Function CFB for various stages of OA.
Figure 40:
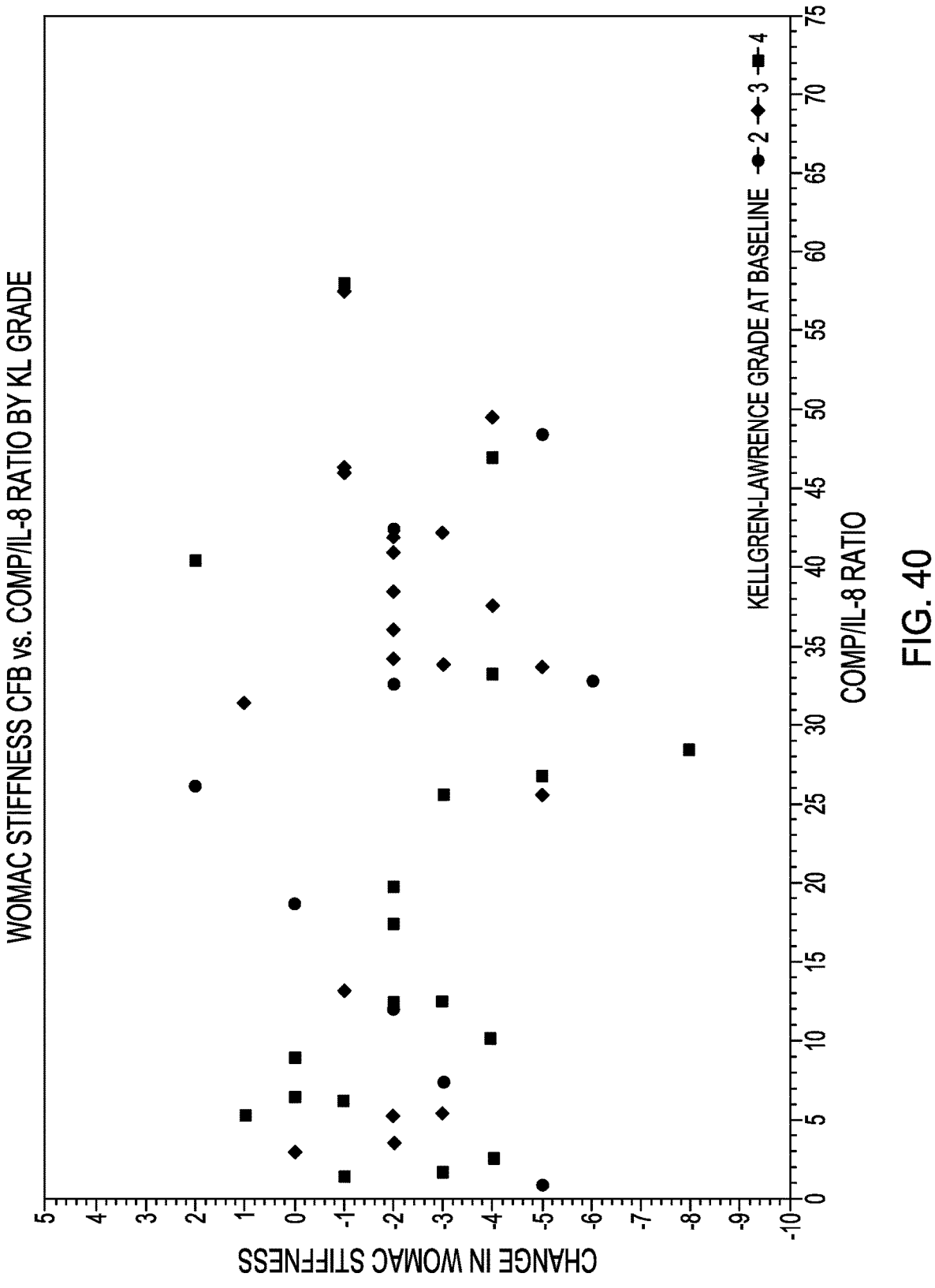
FIG. 40 illustrates a plot of synovial fluid samples by COMP:IL-8 ratio and WOMAC Stiffness for various stages of OA.

Analysis of variance was performed using sample data from Examples 4 and 5. FIG. 38 shows synovial fluid samples staged KL 2, KL 3, and KL 4 plotted against COMP/IL-8 ratio, WOMAC Pain and Change in WOMAC Pain. FIG. 39 shows synovial fluid samples staged KL 2, KL 3 and KL 4 plotted against COMP/IL-8 ratio, WOMAC Function and Change in WOMAC Function. FIG. 40 shows synovial fluid samples staged KL 2, KL 3 and KL 4 plotted against COMP/IL-8 ratio, WOMAC Stiffness and Change in WOMAC Stiffness.

TABLE 33

Synovial fluid sample variance by COMP, IL-8, COMP/IL-8
ratio with treatment, demographic, and baseline symptoms

| Dependent Var. | Source | F-Value | P-Value |
|---|---|---|---|
| COMP | Treatment | 1.57 | 0.2175 |
| | Gender | 0.23 | 0.6315 |
| | Race | 2.62 | 0.0399 |
| | BMI | 3.08 | 0.0874 |
| | Baseline KL | 0.39 | 0.6782 |
| | Baseline WOMAC Pain | 0.37 | 0.5465 |
| | Baseline WOMAC Function | 0.02 | 0.8930 |
| | Baseline WOMAC Stiffness | 0.20 | 0.6547 |
| COMP/ | Treatment | 0.76 | 0.3882 |
| IL-8 Ratio | Gender | 0.05 | 0.8306 |
| | Race | 0.90 | 0.4894 |
| | BMI | 0.06 | 0.8143 |
| | Baseline KL | 3.38 | 0.0453 |
| | Baseline WOMAC Pain | 0.14 | 0.7106 |
| | Baseline WOMAC Function | 0.19 | 0.6685 |
| | Baseline WOMAC Stiffness | 0.40 | 0.5329 |
| IL-8 | Treatment | 0.29 | 0.5911 |
| | Gender | 0.35 | 0.5560 |
| | Race | 0.59 | 0.7090 |
| | BMI | 0.41 | 0.5280 |
| | Baseline KL | 0.74 | 0.4830 |
| | Baseline WOMAC Pain | 3.46 | 0.0708 |
| | Baseline WOMAC Function | 0.01 | 0.9375 |
| | Baseline WOMAC Stiffness | 3.31 | 0.0769 |

TABLE 34

Analysis of Baseline KL Least Square Means for
COMP, IL-8 and COMP/IL-8 ratio, with treatment,
demographic, and baseline symptoms

| Effect | | LS Mean COMP/IL-8 | LS Mean COMP | LS Mean IL-8 |
|---|---|---|---|---|
| Baseline KL | 2 | 35.60 | 4168.5 | 13.49 |
| | 3 | 35.90 | 4597.1 | 242.27 |
| | 4 | 22.11 | 4285.2 | 447.44 |
| Gender | F | 30.62 | 4248.4 | 157.27 |
| | M | 31.79 | 4452.1 | 311.52 |
| Race | African-American | 20.70 | 3116.7 | 592.62 |
| | Asian/Pacific Islander | 35.51 | 3182.1 | −322.3 |
| | Not Specified | 30.40 | 5606.3 | 393.74 |
| | Other | 37.79 | 5384.2 | 183.34 |
| | White (Hispanic) | 38.52 | 5269.7 | 66.82 |
| | White (Non-Hispanic) | 24.31 | 3542.6 | 492.15 |
| Treatment | Saline (Controls) | 28.86 | 4091.3 | 165.43 |
| | N-Stride APS | 33.55 | 4609.2 | 303.36 |

TABLE 35

| | Correlation w/COMP-IL-8 Ratio | P-Value COMP-IL-8 Ratio | Correlation w/COMP | P-Value COMP | Correlation w/IL-8 | P-Value IL-8 |
|---|---|---|---|---|---|---|
| Variable | | | | | | |
| BMI | −0.03139 | 0.8234 | 0.21396 | 0.1203 | 0.06565 | 0.6372 |
| Baseline WOMAC Function | −0.16163 | 0.2476 | 0.05869 | 0.6733 | 0.16764 | 0.2256 |
| Baseline WOMAC Pain | −0.03269 | 0.8162 | 0.13810 | 0.3193 | 0.019168 | 0.1650 |
| Baseline WOMAC Stiffness | 0.02541 | 0.8567 | 0.10030 | 0.4705 | 0.09656 | 0.4873 |

Pearson Correlation analysis of COMP, IL-8, and COMP/IL-8 ratio with treatment, demographic and treatment These analyses have found that COMP/IL-8 ratio decreases with OA disease progression. Thus, the COMP/IL-8 ratio can be used to stage OA or to monitor OA progression. The COMP/IL-8 ratio can also be used to monitor treatment effect.

Example 9

Staging Osteoarthritis, and Monitoring Disease Progression or Treatment

In the biomarker screening as performed in Examples above, we identified biomarkers levels in synovial fluid that increase and we identified biomarker levels that decrease as OA progresses from early to mid-stage, from mid-stage to late-stage and from early-stage to late-stage, based on Kellgren-Lawrence scale. Results of screening of some of these biomarkers are shown in FIGS. 15A-15C and FIGS. 17A-17H. As noted in Example 6, COMP/IL-8 ratio decreases with increasing OA severity/progression, suggesting COMP/IL-8 ratio as a method to stage OA severity, and monitor OA progression and/or treatment.

Biomarker that increase with progression of OA, i.e., advancing stage of OA and/or worsening of OA symptoms are identified in Table 36 below. Biomarker levels in synovial fluid that decrease from early to mid-stage, from mid-stage to late-stage and from early-stage to late-stage, based on Kellgren-Lawrence scale, are identified in Table 37 below. Monitoring expression of one or a combination of biomarkers of osteoarthritis that increase or decrease can be used to assist in staging the severity of OA disease in individual subjects over time, to determine whether OA disease is progressing, and/or to determine if lifestyle and/or therapeutic interventions, e.g., physical therapy, analgesics, DMODs, hyaluronic acid, PRP, or other therapeutic compositions are effective in treating the disease, delaying progression of the disease or reversing cartilage degradation. Monitoring expression of one or a combination of biomarkers of osteoarthritis that increase or decrease can also be used to assess the possibility that prospective therapeutic agents will be effective in treating OA and/or to determine the benefit of treatment regimens and/or therapeutic agents in treating OA.

TABLE 36

Biomarkers Increasing with OA Progression (ranked from top to bottom by magnitude of change; KL = Kellgren-Lawrence scale)

| Early to Mid-Stage OA KL 0/1 to KL 2/3 | Mid-to Late-Stage OA KL 2/3 to KL 4 | Early to Late-Stage OA K L 0/1 to KL 4 |
|---|---|---|
| TNFSF9 | IL36RN | IL36RN |
| CGA | CXCL1 | TNFSF9 |
| MST1 | LAIR1 | CXCL1 |
| ADGRG1 | FST | MSTI |
| THBS2 | IL1F10 | ADGRG1 |
| LAMP1 | NRXN3 | CGA |
| SIGIRR | FCRL1 | FCRL1 |
| PTX3 | PDCD1 | FST |
| FABP2 | BAMBI | FABP2 |
| CD320 | ADGRG1 | LAMP1 |

TABLE 37

Biomarkers Decreasing with OA Progression (ranked from top to bottom by magnitude of change; KL = Kellgren-Lawrence scale)

| Early to Mid-Stage OA KL 0/1 to KL 2/3 | Mid-to Late-Stage OA KL 2/3 to KL 4 | Early to Late-Stage OA KL 0/1 to KL 4 |
|---|---|---|
| FGF5 | IL-1B | IL-1B |
| TFP12 | CD86 | CD 8 6 |
| GPC5 | MMP-8 | MMP-8 |
| FRZB | AGT | FGF5 |
| CCL22 | CSF3R | GPC5 |
| IL16 | CCL15 | TFP12 |
| EFNB3 | IL-12B | CCL22 |
| NCR2 | | CSF3R |
| TNFSF1B | | IL-16 |
| | | AGT |

Method examples described herein can be machine or computer-implemented at least in part. Some examples can include a computer-readable medium or machine-readable medium encoded with instructions operable to configure an electronic device to perform methods as described in the above examples, including one or more of the algorithms described in above Examples. An implementation of such methods can include code, such as microcode, assembly language code, a higher-level language code, or the like.

Such code can include computer readable instructions for performing various methods. The code may form portions of computer program products. A code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method of evaluating a synovial fluid, comprising:
extracting a synovial fluid sample from a painful or inflamed joint of a subject;
determining a level of a first biomarker in the synovial fluid sample using an analytical technique selected from enzyme-linked immunosorbent assay (ELISA) or mass spectrometry, the first biomarker selected from cartilage oligomeric matrix protein (COMP), osteopontin (OPN), osteoprotegerin (O1G), and osteocalcin (OC);
determining a level of a second biomarker in the synovial fluid sample using an analytical technique selected from enzyme-linked immunosorbent assay (ELISA), immunoturbidimetric assay, or mass spectrometry, the second biomarker selected from interleukin-8 (IL-8), interleukin-6 (IL-6), C-reactive protein (CRP), matrix metalloproteinase-9 (MMP-9), matrix metalloproteinase-3 (MMP-3), neutrophil gelatinase-associated lipocalin (NGAL), and a platelet-derived growth factor (PDGF);
determining a sample biomarker ratio of the levels of the first biomarker and the second biomarker in the synovial fluid sample;
comparing the sample biomarker ratio to a reference ratio of the levels of the first biomarker and the second biomarker in a reference synovial fluid; and
and
administering a treatment to the subject based on the comparing step, wherein when the sample biomarker ratio is greater than or equal to the reference ratio, the treatment comprises a therapy for osteoarthritis selected from the group consisting of: viscosupplementation, hyaluronic acid, platelet-rich plasma, a disease-modifying osteoarthritis drug, and a corticosteroid, and wherein when the sample biomarker ratio is less than the reference ratio, the treatment comprises a therapy for inflammatory arthropathy selected from the group consisting of: a disease-modifying antirheumatic drug, a biologic response modifier, a corticosteroid, and a nonsteroidal anti-inflammatory drug.

2. The method of claim 1, wherein when the sample biomarker ratio is greater than or equal to the reference ratio the subject is confirmed to have osteoarthritis.

3. The method of claim 1, further comprising determining the presence of a third biomarker in the synovial fluid sample when the sample biomarker ratio is less than the reference ratio.

4. The method of claim 1, wherein when the level of the first biomarker in the synovial fluid sample is less than a reference level of the first biomarker osteoarthritis can be excluded from a diagnosis of the subject's joint pain or inflammation.

5. The method of claim 1, wherein when the level of the second biomarker in the synovial fluid sample is greater than or equal to a reference level of the second biomarker an inflammatory arthropathy or traumatic injury is present in the subject's joint.

6. A method of evaluating a synovial fluid, comprising:
extracting a synovial fluid sample from a painful or inflamed joint of a subject;
determining a level of a first biomarker in the synovial fluid sample using an analytical technique selected from enzyme-linked immunosorbent assay (ELISA) or mass spectrometry, the first biomarker selected from cartilage oligomeric matrix protein (COMP), osteopontin (OPN), osteoprotegerin (O1G), and osteocalcin (OC);
comparing the level of the first biomarker in the synovial fluid sample to a reference level of the first biomarker;
determining a level of a second biomarker in the synovial fluid sample using an analytical technique selected from enzyme-linked immunosorbent assay (ELISA) or mass spectrometry when the level of the first biomarker is greater than or equal to the reference level of the first biomarker, the second biomarker selected from interleukin-8 (IL-8), interleukin-6 (IL-6), C-reactive protein (CRP), matrix metalloproteinase-9 (MMP-9), matrix metalloproteinase-3 (MMP-3), neutrophil gelatinase-associated lipocalin (NGAL), and a platelet-derived growth factor (PDGF); and
administering a treatment to the subject, wherein when the level of the first biomarker is greater than or equal to the reference level of the first biomarker, the treatment comprises a therapy for osteoarthritis selected from the group consisting of: viscosupplementation, hyaluronic acid, platelet-rich plasma, a disease-modifying osteoarthritis drug, and a corticosteroid, and wherein when the level of the first biomarker is less than the reference level of the first biomarker, the treatment comprises a therapy for inflammatory arthropathy selected from the group consisting of: a disease-modifying antirheumatic drug, a biologic response modifier, a corticosteroid, and a nonsteroidal anti-inflammatory drug.

7. The method of claim 6, further comprising comparing the level of the second biomarker to a reference level of the second biomarker.

8. The method of claim 6, further comprising determining a biomarker ratio of the level of the first biomarker and the level of the second biomarker in the synovial fluid sample and comparing the biomarker ratio with a reference ratio of the levels of the first biomarker and the second biomarker in the reference.

9. The method of claim 6, wherein when the level of the first biomarker in the synovial fluid sample is less than the reference level of the first biomarker osteoarthritis is excluded from a diagnosis of the subject's joint pain or joint inflammation.

10. A method of evaluating joint pain or joint inflammation in a subject, comprising:
extracting a synovial fluid sample from the joint;
determining a level of cartilage oligomeric matrix protein (COMP) in the synovial fluid sample using an analytical technique selected from enzyme-linked immunosorbent assay (ELISA), immunoturbidimetric assay, or mass spectrometry; and
determining a level of interleukin-8 (IL-8) in the synovial fluid sample using an analytical technique selected from enzyme-linked immunosorbent assay (ELISA) or mass spectrometry when the level of COMP is greater than or equal to 1,500 ng/ml and administering a therapy for osteoarthritis selected from the group consisting of: viscosupplementation, hyaluronic acid, platelet-rich plasma, a disease-modifying osteoarthritis drug, and a corticosteroid to the subject, or determining the presence of anti-cyclic citrullinated peptide (anti-CCP1) or rheumatoid factor (RF) in the synovial fluid sample using an analytical technique selected from enzyme-linked immunosorbent assay (ELISA), immunoturbidimetric assay, or mass spectrometry when the level of COMP is less than 1,500 ng/mL and administering a therapy for inflammatory arthropathy selected from the group consisting of: a disease-modifying antirheumatic drug, a biologic response modifier, a corticosteroid, and a nonsteroidal anti-inflammatory drug to the subject.

11. The method of claim 10, further comprising determining the presence of or absence of monosodium urate (MSU) crystals or calcium pyrophosphate dihydrate (CPPD) crystals in the synovial fluid sample.

12. The method of claim 10, further comprising determining a red blood cell (RBC) count, a white blood cell (WBC) count, the percentage of polymorphonuclear WBCs, the presence of alpha-defensin (AD), the presence of lactate, or the presence of neutrophil elastase in the synovial fluid sample.

13. The method of claim 10, further comprising determining the absorbance at 280 nm (A280) of the synovial fluid sample and comparing the A280 of the sample with a reference A280.

14. The method of claim 10, wherein when the level of COMP is less than 1,500 ng/ml osteoarthritis is excluded from a diagnosis of the subject's joint pain or joint inflammation.

15. The method of claim 10, further comprising determining a concentration ratio of COMP:IL-8 when the level of COMP is greater than or equal to 1,500 ng/mL.

16. The method of claim 10, wherein a concentration ratio of COMP:IL-8 greater than or equal to 2.0 ng/pg or greater than or equal to 2,000 indicates the subject has osteoarthritis.

17. The method of claim 10, wherein a level of IL-8 less than 600 µg/mL indicates the subject does not have an inflammatory arthropathy or an acute traumatic injury to the joint.

18. The method of claim 10, further comprising treating the subject for osteoarthritis when the level of COMP is greater than or equal to 1,500 ng/mL.

19. The method of claim 10, further comprising treating the subject for an inflammatory arthropathy or acute traumatic injury when the level of COMP is less than 1,500 ng/mL.

20. The method of claim 10, further comprising treating the subject for an inflammatory arthropathy when a concentration ratio of COMP:IL-8 is less than 4.3 ng/pg or less than 4300, or treating the subject for osteoarthritis when the ratio of COMP:IL-8 is greater than or equal to 4.3 ng/pg or greater than or equal to 4300.

\* \* \* \* \*